US005486762A

United States Patent [19]
Freedman et al.

[11] Patent Number: 5,486,762
[45] Date of Patent: Jan. 23, 1996

[54] APPARATUS INCLUDING MULTI-WAIT TIME PULSED NMR LOGGING METHOD FOR DETERMINING ACCURATE $T_2$-DISTRIBUTIONS AND ACCURATE $T_1/T_2$ RATIOS AND GENERATING A MORE ACCURATE OUTPUT RECORD USING THE UPDATED $T_2$-DISTRIBUTIONS AND $T_1/T_2$ RATIOS

[75] Inventors: Robert Freedman, Houston; Christopher E. Morriss, The Woodlands, both of Tex.

[73] Assignee: Schlumberger Technology Corp., Houston, Tex.

[21] Appl. No.: 291,960

[22] Filed: Aug. 15, 1994

Related U.S. Application Data

[63] Continuation-in-part of Ser. No. 127,978, Sep. 28, 1993, Pat. No. 5,381,092, which is a continuation of Ser. No. 970,332, Nov. 2, 1992, Pat. No. 5,291,137.

[51] Int. Cl.⁶ .................................................. G01R 33/20
[52] U.S. Cl. ............................................................ 324/303
[58] Field of Search ..................................... 324/300, 303, 324/307, 309, 318, 322; 335/296

[56] References Cited

U.S. PATENT DOCUMENTS

| | | | |
|---|---|---|---|
| 3,617,867 | 11/1971 | Herzog | 324/303 |
| 4,350,955 | 9/1982 | Jackson et al. | 324/303 |
| 4,710,713 | 12/1987 | Strikman | 324/303 |
| 4,714,881 | 12/1987 | Given | 324/303 |
| 4,717,876 | 1/1988 | Masi et al. | 324/303 |
| 4,717,877 | 1/1988 | Taicher et al. | 324/303 |
| 4,717,878 | 1/1988 | Taicher et al. | 324/303 |
| 4,933,638 | 6/1990 | Kenyon et al. | 324/303 |
| 5,023,551 | 6/1991 | Kleinberg et al. | 324/303 |
| 5,055,787 | 10/1991 | Kleinberg et al. | 324/303 |
| 5,055,788 | 10/1991 | Kleinberg et al. | 324/303 |
| 5,291,137 | 3/1994 | Freedman | 324/303 |
| 5,381,092 | 1/1995 | Freedman | 324/303 |
| 5,389,877 | 2/1995 | Sezginer et al. | 324/303 |

OTHER PUBLICATIONS

SPE 26472 entitled "Restrictive Diffusion From Uniform Gradient NMR Well Logging", dated Oct. 3–6, 1993 Society of Petroleum Engineers.

IEEE Geoscience and Remote Sensing Society Newsletter, pp. 576–590, dated Sep. 1992, pp. 7–15, entitled "Data Compression in Remote Sensing Applications".

(List continued on next page.)

Primary Examiner—Sandra L. O'Shea
Assistant Examiner—Raymond Y. Mah
Attorney, Agent, or Firm—John H. Bouchard

[57] ABSTRACT

When a pulsed nuclear magnetic resonance (NMR) well logging tool is traversing a wellbore, a NMR well logging method includes magnetizing the hydrogen nuclei in a formation traversed by the tool with a static magnetic field, waiting for a first period of time $W_1$, energizing the formation with oscillating RF pulses, collecting a first plurality of spin echo signals, waiting a second period of time $W_2$ which is different from the first period of time $W_1$, energizing the formation with oscillating RF pulses, collecting a second plurality of spin echo signals, waiting a third period of time $W_3$ which is different from both the second period of time $W_2$ and the first period of time $W_1$, energizing the formation with oscillating RF pulses, collecting a third plurality of spin echo signals, etc. The first, second and third, etc. plurality of spin echo signals corresponding to the different wait times are input to a signal processing apparatus disposed in the tool. Window sums of spin-echo signals are computed and transmitted uphole to a surface oriented signal processing apparatus. In response to the window sums, the surface signal processing apparatus determines an apparent formation $T_2$-distribution for each wait time in the multi-wait time pulse sequence. The apparent $T_2$-distributions are used to construct a cost function. When the cost function is minimized, the surface oriented signal processing apparatus determines estimates of the true $T_1/T_2$ ratios and intrinsic $T_2$-distributions of the formations being logged. The surface signal processing apparatus uses the new $T_2$-distribution to generate new, more accurate, output record medium.

30 Claims, 41 Drawing Sheets

OTHER PUBLICATIONS

SPE 20561 entitled "Spin Echo Magnetic Resonance Logging: Porosity and Free Fluid Index Determination", pp. 321–334, dated Sep. 23–26, 1990, Society of Petroleum Engineers.

Sezginer, A., Kleinberg, R. L., Fukuhara, A., and Latour, L. L., "Very Rapid Measurement of Nuclear Magnetic Resonance Spin–Lattice Relaxation Time and Spin–Spin Relaxation Time," J. of Magnetic Resonance, v. 92, 504–527 (1992).

Kleinberg, R. L. Sezginer, A., Griffin, D. D. and Fukuhara, M., "Novel NMR Apparatus For Investigating An External Sample," J. of Magnetic Resonance, v. 97, 466–485 (1992).

Gallegos, D. P. and Smith, D. M., "A NMR Technique for the Analysis of Pore Structure: Determination of Continuous Pore Size Distributions", J. of Colloid and Interface Science, v. 122, No., 1, pp. 143–153, Mar. 1988.

Brown, R. J. S., Borgia, G. C., Fantazzini, P., and Mesini, E., "Problems In Identifying Multimodal Distributions Of Relaxation Times for NMR In Porous Media," Magnetic Resonance Imaging, vol. 9, pp. 687–693 (1991).

Kenyon, W. E. Howard, J. J., Sezginer, A., Straley, C., Matteson, A., Horkowitz, R., and Erlich, R., "Pore–size Distribution and NMR in Microporous Cherty Sandstones, Tran. of the SPWLA of the 30th Ann. Logging Symp.," Paper LL, Jun. 11–14, 1989.

Latour, L. L., Kleinberg, R. L. and A. Sezginer, "Nuclear Magnetic Resonance Properties of Rocks at Elevated Temperatures," J. of Colloid and Interface Science, v. 150, 535 (1992).

Twomey, S., "Introduction To the Mathematics of Inversion In Remote Sensing And Indirect Measurement," published by Elevated Scientific Publishing Company, 1977.

Straley, C., Morriss, C. E. Kenyon, W. E., and Howard, J. J., "NMR in Partially Saturated Rocks: Laboratory Insights on Free Fluid Index and Comparison with Borehole Logs", Trans. of the SPWLA 32nd Ann. Logging Symp. Paper CC, Jun. 16–19, 1991.

Butler, J. P., Reeds, J. A. and Dawson, S. V., "Estimating Solutions of First Kind Integral Equations with Non–Negative Constraints and Optimal Smoothing", SIAM J. Numerical Anal., v. 18, No. 3, 381–397, 1991.

Kleinberg, R. L., Straley, C., Kenyon, W. E., Akkurt, R. and Farooqui, S. A., 1993b, Nuclear Magnetic resonance of rocks: $T_1$ vs. $T^2$: SPE 26470, Proceedings 1993 SPE Ann. Tech. Conf. And Exhibition, Houston, Tex., Oct. 3–6, 553–563.

Kleinberg, R. L., Farooqui, S. A., and Horsfield, M. A., 1993a, $T_1/T_2$ ratio and frequency dependence of NMR relaxation in porous sedimentary rocks: J. of Colloid and Interface Science, v. 158, 195–198.

Farrar, T. C. and Becker, E. D., 1971, Pulse and fourier transform NMR: Academic Press, 27–29.

Morriss, C. E. MacInnis, J., Freedman, R., Smaardyk, J., Straley, C., Kenyon, W. E., Vinegar, H. J., and Tutunjian, P. N., 1993, Field test of an experimental pulsed nuclear magnetism tool, paper GGG in 34th Annual Logging Symposium Transactions: Soc. of Professional Well Log Analysts.

$B_0 = 0$
$M \cong 0$ (WITHOUT MAGNET)

$B_0 \neq 0$
$M \neq 0$ (WITH MAGNET)

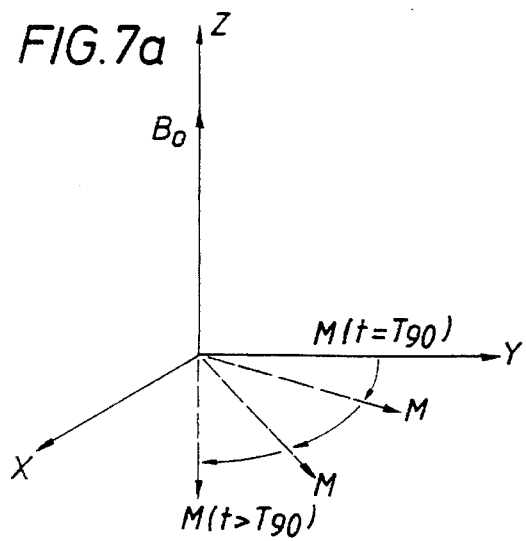
FIG.7a
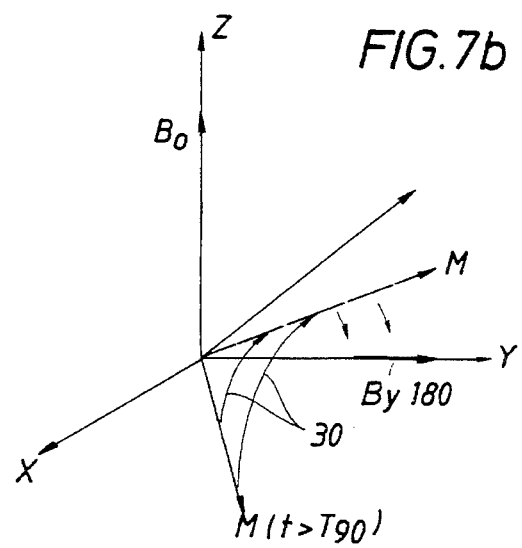
FIG.7b
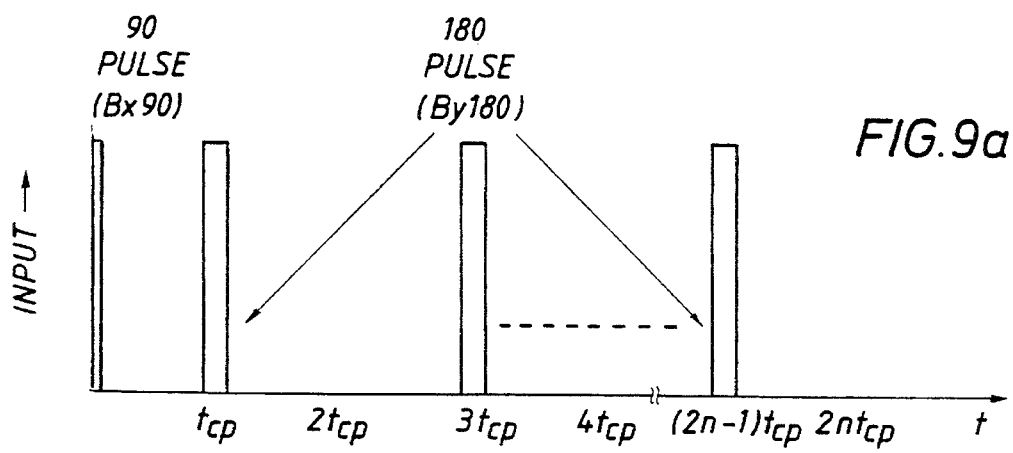
FIG.9a
FIG.9b

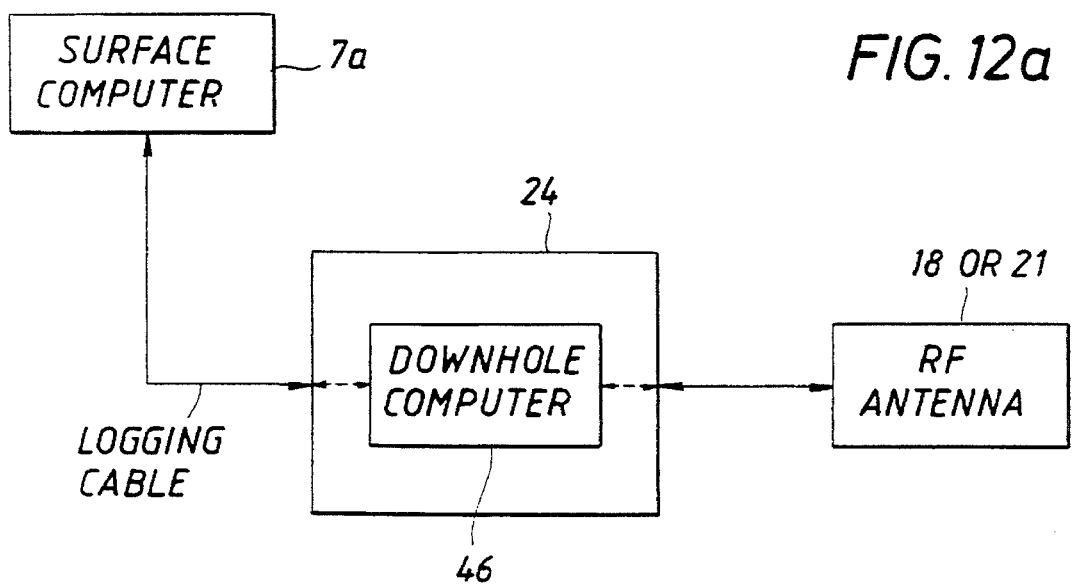
FIG. 12a
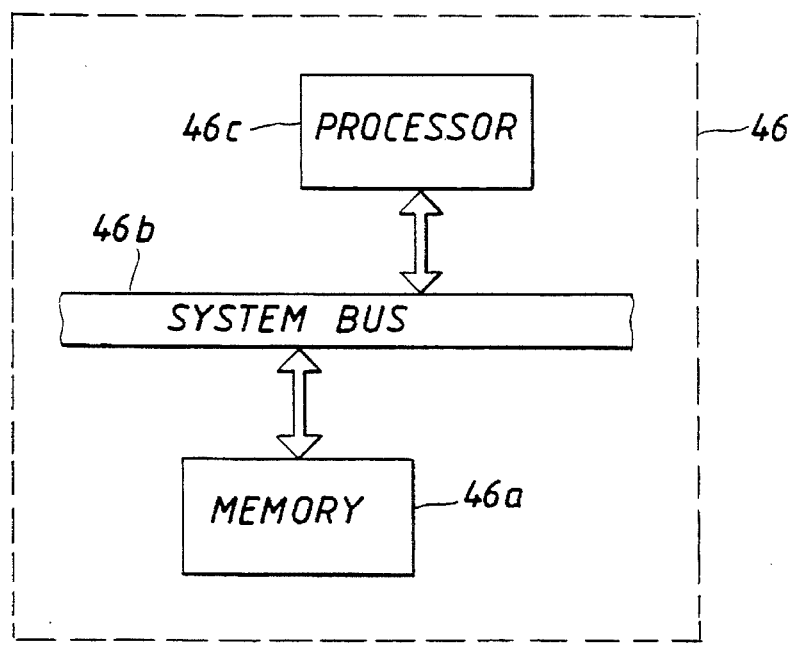
FIG. 12b1
FIG. 12b2

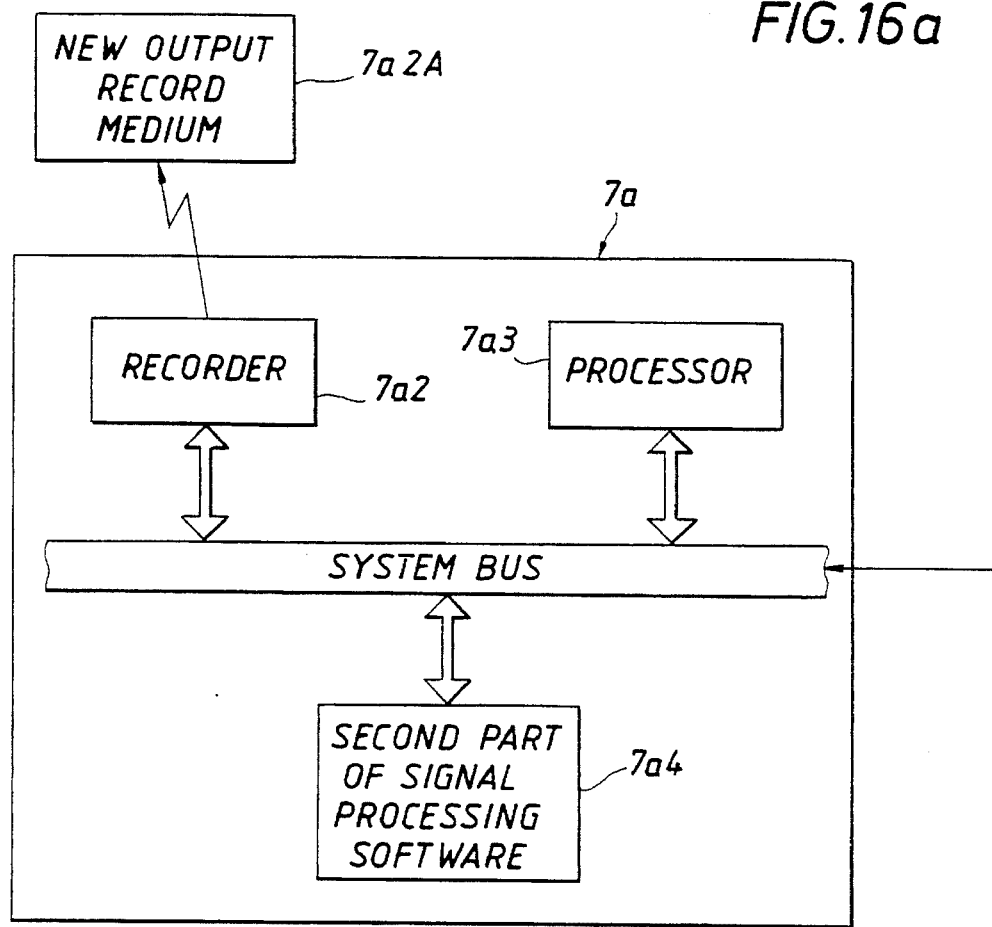
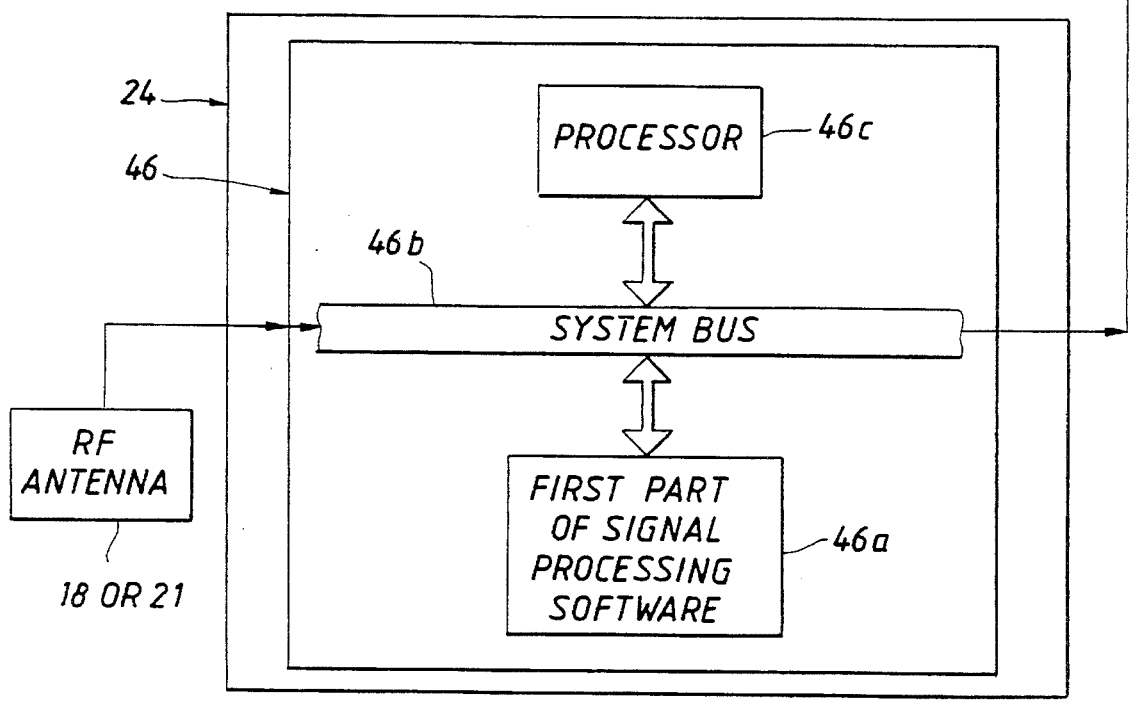
FIG. 16a

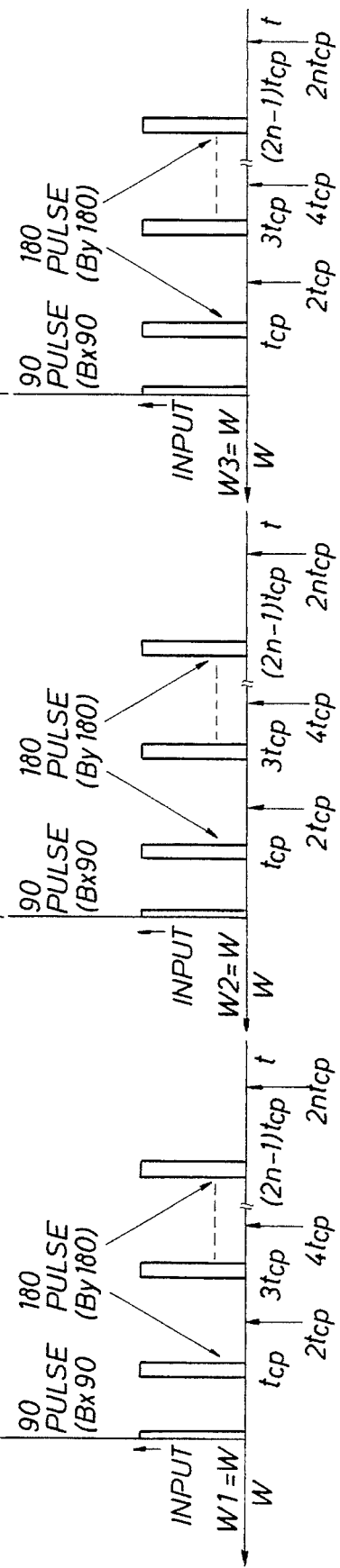

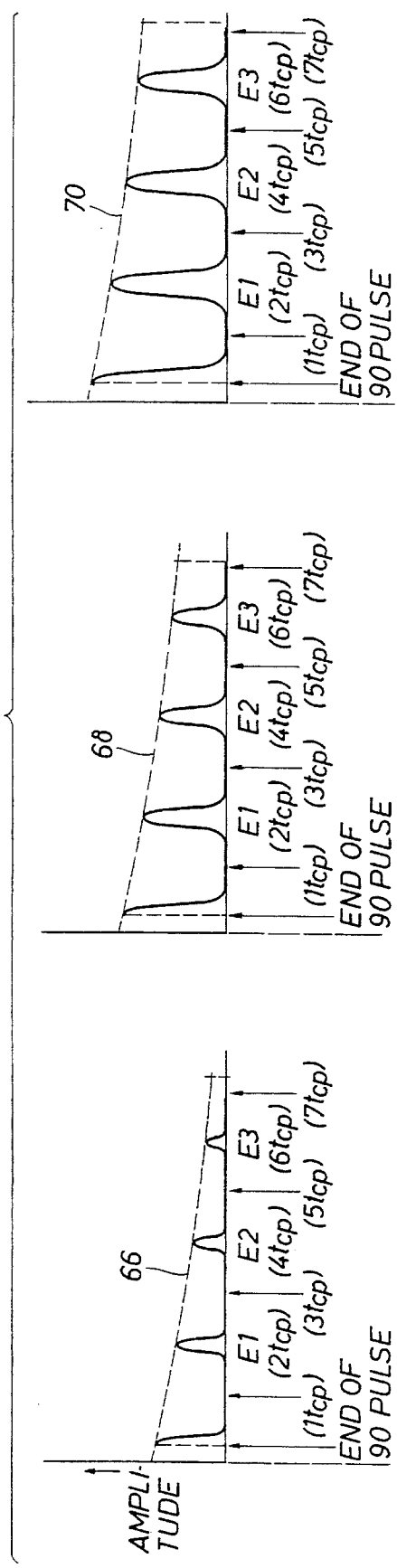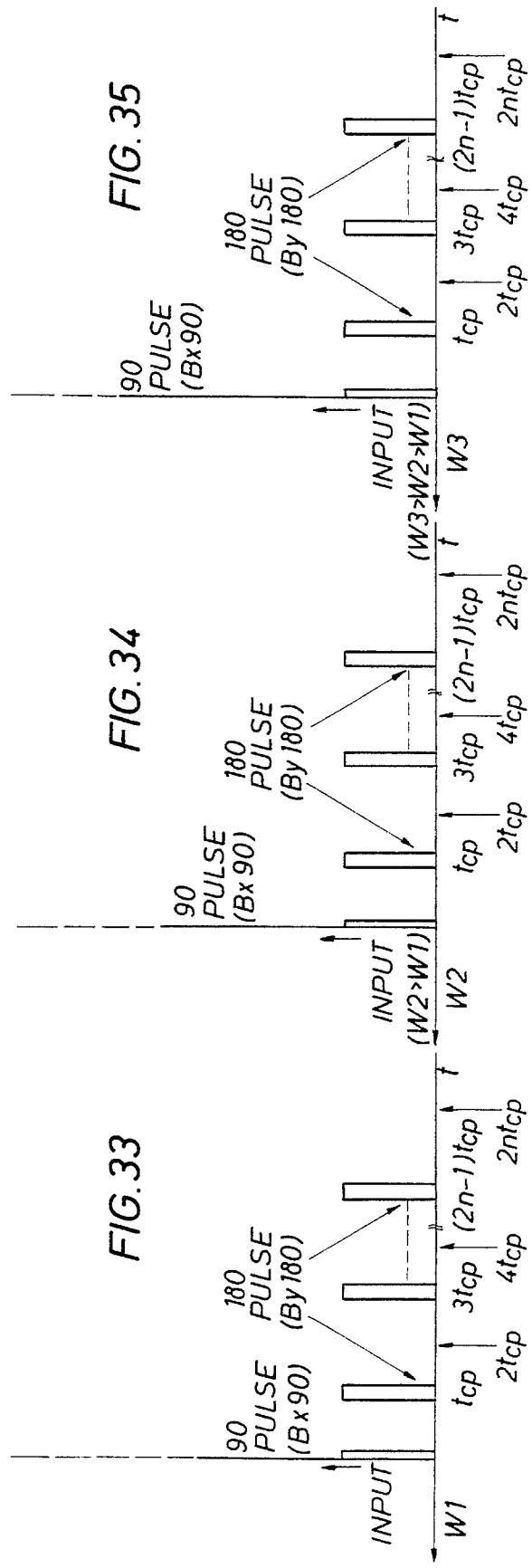

APPARATUS INCLUDING MULTI-WAIT TIME PULSED NMR LOGGING METHOD FOR DETERMINING ACCURATE $T_2$-DISTRIBUTIONS AND ACCURATE $T_1/T_2$ RATIOS AND GENERATING A MORE ACCURATE OUTPUT RECORD USING THE UPDATED $T_2$-DISTRIBUTIONS AND $T_1/T_2$ RATIOS

CROSS REFERENCE TO RELATED APPLICATIONS

This application is a continuation in part of prior pending application Ser. No. 08/127,978, filed Sep. 28, 1993, now U.S. Pat. No. 5,381,092 which prior pending application is a continuation of prior application Ser. No. 07/970,332, filed Nov. 2, 1992, entitled "Processing Method and Apparatus for Processing Spin Echo In-Phase and Quadrature Amplitudes From a Pulsed Nuclear Magnetism Tool and Producing new Output Data to be Recorded on an Output Record," now U.S. Pat. No. 5,291,137 issued to Freedman.

BACKGROUND OF THE INVENTION

The subject matter of the present invention relates to a new Pulsed Nuclear Magnetic Resonance (NMR) well logging apparatus using a multi-wait time pulsed nuclear magnetic resonance (NMR) logging method for processing a plurality of multi-wait time spin echo pulse sequences which are output from a pulsed nuclear magnetic resonance (NMR) tool when the tool is traversing a wellbore.

Commercial and experimental pulsed NMR logging methods and apparatus, which acquire depth logs from a continuously moving logging sonde, have employed the Carr-Purcell-Meiboom-Gill (CPMG) pulse sequence. The CPMG pulse sequence is defined in eq. (1) of the this specification and in U.S Pat. No. 5,291,137 issued to Freedman (hereafter called "the Freedman patent"). Recalling eq. 1 of the Freedman patent and part A of this specification, the CPMG pulse sequence for a phase alternated pair can be written in the form:

$$CPMG^{(\pm)}: W-90°(\pm x)-(t_{cp}-180°(y)-t_{cp}-(echo)_j)_{j=1,2,\ldots,J}. \quad (1)$$

For purposes of the present discussion, the important ingredient in {:he above equation describing the CPMG pulse sequences is the wait time (W) that precedes each set of radio frequency (RF) pulses that produce the spin echoes. A detailed description of the action of the RF pulses is given in part A of this specification. Here we note that a watt time is required so that the nuclear magnetization which produces the spin-echo signals can approach its thermal equilibrium value (in the magnetic field produced by a permanent magnet in the tool sonde). During depth logging with a continuously moving logging tool, the pulse sequence in eq. 1 is repeated, as the tool traverses the borehole, using a single wait time (W) which is approximately 1.0 second in duration. In many reservoir rock formations, the magnetization attains only a fraction of its thermal equilibrium value (e.g., its maximum attainable value at a given temperature) during the wait time and therefore the logs of the NMR properties must be corrected to account for the fact that the wait time is too short. Increasing the wait time is not a viable solution because it is inefficient and leads to reduced logging speeds which is undesirable for a commercial well logging service.

The single wait time CPMG pulse sequence described above produces spin-echo waveforms that, by signal processing, are used to compute $T_2$-distributions of the the porous rock formations traversed by the NMR tool. The $T_2$-distributions are used to compute the NMR logs. Because only a single wait time (W) is utilized, the spin echo waveforms have no direct sensitivity to the $T_1$-distributions which determine the rate at which the magnetization approaches its thermal equilibrium value during the wait time (W). Thus an accurate correction for insufficient wait time is not possible using a single wait time pulsed NMR logging method. The Freedman patent introduced a parameter called the $T_1/T_2$ ratio (denoted in the Freedman patent by the Greek symbol ξ) which was utilized in the signal processing algorithm as a means for correcting the log outputs for insufficient wait time. The correction is based on an empirical relationship established by Kleinberg, et al. (see references 11 and 12 in part B of this specification) which relates the $T_1$ and $T_2$-distributions of porous rock samples. The Kleinberg, et al. work in references 11 and 12 showed that at the low frequencies (e.g., in the 2 MHz range) at which pulsed NMR logging tools operate, the two relaxation time distributions are approximately congruent (i.e., have the same shape and size). Moreover it was shown that $T_1 \equiv \xi T_2$. The Kleinberg, et al. publication in reference 11 shows that the true value of the ratio ε varies from one rock sample to the next. The correction for finite wait time used in the Freedman patent assumed a constant (and incorrect) value for ε since the true value is not known and can not be determined using the single wait time CPMG pulse sequence disclosed in the teachings of the Freedman patent.

It is useful to review the Freedman patent since the invention disclosed here utilizes the teachings of the Freedman patent and also discloses improved new apparatus and methods for eliminating the inherent accuracy problem associated with the teachings of the Freedman patent.

In the U.S. Pat. No. 5,291,137 issued to Freedman, a nuclear magnetic resonance (NMR) tool known as the Combinable Magnetic Resonance Tool (CMR tool), also formerly known as the Pulsed Nuclear Magnetism Tool (PNMT), is disposed in a wellbore (hereinafter, the CMR tool will be known as the "NMR tool"). The NMR tool produces a nuclear magnetization in a formation traversed by the wellbore by applying a static magnetic field $B_0$ to the formation. The magnetic field is produced by a permanent magnet located in the logging tool. The nuclear magnetization is produced during a predetermined wait time W which is followed by a set of radio frequency (rf) pulses which produce the measured spin-echo signals from the rock formations. Following the rf pulses the nuclear magnetization is practically zero and another wait time is required to re-establish the magnetization prior to application of the next set of rf pulses. During the wait time, the magnetic moments of the protons contained in the fluids (gas, oil and water) align themselves along the direction of the static magnetic field $B_0$. Ideally, the wait time W would be chosen to be sufficiently long so that the magnetic moments are completely aligned with the field $B_0$ as shown schematically in FIG. 5 of the Freedman patent. In practice, this can require wait times as long as 10 seconds in some reservoirs but these wait times would be impractical for a moving logging tool. It is undesirable to increase the wait time because for a desired vertical resolution of the NMR measurement the logging speeds would be decreased in proportion and would be too slow for a commercial logging service. In practice wait times are selected to be generally less than 3 seconds for continuous logging so that a correction for insufficient wait time (or equivalently, for incomplete recovery of the total nuclear magnetization following the set of rf pulses) must be applied in many situations.

After the wait time W, the logging tool begins energizing the formation with a plurality of rf pulses starting with the Bx90 pulse and continuing with the By180 pulses as shown in FIG. 9a of the Freedman patent. Then, the NMR tool begins to receive a plurality of spin echo pulses from the formation as shown in FIG. 9b of the Freedman patent. A predetermined total number (say J) of spin-echoes are collected by application of J By180 pulses. After collection of the J spin-echoes the total nuclear magnetization is practically zero and a wait time W initiates the next CPMG and so forth as the tool traverses the borehole. Note that the wait times used to initiate each CPMG are identical (i.e., equal to W). The rf pulses and spin-echoes of a CPMG waveform are shown schematically in FIGS. 9a and 9b of the Freedman patent, respectively.

In order to compensate for the insufficient wait time, the processing method and apparatus disclosed in the Freedman patent utilizes a correction parameter $\xi$ (hereinafter, the parameter $\xi$ used in the Freedman patent will be denoted by $\xi_0$) which is an approximation to the true $T_1/T_2$ ratio of the rock formations being logged.

However, an additional problem exists: the parameter $\xi_0$ approximating the true $T_1/T_2$ ratio is always assumed to be a constant value. Even if the $\xi_0$ parameter were allowed to vary with the measurement depth, there still exists no method for accurately determining the proper value from measurements made in a borehole using a single wait time pulse sequence. The use of approximate ratios ($\xi_0$) which differ from the true ratios ($\xi$) can lead to inaccurate results. In real terms, true $T_1/T_2$ ratio varies from one rock sample to another. An experimental study by Kleinberg, et. al. (see ref. 11 in part B of this specification) found for a wide range of rock types that the ratios varied approximately from 1.0 to 2.6. The ratios differ depending upon the particular rock material of the particular formation being excited. Therefore, it is incorrect to use a constant value, $\xi_0$, for the ratio.

Since the function used to correct for insufficient wait time (see eq. (5) of the Freedman patent) which compensates for the insufficient wait time (W) utilizes a constant and/or assumed value of the ratio parameter, the resultant $T_2$-distributions or equivalently, the set of spectral amplitudes ($\{\alpha_l\}$) in the Freedman patent can be inaccurate.

Recall that the $N_s$ spectral amplitudes, denoted collectively by the set $\{\alpha_l\}$, are computed by constructing and minimizing the negative logarithm of a maximum likelihood function shown in eq. (42) and in block 4A3 of FIG. 13 of the Freedman patent. Recall also that the negative logarithm of the likelihood function (−ln L) in eq. (42) is a function of the aforementioned assumed ratio ($\xi_0$).

In the Freedman patent, the set of spectral amplitudes $\{\alpha_l\}$ were used to generate the output record medium shown in FIG. 16 of the Freedman patent. Therefore, since the spectral amplitudes are inaccurate, the output record medium shown in FIG. 16 of the Freedman patent is also somewhat inaccurate.

Through the use of computer simulations, this specification demonstrates that pulsed NMR logging methods utilizing single wait time pulse seqences include an uncontrolled approximation which can lead to significant accuracy errors in the output logs. This problem represents a deficiency in all other methods for obtaining depth logs that use single wait time pulse sequences. The root of the problem can be traced to the arbitrary variability of the true $T_1/T_2$ ratios (i.e., the variability of $T_1$) in rocks and specifically to the use of a constant and/or assumed ratio, say $\epsilon_0$, to process the logs which is not equal to the true value, $\xi$. To avoid confusion with notation it is worth pointing out that the constant ratio in the Freedman patent was denoted by $\xi$ instead of $\xi_0$ which is used in the present invention to differentiate between the assumed value and the true value.

In accordance with the present invention, part B of this specification discloses a new apparatus for acquiring multi-wait time CPMG pulse sequences and a method for processing the resulting spin-echo waveforms which eliminates the accuracy problems inherently associated with single wait time pulse sequences, the new apparatus functioning to generate a multi-wait time pulse sequence which can be succinctly defined using eq. (72) of part B of this specification. That is, the multi-wait time pulse sequence is described by the following notation:

$$CPMG^{(\pm)}:\{n_p\{W_p-90°(\pm x)-(t_{cp}-180°(y)-t_{cp}-(echo))_{j=1,2,\ldots} \\ ,J_p\}\}_{p=1,2,\ldots,N_{wt}} \quad (72)$$

which consists, in its general form, of $n_p$ phase alternated pair (PAP) CPMG waveforms, each initiated with a wait pair $W_p$ where $p=1, 2, \ldots N_{wt}$. The integers $n_p$ specify the number of repeats of PAP waveforms with wait time $W_p$ in a multi-wait time pulse sequence. For short wait times the repeat PAP waveforms can be averaged to improve the S/N ratio of the measurement. The integer $N_{wt}$ specifies the number of different wait times in the multi-wait time pulse sequence and $J_p$ is the total number of echoes collected for wait time $W_p$. Note that if $N_{wt}=1$, the above multi-wait time pulse sequence is equivalent to the single wait time pulse sequence of the Freedman patent. A multi-wait time pulse sequence is defined here to correspond to $N_{wt}>1$. Part B of this specification discloses a method for using the plurality of PAP waveforms corresponding to the different wait times, $W_p$, using the teachings of the Freedman patent to compute sets of estimated apparent spectral amplitudes denoted by, $\{\hat{\alpha}_{l,p}\}$, for each wait time. These apparent spectral amplitudes are in many situations inaccurate when the wait times, $W_p$, are too short for the magnetization to achieve complete recovery and because the estimates are made using an assumed and inaccurate value of the $T_1/T_2$ ratio ($\xi_0$). For a multi-wait time pulse sequence, the apparent spectral amplitudes, $\{\hat{\alpha}_{l,p}\}$, and assumed ratio, $\xi_0$, are input as parameters into a cost function derived in part B of this specification. The cost function is set forth in eq. (73) of this specification. The cost function also depends on variables representing the true (i.e., intrinsic) spectral amplitudes, ($\{\alpha_l\}$), and the true $T_1/T_2$ ratio ($\xi$) of the rock formation producing the measured spin-echo signals. Simultaneous minimization of the cost function with respect the aforementioned variables provides estimates of the true $T_1/T_2$ ratios (the estimates are denoted by $\hat{\xi}$) and an updated $T_2$-distribution denoted by the spectral amplitudes, $\{\hat{\alpha}_l\}$. The updated spectral amplitude estimates are used to compute updated log outputs. This process is shown schematically in the flowchart of FIG. 36.

The most relevant prior art related to the present disclosure is U.S. Pat. No. 5,023,551 issued to Kleinberg et al. entitled "Nuclear Magnetic Resonance Pulse Sequences for Use With Borchole Logging Tools." Kleinberg, et al. disclose a multi-wait time pulse sequence which combines fast inversion recovery and CPMG spin-echo sequences (referred to in the patent as the "FIR/CPMG" pulse sequence) for the purpose of making non-linear estimations of longitudinal relaxation times ($T_1$), transverse relaxation times ($T_2$), and total signal amplitudes (or equivalently formation porosities) from various models including stretched exponential and multi-exponential models. The continuous logs of the aforementioned quantities obtained from the FIR/CPMG pulse sequence were later shown by Kleinberg, et al., in a paper presented at the 1993 Society of Petroleum Engineers Annual Meeting (see reference 11 of part B of this specification), to be non-repeatable at bed boundary interfaces. The repeatability problem can be traced to the long measurement times required by the FIR/CPMG pulse sequence and the poor signal to noise of the non-linear estimations required by the teachings of the Kleinberg, et al. patent. The aforementioned work of Kleinberg, et al. and also similar works which utilized FIR/CPMG pulse sequences for laboratory studies, and which are cited in reference 6 of part A and reference 12 of part B of this specification, proved to be impractical for borehole logging tools. The Kleinberg, et al. U.S. Pat. No. 5,023,551 discloses in claim 42 a "saturation recovery/CPMG" pulse sequence in which the inversion pulses are omitted from the FIR/CPMG pulse. However, although the Kleinberg claim 42 pulse sequence appears to be identical to the pulse sequence in eq. (72) discussed above, Kleinberg's claim 42 pulse sequence does not disclose the integers $n_p$ which represents the explicit repeats of CPMG pulse sequences with different wait times, $W_p$. Futhermore, the saturation recovery/CPMG pulse sequence was not disclosed by Kleinberg, et al. in connection with any means for generating a more accurate output record medium by computing more accurate estimates of true $T_2$-distribution (e.g., spectral amplitudes), $\{\hat{\alpha}_l\}$ and estimates of true $T_1/T_2$ ratios ($\hat{\xi}$).

SUMMARY OF THE INVENTION

Accordingly, it is a primary object of the present invention to provide a new method and apparatus for generating a more accurate output record medium when a nuclear magnetic resonance (NMR) well logging tool disposed in a wellbore performs a multi-wait time pulsed NMR. logging operation in the wellbore.

It is a further object of the present invention to provide a new method and apparatus for determining new output data in response to output signals generated by a NMR well logging tool when the tool is traversing a wellbore and for generating a more accurate output record medium in response to the new output data.

It is a further object of the present invention to provide a new method and apparatus for determining new output data in response to spin echo pulse sequences received by a NMR well logging tool traversing a wellbore and for generating a more accurate output record medium in response to the new output data, the spin echo pulse sequences being received by the NMR tool when the tool: (1) is traversing a wellbore, (2) waits a first period of time ($W_1$), (3) pulses a formation traversed by the wellbore with RF pulses, (4) collects a first set of the spin echo pulse sequences, (5) waits a second period of time ($W_2$) which is different than the first period of time, (6) pulses the formation with RF pulses, and (7) collects a second set of the spin echo pulse sequences.

It is a further object of the present invention to provide a new method and apparatus for determining new output data in response to spin echo pulse sequences received by a NMR well logging tool traversing a wellbore and for generating a more accurate output record medium in response to the new output data, the spin echo pulse sequences being received by the NMR tool when the tool: (1) is traversing a wellbore, (2) waits a first period of time ($W_1$), (3) pulses a formation traversed by the wellbore with RF pulses, (4) collects a first set of the spin echo pulse sequences, (5) waits a second period of time ($W_2$) which is different than the first period of time, (6) pulses the formation with RF pulses, (7) collects a second set of the spin echo pulse sequences, (8) waits a third period of time ($W_3$) which is different than the first and second periods of time, (9) pulses the formation with RF pulses, and (10) collects a third set of the spin echo pulse sequences.

It is a further object of the present invention to provide a new method and apparatus for determining new output data in response to spin echo pulse sequences received by a NMR well logging tool traversing a wellbore and for generating a more accurate output record medium in response to the new output data, the spin echo pulse sequences being received by the NMR tool when the tool: (1) is traversing a wellbore, (2) waits a first period of time ($W_1$), (3) pulses a formation traversed by the wellbore with RF pulses, (4) collects a first set of the spin echo pulse sequences and repeats, a first predetermined number of times, steps (2)–(4) above, (5) waits a second period of time ($W_2$) which is different than the first period of time, (6) pulses the formation with RF pulses, (7) collects a second set of the spin echo pulse sequences and repeats, a second predetermined number of times, steps (5)–(7) above, (8) waits a third period of time ($W_3$) which is different than the first and second periods of time, (9) pulses the formation with RF pulses, and (10) collects a third set of the spin echo pulse sequences and repeats, a third predetermined number of times, steps (8)–(10) above.

It is a further object of the present invention to determine new data including a set of new and more accurate values of true spectral amplitudes or equivalently a more accurate $T_2$-distribution, $\{\alpha_l\}$, and a new more accurate $T_1/T_2$ ratio, $\xi$, from sets of previously determined apparent values of spectral amplitudes or equvalently apparent $T_2$-distributions, $\{\alpha_{l,p}\}$, and to generate a more accurate output record medium from the new more accurate spectral amplitudes, $\{\alpha_l\}$, in response to a plurality of spin echo multi-wait time pulse sequences which are generated from a NMR well logging tool when the NMR tool: (1) is traversing a wellbore, (2) waits a first period of time ($W_1$), (3) pulses a formation traversed by the wellbore with RF pulses, (4) collects a first set of the spin echo pulse sequences, (5) waits a second period of time ($W_2$) which is different than the first period of time, (6) pulses the formation with RF pulses, (7) collects a second set of the spin echo pulse sequences, (8) waits a third period of time ($W_3$) which is different than the first and second periods of time, (9) pulses the formation with RF pulses, and (10) collects a third set of the spin echo pulse sequences.

It is a further object of the present invention to determine new data including a new more accurate set of values of spectral amplitudes or equivalently a more accurate $T_2$-distribution, $\{\alpha_l\}$, and a new more accurate $T_1/T_2$ ratio, $\xi$, from sets of previously determined values of apparent spectral amplitudes or equivalently apparent $T_2$-distributions, $\{\alpha_{l,p}\}$ determined assuming an approximate value, $\xi_0$, for the $T_1/T_2$ ratio, and to generate a more accurate output record medium from the new and more accurate spectral amplitudes, $\{\alpha_l\}$, in response to a plurality of spin echo multi-wait time pulse sequences which are generated from a NMR well logging tool when the NMR tool: (1) is traversing a wellbore, (2) waits a first period of time ($W_1$), (3) pulses a formation traversed by the wellbore with RF pulses, (4) collects a first set of the spin echo pulse sequences and repeats, a first predetermined number of times, steps (2)–(4) above, (5) waits a second period of time ($W_2$) which is different than the first period of time, (6) pulses the formation with RF pulses, (7) collects a second set of the spin echo pulse sequences and repeats, a second predetermined number of times, steps (5)–(7) above, (8) waits a third period of time ($W_3$) which is different than the first and second periods of time, (9) pulses the formation with RF pulses, and (10) collects a third set of the spin echo pulse sequences and repeats, a third predetermined number of times, steps (8)–(10) above.

It is a further object of the present invention to determine a new more accurate value of the true $T_1/T_2$ ratio, $\xi$, and a new set of more accurate values of the true spectral amplitudes or equivalently a more accurate $T_2$-distribution, $\{\alpha_l\}$, computed from the previously determined sets of apparent spectral amplitudes or equivalently sets of apparent $T_2$-distributions, $\{\alpha_{l,p}\}$, each set of apparent amplitudes corresponding to a wait time $W_p$ in a multi-wait time pulse sequence consisting of at least two different wait times, the new $T_1/T_2$ ratio, $\xi$, and the new set of spectral amplitudes, $\{\alpha_l\}$, being determined by the values which minimize a cost function, the new values of the spectral amplitudes, $\{\alpha_l\}$, being used instead of the previously determined sets of spectral amplitudes, $\{\alpha_{l,p}\}$, to generate a more accurate output record medium from the spin echo multi-wait time pulse sequences received by a NMR tool when the NMR well logging tool is traversing the wellbore.

It is a further object of the present invention to determine a new more accurate value of the true $T_1/T_2$ ratio, $\epsilon$, and a new set of more accurate values of the true spectral amplitudes or equivalently a more accurate $T_2$-distribution, $\{\alpha_l\}$, computed from the previously determined sets of apparent spectral amplitudes or equivalently sets of apparent $T_2$-distributions, $\{\alpha_{l,p}\}$, each set of apparent amplitudes corresponding to a wait time $W_p$ in a multi-wait time pulse sequence consisting of at least two different wait times, the new $T_1/T_2$ ratio, $\xi$, and the new set of spectral amplitudes, $\{\alpha_l\}$, being determined by the values which minimize a cost function, the new values of the spectral amplitudes, $\{\alpha_l\}$, and the new values of the ratios, $\xi$, being used to determine $T_1$-distributions from the spin echo multi-wait time pulse sequences received by a NMR tool when the NMR well logging tool is traversing the wellbore.

In accordance with these and other objects of the present invention with reference to the new FIGS. 27–77 of the drawings, the Nuclear Magnetic Resonance (NMR) well logging tool introduced in U.S. Pat. No. 5,291,137. issued to Freedman included a permanent magnet which produces a static magnetic field, $B_0$ in the formation surrounding the borehole. This magnetic field tends to align the magnetic moment vet:tots in the formation in the manner shown in FIG. 5. After a set of spin-echo signals are acquired from the formation being traversed by the logging tool, the total magnetization in the formation is practically zero. Therefore, before a new set of spin-echo signals can be acquired, a wait time W is required before re-energizing the formation with a plurality of oscillating radio frequency magnetic field pulses, Bx90 and By180 (hereinafter called "RF pulses"). These RF pulses are also known as the "Carr-Purcell-Meiboom-Gill (CPMG) pulse sequence". The amount of time required to align the magnetic moment vectors in the formation in the manner shown in FIG. 5 is approximately $5 \times T_1$, where $T_1$ is the "longitudinal relaxation time." However, the NMR well logging tool which is traversing a wellbore cannot wait that long a period of time, that is, it cannot wait for a time period, $W \equiv 5 \times T_1$, to elapse before re-energizing the formation with the RF pulses. Therefore, since the NMR logging tool cannot wait a long enough period of time before re-applying the RF pulses, in order to compensate for the insufficient wait time, the signal processing software of FIG. 13 corrected for this discrepancy by including correction factor which was based on an assumed and incorrect value of the formation $T_1/T_2$ ratio denoted by $\xi_0$. The correction factor, in which the incorrect ratio is used, is given by eq. (5) of part A of this specification and the Freedman Patent. The function in eq. (5) corrects for insufficient wait time W. This correction is used in constructing the logarithm of a likelihood function shown in block 4A3 of FIG. 13. The use an inaccurate correction for insufficient wait times means that the output record medium, as shown in FIG. 16, which is computed from a set of spectral amplitudes obtained by minimizing the likelihood function is, to some extent, inaccurate.

In order to correct the somewhat inaccurate output record medium of FIG. 16, in accordance with the present invention, a NMR well logging tool is traversing a wellbore and the tool is raised upwardly in the wellbore during a logging operation. During the logging operation, the tool will practice a pulsed NMR multi-wait time pulse sequence which contains at least two different wait times which are different. The multi-wait time pulse sequence is similar to the "saturation recovery/CPMG" NMPR pulse sequence disclosed in U.S. Pat. No. 5,023,551 issued to Kleinberg, et al. During the practice of this multi-wait time NMR well logging method, the NMR well logging tool in the wellbore receives a set of "multi-wait time" spin echo pulse sequence data. This data is input to a new signal processing system in the NMR well logging tool in accordance with the present invention. The new signal processing system, illustrated in FIGS. 10, 11, 12a, 12b1–12b2, and 36, includes a new signal processing software. The new signal processing software comprises the previously disclosed signal processing software represented by the flowchart shown in FIG. 13, but modified by adding a decision triangle and an additional software block to the second part 7a4A of the signal processing software which is resident in the surface oriented processing system 7a shown in FIG. 11. The decision triangle is entitled, "$N_{wt}>1?$", and the additional software block is entitled "Construct Cost Function and Perform Minimization". In the new "Construct Cost Function and Perform Minimization" block, a cost function is constructed and then minimized. When the cost function is minimized, new values of the $T_1/T_2$ ratio, $\hat{\xi}$, and new set of spectral amplitudes, $\{\hat{\alpha}_l\}$, are produced. These new values of the $T_1/T_2$ ratio and spectral amplitudes are used to generate a more accurate output record medium similar to the output record shown in FIG. 16.

The pulsed NMR well logging method referred to above includes the following steps. The NMR well logging tool having a magnet which produces a static magnetic field, $B_0$, is traversing a wellbore. The tool is then raised upwardly in the wellbore during the logging operation. The static magnetic field produces a nuclear magnetization in the formation traversed by the wellbore. The NMR tool waits for a first period of time, $W_1$, to elapse, and then it energizes the formation with a series of oscillating radio frequency magnetic fields (RF pulses). The NMR tool collects a first set of spin echo pulses, and then the NMR tool waits for a second period of time, $W_2$, to elapse, where $W_2$ is different than $W_1$. The NMR tool then energizes the formation with the RF pulses and it collects a second set, of spin echo pulses. The NMR tool waits for a third period of time, $W_3$, to elapse, where $W_3$ is different from both $W_2$ and $W_1$. When the third period of time $W_3$ elapses, the NMR tool energizes the formation with the RF pulses. The NMR tool then collects a third set of spin echo pulses, etc. The plurality of "multiwait time" spin echo pulse sequence data correspond, respectively, to the plurality set of wait times, $W_p$, where $p=1, 2, 3, \ldots, N_{wt}$, and consists of the first set of spin echo pulses associated with a first wait time $W_1$ followed by the second set of spin echo pulses associated with a second wait time $W_2$ followed by the third set of spin echo pulses associated with a third wait time $W_3$, etc. In a given formation, as the wait times, $W_1 < W_2 <, \ldots, < W_{N_{wt}}$, are increased the amplitudes of the first, second, etc. spin echo pulses will continue to increase in an exponential manner as long as the successive wait times are insufficient to totally saturate the magnetization at its thermal equilibrium value. A multi-wait time pulse sequence containing pulses with three distinct wait times is shown in FIGS. 33, 34, and 35 and the associated spin-echo signals are shown in FIG. 32 of this specification.

For each multi-wait time spin echo pulse sequence that is input to and processed by the new signal processing software of FIG. 36, the following preliminary data are generated for each wait time $W_p$ in the sequence according to the teachings of the Freedman patent (1) signal plus noise spin-echo amplitudes, $\tilde{A}_{j,p}^{(+)}$, (2) noise amplitudes, $\tilde{A}_{j,p}^{(-)}$, (3) of window sums $\tilde{I}_{m,m+l,p}$, and (4) a set of apparent spectral amplitudes $\{\alpha_{l,p}\}$, where the subscript p is an integer denoting the particular wait time, $W_p$, between the complete receipt of the previously received spin echo pulses and the re-application of the RF pulses, e.g., $p=1, 2, 3, \ldots, N_{wt}$. For a particular wait time $W_p$, in response to the aforementioned preliminary data, since $N_{wt}$ is greater than 1 (there is more than one wait time), the new "Construct Cost Function and Perform Minimization" block of the new signal processing apparatus of FIG. 36 constructs a cost function, $C(\xi_v, \{\alpha_{v,l}\})$. The cost function is a function of the following variables: (1) a variable, $\xi_v$, representing the true formation $T_1/T_2$ ratio denoted which must be determined, (2) a set of variables, $\{\alpha_{l,p}\}$ representing the formation $T_2$-distribution, which must be determined. Additionally, the cost function contains as fixed parameters the previously determined sets of spectral amplitudes $\{\alpha_{l,p}\}$ output from the "Construct and Minimize —In L" block, and the previously assumed constant and usually incorrect value of the formation $T_1/T_2$ ratio, $\epsilon_0$. The cost function is then minimized with respect to the aforementioned variables. When minimizing the cost function, various values of the variables, $\xi_v$, and the sec, $\{\alpha_{v,l}\}$, are input into the cost function, $C(\xi_v, \{\alpha_{v,l}\})$ equation, and the calculated values of $C(\xi_v, \{\alpha_{v,l}\})$ are recorded for selected feasible values of $\xi$ and $\{\alpha_l\}$. The values of the variables, $\xi_v$, and $\{\alpha_{v,l}\}$ which correspond to the minimum value of $C(\xi_v, \{\alpha_{v,l}\})$ are selected as the new accurate outputs, corresponding to $\hat{\xi}$ and $\{\hat{\alpha}_l\}$. These new values are output from the "Construct Cost Function and Perform Minimization" block and are used to generate a more accurate output record medium similar to the; output record medium 7a2A shown in FIG. 16 of the Freedman patent, that can be used to determine reservoir properties of the earth formation being logged, such as for example, permeability, porosity, free-fluid and pore size distribution.

Further scope of applicability of the present invention will become apparent from the detailed description presented hereinafter. It should be understood, however, that the detailed description and the specific examples, while representing a preferred embodiment of the present invention, are given by way of illustration only, since various changes and modifications within the spirit and scope of the invention will become obvious to one skilled in the art from a reading of the following detailed description.

BRIEF DESCRIPTION OF THE DRAWINGS

A full understanding of the present invention will be obtained from the detailed description of the preferred embodiment presented hereinbelow, and the accompanying drawings, which are given by way of illustration only and are not intended to be limitative of the present invention, and wherein:

FIGS. 7a–7b illustrate the precession of the individual magnetic moments vector $\mu_1$ and the effects on this magnetic moments vector $\mu_1$ of the presence of two other magnetic fields: the static magnetic field $B_0$ and a radio frequency magnetic field By180, the direction of which is transverse to the magnetic field $B_0$ and is directed along the y-axis;

FIGS. 9a–9b illustrate the spin-echo transmitter and receiver voltage pulses produced by the logging tool in time relation to: (1) a first magnetic field pulse which is directed along the x- axis of FIG. 6 and has a pulse duration of T90 (the first magnetic field pulse being hereinafter termed "Bx90" or "the 90 pulse"), and (2) a second magnetic field pulse directed along the y-axis and having a pulse duration of T180 which rotates all of the proton spins 180 degrees about the y-axis (the second magnetic field pulse being hereinafter termed By180);

FIGS. 12a, 12b1 and 12b2 illustrate a more detailed construction of the electronics cartridge of FIG. 10 which stores the first part of the signal processing method and apparatus of the present invention;

FIG. 16a illustrates a more detailed block diagram of the surface computer and the downhole computer of FIG. 12a utilized in conjunction with FIG. 13 for providing a functional description of the present invention;

FIG. 27 illustrates a plurality of spin echo pulse sequences having equal amplitudes prior to implementation of the present invention and indirectly referred to in U.S. Pat. No. 5,291,137 to Freedman generated by a plurality of single wait time pulse sequences which are separated by wait times W of equal duration;

FIGS. 28–30 illustrate the RF pulses, Bx90 and By180, for a single wait time CPMG pulse sequence, which energize the formation traversed by the wellbore following each equal duration wait time W and which stimulate the generation of the equal amplitude spin echo pulse sequences of FIG. 27;

FIG. 32 illustrates a plurality of spin echo signals having different amplitudes generated when a multiwait time CPMG pulse sequence is applied including a plurality wait times $W_1, W_2, W_3, \ldots, W_p$, where each succeeding wait time is different (e.g., longer) in duration than its preceding wait time;

FIGS. 33–35 illustrate the RF pulses or CPMG pulse sequences, Bx90 and By180, which energize the formation traversed by the wellbore following each different duration wait time $W_1$ to $W_3$ and which stimulate the generation of the spin echo pulses sequences having different amplitudes as shown in FIG. 32;

FIG. 63 representing input B-distribution where $\xi=2.5$, wait time $=3.0$ sec, 1800 echoes, 1 percent noise, $\xi_0=2.5$ for dashed curve and $\xi_0=1.5$ for dotted curve;

DETAILED DESCRIPTION OF THE PREFERRED EMBODIMENT

This specification is divided into two parts:

(1) Part A representing the entire Description of the Preferred Embodiment and the Detailed Description of the Preferred Embodiment set forth in U.S. Pat. No. 5,291,137 to Freedman entitled "Processing Method and Apparatus for Processing Spin Echo In-phase and Quadrature Amplitudes from a Pulsed Nuclear Magnetism Tool and Producing New Output Data to be Recorded on an Output Record," and (2) Part B representing the Description of the Preferred Embodiment and the Detailed Description of the Preferred Embodiment of the specification of the present invention entitled "Apparatus Including Multi-Wait Time Pulsed NMR Logging Method For Determining Accurate $T_2$-Distributions And Accurate $T_1/T_2$ Ratios And Generating a More Accurate Output Record Using The Updated $T_2$-Distributions And $T_1/T_2$ Ratios."

A. Processing Method and Apparatus for Processing Spin Echo In-phase and Quadrature Amplitudes from a Pulsed Nuclear Magnetism Tool and Producing New Output Data to be Recorded on an Output Record The specification of part A is divided into two parts:

(1) a Description of the Preferred Embodiment, which provides a general, more understandable description of the new signal processing method and apparatus of the present invention; and (2) a Detailed Description of the Preferred Embodiment, which provides a more detailed description of the new signal processing method and apparatus of the present invention.

DESCRIPTION OF THE PREFERRED EMBODIMENT

Figure 1:
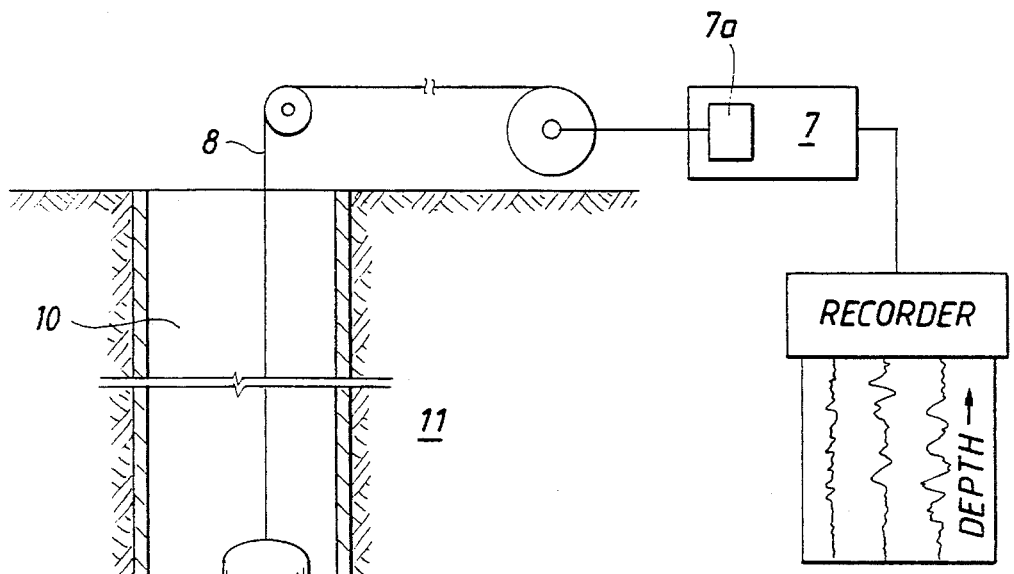
FIG. 1 illustrates a nuclear magnetic resonance (NMR) logging system including a NMR logging tool disposed in a wellbore and a processing system disposed at the wellbore surface for processing signals transmitted uphole by the logging tool.

Referring to FIG. 1, a nuclear magnetic resonance (NMR) logging system is illustrated, the NMR logging system including a NMR logging tool 13 disposed in a wellbore and a processing system 7a disposed at the wellbore surface for processing signals transmitted uphole by the logging tool.

In FIG. 1, a borehole 10 is shown adjacent to formations 11, 12, the characteristics of which are to be determined. Within borehole 10 there is shown a logging tool 13 connected via a wireline 8 to surface equipment 7. The surface equipment 7 includes a processing system 7a which stores therein a signal processing method and apparatus embodied in the form of software. The processing system 7a will be discussed in more detail with reference to FIGS. 12 and 13 of the drawings. Tool 13 preferably has a face 14 shaped to intimately contact the borehole wall, with minimal gaps or standoff. The tool 13 also has a retractable arm 15 which can be activated to press the body of the tool 13 against the borehole wall during a logging run, with the face 14 pressed against the wall's surface. Although tool 13 is shown in the preferred embodiment of FIG. 1 as a single body, the tool may obviously comprise separate components such as a cartridge, sonde or skid, and the tool may be combinable with other logging tools as would be obvious to those skilled in the art. Similarly, although wireline 8 is the preferred form of physical support and communicating link for the invention, alternatives are clearly possible, and the invention can be incorporated in a drill stem, for example, using forms of telemetry which may not require a wireline. The formations 11, 12 have distinct characteristics such as formation type, porosity, permeability and oil content, which can be determined from measurements taken by the tool. Deposited upon the borehole wall of formations 11, 12 is typically a layer of mudcake 16 which is deposited thereon by the natural infiltration of borehole fluid filtrate into the formations. In the preferred embodiment shown in FIG. 1, tool 13 comprises a first set magnet array 17 and an antenna 18 positioned between the array 17 and the wall engaging face 14. Magnet array 17 produces a static magnetic field $B_0$ in all regions surrounding the tool 13. The antenna 18 produces, at selected times, an oscillating radio frequency magnetic field B1 (previously denoted as "Bx90" and By180") which is focussed into formation 12, and is superposed on the static field $B_0$ within those parts of formation opposite the face 14. The field B1 is perpendicular to the field $B_0$. The Volume of Investigation, 19, of the tool for the first set magnet array 17 shown in dotted lines FIG. 1, is a vertically elongated region directly in front of tool face 14 in which the magnetic field produced by the magnet array 17 is substantially homogeneous and the spatial gradient thereof is approximately zero. The tool 13 may also comprise, as an option, a second set magnet array 20 and an antenna 21 positioned between the array 20 and the wall engaging face 14. Magnet array 20 produces another static magnetic field $B_0$ in all regions surrounding the tool 13. The antenna 21 produces, at selected times, an oscillating radio frequency magnetic field B1 which is again focussed into formation 12, and is superposed on the static field $B_0$ within those parts of formation opposite the face 14. The Volume of Investigation 22 of the tool for the second set magnet array 20, shown in dotted lines in FIG. 1, is a vertically elongated region directly in front of tool face 14 in which the magnetic field produced by the magnet array 20 is substantially homogeneous and the spatial gradient thereof is approximately zero. Due to the particular magnet arrangement; for the second set magnet array 20, the Volume of Investigation 22 is at a depth in the formation 12 which is greater than the depth at which the Volume of Investigation 19 is located. A prepolarizing magnet 23, shown in dotted lines, may be positioned directly above the array 17 in a modified embodiment of the invention in accordance with the teachings of the aforementioned Kenyon, et al patent. An electronics cartridge 24 is positioned above the magnet 23. The electronics cartridge 24 includes a downhole microcomputer. The electronics cartridge 24, including the downhole microcomputer, will be discussed in more detail with reference to FIGS. 12a–12b of the drawings.

In operation, referring to FIG. 1, the tool 13 makes a measurement in the Volume of Investigation 19 by magnetically reorienting the nuclear spins of particles in formation 12 with a pulse of oscillating magnetic field B1 (previously denoted as "Bx90" and "By180"), and then detecting the precession of the tipped particles in the static, homogeneous field $B_0$ within the Volume of Investigation 19, over a period of time. As seen in FIG. 1, this Volume of Investigation does not overlap the surface of the wall engaging face 14 as in some previous logging tools, and does not overlap the mudcake 16 on the borehole wall. In a pulse echo type of measurement, a pulse of RF current is passed through the antenna 18 to generate a pulse of RF field B1 where the RF frequency is selected to resonate only hydrogen nuclei subjected to a static magnetic field strength equal or nearly equal to the field $B_0$ within the Volume of Investigation 19. The signals induced in antenna 18 subsequent to the RF pulse B1 represent a measurement of nuclear magnetic precession and decay within the Volume, automatically excluding any undesirable contributions from the borehole fluid, mudcake, or surrounding formations where the field strength of $B_0$ is substantially different. The tool 13 makes a measurement in the Volume of Investigation 22 in the same manner discussed above with respect to the Volume of Investigation 19 but utilizing the second set magnet array 20 and the antenna 21.

The general principles associated with nuclear magnetic resonance well logging, utilized by the NMR logging system of FIG. 1, will be discussed in the following paragraphs with reference to FIGS. 2 through 10 of the drawings.

Figure 2:
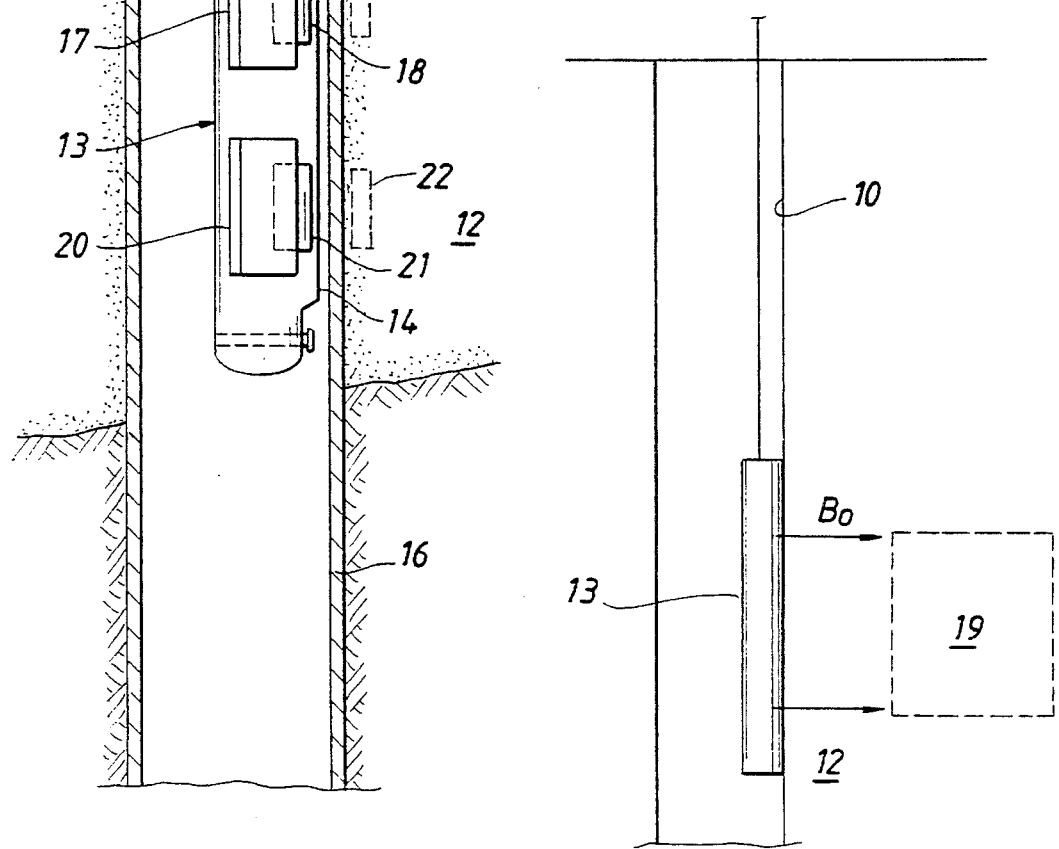
FIG. 2 illustrates a sketch of the logging tool in the, wellbore producing a static magnetic field $B_0$ into a formation traversed by the wellbore.

In FIG. 2, a NMR tool 13 contacts a wall of the borehole 10. A magnet disposed within the tool 13 generates a static magnetic field $B_0$, which field $B_0$ is directed toward a volume of investigation 19 disposed within a portion of the formation 12 traversed by the borehole 10.

Figure 3:
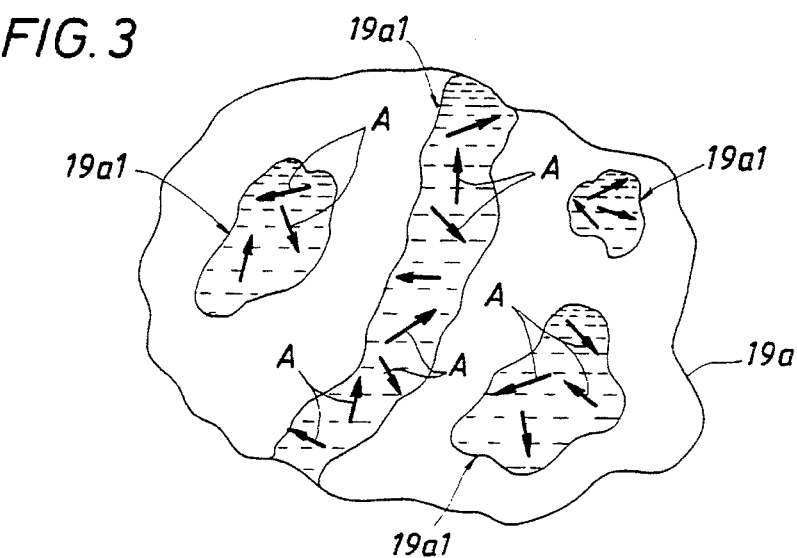
FIGS. 3–5 illustrate sections of the formation adjacent the logging tool in the wellbore and the effects of the magnetic field $B_0$ on the composite magnetic moment vector M representative of the sum of a plurality of individual magnetic moments associated with a corresponding plurality of protons disposed within elements of the formation.

FIG. 3 illustrates a cross section 19a of the volume of investigation 19 of FIG. 2. The cross section 19a includes a plurality of pores 19a1, each of which contain oil and/or water, the oil and/or water being further comprised of a plurality of protons, each proton having a magnetic spin or magnetic moment ($\mu_i$) identified in FIG. 3 by the arrow A shown in FIG. 3. Since there are a plurality of protons in each of the pores 19a1, there are a corresponding plurality of magnetic moments ($\mu_1, \mu_2, \mu_3, \ldots, \mu_n$) in each pore 19a1, where n equals the number of protons in each pore.

Figure 4:
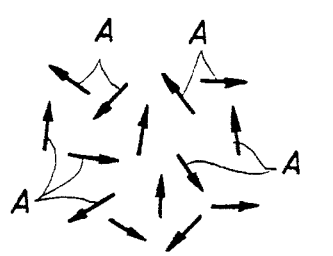

FIG. 4 illustrates a plurality of magnetic moments, $\mu_i$ (identified in FIG. 4 by a plurality of arrows "A") associated with a corresponding plurality of protons disposed within a particular one of the pores 19a1 of the volume of investigation 19 when the static magnetic field $B_0$ is zero. Note that the magnetic moments (ui) A all point in different directions. Therefore, a composite magnetic moment, M, defined to be the vector sum of all individual magnetic moments A (that is, $$M = \Sigma^n_{i=1} \mu_i)$$

is approximately zero.

Figure 5:
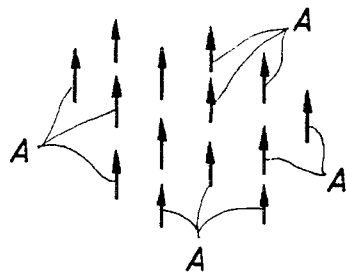

However, FIG. 5 illustrates the same plurality of magnetic moments A of FIG. 4, but now the magnetic field $B_0$ is not equal to zero. Note that, in FIG. 5, the magnetic moments ($\mu_i$) A align together in the same direction when the magnetic field $B_0$ is not equal to zero. Therefore, the composite magnetic moment M is not approximately equal to zero, but rather, is equal to a sum which is defined to be the sum of all individual magnetic moments A. Since each individual magnetic moment A can be quantified by the term $\mu_i$, the composite magnetic moment M is equal to the sum of all individual magnetic moments $\mu_i$, where i=1, 2, 3 . . . , n, associated with the n individual protons disposed within a pore space 19a1 associated with the volume of investigation 19, that is, $$M = \Sigma^n_{i=1} \mu_i.$$

Figure 6:
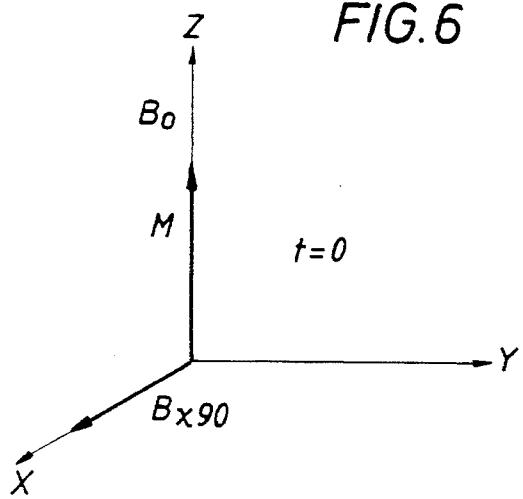
FIGS. 6–7 illustrate the effects on the proton's composite magnetic moment M of the presence of two magnetic fields: the static magnetic field $B_0$ and a radio frequency magnetic field Bx90, the direction of which is transverse to the static magnetic field $B_0$ and along the x-axis, the field Bx90 being applied along the x-axis for a duration $T_{90}$ which causes a 90 degree rotation of the composite magnetic moment vector M about the x-axis.

Referring to FIG. 6, assume that the composite magnetic moment M for the volume of investigation 19 of FIG. 3–5 is aligned along the z-axis; assume further that the static magnetic field $B_0$ is also aligned along the z-axis. Then, assume that an oscillating radio frequency magnetic field pulse "B1" or "Bx90" is applied along the x-axis, transverse to the z-axis.

Figure 7:
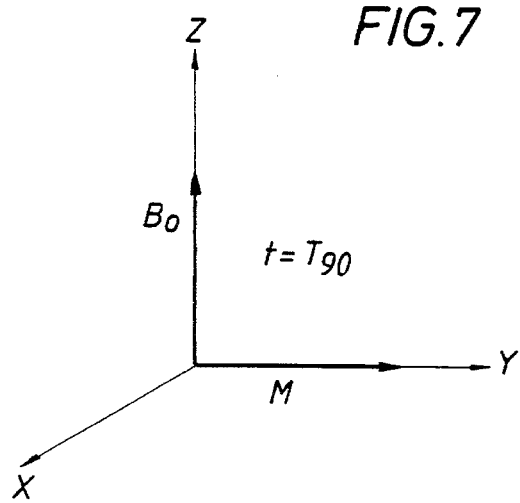

Referring to FIG. 7, recalling the assumptions mentioned above with reference to FIG. 6, since the pulse duration of the oscillating magnetic field pulse "Bx90" is 90 degrees and is applied along the x-axis in the presence of the static magnetic field $B_0$, the composite magnetic moment M rotates 90 degrees from the z-axis to the y-axis, as shown in FIG. 7.

Referring to FIGS. 7a–7b, the magnetic moment vector M is initially disposed along the y-axis as shown in FIG. 7, and begins to "precess" (or rotate) clockwise within the x-y plane, as shown in FIG. 7a. However, in FIG. 7b, if an oscillating magnetic field pulse By180 is applied along the y-axis (for a period of time equivalent to a 180 degree pulse duration), the magnetic moment vector M rotates or flips 180 degrees from one quadrant within the x-y plane to another quadrant within the x-y plane, as illustrated by element numeral 30 in FIG. 7b. The significance of this concept will become clear with reference to FIGS. 8a–8L of the drawings.

Referring to FIG. 8a–8m, recall that the composite magnetic moment M is defined to be the vector sum of all the individual magnetic moments $\mu_i$ (identified by the letter A) of all protons within a pore space 19a1 in FIG. 3, that is, $$M = \Sigma^n_{i=1} \mu_i,$$

where i=1, 2, . . . , n. In FIGS. 7a–7b, it was shown that, in the presence of the static magnetic field $B_0$, the composite magnetic moment vector M processed in the x-y plane, then flipped to another quadrant in response to the By180 oscillating magnetic field pulse.

Since the composite magnetic moment vector M is the sum of all individual magnetic moments, $\mu_i$, in actuality, all of the individual magnetic moments $\mu_i$, being disposed within the static magnetic field $B_0$, individually precess in the x-y plane; and, then, each individual magnetic moment $\mu_i$ flips to another quadrant in response to the By180 oscillating magnetic field pulse.

However, the static magnetic field $B_0$ is not homogeneous, that is, some parts of the static magnetic field $B_0$ are stronger in terms of field strength than other parts of the field $B_0$. Therefore, if one individual magnetic moment $\mu_i$ is disposed within a stronger part of the static magnetic field $B_0$, and another individual magnetic moment $\mu_2$ is disposed within a weaker part of the static magnetic field $B_0$, the rate of precession or rotation within the x-y plane of the one magnetic moment $\mu_1$ will be greater than the rate of precession of $\mu_2$.

FIGS. 8a–8m illustrate the effects on the precession rate of the one individual magnetic moment $\mu_1$ which is located within a stronger part of the field $B_0$ relative to another individual magnetic moment $\mu_2$ which is located within a weaker part of the field $B_0$; furthermore, FIGS. 8a–8L illustrate the effects on the one individual magnetic moment $\mu_1$ and the other individual magnetic moment $\mu_2$ of a further, oscillating magnetic field pulse By180 which "rotates" or "flips" the magnetic moments $\mu_1$ and $\mu_2$ 180 degrees about the y-axis thereby causing the magnetic moments $\mu_1$ and $\mu_2$ to refocus and to produce one of the spin-echo receiver voltage pulses of FIG. 9b.

Figure 8A:
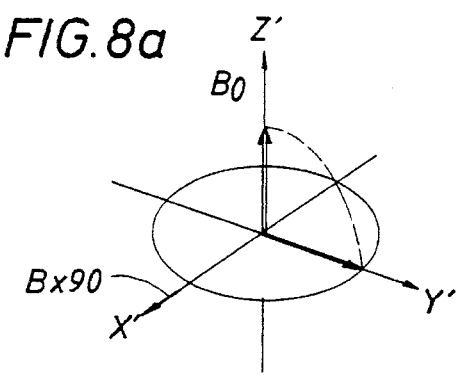
FIGS. 8a–8m illustrate the effects on the precession rate of an individual magnetic moment "An" which is located within a stronger field strength of the static magnetic field $B_0$, relative to another individual magnetic moment "Af" which is located within a weaker field strength of the static magnetic field $B_0$, since the field $B_0$ is non-homogeneous and the individual magnetic moments precess at different rates about the z-axis, the direction of the magnetic field $B_0$ vector, and the effects on the magnetic moments An and Af of a further magnetic field pulse By180 which "rotates" the magnetic moments An and Af 180 degrees about the y-axis thereby causing the magnetic moments An and Af to refocus and to produce the spin-echo receiver voltage pulses of FIG. 9b.

In FIG. 8a, the plurality of individual magnetic moments ($\mu_i$) A (and thus, the composite magnetic moment M) rotate 90 degrees in the z-y plane, as shown in FIGS. 6–7 of the drawings, in response to the static, radio frequency magnetic field pulse "Bx90" which is applied along the x-axis for a time equivalent to a 90 degree pulse duration.

Figure 8B:
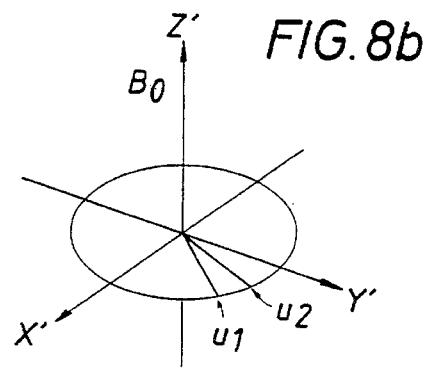

In FIG. 8b, the one individual magnetic moment $\mu_1$, the magnetic moment associated within one particular proton which is disposed within a stronger part of the magnetic field $B_0$, precesses or rotates, in a clockwise direction, at a faster rate than does the other individual magnetic moment $\mu_2$, the other individual magnetic moment associated with another proton that is located within a weaker part of the magnetic field $B_0$.

Figure 8C:
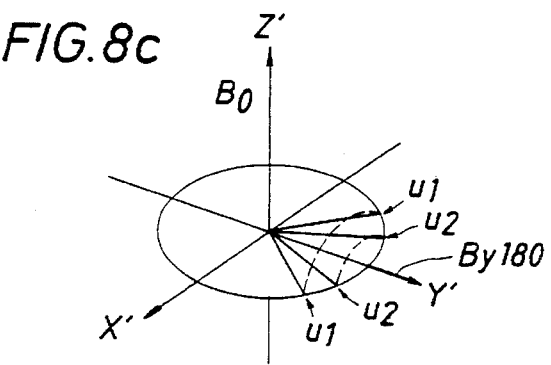
Figure 8D:
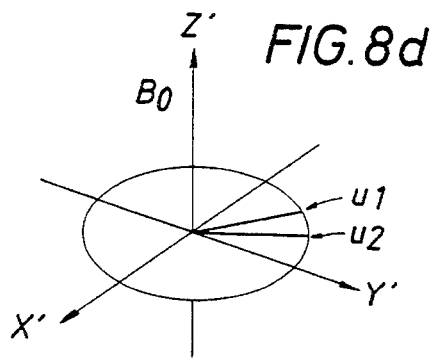
Figure 8E:
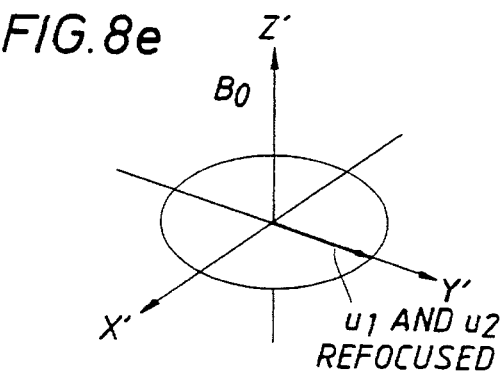
Figure 8F:
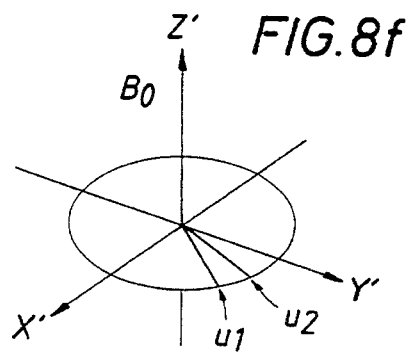
Figure 8G:
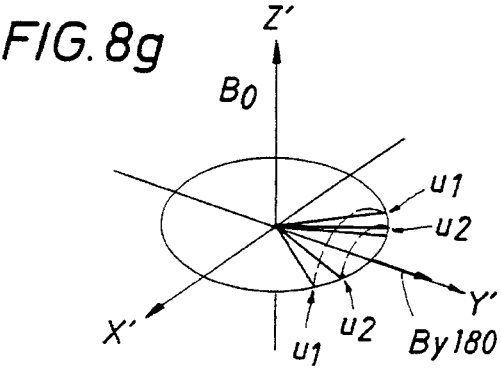
Figure 8H:
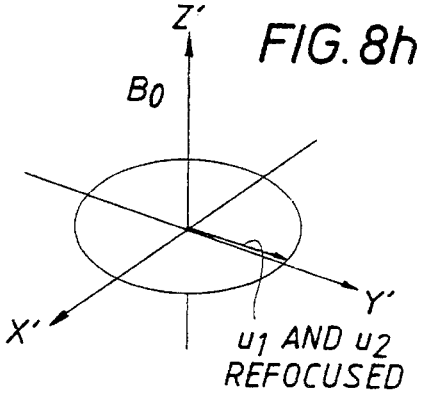
Figure 8I:
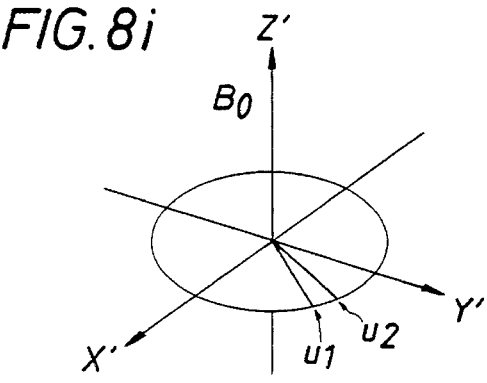
Figure 8J:
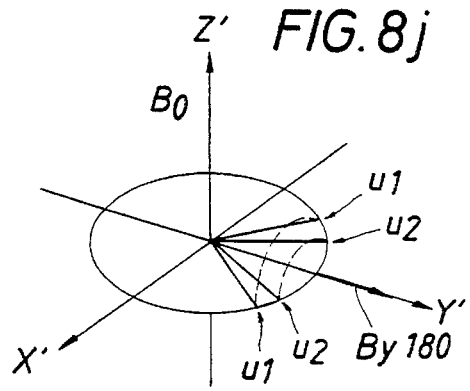
Figure 8K:
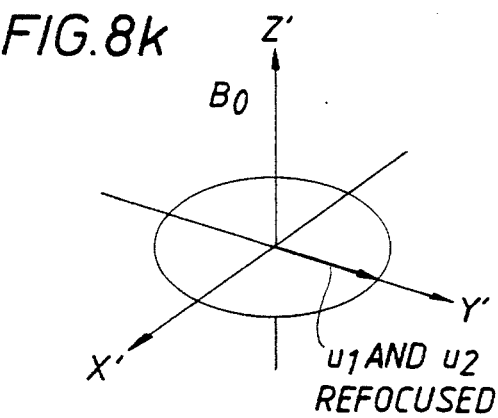
Figure 8L:
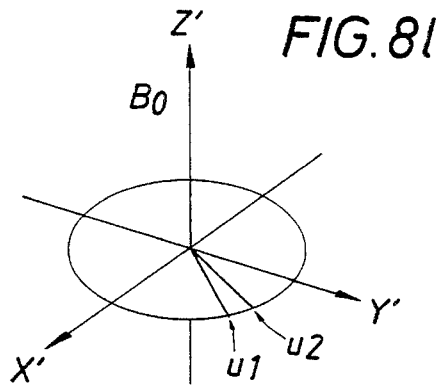
Figure 8M:
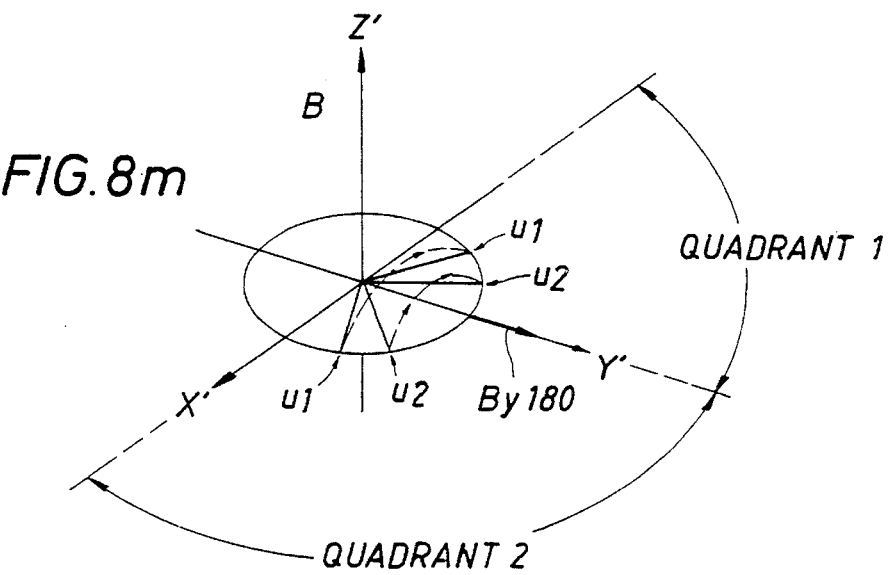

In FIGS. 8c and 8m, a further, oscillating magnetic field pulse By180 is applied at a time $t_{cp}$ after application of the magnetic field pulse Bx90 (which is assumed to be applied at a time t=0) along the y-axis for a period of time equivalent to a pulse duration of 180 degrees; in response to the further magnetic field pulse By180, the individual magnetic moments $\mu_1$ and $\mu_2$ rotate or flip about the y-axis by an amount equal to 180 degrees thereby removing the two individual magnetic moments $\mu_1$ and $\mu_2$ from quadrant number 2 and locating the two individual magnetic moments $\mu_1$ and $\mu_2$ in quadrant number 1 of the x-y plane, as shown in FIG. 8c.

In FIG. 8d, both of the individual magnetic moments $\mu_1$ and $\mu_2$ continue to rotate in the clockwise direction but the one magnetic moment $\mu_1$ continues to rotate or precess at a faster rate than does the other magnetic moment $\mu_2$.

In FIG. 8e, since, as shown in FIG. 8c, the two individual magnetic moments $\mu_1$ and $\mu_2$ flipped from quadrant 2 to quadrant 1 of the x-y plane in response to the oscillating magnetic field By180, the two individual magnetic moments $\mu_1$ and $\mu_2$ refocus (align together as one magnetic moment vector) thereby producing a first spin-echo signal (echo 1) at a time $2t_{cp}$, which spin-echo signal is picked up by the antennas 18 or 21 of the NMR tool 13 of FIG. 1 and is transmitted uphole to the processing system 7a. The first spin-echo signal (echo 1) is shown in FIG. 9b of the drawings.

In FIG. 8f, the one magnetic moment $\mu_1$ proceeds to precess ahead or in front of the other magnetic moment $\mu_2$ since the rate of precession of the one magnetic moment $\mu_1$ is still greater than the rate of precession of the other individual magnetic moment $\mu_2$.

FIGS. 8g and 8m, a further oscillating magnetic field pulse By180 is applied at a time $3t_{cp}$ along the y-axis for a period of time equivalent to a pulse duration of 180 degrees; in response to the further magnetic field pulse By180, the two individual magnetic magnetic moments $\mu_1$ and $\mu_2$ rotate or flip about the y-axis by an amount equal to 180 degrees (similar to the action depicted in FIG. 8c) thereby removing the two magnetic moments $\mu_1$ and $\mu_2$ from quadrant number 2 and locating the two magnetic moments $\mu_1$ and $\mu_2$ into quadrant number 1 of the x-y plane, as shown in FIG. 8g.

In FIG. 8h, the two individual magnetic moments $\mu_1$ and $\mu_2$ refocus again, similar to the action depicted in FIG. 8e, thereby producing a second spin-echo signal (echo 2) at a time $4t_{cp}$, which second spin-echo signal is picked up by antennas 18 and 21 of the NMR tool 13 of FIG. 1 and transmitted uphole to the processing system 7a. FIG. 9b illustrates the echo 2, second spin-echo signal.

In FIG. 8i, the one individual magnetic moment $\mu_1$ proceeds ahead of the other individual magnetic moment $\mu_2$ since the rate of precession of the one magnetic moment $\mu_1$ is greater than the rate of precession of the other magnetic moment $\mu_2$.

In FIGS. 8j and 8m, the two individual magnetic moments $\mu_1$ and $\mu_2$ flip or rotate 180 degrees about the y-axis from quadrant 2 to quadrant 1 of the x-y plane in response to application of the oscillating magnetic field pulse By180, applied along the y-axis at a time $5t_{cp}$.

In FIG. 8k, the two individual magnetic moments $\mu_1$ and $\mu_1$ refocus again thereby producing a third spin-echo signal (echo 3) at a time $6t_{cp}$, which third spin-echo signal (echo 3) is picked up by antennas 18 and 21 of NMR tool 13 and transmitted uphole to processing system 7a. The echo 3, third spin-echo signal is illustrated in FIG. 9b.

In FIG. 8L, the one individual magnetic moment $\mu_1$ proceeds ahead of the other individual magnetic moment $\mu_2$ since the rate of precession of the one magnetic moment $\mu_1$ is greater than the rate of precession of the other magnetic moment $\mu_2$.

Therefore, three spin-echo signals have been produced, the first spin-echo signal (echo 1) being produced in connection with FIG. 8e, the second spin-echo signal (echo 2) being produced in connection with FIG. 8h, and the third spin-echo signal (echo 3) being produced in connection with FIG. 8k.

Referring to FIGS. 9a–9b, the aforementioned first and second spin-echo signals, echo 1 and echo 2, are illustrated in time relation to the oscillating magnetic field pulse Bx90 (90 pulse) which is directed along the x-axis of FIG. 6 and has a pulse duration of 90 degrees, and to the further oscillating magnetic field pulse By180 (180 pulse) directed along the y-axis and having a pulse duration of 180 degrees. FIG. 9b illustrates a plurality of spin-echo signals associated with either the ($\tilde{R}_j$) in-phase channel or the ($\tilde{X}_j$) quadrature channel. When FIGS. 9a–9b are examined jointly with FIGS. 8a–8m, it is evident that the nth spin-echo signal is produced at a time $2nt_{cp}$ following application of the magnetic field pulses By180 at $(2n-1)t_{cp}$, where n=1,2,3, . . . J. The first spin-echo signal (echo 1) is generated after a time $t_{cp}$ elapses following application of the first magnetic field pulse By180 and the second spin-echo signal (echo 2) is generated after a time $t_{cp}$ elapses following application of the second magnetic field pulse By180.

Figures 10, 11:
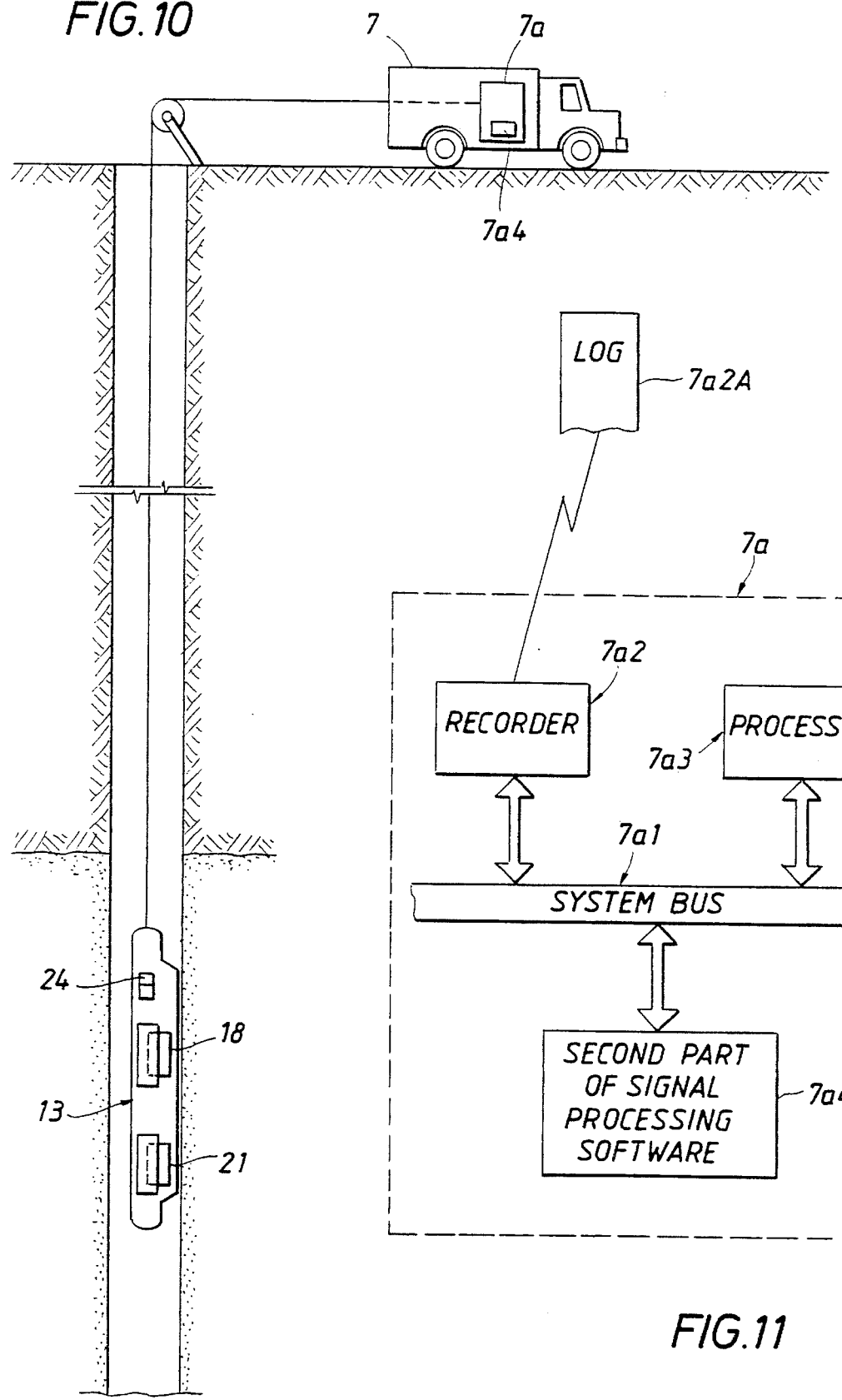
FIG. 10 illustrates NMR logging tool disposed in a borehole including an electronics cartridge which stores the first part of the signal processing method and apparatus in accordance with the present invention, and the processing system disposed on the surface of the borehole which stores the second part of the signal processing method and apparatus in accordance with the present invention.
FIG. 11 illustrates a more detailed construction of the surface oriented processing system of FIG. 10 which stores the second part of the signal processing method and apparatus of the present invention.

Referring to FIG. 10, a nuclear magnetic resonance (NMR) logging system is illustrated, the logging system including a NMR logging tool 13 disposed in a wellbore and surface equipment in the form of a well logging truck 7 situated on the surface of the wellbore, the well logging truck 7 including a processing system 7a in the form of a computer 7a situated within the well logging truck 7.

In FIG. 10, the NMR logging tool 13 includes antennas 18 and 21 and an electronics cartridge 24 responsive to signals received by the antennas 18 and 21 for processing the signals before transmission of the signals uphole to the computer 7a in the well logging truck. The electronics cartridge 24 of the logging tool 13 stores a first part of the signal processing (software) method and apparatus in accordance with one aspect of the present invention, and the computer 7a stores a second part of the signal processing (software) method and apparatus in accordance with another aspect of the present invention.

Figure 16:
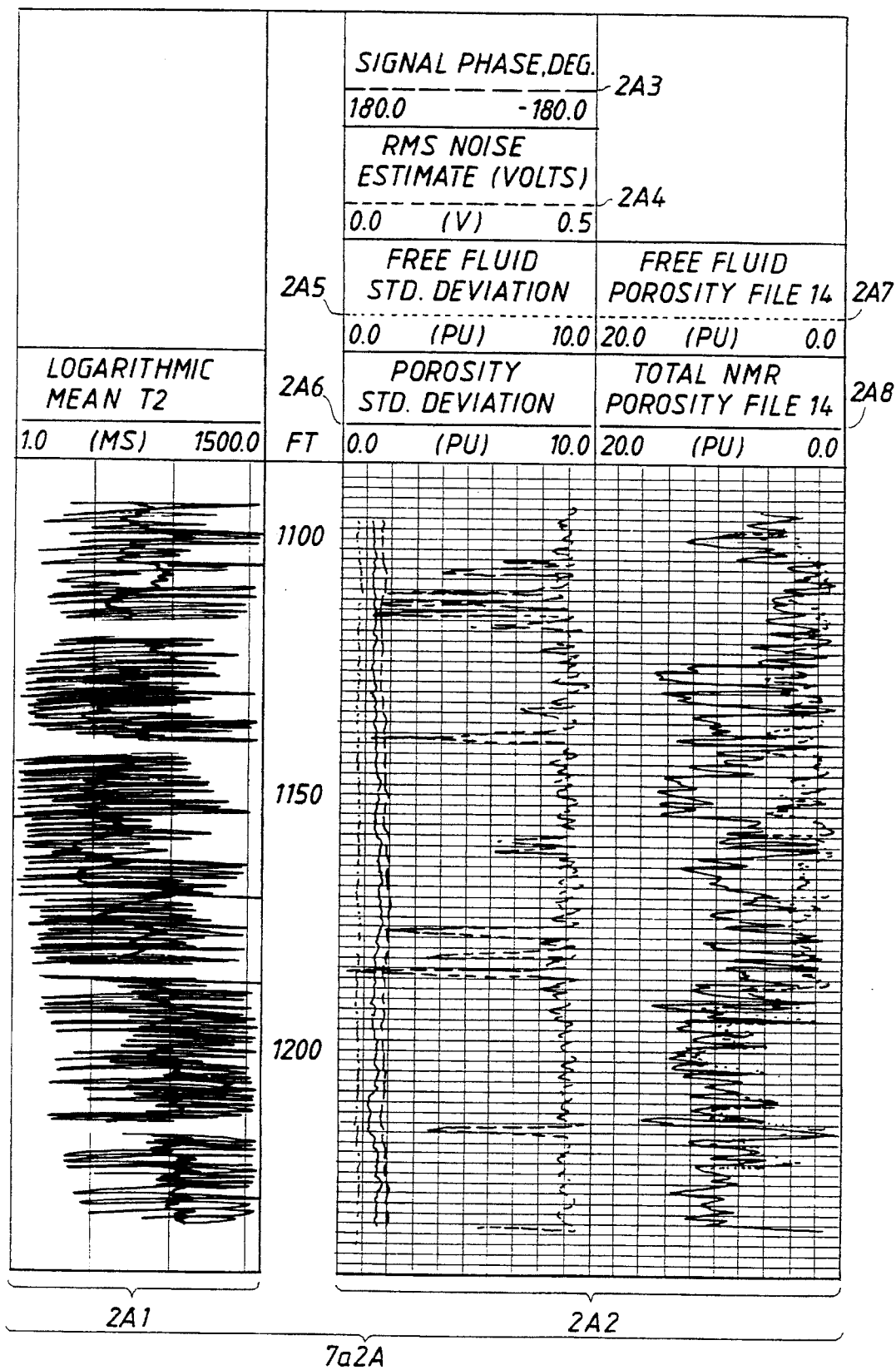
FIG. 16 illustrates a new output record medium, comprising a plurality of new logs, generated by the processing system disposed at the wellbore surface in accordance with another aspect of the present invention.
Figure 17:
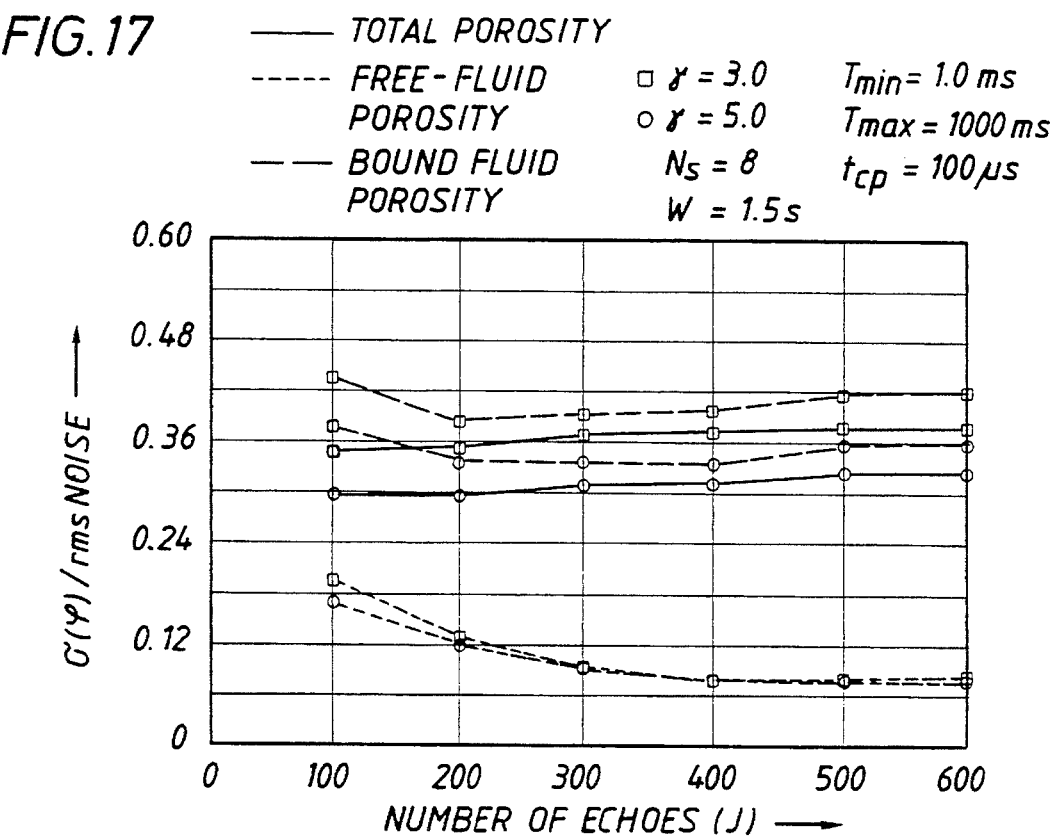
FIG. 17 illustrates the standard deviation in porosity estimates versus the total number of echoes for two values of $\gamma$.
Figure 18:
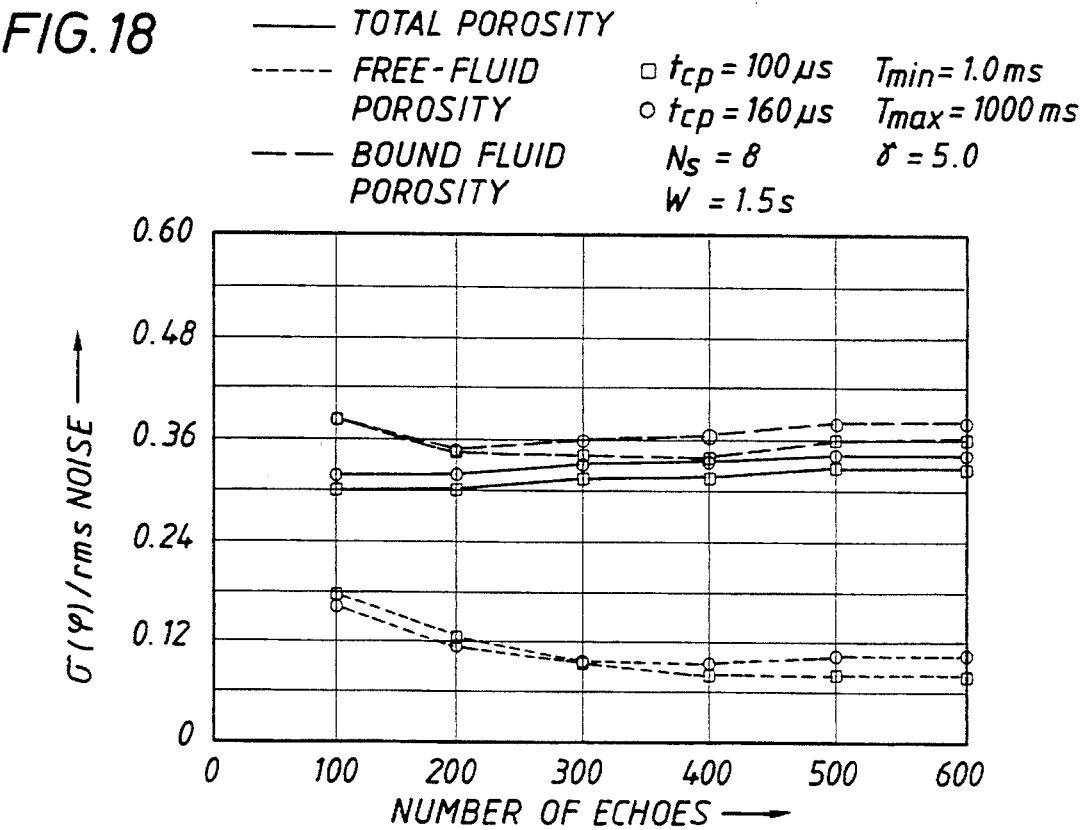
FIG. 18 illustrates the standard deviation in porosity estimates versus the total number of echoes for two values of $t_{cp}$.
Figure 19:
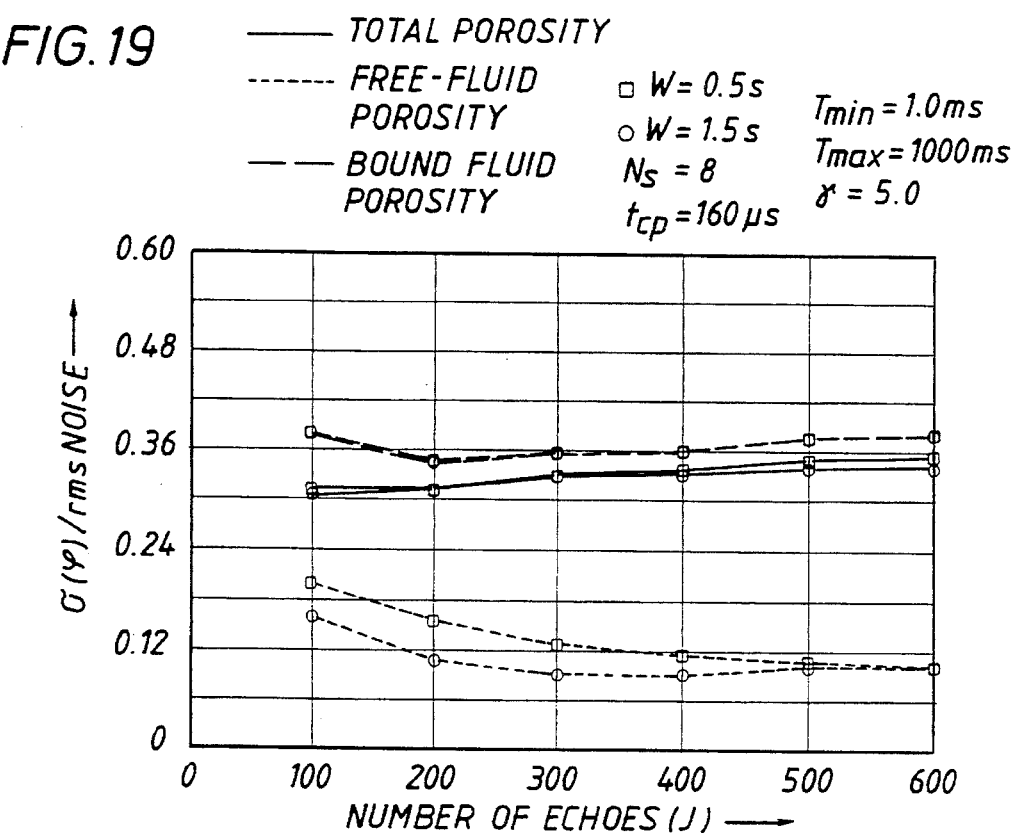
FIG. 19 illustrates the standard deviation in porosity estimates versus the total number of echoes for two values of W.
Figure 20:
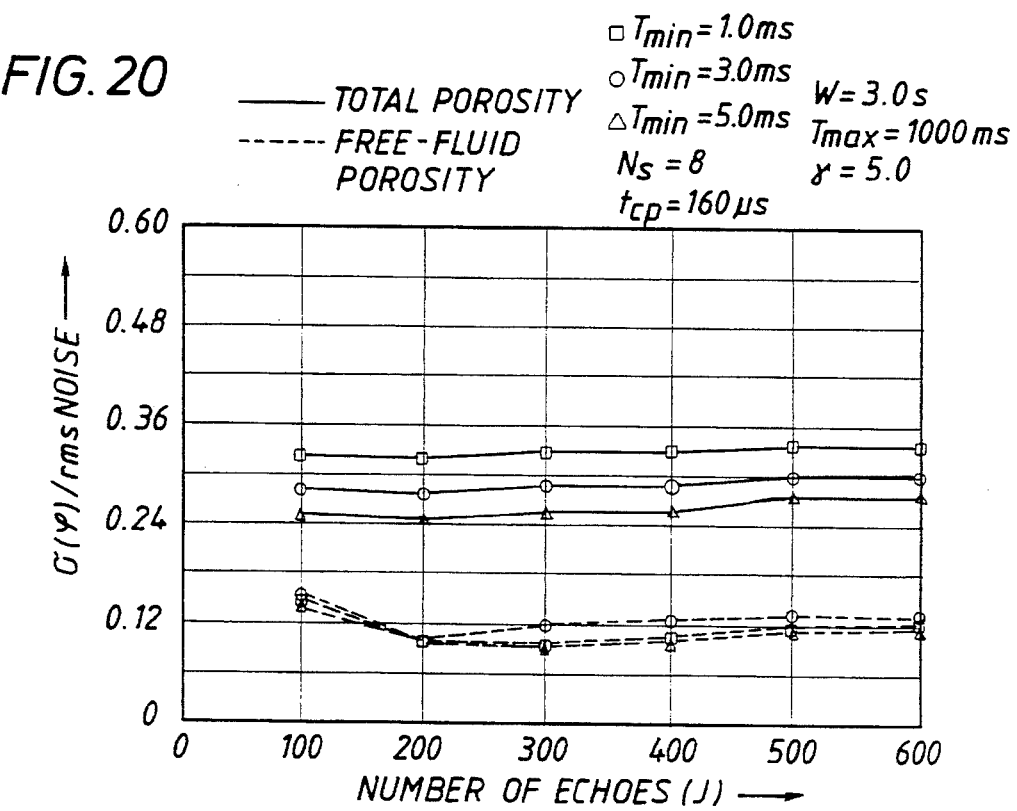
FIG. 20 illustrates the standard deviation in porosity estimates versus the total number of echoes for three values of $T_{min}$.

In FIG. 11, the computer 7a includes a system bus 7a1, a processor 7a3 connected to the system bus 7a1 for generating new output data in accordance with one aspect of the present invention, a memory 7a4 connected to the system bus 7a1 for storing the second part of the signal processing (software) method and apparatus of the present invention, and a recorder 7a2 connected to the system bus for receiving the new output data from the processor and generating a new output record medium 7a2A, to be discussed with reference to FIG. 16 of the drawings, in accordance with another aspect of the present invention. The computer 7a may include or consist of any one of the following computer systems manufactured by Digital Equipment Corporation (DEC), Maynard, Mass.: (1) DEC VAX 6430, (2) DEC PDP-11, or (3) DEC Vaxstation 3100, or it may include any other suitable computer system.

Referring to FIGS. 12a, 12b1, and 12b2, a contruction of the electronics cartridge 24 of FIG. 10 is illustrated. A more detailed construction of the hardware associated with the NMR logging system of FIGS. 1, 12a, 12b1, and 12b2, and in particular, of the construction of the electronics cartridge 24, is set forth in a prior pending application entitled "Borehole Measurement of NMR Characteristics of Earth Formations," corresponding to attorney docket number 20.2610, filed Nov. 2, 1992, the disclosure of which is incorporated by reference into this specification.

In FIG. 12a, the surface computer 7a is electrically connected via logging cable to the electronics cartridge 24 of FIG. 10. The electronics cartridge 24 includes a downhole computer 46. The downhole computer 46 is ultimately electrically connected to the antennas 18 and 21.

In FIGS. 12b1, the downhole computer 46 of electronics cartridge 24 includes a system bus 46b to which a processor 46c is electrically connected and a memory 46a is electrically connected.

In FIG. 12b2, the memory 46a stores the first part of the signal processing method and apparatus of the present invention.

Figure 13:
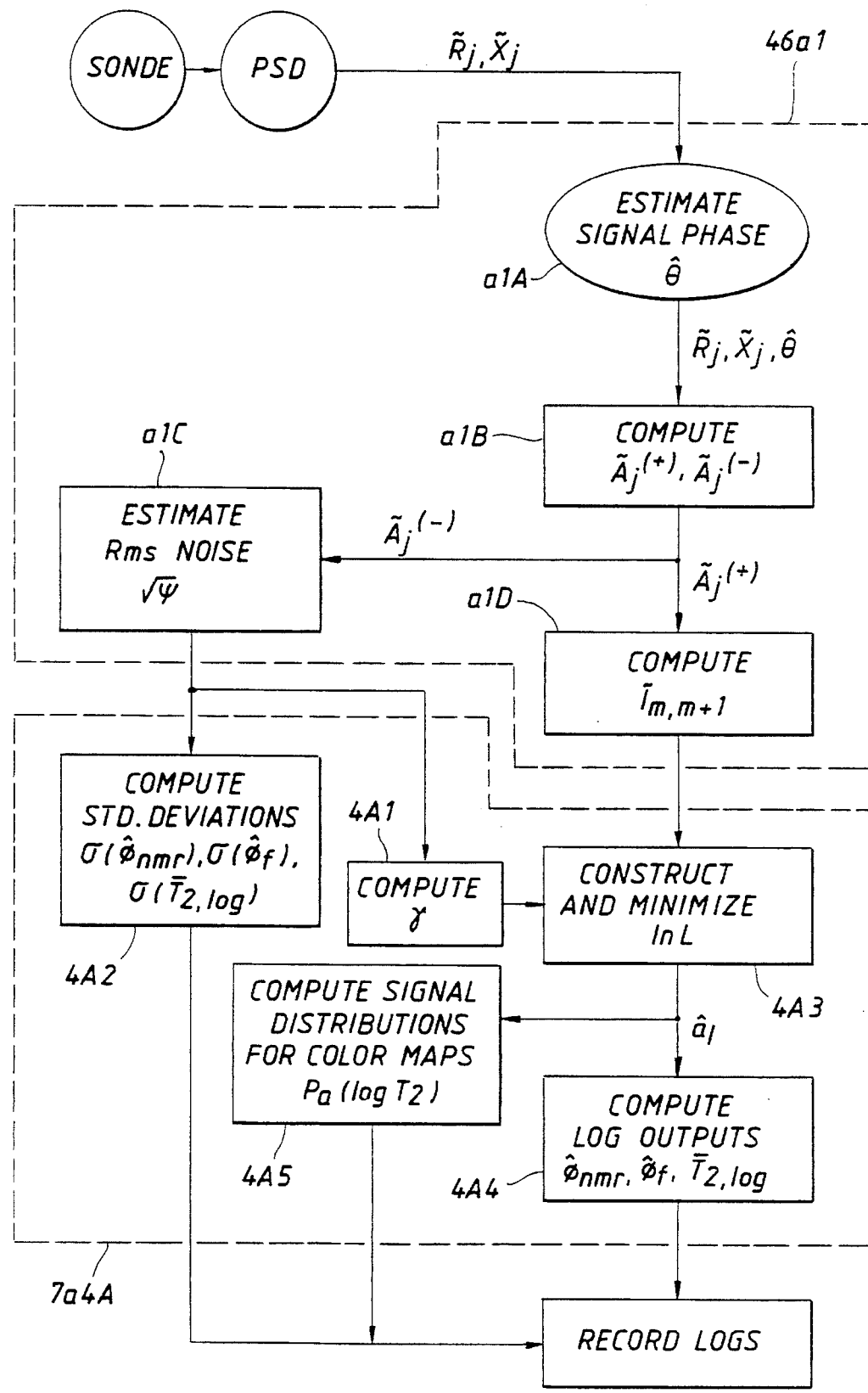
FIG. 13 illustrates a block diagram or flow chart of the first part of the signal processing method and apparatus of the present invention stored in the electronics cartridge of the NMR tool and the second part of the signal processing method and apparatus of the present invention stored in the surface oriented processing system of FIG. 10, which first part and second part of the signal processing method and apparatus is embodied in the form of software stored in a memory of the electronics cartridge and the surface oriented processing system, respectively.

Referring to FIG. 13, a flow chart of the first part and the second part of the signal processing (software) method and apparatus of the present is illustrated.

This specification is divided into a Description of the Preferred Embodiment, and a Detailed Description of the Preferred Embodiment. The flow chart of FIG. 13 and the following discussion is part of the Description of the Preferred Embodiment and provides a general discussion of the signal processing method and apparatus of the present invention. The Detailed Description of the Preferred Embodiment set forth below provides a more detailed discussion or the aforementioned signal processing method and apparatus of the present invention. In the following general discussion, occasional reference to equations and other specific description set forth in the Detailed Description of the Preferred Embodiment will be required.

The signal processing method and apparatus of the present invention, embodied in the form of a software package, includes two parts: a first part 46a1 stored in the memory 46a of the downhole computer 46 of electronics cartridge 24 of FIGS. 12a–12b2 and a second part 7a4A stored in the memory 7a4 of the well logging truck computer 7a of FIG. 10 situated at the surface of the wellbore.

In FIG. 1, the receiving antennas 18 and 21 of logging tool 13 measure the magnetic moments of individual protons in the volumes 19 and 22 of the formation traversed by the borehole 10 and generate a plurality of spin-echo receiver voltage pulses (FIG. 9b) representative of the magnetic moments. The electronics cartridge 24 begins processing the two-channel receiver voltage pulses by integrating each of the spin-echo receiver voltage pulses over a time interval, there being a total of J time intervals, each time interval being centered about a time $t_j=j\Delta$, where j=1, 2, . . . J. The integrated signals are recorded as spin-echo in-phase ($\tilde{R}_j$) and quadrature ($\tilde{X}_j$) amplitudes, time series channels or waveforms.

Referring to FIG. 13, the first part 46a1 of the signal processing method and apparatus of the present invention is illustrated.

In FIG. 13, the first part 46a1 of the signal processing method and apparatus of the present invention receives the aforementioned in-phase ($\tilde{R}_j$) and quadrature ($\tilde{X}_j$) amplitudes, and a signal phase (θ) is estimated associated with these amplitudes, block a1 A. Equation 9 of the Detailed Description set forth below provides the equation of the signal phase (theta) as a junction of the in-phase ($\tilde{R}_j$) and quadrature ($\tilde{X}_j$) amplitudes, as follows:

$$\hat{\theta} = \arctan \left[ \frac{\sum_{j=1}^{J} \tilde{X}_j}{\sum_{j=1}^{J} \tilde{R}_j} \right], \qquad (9)$$

Since the in-phase ($\tilde{R}_j$) amplitudes, the quadrature ($\tilde{X}_j$) amplitudes, and the signal phase estimate ($\hat{\theta}$) are known for each spin-echo receiver voltage pulse, the signal plus noise amplitude $\tilde{A}_j^{(+)}$, and the amplitude $\tilde{A}_j(-)$, for each spin-echo receiver voltage pulse, may now be determined, block a1B, by utilizing equations 22 and 23 of the Detailed Description, as follows:

$$\tilde{A}_j^{(+)} = \tilde{R}_j \cos\hat{\theta} + \tilde{X}_j \sin\hat{\theta}, \qquad (22)$$

and $$\tilde{A}_j^{(-)} = \tilde{R}_j \sin\hat{\theta} - \tilde{X}_j \cos\hat{\theta}. \qquad (23)$$

The RMS noise, the square root of $\psi$ or, $\sqrt{\psi}$, can be estimated from the noise amplitude $\tilde{A}_j^{(-)}$, block a1C, by utilizing a practical implementation of equation 31 of the Detailed Description, as follows:

$$\frac{1}{J} \sum_{j=1}^{J} \tilde{A}_j^{(-)2} \equiv \psi,$$

where equation (31) is set forth as follows:

$$<(\tilde{A}_j^{(-)})^2> \approx \psi, \quad (31)$$

The window sum $\tilde{I}_{mm+1}$ can be computed from the signal plus noise amplitudes $\tilde{A}_j^{(+)}$, block a1D, by utilizing equations 22 and 35 of the Detailed Description, as follows:

$$\tilde{I}_{m,m+1} = \sum_{j=N_{m+pm}}^{N_{m+1}} \tilde{A}_j^{(+)}, \quad (35)$$

As a result, when the downhole computer 46 of FIG. 12 executes the first part 46a1 of the signal processing software of FIG. 13, two outputs are generated: the window sum, $\tilde{I}_{m,m+1}$, which is determined from equation 35 and the RMS noise ($\sqrt{\psi}$) which is determined from equation 31.

The following paragraphs present a more detailed explanation of the window sum, $\tilde{I}_{m,m+1}$, determined from equation 35.

Figure 14:
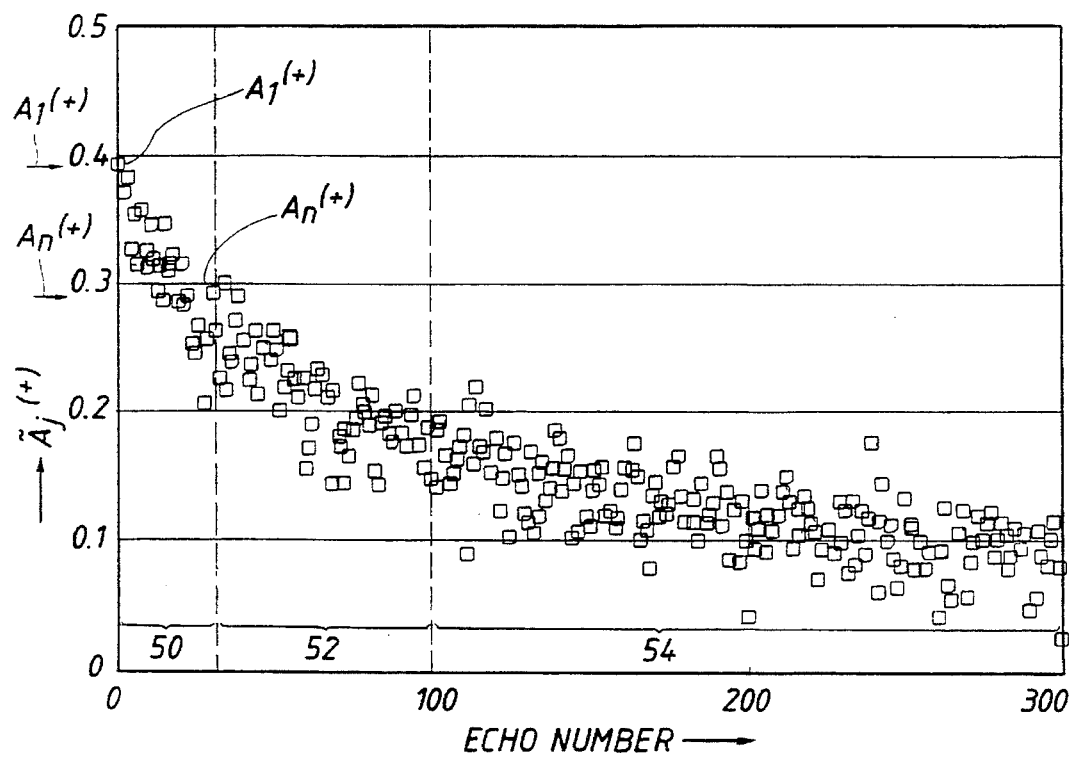
FIG. 14 illustrates a plurality of the spin-echo signal plus noise amplitudes, $\tilde{A}_j^{(+)}$, corresponding, respectively, to the plurality of spin-echo signals of FIG. 9b, each spin-echo signal plus noise amplitude $\tilde{A}_j^{(+)}$ being identified by an echo number, the echo numbers being divided into a plurality of time windows.

Referring to FIG. 14, an example of signal plus noise amplitudes, $\tilde{A}_j^{(+)}$ that have been determined from spin-echo signals (echo 1, echo 2, . . .) like those shown schematically as either R or X-channel spin-echo pulses in FIG. 9b is illustrated in FIG. 14 The spin-echo signal plus noise amplitudes $\tilde{A}_j^{(+)}$ are separated in time by $2t_{cp}$ from each other.

Figure 15:
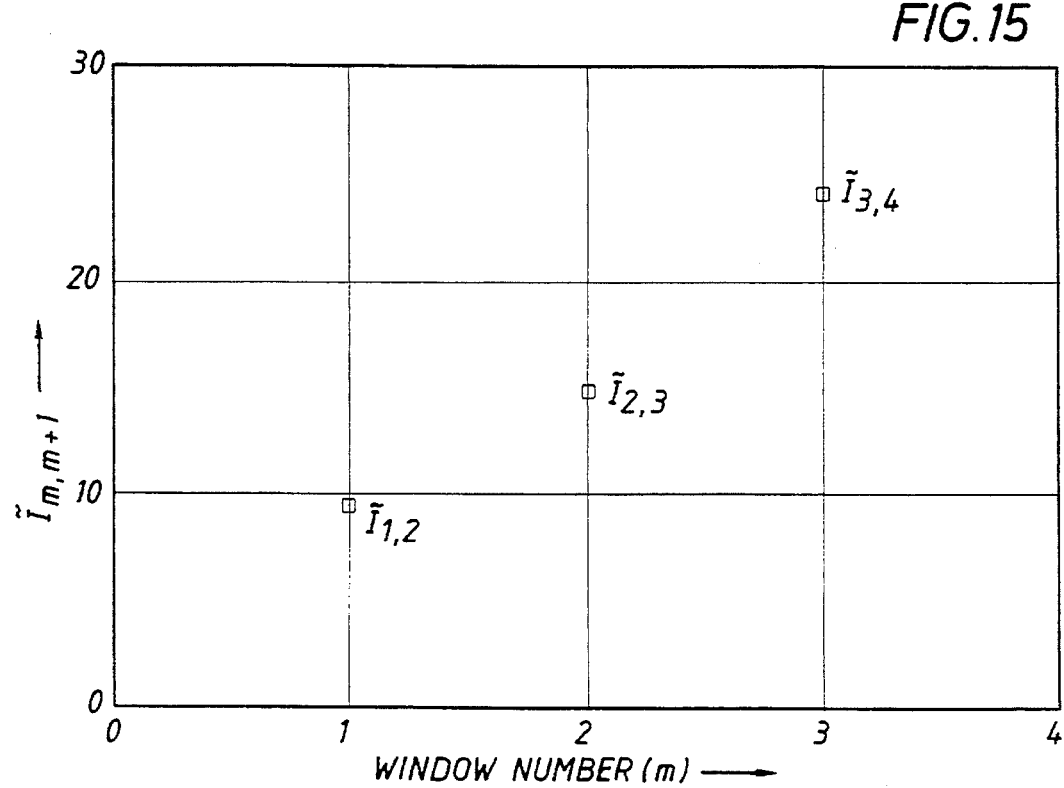
FIG. 15 illustrates a plurality of window sums $\tilde{I}_{m,m+1}$ corresponding, respectively, to the plurality of time windows of FIG. 14.

Referring to FIGS. 14 and 15, the technique for determining a particular window sum ($\tilde{I}_{m,m+1}$) from a plurality of signal plus noise amplitudes ($\tilde{A}_1^{(+)}, \tilde{A}_2^{(+)}, \tilde{A}_3^{(+)}, \ldots \tilde{A}_n^{(+)}$) is illustrated.

Recalling that a window sum $\tilde{I}_{m,m+1}$ is determined as set forth in equation 35 of the Detailed Description of the Preferred Embodiment set forth below, referring to FIGS. 14 and 15, a first window sum, $\tilde{I}_{1,2}$, where m=1, may be determined by summing a plurality of individual signal plus noise amplitudes, $\tilde{A}_1^{(+)}, \tilde{A}_2^{(+)}, \tilde{A}_3^{(+)}, \ldots \tilde{A}_n^{(+)}$, which are disposed within a first time window 50 shown in FIG. 14. A second window sum $\tilde{I}_{2,3}$ is determined in association with a second time window 52 and a third window sum $\tilde{I}_{3,4}$ is determined in association with a third time window 54 in the same manner as indicated above by summing the associated signal plus noise amplitudes, $\tilde{A}_3^{(+)}$, which are disposed within the second and third time windows, respectively.

The window sums are transmitted uphole from the NMR tool 13 of FIGS. 1 and 10 to the processing system or well logging truck computer 7a disposed on the wellbore surface as shown in FIG. 10. There are, $N_w$, window sums, where $N_w$ is typically three to five in number. Therefore, since only $N_w$ window sums are being transmitted uphole instead of 2J amplitudes (there being $\tilde{R}_j$ amplitudes and $\tilde{X}_j$ amplitudes, where j=1, 2, 3, . . . J), the telemetry requirements needed to transmit the $N_w$ window sums uphole to the truck computer 7a, relative to the telemetry requirements needed to transmit the 2J amplitudes uphole, is significantly reduced.

Referring again to FIG. 13, the second part 7a4A of the signal processing method and apparatus of the present invention is illustrated.

In FIG. 13, recall that the RMS noise ($\sqrt{\psi}$) is output from the first part 46a1 of the signal processing method and apparatus of the present invention. The RMS noise is used for two purposes:

1 1. to compute $\gamma$, block 4A1—the computation of $\gamma$ is discussed in connection with equation (42) of the Detailed Description and is set forth in Appendix A of the Detailed Description of the Preferred Embodiment, entitled "An Algorithm for Optimal Selection of $\gamma$"; in Appendix A, note that the best value of $\gamma$ can be found by finding the roots of equation (A.26) or of similarly derived equations; and 2. to compute standard deviations $\sigma(\hat{\phi}_{nmr})$, $\sigma(\hat{\phi}_f)$ and $\sigma(\overline{T}_{2,log})$, block 4A2—the standard deviation, $\sigma(\hat{\phi}_{nmr})$, may be determined from equation (58) of the Detailed Description of the preferred embodiment set forth below; the standard deviation, $\sigma(\hat{\phi}_f)$, may be determined from equation (61) of the Detailed Description; and the standard deviation, $\sigma(\overline{T}_{2,log})$, may be determined from equation (65) of the Detailed Description set forth below.

The parameter, $\gamma$, computed in block 4A1, is used to construct and minimize the likelihood function (−ln L), block 4A3. The likelihood function (−ln L) is represented by the following equation, which is equation (42) of the Detailed Description set forth below:

$$-\ln L = \sum_{m=1}^{N_w} \frac{(\tilde{I}_{m,m+1} - I_{m,m+1}\{\alpha_l\})^2}{2\psi[N_{m+1} - N_m + \delta_{m,1}]} + \frac{\gamma}{2\psi} \sum_{l=1}^{N_s} \alpha_l^2, \quad (42)$$

The spectral amplitudes, $\{\alpha_l\}$, are determined by minimization of equation (42) subject to a positivity constraint, as indicated in the Detailed Description set forth below in connection with equation 42.

The spectral amplitudes, $\{\alpha_l\}$, are used for two purposes: to compute log outputs $\phi_{nmr}$, $\phi_f$, and $\overline{T}_{2,log}$; and to compute signal distributions $P_a(\log T_2)$ represented by color maps 2A1 of FIG. 16, to be discussed below.

To compute log outputs $\phi_{nmr}$, $\phi_f$, and $T_{2,log}$, block 4A4, the log output, $\phi_{nmr}$, is determined from equation (43), as follows:

$$\phi_{nmr} = K_{tool} \int_{T_{min}}^{T_{max}} dT_2 P(T_2) \equiv K_{tool} \sum_{l=1}^{N_s} \alpha_l, \quad (43)$$

where $K_{tool}$ is a tool constant for converting volts to porosity.

The log output, $100_f$, is determined from equation (44), as follows:

$$\phi_f = K_{tool} \sum_{l=N_c}^{N_s} \alpha_l + \Delta\phi, \quad (44)$$

The log output, $T_{2,log}$, is determined from equations (54) and (55), as follows:

$$\overline{m} = \frac{\sum_{l=1}^{N_s} \delta P_\alpha(\log T_{2,l}) \log T_{2,l}}{\sum_{l=1}^{N_s} \delta P_\alpha(\log T_{2,l})} = \frac{\sum_{l=1}^{N_s} \alpha_l \log T_{2,l}}{\sum_{l=1}^{N_s} \alpha_l}. \quad (54)$$

and, $$\overline{T}_{2,log} = 10^{\overline{m}}. \quad (55)$$

To compute signal distributions, $P_a(\log T_2)$, which represent color maps 2A1 of FIG. 16, block 4A5, the computation of the signal distributions $P_a(\log T_2)$ is performed using equation (50) as follows:

$$P_\alpha(\log T_{2,l}) = \frac{2\alpha_l r}{c(r^2 - 1)}. \quad (50)$$

Referring to FIG. 16, a new output record medium 7a2A is illustrated. This new output record medium, a new log adapted to be given to a client for evaluation of the formation traversed by the wellbore, is generated in response to the receipt of the following information:

1. the log outputs $\hat{\phi}_{nmr}$, $\hat{\phi}_f$, and $T_{2,log}$ of block 4A4;

2. the signal distributions for color maps, $P_a(\log T_2)$, of block 4A5; and 3. the standard deviations $\sigma(\hat{\phi}_{nmr})$, $\sigma(\hat{\phi}_f)$ and $\sigma(T_{2,log})$, of block 4A2.

The new output record medium 7a2A of FIG. 16 records the following new data or information presented in the form of logs as a function of depth in the wellbore (see element 2A2 in FIG. 16) and in the form of a color map (see element 2A1 of FIG. 16);

1. signal phase 2A3 from block a1A; 2. RMS noise estimate 2A4 from block a1C; 3. free fluid standard deviation 2A5 from block 4A2; 4. porosity standard deviation 2A6 from block 4A2; 5. free fluid porosity 2A7 from block 4A4; 6. total NMR porosity 2A8 from block 4A4; and 7. color Map 2A1.

The new output record medium 7a2A is given to a customer or client for the purpose of determining the presence or absence of underground deposits of hydrocarbons and the reservoir quality of the formation traversed by the wellbore 10 of FIG. 1.

A functional description of the operation of the signal processing method and apparatus in accordance with the present invention is set forth in the following paragraphs with reference to FIG. 16a and FIG. 13 of the drawings.

In FIGS. 16a and 13, the RF antennas 18 and/or 21 measure the precession of the protons in the pores 19a1 of the volume of investigation 19 of FIG. 3 and generate spin-echo receiver voltage pulses similar to the spin-echo receiver voltage pulses "echo 1", "echo 2", and "echo 3" illustrated in FIG. 9b of the drawings. Phase sensitive detection (PSI)) circuits disposed within the electronics cartridge 24 integrate each of the spin echo receiver voltage pulses over a time interval, and the integrated signals are recorded as spin-echo in-phase ($\tilde{R}_j$) and quadrature ($\tilde{X}_j$) amplitudes. The processor 46c or the downhole computer 46 in the electronics cartridge 24 disposed within the NMR tool 13 in the wellbore begins executing the first part 46a1 of the signal processing (software) method and apparatus of FIG. 13 stored within the memory 46a of the downhole computer 46. When the processor 46c completes the execution of the first part of the signal processing software 46a1 stored in memory 46a, the following data and information is determined:

1. the signal phase (θ) is estimated from the 2J in-phase ($\tilde{R}_j$) and quadrature ($\tilde{X}_j$) amplitudes corresponding to J spin-echo receiver voltage pulses in the R and X-channels using equation 9 as a function of the in-phase and quadrature amplitudes set forth in the detailed description, block a1A of FIG. 13;

2. a spin-echo signal plus noise amplitude $\tilde{A}_j^{(+)}$ is determined for each in-phase ($\tilde{R}_j$) amplitude, quadrature ($\tilde{X}_j$) amplitude, and signal phase (θ) using equation 22 in the Detailed Description; and the amplitude $\tilde{A}_j^{(-)}$ is also determined from in-phase ($\tilde{R}_j$) amplitude, quadrature ($\tilde{X}_j$) amplitude, and signal phase (θ) using equation 23 in the Detailed Description, block a1B of FIG. 13; furthermore, there are J in-phase amplitudes ($\tilde{R}_j$) and J quadrature amplitudes ($\tilde{X}_j$); and, as a result, there are J spin-echo signal plus noise amplitudes $\tilde{A}_j^{(+)}$ and there are J amplitudes $\tilde{A}_j^{(-)}$;

3. the $N_w$ window sums $\tilde{I}_{m,m+1}$ are determined from the $\tilde{A}_j^{(+)}$ signal plus noise amplitudes using equation 35, where $N_w$ is typically three to five in number, thereby reducing telemetry requirements for transmission of window sums uphole to the surface computer 7a, block a1D of FIG. 13; and 4. the RMS noise, $\sqrt{\psi}$, is determined from the J amplitudes $\tilde{A}_j^{(-)}$ using the practical implementation of equation 31 or equation per se, block a1C of FIG. 13.

Two sets of data are transmitted uphole from the NMR tool 13 to the surface computer 7a: the $N_w$ window sums, $\tilde{I}_{m,m+1}$, and the RMS noise, $\sqrt{\psi}$ The processor 7a3 of the surface computer 7a receives the Nw window sums, $\tilde{I}_{m,m+1}$, and the RMS noise, $\sqrt{\psi}$, from the downhole computer 46 of the NMR tool 13 disposed downhole; in response, the processor 7a3 begins to execute the second part of the signal processing software 7a4A of FIG. 13 stored in memory 7a4 of the surface computer 7a. When the processor 7a3 completes execution of the second part of the signal processing software 7a4A, the following additional data and information is determined:

1. the standard deviations $\sigma(\hat{\phi}_{nmr})$, $\sigma(\hat{\phi}_f)$ and $\sigma(\overline{T}_{2,log})$, are determined, block 4A2 of FIG. 13, the standard deviation $\sigma(\hat{\phi}_{nmr})$, being determined from equation (58) of the Detailed Description, the standard deviation $\sigma(\hat{\phi}_f)$ being determined from equation (61) of the Detailed Description, and the standard deviation $\sigma(T_{2,log})$, being determined from equation (65) of the Detailed Description of the Preferred Embodiment set forth below.

2. the parameter, γ, is determined from the RMS noise $\sqrt{\psi}$; block 4A1 of FIG. 13, in the manner described in Appendix A of the Detailed Description and in connection with equation 42 in the Detailed Description;

3. once the parameter, γ, is determined, a likelihood function (−ln L) is constructed and minimized, the likelihood function being represented by equation 42 of the Detailed Description, which equation is a function of the parameter, γ, block 4A3 of FIG. 13;

4. the spectral amplitudes, $\{\alpha_l\}$, are determined by minimization of the likelihood function (−ln L) of equation 42, and the spectral amplitudes, $\{\alpha_l\}$, are used for two purposes: to compute log outputs $\hat{\phi}_{nmr}$, $\hat{\phi}_f$, and $T_{2,log}$ of block 4A4 of FIG. 13, and to compute the signal distributions $P_a(logT_2)$, which signal distributions are illustrated in the form of the color maps 2A1 of FIG. 16, block 4A5 of FIG. 13;

The processor 7a3 of FIG. 16a instructs the recorder 7a2 to generate the new output record medium 7a2A of FIG. 16 using the aforementioned recently determined standard deviations $\sigma(\hat{\phi}_{nmr})$, $\sigma(\hat{\phi}_f)$ and $\sigma(T_{2,log})$; the signal distributions, $P_a(logT_2)$; and the log outputs $\hat{\phi}_{nmr}$, $\hat{\phi}_f$, and $T_{2,log}$, the new output record medium 7a2A of FIG. 16 displaying the following new information:

1. signal phase 2A3 from block a1A; 2. RMS noise estimate 2A4 from block a1C; 3. free fluid standard deviation 2A5 from block 4A2; 4. porosity standard deviation 2A6 from block dA2; 5. free fluid porosity 2A7 from block 4A4; 6. total NMR porosity 2A8 from block 4A4; and 7. color map 2A1.

DETAILED DESCRIPTION OF THE PREFERRED EMBODIMENT

Introduction

The development of Pulsed Nuclear Magnetic Resonance logging tools to acquire downhole spin-echo measurements in earth formations penetrated by boreholes is a new technology. The measurement principles and pulse sequences have been recently published.[1,2] This new logging technology provides detailed formation evaluation information previously obtainable only from costly laboratory analysis of conventional core data. This information presently includes but is not limited to: (1) total NMR porosity ($\phi_{nmr}$), (2) free-fluid porosity ($\phi_f$) (i.e., part or total porosity which is movable), (3) bound fluid porosity ($\phi_b$), (4) spin-spin ($T_2$) relaxation time distributions which are related to pore size distributions in sandstones, and (5) continuous permeability logs in sandstones. To extract this information from the measured spin-echoes requires a signal processing algorithm which is capable of providing an accurate and repeatable spectral decomposition of the measured data. The algorithm must be efficient and robust for real time processing of data as it is continuously acquired by a moving logging tool. This report describes a new algorithm which statisfies these conditions and provides PNMT logs which agree well with conventional core and other log data. Other approaches to spectral decomposition of NMR data have been reported[3-6]. Kenyon, et al.[5] used the algorithm reported by Gallegos and Smith[3] to compute $T_1$ distributions in rocks from laboratory NMR inversion recovery data. Latour, et al.[6] used a computationally expensive singular value decomposition algorithm to compute relaxation time distributions in rocks from laboratory NMR data.

It is well-known that sedimentary rocks have a distribution of pore sizes. This results in NMR signals in rocks which decay with a distribution of relaxation times. Mathematically, the signal processing problem is to determine the distribution functions from the measured data (i.e., solve an inverse problem). The aforementioned formation evaluation parameters are computed from the distribution functions. Generally, there exists a joint distribution function, i.e., a function of both the longitudinal ($T_1$) and transverse ($T_2$) spin relaxation times, however, laboratory measurements have shown that these distributions in sedimentary rocks are correlated.[6] The correlation is valid at NMR frequencies in the range of 2 MHz and is applicable to the borehole measurements described in this report.

Pulse Sequence And Parameters

It suffices to describe the pulse sequence and typical measurement parameters used in practice. The spin-echo measurement employed is the well-known Carr-Purcell-Meiboom-Gill (CPMG) sequence. This sequence measures the decay of the amplitude of the transverse magnetization following a 90° (+x) r.f. pulse which rotates the magnetization into a plane transverse to an applied static magnetic field ($H_0\hat{z}$). The frequency of the r.f. pulses is equal to the median Larmor proton precession frequency. The nuclear spins contributing to the transverse magnetization precess at different Larmor frequencies in the inhomogeneous d.c. magnetic field. The free-induction decay (FID) signal which is generated by the 90° (+x) pulse decays to zero within microseconds because of spin dephasing produced by the spread in Larmor frequencies. The FID signal occurs too soon following the 90° (+x) to be measured by the PNMT electronics. At times $t_j=(2j-1)t_{cp}$ following the 90° (+x) pulse, a set of 180° (y) r.f. pulses are applied which cause the transverse magnetization to refocus at times $t_j=2jt_{cp}$ for j=1, 2, ..., J producing J spin-echo signals. Note that the r.f. magnetic field of the 180° pulses is transverse to both $H_0$ and the r.f. magnetic field of the 90° pulses. The spin-echoes are equally spaced in time with spacing $\Delta=2t_{cp}$. The train of spin-echoes represents a signal whose decay contains contributions from all components of the intrinsic $T_2$-distribution. Here intrinsic refers to a distribution that includes effects of microscopic spin-spin interactions as observed in bulk liquids as well as surface relaxation from the confining pores. It is the latter effects that frequently dominate in reservoir rocks and provide the link between $T_2$-distributions and pore size distributions. The effects, on the spin-echo decay, of molecular diffusion in the static field gradient can be made negligble for the PNMT by making the Carr-Purcell time $t_{cp}$ sufficiently short. The CPMG sequence described above can be improved by using phase alternated pairs (PAPS) of CPMGs to eliminate baseline shifts. Phase alternated pairs of CPMGs differ by shifting the phase of the 90° pulses by 180 degrees. The PNMT PAPS pulse sequences can therefore be written succinctly in an obvious notation, $$\text{CPMG}^{(\pm)}: W - 90°(\pm x) - (t_{cp} - 180°(y) - t_{cp} - (\text{echo}))_{j=1,2,\ldots,J} \quad (1)$$

where W is a wait time that must precede each CPMG so that the longitudinal magnetization can recover prior to the initial 90° pulse. The PAPS pairs are combined by taking one-half their difference. This eliminates baseline offsets. Note each PAPS is constructed by signal averaging two CPMG sequences which reduces the rms noise by a factor $\sqrt{2}$.

Typical values of the pulse parameters are $t_{cp}$=100–500 μs, W=0.5–1.5 s, and J=100–1000 echoes.

Statement of The Signal Processing Problem

The spin-echo amplitudes are obtained by hardware integration of the receiver voltages over J time windows each centered about $t_j=j\Delta$ for j=1, 2, ..., J. The PNMT tool uses phase sensitive detection to measure the in-phase ($\tilde{R}_j$) and quadrature ($\tilde{X}_j$) components of the signal-plus-noise amplitudes. As shown in the next section, the signal phase θ is estimated from the $\tilde{R}_j$ and $\tilde{X}_j$ amplitudes which are then combined to provide the signal-plus-noise amplitudes $\tilde{A}_j^{(+)}$. A phenomenological model for the signal-plus-noise amplitude of the j-th echo can be written in the form:

$$\tilde{A}_j^{(+)} = \int dT_1 \int dT_2 \, P_j(T_1, T_2) f(W, T_1) \exp\left(-\frac{j\Delta}{T_2}\right) + N_j^{(+)}, \quad (2)$$

where $P_j(T_1, T_2)$ is the joint relaxation time distribution function and the integals are over the domain of the distribution function. As noted previously, experiments have shown that to within a good approximation, the joint distribution function in reservoir rocks has the form, $$R_j(T_1, T_2) = P(T_2)\delta(T_1 - \xi T_2),$$

where $\xi$~1.5. That is, the $T_1$ and $T_2$ distributions are practically identical except for a constant scaling factor. Substitution of eq. (3) into (2) and performing the integration over $T_1$ leads to $$\tilde{A}_j^{(+)} = \int_{T_{min}}^{T_{max}} dT_2 \, P(T_2) f(W, \xi T_2) \exp\left(-\frac{j\Delta}{T_2}\right) + N_j^{(+)}, \quad (4)$$

where for $\hat{A}_j^{(+)}$ expressed in volts, $P(T_2)dT_2$ is the signal amplitude in volts contributed by spectral components with transverse relaxation times in the interval $T_2$ to $T_2+dT_2$. The domain of tile function $P(T_2)$ is the closed interval [$T_{min}$, $T_{max}$]. The function $f(W, \xi T_2)$ accounts for the incomplete recovery of the longitudinal magnetization during the wait time W and is defined by, $$f(W, \xi T_2) = \left(1 - \exp\left(-\frac{W}{\xi T_2}\right)\right). \quad (5)$$

The integrals in eqs. (2) and (4) are the amplitudes of the transverse magnetization observed at the j-th echo and $N_j^{(+)}$ is the thermal noise in the tool electronics.

Equation (4) is a Fredholm integral equation of the first kind for the distribution function $P(T_2)$. The solution of eq. (4) for $P(T_2)$ from the measured spin-echo signal-plus-noise amplitudes is the signal processing problem that must be confronted to obtain maximum information from the PNMT data. This type of problem represents an inverse problem of the type frequently encountered in remote sensing problems.[7] The relaxation time distribution is the central quantity of interest since essentially all of the petrophysical quantities of interest can be computed from this function.

Pre-Processing of Spin-Echo Data

As noted previously, the amplitudes of the spin-echoes are integrated over time windows and the integrated signals are recorded as $\tilde{R}_j$ and $\tilde{X}_j$ time series channels or waveforms. Each time series or CPMG(+) is combined with its phase alternated pair CPMG(−). The PAPS pairs are accumulated as the tool moves and then averaged and output into depth bins. Thus, in each depth bin the data typically consists of several hundred echoes $\tilde{R}_j$ and $\tilde{X}_j$ for $j=1, 2, \ldots, J$ where $J$ is the total number of echoes collected. Prior to applying the signal processing algorithm, the data in each depth bin are pre-processed. First, an estimate $\hat{\theta}$ of the signal phase is computed. Using $\hat{\theta}$ the $\tilde{R}_j$ and $\tilde{X}_j$ data are combined into two random time series $\tilde{A}_j^{(+)}$ and $\tilde{A}_j^{(-)}$. The random variables $\tilde{A}_j^{(+)}$ have the statistical properties of the phase coherent signal-plus-noise and are used to estimate the relaxation time distribution (i.e., by solving a discretized version of eq. (4)). The random variables $\tilde{A}_j^{(-)}$ have the statistical properties of the noise and are used to estimate the rms noise, $\sqrt{\psi}$, on a single echo of the PAPs pairs in each depth bin. In each depth bin the number of PAPs pairs accumulated and averaged depends on the pulse sequence parameters and the logging speed.

Statistical Properties of the Noise

The spin-echo in-phase and quadrature amplitudes can be written in the form, $$\tilde{R}_j = S_j \cos\theta + N_j^{(c)}, \tag{6}$$

$$\tilde{X}_j = S_j \sin\theta + N_j^{(s)}, \tag{7}$$

where $\theta$ is the signal phase and $S_j$ is the signal. $N_j^{(c)}$ and $N_j^{(s)}$ are thermal noise voltage fluctuations in the R and X receiver channels, respectively. The thermal noise fluctuations are uncorrelated, zero mean Gaussian random variables with the following statistical properties:

$$\langle N_j^{(c)} \rangle = \langle N_j^{(s)} \rangle = 0, \tag{8a}$$

$$\langle N_j^{(c)} N_k^{(s)} \rangle = 0 \tag{8b}$$

$$\langle N_j^{(c)} N_k^{(c)} \rangle = \langle N_j^{(s)} N_k^{(s)} \rangle = \delta_{j,k} \psi. \tag{8c}$$

The angular brackets are used to denote statistical or ensemble averages and $\delta_{j,k}$ is the Kronecker delta function. Note that thermal noise fluctuations are a time translationally invariant stochastic process. Therefore it follows from the ergodic theorem that statistical averages can be replaced by time averages. In eq. (8c), is the noise variance on a single echo.

Signal Phase Estimator

An unbiased estimator $\hat{\theta}$ of the signal phase is computed from the in-phase and quadrature amplitudes, $$\hat{\theta} = \arctan\left[\frac{\sum_{j=1}^{J} \tilde{X}_j}{\sum_{j=1}^{J} \tilde{R}_j}\right], \tag{9}$$

To compute the mean and variance of $\hat{\theta}$, sum eqs. (6) and (7) over all echoes, i.e., $$\sum_{j=1}^{J} \tilde{R}_j = \sum_{j=1}^{J} S_j \cos\theta + \sum_{j=1}^{J} N_j^{(c)}, \tag{10}$$

and, $$\sum_{j=1}^{J} \tilde{X}_j = \sum_{j=1}^{J} S_j \sin\theta + \sum_{j=1}^{J} N_j^{(s)}, \tag{11}$$

from which it follows that, $$\cos\hat{\theta} = \cos\theta + \frac{\sum_{j=1}^{J} N_j^{(c)}}{\sum_{j=1}^{J} S_j}, \tag{12}$$

and $$\sin\hat{\theta} = \sin\theta + \frac{\sum_{j=1}^{J} N_j^{(s)}}{\sum_{j=1}^{J} S_j}, \tag{13}$$

where I have defined, $$\cos\hat{\theta} \equiv \frac{\sum_{j=1}^{J} \tilde{R}_j}{\sum_{j=1}^{J} S_j}, \tag{14}$$

and, $$\sin\hat{\theta} \equiv \frac{\sum_{j=1}^{J} \tilde{X}_j}{\sum_{j=1}^{J} S_j}. \tag{15}$$

Combining eqs. (12) and (13) one finds to lowest order in the noise fluctuations that, $$\tan\hat{\theta} - \tan\theta \simeq \left[\frac{\sum_{j=1}^{J} N_j^{(s)}}{\sum_{j=1}^{J} S_j \cos\theta} - \frac{\sum_{j=1}^{J} N_j^{(c)} \sin\theta}{\sum_{j=1}^{J} S_j \cos^2\theta}\right], \tag{16}$$

from which it follows that $$\hat{\theta} \simeq \theta + \frac{\sum_{j=1}^{J} N_j^{(s)} \cos\theta}{\sum_{j=1}^{J} S_j} - \frac{\sum_{j=1}^{J} N_j^{(c)} \sin\theta}{\sum_{j=1}^{J} S_j}, \tag{17}$$

where in obtaining the above equation I have used the result, $$\tan\hat{\theta} - \tan\theta \simeq \frac{(\hat{\theta} - \theta)}{\cos^2\theta}, \tag{18}$$

which is valid for $\hat{\theta} \approx \theta$. It follows easily from eq. (17) and the statistical properties of the noise that, $$\langle\hat{\theta}\rangle = \theta, \tag{19}$$

so that $\hat{\theta}$ is an unbiased estimator of the signal phase $\theta$. One also finds using the noise properties that, $$\langle\hat{\theta}^2\rangle = \theta^2 + \frac{\psi}{(\sum_{j=1}^{J} S_j)^2}. \tag{20}$$

Finally, it follows from eqs. (19) and (20) that the variance in the phase estimator $\theta$ is given by, $$\sigma^2(\hat{\theta}) = \frac{\psi}{(\sum_{j=1}^{J} S_j)^2}. \tag{21}$$

It should be noted that the phase estimator $\hat{\theta}$ is sensible provided that the signal-to-noise ratio is not too small. In practice, the signal phase is found to be relatively constant in zones with porosities greater than a few p.u. and exhibits random fluctuations in zones with no appreciable signal. It is a useful tool diagnostic since it should not vary with the formation and should be relatively constant in porous zones during a logging run.

Computation of $\tilde{A}_j^{(+)}$ and $\tilde{A}_j^{(-)}$

Using $\hat{\theta}$, it is convenient to construct two random time series from the $\tilde{R}_j$ and $\tilde{X}_j$. These are the signal-plus-noise amplitudes $\tilde{A}_j^{(+)}$ introduced in eq. (2) and $\tilde{A}_j^{(-)}$ which can be used to estimate $\psi$ from the data. These random time series are defined by, $$\tilde{A}_j^{(+)} \tilde{R}_j \cos \hat{\theta} + \tilde{X}_j \sin \hat{\theta}, \quad (22)$$

and $$\tilde{A}_j^{(-)} = \tilde{R}_j \sin \hat{\theta} - \tilde{X}_j \cos \hat{\theta}. \quad (23)$$

The rationale for introducing $\tilde{A}_j^{(+)}$ is that it has the statistical properties of a phase coherent signal. The above pair of equations has a simple vectorial interpretation, e.g., in eq. (22) the two terms on the right are the projections of the R and X components along the total signal whereas the terms in eq. (23) are projections perpendicular to the total signal. To calculate its expectation value first note that, $$\tilde{A}_j^{(+)} = S_j \cos(\hat{\theta} - \theta) + N_j^{(+)} \approx S_j + N_j^{(+)}, \quad (24)$$

where I have used eqs. (6), (7) and (22) and defined, $$N_j^{(+)} = N_j^{(c)} \cos \hat{\theta} + N_j^{(s)} \sin \hat{\theta}. \quad (25)$$

I have dropped terms in eq. (24) of order $(\hat{\theta} - \theta)^2$ which are assumed to be negligble. The expectation value of eq. (24) is obtained from the statistical properties of the noise. i.e., eqs. (8).

$$\langle \tilde{A}_j^{(+)} \rangle \approx S_j. \quad (26)$$

One also finds that, $$\langle (\tilde{A}_j^{(+)})^2 \rangle \approx S_j^2 + \psi, \quad (27)$$

from which it follows that the variance in $\tilde{A}_j^{(+)}$ is $\psi$. I shall make use of these results in the development of the algorithm for computing the spectral distribution function. Next it is shown that $\tilde{A}_j^{(-)}$ has the properties of the noise. Substituting eqs. (6), (7) into (23) one finds that, $$\tilde{A}_j^{(-)} = S_j \sin(\hat{\theta} - \theta) + N_j^{(-)} \approx N_j^{(-)}, \quad (28)$$

where $$N_j^{(-)} = N_j^{(c)} \sin \hat{\theta} - N_j^{(s)} \cos \hat{\theta}. \quad (29)$$

Using the statistical properties of the noise one finds that, $$\langle \tilde{A}_j^{(-)} \rangle \approx 0, \quad (30)$$

and, $$\langle (\tilde{A}_j^{(-)})^2 \rangle \approx \psi, \quad (31)$$

from which it follows that the variance in $\tilde{A}_j^{(-)}$ is $\psi$. Thus, as noted previously, the random time series for $\tilde{A}_j^{(-)}$ can be used to estimate the rms noise $\sqrt{\psi}$.

Spectral Decomposition Algorithm

Discretization of the Signal

First, the signal $S_j$ which is given by the integral in eq. (4) is discretized, i.e., $$\tilde{A}_j^{(+)} = \sum_{l=1}^{N_s} \alpha_l f_l \exp\left[ -\frac{t_j}{T_{2,l}} \right] + N_j^{(+)}, \quad (32)$$

where it is assumed that there are $N_a$ components (i.e., basis functions) in the spectrum with relaxation times given by, $$T_{2,l} = T_{min} \left( \frac{T_{max}}{T_{min}} \right)^{\frac{l-1}{N_s-1}}, \quad (33)$$

for $l=1, 2, \ldots, N_s$. Note that the $T_{2,l}$ are equally spaced on a logarithmic scale. In eq. (32), I have defined the polarization functions, $$f_l = \left( 1 - \exp\left( -\frac{W}{\xi T_{2,l}} \right) \right). \quad (34)$$

The signal processing problem therefore becomes the determination of the $N_s$ spectral amplitudes at $\alpha_l \equiv P(T_{2,l}) \delta_l$ where $\delta_l = (T_{2,l+1} - T_{2,l-1})2$.

Data Compression

In this section, the data $\tilde{A}_j^{(+)}$ arc reduced by introducing sums of echoes over time windows. As noted earlier, the different windows have different sensitivities to the various components of the spectrum. Consider $N_w$ non-overlapping windows. Define the window sum, $\tilde{I}_{m,m+1}$, over $(N_{m+1} - N_m + \delta_{m,1})$ echoes in the m-th window, i.e., $$\tilde{I}_{m,m+1} = \sum_{j=N_m+\rho_m}^{N_{m+1}} \tilde{A}_j^{(+)}, \quad (35)$$

where $\rho_m = (1 - \delta_{m,1})$ for $m = 1, 2, \ldots N_w$ and $\delta_{m,1}$ is the familiar Kronecker delta function (e.g., equals 1 for $m=1$ and 0 otherwise). Here $(N_{m+\rho_m})$ and $N_{m+1}$ are the echo numbers (i.e., endpoints) of the m-th window. More explicitly, for the first window $$\tilde{I}_{1,2} = \sum_{j=N_1}^{N_2} \tilde{A}_j^{(+)},$$

where $N_1$ and $N_2$ are the echo numbers of the endpoints of the first window. For the second window, $$\tilde{I}_{2,3} = \sum_{j=N_2+1}^{N_3} \tilde{A}_j^{(+)},$$

and, in general, for the n-th window where $n>1$, $$\tilde{I}_{n,n+1} = \sum_{j=N_n+1}^{N_{n+1}} \tilde{A}_j^{(+)}.$$

Recalling eq. (32), one can write (35) in the form, $$\tilde{I}_{m,m+1} = \sum_{l=1}^{N_s} \alpha_l f_l F_{m,m+1}(T_{2,l}, N_m, N_{m+1}, \Delta) + \tilde{N}_{m,m+1}, \quad (36)$$

where I have defined window spectral sensitivity functions $F_{m,m+1}$ given by geometric series, i.e., $$F_{m,m+1}(T_{2,l}, N_m, N_{m+1}, \Delta) = \sum_{j=N_m+\rho_m}^{N_{m+1}} \exp\left[ -\frac{j\Delta}{T_{2,l}} \right] \quad (37)$$

and also defined the sums over noise, $$\tilde{N}_{m,m+1} = \sum_{j=N_m+\rho_m}^{N_{m+1}} N_j^{(+)}. \quad (38)$$

In each window the set of sensitivity functions defined above for $l=1, \ldots N_a$ provide the relative sensitivity of each window to the different components in the spectrum.

Performing the summation in eq. (37), one finds that the sensitivity functions can be expressed in a form convenient for computation, i.e., $$F_{m,m+1}(x_l, N_m, N_{m+1}) = \quad (39)$$

$$\frac{\exp(-x_l)}{(1 - \exp(-x_l))} \left[ \exp[-(N_m - \delta_{m,1}) x_l] - \exp[-N_{m+1} x_l] \right],$$

where $x_l = \Delta/T_{2,l}$. In practice, it has been found that for

PNMT log data that usually 3 windows are sufficient (i.e., the log outputs are not altered by adding more windows). Likewise for continuous logging it has been found that $N_s=8$ is sufficient. This is discussed further in a section that examines the statistical uncertainties in the log outputs.

Statistical Properties of Window Sums

The statistical properties of the reduced set of random variables $\tilde{I}_{m,m+1}$ are determined from the known statistical properties of the noise. One finds from eq. (36) that their expectation values are given by, $$<\tilde{I}_{m,m+1}> = \sum_{l=1}^{N_s} \alpha_l f_l F_{m,m+1}(T_{2,l}, N_m, N_{m+1}, \Delta) \equiv I_{m,m+1}\{\alpha_l\}, \quad (40)$$

where the curly brackets on the right are used to indicate that the expectation value is a functional (i.e., a scalar whose value depends on a function) of the spectral amplitudes. The above expression has a simple physical interpretation, i.e., the expected value of the sum of the signal over the m-th window is the weighted sum of the sensitivity functions of the various spectral components each weighted by its amplitude. The variances in the window sums are easily calculated. One finds that, $$\sigma^2(\tilde{I}_{m,m+1}) = \psi(N_{m+1} - N_m + \delta_{m,1}) \equiv I_{m,m+1}\{\alpha_l\}, \quad (40)$$

Here $\psi$ is the variance of the noise in a single echo which is the same for all echoes. The variance of the window sum in the above equation is simply the number of echoes in the window times the variance in a single echo. Note that this result is evident from elementary statistics since the variance in a sum of uncorrelated random variables is simply the sum of the variances. For non-overlapping windows the window sums over different windows are uncorrelated, i.e., $$<\delta\tilde{I}_{m,m+1}\delta\tilde{I}_{m,m+1}> = \delta_{m,m}\psi\hat{\sigma}_{m,m+1}^2, \quad (41a)$$

where from eq. (36), $\delta\tilde{I}_{m,m+1} = \tilde{N}_{m,m+1}$.

Spectral Estimation

The window sums defined in eq. (35) are independent Gaussian random variables with expectation values and variances given by eqs. (40) and (41), respectively. The logarithm of the likelihood function for the $N_w$ window sums is given by, $$-\ln L = \sum_{m=1}^{N_w} \frac{(\tilde{I}_{m,m+1} - I_{m,m+1}\{\alpha_l\})^2}{2\psi[N_{m+1} - N_m + \delta_{m,1}]} + \frac{\gamma}{2\psi} \sum_{l=1}^{N_s} \alpha_l^2, \quad (42)$$

where the expected values $<\tilde{I}_{m,m+1}> \equiv I_{m,m+1}\{\alpha_l\}$ were defined earlier and are functions of the spectral parameters which we want to estimate. The last term is a phenomenological regularization term introduced to prevent noise amplification artifacts. It is a penalty constraint that prevents the $L_2$ norm of the amplitudes from becoming too large. The $L_2$ regularization is commonly employed but other criteria can be imposed. The spectral amplitudes are relatively insensitive to the dimensionless parameter $\gamma$. A value $\gamma \approx 5$ is usually used for PNMT log data. How to best choose $\gamma$ is not a trivial question. The best fit to the data occurs if $\gamma=0$, however, the solution is not stable. It would be the best solution in the absence of noise. In the presence of noise, the squared residuals of the fit of the data in each window should be equal to the variance in the window sums in eq. (41). This represents the best fit based on the statistics of the model. Increasing $\gamma$ reduces the variance in the estimates but can lead to solutions that do not fit the data if $\gamma$ is too large. An algorithm for a priori estimation of an "optimal" $\gamma$ determined at each depth from the data is developed in Appendix A. The spectral amplitudes $\{\alpha_l\}$ are determined by minimization of eq. (42) subject to a positivity constraint. The estimation is extremely fast on a computer as only a few (e.g., 3) windows are needed. The computation time is essentially independent of the number of echoes.

The above algorithm leads to a tremendous data reduction since the spectrum is obtained from only a few random variables instead of hundreds or thousands of echoes. This huge data reduction has obvious potential benefits for efficient data acquisition and storage. A set (e.g., 10–100) of window sums can be rapidly computed downhole and transmitted uphole for processing. This set can be combined into gates for uphole processing. This leads to a substantial reduction in PNMT telemetry requirements which is important for commercial tools run in combination. Downhole preprocessing can be used to assess data quality and flags established for sending all of the echoes uphole if necessary.

Total, Free and Bound Fluid Porosities

The spectral analysis described above leads immediately to logs of total, bound and free fluid porosities and mean transverse spin relaxation time. The total NMR porosity $\phi_{nmr}$ can be computed by integration of the distribution function $P(T_2)$ defined in eq. (4), i.e., $$\phi_{nmr} = K_{tool} \int_{T_{min}}^{T_{max}} dT_2 P(T_2) \equiv K_{tool} \sum_{l=1}^{N_s} \alpha_l, \quad (43)$$

where $K_{tool}$ is a tool constant for converting volts to porosity. Similarly, the free-fluid porosity is given by, $$\phi_f = K_{tool} \sum_{l=N_c}^{N_s} \alpha_l + \Delta\phi, \quad (44)$$

where for the free fluid porosity (denoted by UBF on PNMT logs), the summation is over a subset of components, $l=N_c$, $N_c+1, \ldots, N_s$ for which $T_{2,l} \geq T_c$. Centrifuge experiments by Straley, et al[8] have found that in many sandstones $T_c \approx 33$ milliseconds. The bound-fluid porosity is simply given by $\phi_{bf} = \phi_t - \phi_f$. The term $\Delta\phi$ is a small correction which accounts for the fact that the cut-off $T_c$ does not lie on the endpoint of the free fluid integration interval. An analytic expression is derived in Appendix C for the $\Delta\phi$ correction. Note that this correction does not affect $\phi_t$, i.e., only the partitioning of the free and bound fluid porosities.

Distributions And Mean Relaxation Times

The porosity distribution function $P(T_2)$ is with respect to $T_2$. For displaying maps of porosity distributions versus relaxation time, it is useful to define a logarithmic distribution $P_a(\log T_2)$ since the relaxation times span several decades. In terms of the logarithmic distribution function, $$\phi_{nmr} = K_{tool} \int_{\log T_{min}}^{\log T_{max}} d(\log T_2) P_a(\log T_2), \quad (45)$$

where $K_{tool} P_a(\log T_2) d(\log T_2)$ is the porosity in the interval flog $[\log T_2, \log T_2 + d(\log T_2)]$. The distributions with respect to $T_2$ and $\log T_2$ are related, i.e., $$P(T_2) = \frac{c P_a(\log T_2)}{T_2}, \quad (46)$$

with $c = (\ln 10)^{-1}$ as can be shown using eqs. (43) and (45). Using the discretization of $P(T_2)$ introduced earlier, the discretized distribution with respect to the $T_{2,l}$, defined in eq. (33) is given by, $$P(T_{2,l}) = \frac{\alpha_l}{\delta_l}, \qquad (47)$$

with $\delta_l = (T_{2,l+1} - T_{2,l-1})/2$. Using eq. (33), it follows from simple algebra that, $$\delta_l = \frac{T_{2,l}(r^2 - 1)}{2r}, \qquad (48)$$

where I have defined, $$r = \left(\frac{T_{max}}{T_{min}}\right)^{\frac{1}{N_s - 1}}. \qquad (49)$$

Combining eqs. (46)–(48), one finds that, $$P_\alpha(\log T_{2,l}) = \frac{2\alpha_l r}{c(r^2 - 1)}. \qquad (50)$$

Note that to within a constant factor, independent of l, the logarithmic distribution is proportional to the amplitude distribution $\{\alpha_l\}$.

The main results concerning distributions are eqs. (47) and (50). In summary, to display the distribution $P(T_2)$, use eq. (47) to compute $P(T_{2,l})$ and plot it versus $T_{2,l}$, on a linear scale. To display, the logarithmic distribution use eq. (50) to compute $P_\alpha(\log T_{2,l})$ and plot it versus $T_{2,l}$ on a logarithmic scale. More simply, plot the $\{\alpha_l\}$ distribution on a logarithmic $T_{2,l}$ scale to obtain the logarithmic distribution to within a constant scale factor.

A mean relaxation time $\overline{T}_2$ can be defined for the distribution $P(T_2)$. That is, $$\overline{T}_2 = \frac{\int_{T_{min}}^{T_{max}} dT_2 P(T_2) T_2}{\int_{T_{min}}^{T_{max}} dT_2 P(T_2)}, \qquad (51)$$

or in discretized form, $$\overline{T}_2 = \frac{\sum_{l=1}^{N_s} \alpha_l T_{2,l}}{\sum_{l=1}^{N_s} \alpha_l}. \qquad (52)$$

Analagously, a logarithmic mean relaxation time $\overline{T}_{2,log}$, can be defined. First, one defines a mean logarithm $\overline{m}$ for the $P_\alpha(\log T_2)$ distribution, i.e., $$\overline{m} = \frac{\int_{T_{min}}^{T_{max}} d(\log T_2) P_\alpha(\log T_2) \log T_2}{\int_{T_{min}}^{T_{max}} d(\log T_2) P_\alpha(\log T_2)}, \qquad (53)$$

or in discretized form, $$\overline{m} = \frac{\sum_{l=1}^{N_s} \delta P_\alpha(\log T_{2,l}) \log T_{2,l}}{\sum_{l=1}^{N_s} \delta P_\alpha(\log T_{2,l})} = \frac{\sum_{l=1}^{N_s} \alpha_l \log T_{2,l}}{\sum_{l=1}^{N_s} \alpha_l}. \qquad (54)$$

Note that on a logarithmic scale the spacings, $\delta = \log T_{2,l+1} - \log T_{2,l+1}, \equiv (N_a - 1)^{-1} \log[T_{max}/T_{min}]$, are equal and therefore independent of l. The last equality in the above equation follows from the result in eq. (50). The logarithmic mean relaxation time $\overline{T}_{2,log}$, is obtained by exponentiation, $$\overline{T}_{2,log} = 10^{\overline{m}}.$$

The logarithmic mean relaxation times $\overline{T}_{2,log}$ and porosities $\phi_{nmr}$ are used as inputs into empirically derived equations to provide estimates of permeabilities.

Variances In The Porosity Estimators

The variances in the porosity estimators $\hat{\phi}_{nmr}$, $\hat{\phi}_f$ and $\hat{\phi}_{bf}$ are computed from the covariance matrix $C_{l,k}$. The porosity estimators are obtained from estimates of the spectral amplitudes, i.e., $$\hat{\phi}_{nmr} = K_{tool} \sum_{l=1}^{N_s} \hat{\alpha}_l, \qquad (56)$$

where the hat is used to differentiate the estimators from the true quantities (e.g., in eqs. (43)–(44) true porosities and spectral amplitudes are indicated). The variance $\sigma^2(\hat{\phi}_{nmr})$ is by definition, $$\sigma^2(\hat{\phi}_{nmr}) \equiv \langle \hat{\phi}_{nmr}^2 \rangle - (\langle \hat{\phi}_{nmr} \rangle)^2, \qquad (57)$$

or explicitly by, $$\sigma^2(\hat{\phi}_{nmr}) = K_{tool}^2 \sum_{l=1}^{N_s} \sum_{k=1}^{N_s} C_{l,k}, \qquad (58)$$

where the parameter-parameter covariance matrix, $$C_{l,k} = \langle \delta \hat{\alpha}_l \delta \hat{\alpha}_k \rangle, \qquad (59)$$

has been introduced. The angular brackets denote statistical averages and the fluctuations $\delta \hat{a}_k$ are defined by, $$\delta \hat{a}_k = \hat{a}_k - \langle \hat{a}_k \rangle. \qquad (60)$$

Note the covariance matrix is symmetric and its diagonal elements are the variances in the amplitudes, i.e., $\sigma^2(\hat{a}_l)$. In general, the fluctuations in the amplitude estimates are correlated and therefore the off-diagonal elements of $C_{l,k}$ are non-zero. The derivation of the variances in the free and bound fluid porosities is analogous to the derivation of eq. (58). One finds, for example, that $$\sigma^2(\hat{\phi}_f) = K_{tool}^2 \sum_{l=N_c}^{N_s} \sum_{k=N_c}^{N_s} C_{l,k}. \qquad (61)$$

where $N_c$ is defined in eq. (44). In order to apply eqs. (58) and (61), one needs to compute the covariance matrix. An approximation for the covariance matrix will be derived in a subsequent section. First, however, an approximate calculation of the variance in the logarithmic, mean relaxation time is presented.

Variance In The Logarithmic Mean Relaxation Times

In this section an approximate formula for the variance in $\overline{T}_{2,log}$, is derived. Recalling eqs. (54) and (55) one finds that, $$\overline{T}_{2,log}\{\hat{\alpha}_l\} = \exp\left[\frac{c \sum_l \hat{\alpha}_l \ln T_{2,l}}{\sum_l \hat{\alpha}_l}\right], \qquad (62)$$

where the curly bracket on the left indicates that $\overline{T}_{2,log}$ is a functional of the amplitude estimates $\hat{\alpha}_l$. It is to be understood that the summations on the right are over the whole spectrum, i.e., $l = 1, 2, \ldots, N_s$. The constant $c = (\ln 10)^{-1}$. Expand $\overline{T}_{2,log}$ in a Taylor's series about the expectation values of the amplitude estimates, i.e., $$\overline{T}_{2,log}\{\hat{\alpha}_l\} = \overline{T}_{2,log}(\langle \hat{\alpha}_l \rangle) + \sum_{k=1}^{N_s} \left(\frac{\partial \overline{T}_{2,log}}{\partial \hat{\alpha}_k}\right) \delta \hat{\alpha}_k + \ldots. \qquad (63)$$

Note that in eq. (63), it has been assumed that the fluctuations are sufficiently small that terms of order $(\delta \hat{\alpha}_k)^2$ can be neglected. The derivatives on the right are, of course, evaluated at $\langle \hat{\alpha}_k \rangle$. To proceed, another small fluctuation approximation, i.e., $\langle \bar{T}_{2,log} \rangle \approx \bar{T}_{2,log}(\langle \hat{\alpha}_l \rangle)$ is employed to obtain $$\sigma^2(\bar{T}_{2,log}) \equiv \langle (\delta \bar{T}_{2,log})^2 \rangle = \sum_{k=1}^{N_s} \sum_{l=1}^{N_s} \left( \frac{\partial \bar{T}_{2,log}}{\partial \hat{\alpha}_k} \right) \left( \frac{\partial \bar{T}_{2,log}}{\partial \hat{\alpha}_l} \right) C_{l,k}, \quad (64)$$

where, $\delta \bar{T}_{2,log}\} \langle \bar{T}_{2,log} \rangle$, and eqs. (59) and (63) have been used. The partial derivatives can be evaluated explicitly using eq. (62). One finds after some simple algebra that the standard deviation, $$\sigma(\bar{T}_{2,log}) = \bar{T}_{2,log} \left[ \sum_{l=1}^{N_s} \sum_{k=1}^{N_s} P_l P_k C_{l,k} \right]^{1/2}, \quad (65)$$

where I have defined the quantities, $$P_l = \frac{\delta}{(\Sigma_l \langle \hat{\alpha}_l \rangle)^2} \sum_{k=1}^{N_s} \langle \hat{\alpha}_k \rangle (l-k), \quad (66)$$

where eq. (33) was used in obtaining the above result. Here $\delta$ is the $T_{2,l}$, spacing on a logarithmic scale (e.g., see the remarks following eq. (54)). In actual computations, the expectation values in the above equations are replaced by the maximum likelihood estimates obtained by the minimization of eq. (42). The calculation of the variance in $\bar{T}_2$ can be derived by similar manipulations but is not given here. The notion of a relaxation time becomes meaningless whenever the signal is dominated by the noise. This occurs in low porosity (e.g., for $\phi_{nmr} \approx 1$ p.u.) formations and leads to random fluctuations in $\bar{T}_{2,log}$ usually occurring at long times since noise amplitude fluctuations are non-decaying. In these instances eq. (65) provides a useful criterion for "turning off" the $T_{2,log}$, log curve. A criterion which has proven useful is to disallow the log curve if the factor multiplying $T_{2,log}$, on the right side of eq. (65) exceeds unity.

Calculation of the Parameter-Parameter Covariance Matrix

An exact covariance matrix can be calculated for the algorithm. Using eqs. (A.1)–(A.3) and eq. (42), it is easy to prove that the parameter estimates are related to the "data" via the set of linear equations, $$\hat{\alpha}_l = R_{l,m} \bar{I}_{m,m+1}, \quad (67)$$

for $l=1, 2, \ldots, N_s$ and where the Einstein summation convention of summing over repeated indices is used in this section. In the above equation, I have defined the $N_s \times N_w$ matrix R, $$R_{l,m} = M_{l,k}^{-1} Q_{k,m}, \quad (68)$$

where the $N_s \times N_s$ matrix M is defined by, $$M_{l,k} = \sum_{m=1}^{N_w} \frac{f_k F_{m,m+1}(T_{2,k}) f_l F_{m,m+1}(T_{2,l})}{\hat{\sigma}_{m,m+1}^2} + \gamma \delta_{k,l}. \quad (69)$$

and where the $N_s \times N_w$ matrix Q is defined by, $$Q_{k,m} = \frac{f_k F_{m,m+1}(T_{2,k})}{\hat{\sigma}_{m,m+1}^2}, \quad (70)$$

where $\hat{\sigma}_{m,m+1}^2$ is defined in eq. (41). Using the definition of the parameter-parameter covariance matrix in eq. (59) and eqs. (41) and (41a) one finds that, $$C_{l,k} = R_{l,m} \psi \hat{\sigma}_{m,m+1}^2 R_{m,k}^t. \quad (71)$$

The parameter-parameter covariance matrix in eq. (71) can be used with eqs. (58), (61) and with an analogous equation for $\sigma^2(\hat{\phi}_{ff})$ to study the standard deviations in $\hat{\phi}_t$, $\hat{\phi}_f$ and $\hat{\phi}_{bf}$ for various pulse and processing parameters. Some of these results are shown in FIGS. 17–20. The PNMT logs from repeat runs generally agree very well with the standard deviations computed from the covariance matrix. It should be noted, however, that log repeatability can be affected by many factors other than statistical fluctuations (e.g., hole conditions). Therefore the uncertainties computed using eq. (71) and displayed on the logs may in some cases be optimistic compared to the log uncertainties estimated from statistical analysis of repeat runs. A proof that the matrix M is positive definite and therefore has an inverse is given in Appendix B.

Processing Example From a PNMT Field Test

The algorithm described above has been used to process log data from five Schlumberger client wells logged to date. A flowchart illustrating the various steps in the implementation of the algorithm is shown in FIG. 13.

A detailed discussion of the field examples is beyond the scope of this report. Here, it will suffice to show a short section of processed continuous PNMT log data and the analysis of station data acquired at several depths within the interval. The log data shown was acquired with the PNMT tool moving at 150 ft/hour. FIG. 16 shows a section of log from a well in Texas. The section shown contains a non-hydrocarbon bearing thinly bedded sand/shale sequence. In Track 1, a color map of signal versus relaxation time ($T_2$) plotted on a logarithmic scale is shown. The magnitude of the signal is proportional to the intensity of the color and in this example, the $T_2$ range is from 1 ms to 1500 ms. The red curve in Track 1 is the logarithmic mean ($T_{2,log}$) of the distribution. In Track 2, the rms noise estimate ($\sqrt{\psi}$) in volts, the estimated standard deviations in the total and free-fluid porosities, and the signal phase estimate ($\hat{\theta}$) in degrees are displayed. Note that $\hat{\theta}$ is essentially constant, as expected, except at depths with low porosities (i.e., low signals) where the phase estimator is dominated by random noise. In Track 3, the total and free-fluid porosity estimates are displayed.

Several station stop measurements were made in the logged interval. At station stops, the tool acquires data for several minutes. The data is averaged to reduce the noise so that the quality of the station data is significantly better than the continuous data. The signal processing of the station data is the same as for the continuous data.

Figure 21:
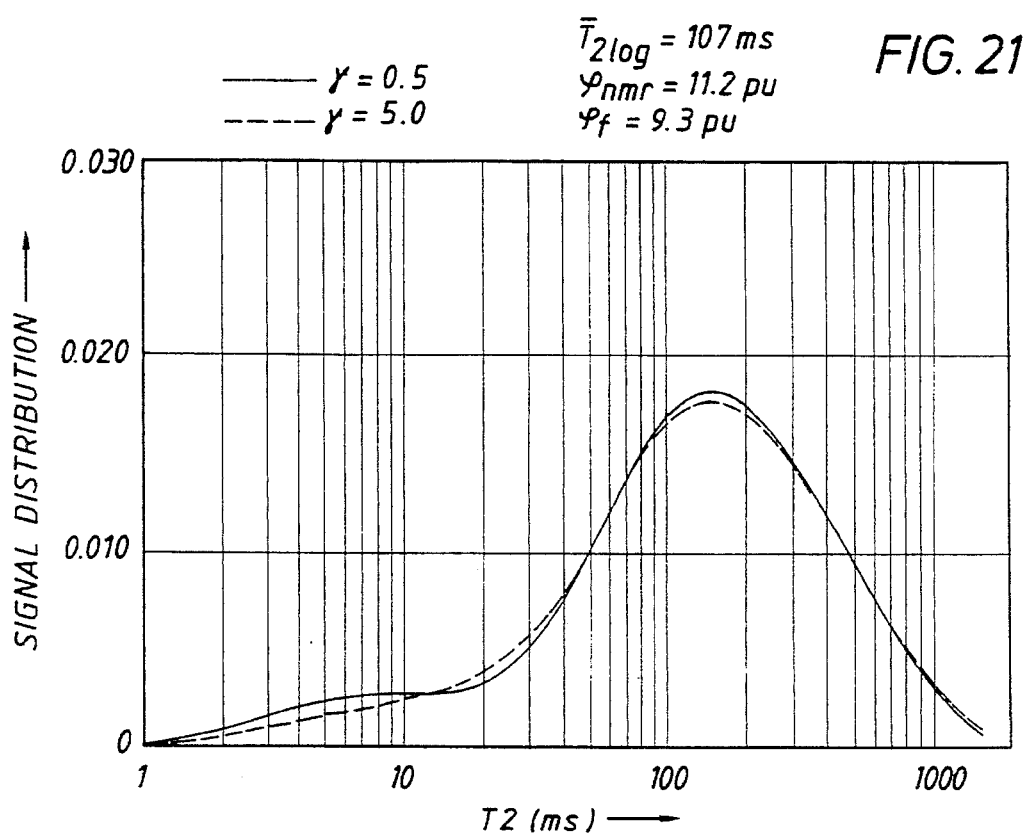
FIG. 21 illustrates a signal distribution computed from station data at 1100 ft for two values of $\gamma$ differing by an order of magnitude.

In FIG. 21, the signal distribution (analogous to the color map shown in FIG. 16) versus $T_2$ is shown for a station stop at 1100 ft. Recall that the area under the signal distribution curve is proportional to porosity. Comparing FIG. 21 with the continuous log observe that the total NMR porosity ($\phi_{nmr}$), free-fluid porosity ($\phi_f$), and logarithmic mean relaxation time ($T_{2,log}$) computed from the station stop data agree well with the continuous log values. The values shown were computed with a regularization parameter, $\gamma=5.0$, as was the continuous log. It should be noted, that it has been found that estimates of $\phi_{nmr}$, $\Phi_f$ and $T_{2,log}$, depend only weakly on the regularization parameter. For example, changing $\gamma$ by an order of magnitude usually results in porosity variations of less than ±0.5 pu. The detailed shape of the signal distribution, however, can be changed significantly in some cases by varying the regularization parameter. This is a consequence of the fact that there are infinitely many solutions which will fit the data. Decreasing $\gamma$ reduces the fit error but can increase the norm of the solution vector.

In FIG. 21, the two signal distributions plotted correspond to two very different values of the regularization parameter. Note that there is practically no difference in the two distributions. Both distributions fit the data to within the noise and have comparable norms. Therefore both solutions are mathematically acceptable.

Figure 22:
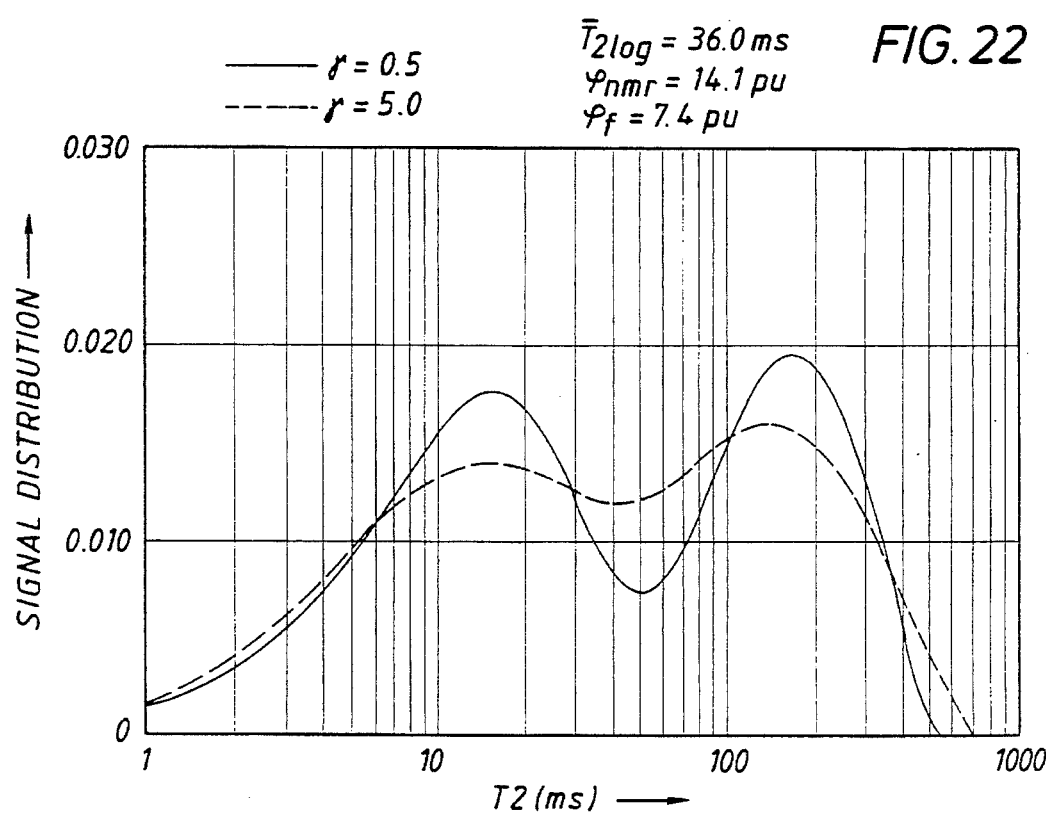
FIG. 22 illustrates a signal distribution at 1125 ft exhibiting a two peak structure reflecting two disparate pore size distributions.

In FIG. 22, results from a station stop at 1125 ft are displayed. The two signal distributions corresponding to values of γ differing by an order of magnitude are qualitatively similar. The distribution computed with γ=0.5 amplifies the two peak structure already apparent in the distribtution computed using γ=5.0. In this example, the two peaks are probably due to signal contributions from two disparate pore distributions in the thinly bedded heterogeneous reservoir at 1125 ft as indicated on the FMS image (not shown here). In oil reservoirs, where the formation is relatively homogeneous over the length of the PNMT tool aperture, separate oil and water signal peaks can be identified in the signal distribution.

Figure 23:
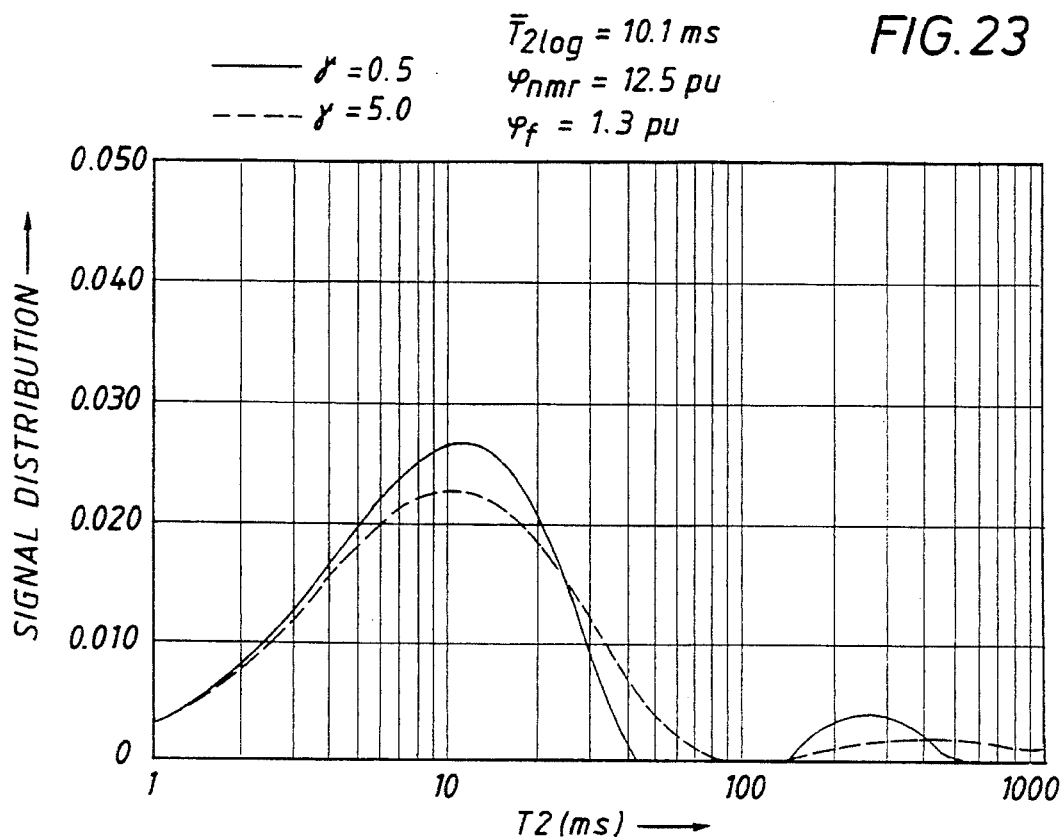
FIG. 23 illustrates a signal distribution at 1148 ft indicating a relatively poor reservoir quality rock.

In FIG. 23, results from a station stop at 1148 ft are shown. Note that, the continuous log outputs agree well with those obtained by processing the station data. Note that, the reservoir quality at this depth is poor compared to that at the previous two stations as evidenced by almost all of the signal being associated with bound fluid porosity.

Figure 24:
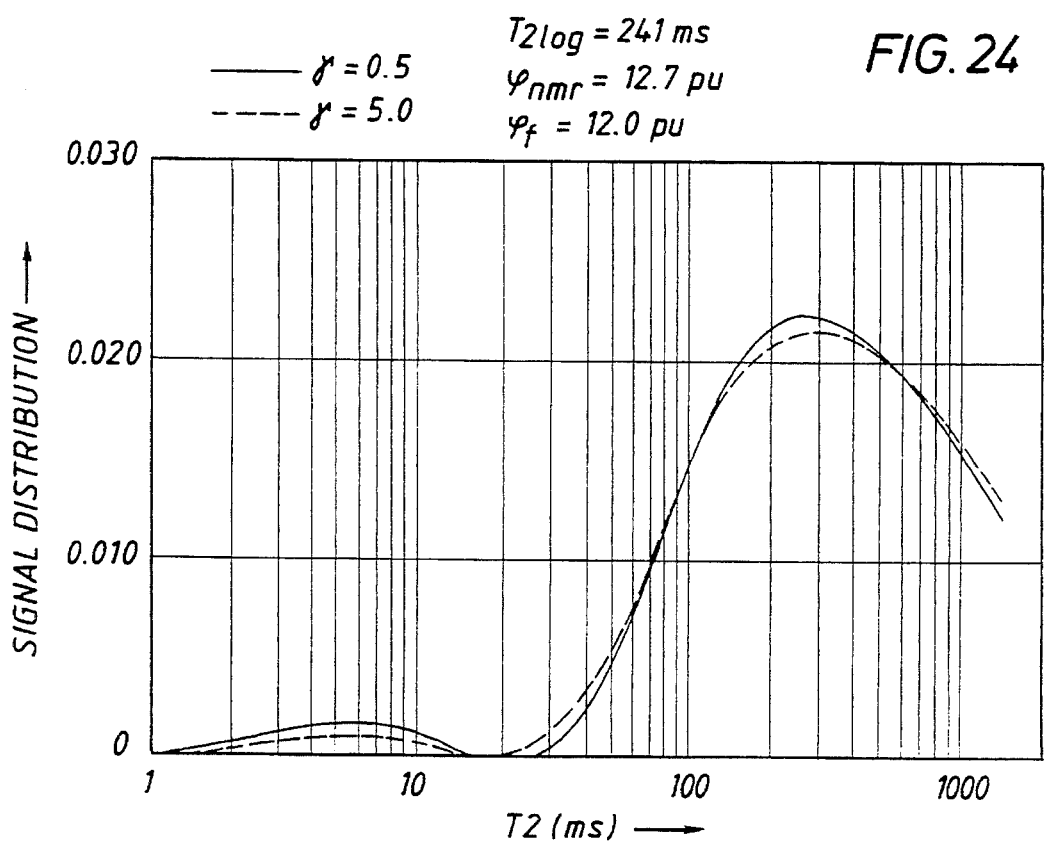
FIG. 24 illustrates a signal distribution at 1200 ft indicating a relatively good quality permeable reservoir rock.
Figure 25:
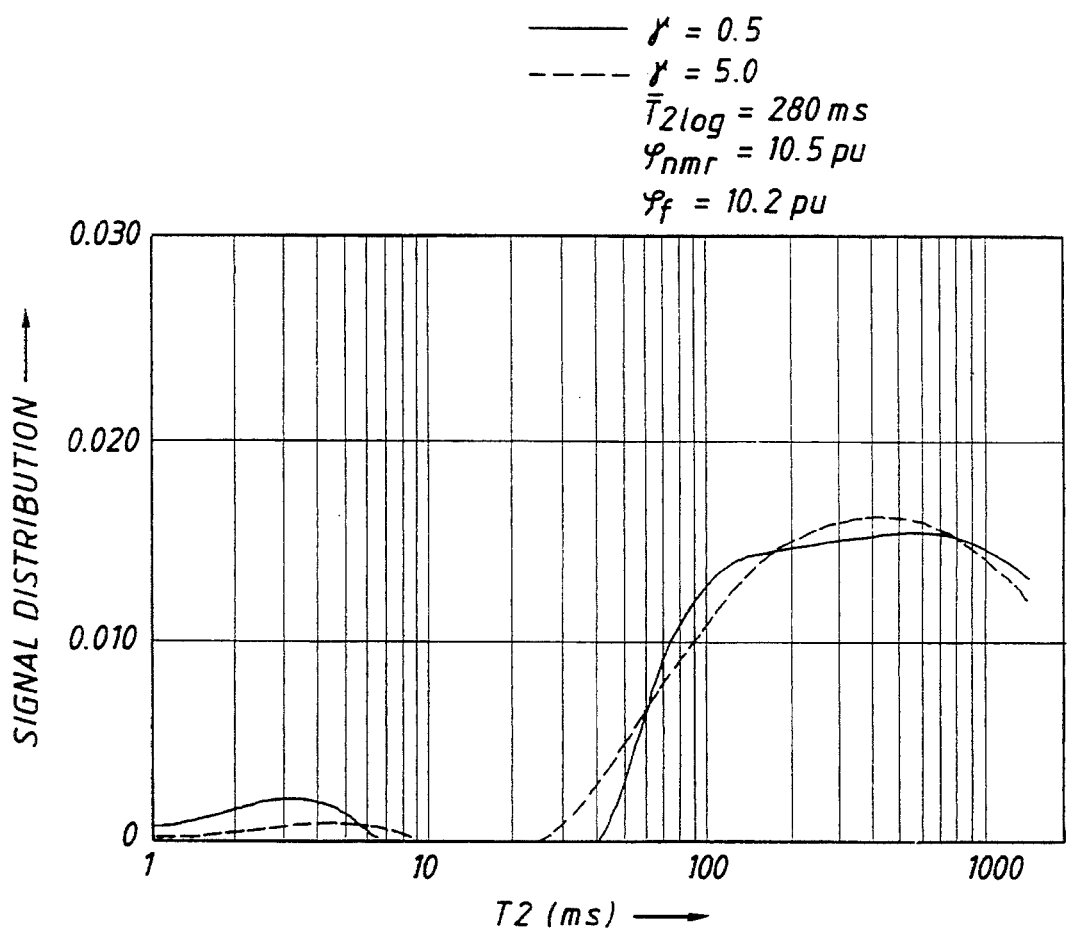
FIG. 25 illustrates a signal distribution at 1229 ft indicating essentially no bound fluid, and a long relaxation time.

In FIGS. 24 and 25 the station stops at 1200 ft and 1229 ft are shown. These distributions, reveal relatively high permeability reservoir rock at these depths. The long relaxation times are indicative of large pore and, pore surfaces free of iron or other magnetic material.

Note Added: After this report was completed FIG. 12 shown on page 20 was added. This figure shows the relative sensitivities (e.g., the sensitivity functions in eq. (39)) of different windows to different spectral components.

REFERENCES

The following references are incorporated into this specification by reference:
1. Sezginer, A., Kleinberg, R. L., Fukuhara, A., and Latour, L. L., "Very Rapid Measurement of Nuclear Magnetic Resonance Spin-Lattice Relaxation Time and Spin-Spin Relaxation Time," J. of Magnetic Resonance, v. 92, 504–527 (1992).
2. Kleinberg, R. L., Sezginer, A., Griffin, D. D., and Fukuhara, M., "Novel NMR Apparatus for Investigating an External Sample," J. of Magnetic Resonance, v. 97, 466–485 (1992).
3. Gallegos, D. P. and Smith, D. M., "A NMR Technique for the Analysis of Pore Structure: Determination of Continuous Pore Size Distributions," J. of Colloid and Interface Science, v. 122, No. 1, pp. 143–153, March, 1988.
4. Brown, R. J. S., Borgia, G. C., Fantazzini, P., and Mesini, E., "Problems In Identifying Multimodal Distributions Of Relaxation Times For NMR In Porous Media," Magnetic Resonance Imaging, Vol. 9, pp. 687–693 (1991).
5. Kenyon, W. E., Howard, J. J., Sezginer, A., Straley, C., Matteson, A., Horkowitz, R, and Erlich, R., "Pore-size Distribution and NMR in Microporous Cherty Sandstones" Trans. of the SPWLA of the 30th Ann. Logging Symp., Paper LL, June 11–14, 1989.
6. Latour, L. L., Kleinberg, R. L. and A. Sezginer, "Nuclear Magnetic Resonance Properties of Rocks at Elevated Temperatures," J. of Colloid and Interface Science, v. 150, 535 (1992).
7. Twomey, S., *Introduction To The Mathematics of Inversion In Remote Sensing And Indirect Measurements*," published by Elsevier Scientific
8. Straley, C., Morriss, C. E., Kenyon, W. E., and Howard, J. J., "NMR in Partially Saturated Rocks: Laboratory Insights on Free Fluid Index and Comparison with Borehole Logs," Trans. of the SPWLA 32nd Ann. Logging Symp., Paper CC, June 16–19, 1991.
9. Butler, J. P., Reeds, J. A. and Dawson, S. V., "Estimating Solutions of First Kind Integral Equations with Non-Negative Constraints and Optimal Smoothing," SIAM J. Numerical Anal., v. 18, no. 3, 381–397, 1981.

Appendix A: An Algorithm for Optimal Selection of γ

In this Appendix an algorithm for selection of an "optimal" regularization parameter $\gamma_{opt}$ is derived. A similar algorithm was derived by Butler, Reeds and Dawson[9] and has been used by Gallegos and Smith[3] to select the regularization parameter. The selection criterion for choosing $\gamma_{opt}$ is based on the notion that an optimal value of smoothing is obtained by minimizing the squared norm of the difference vector $\vec{\delta\alpha} = \vec{\alpha}_\gamma - \vec{\alpha}_{true}$, where $\vec{\alpha}_\gamma$ is the regularized solution and $\vec{\alpha}_{true}$ is the true distribution. Since $\vec{\alpha}_{true}$ is, of course unknown, a compromise is made by replacing $\vec{\alpha}_{true}$ by a hypothetical noise free solution $\vec{\alpha}^0$ for which γ=0. Although, the aforementioned criterion can be rigorously stated, assumptions must be made that introduce elements of empiricism into the algorithm. These elements are also present in other algorithms[9] and therefore the claims of optimality are somewhat subjective.

Maximum likelihood estimates of the $N_s$ spectral amplitudes $\alpha_l$ are obtained by minimization of, −ln L, in eq. (42). The equations to be solved are $$\frac{\partial \ln L}{\partial \alpha_l} = 0, \tag{A.1}$$

for l=1, 2, ..., $N_s$. Substituting eq. (42) into (A.1) leads to the linear system of equations, $$\sum_{k=1}^{N_s} M_{l,k} \alpha_k = d_l, \tag{A.2}$$

where the symmetric matrix $M_{l,k}$ is defined in eq. (69) and the data vector $$d_l = \sum_{m=1}^{N_w} \frac{\tilde{I}_{m,m+1} f_l F_{m,m+1}(T_{2,l})}{\hat{\sigma}^2_{m,m+1}}, \tag{A.3}$$

has been defined. The quantities $f_l, \tilde{I}_{m,m+1}(T_{2,l})$ are defined in eqs. (34), (35) and (39), respectively, and $$\hat{\sigma}_{m,m+1}^2 = N_{m+1} - N_m + \delta_{m,1} \tag{A.4}$$

have been defined. The $\hat{\sigma}_{m,m+1}^2$ are simply the number of echoes in the m-th window. It is useful to write eq. (A.2) in an explicit matrix form, $$M \vec{a}_\gamma = \vec{d}, \tag{A.5}$$

and to also write the companion equation, $$M_0 \vec{a}^{(0)} = \vec{d}^{(0)}, \tag{A.6}$$

where $\vec{\alpha}_\gamma$ is a vector whose $N_s$ components are the spectral amplitudes for a regularization parameter γ, $\vec{d}$ is the data vector defined in eq. (A.3). The matrix $M_0$ is defined by the matrix equation, $$M = M_0 + \gamma I \tag{A.7}$$

where $I \in R^{N_s \times N_s}$ is the identity matrix. In (A.6), $\vec{\alpha}^{(0)}$ is the vector of spectral amplitudes corresponding to hypothetical noise free data and $\vec{d}^{(0)}$ is the noise free data vector, i.e., $$\vec{d} = \vec{d}^{(0)} + \vec{n}, \tag{A.8}$$

where the noise vector $\vec{n}$ is defined by, $$n_l = \sum_{m=1}^{N_w} \frac{\tilde{N}_{m,m+1} f_l F_{m,m+1}(T_{2,l})}{\tilde{\sigma}_{m,m+1}^2}, \tag{A.9}$$

where $\tilde{N}_{m,m+1}$ is defined in eq. (38).

It follows from the theory of matrices that the real symmetric matrix M can be diagonalized by an orthogonal transformation, i.e., $$M = U D_\gamma U^t, \tag{A.10}$$

where $U^t$ is the transpose of U where U is an $N_s \times N_s$ matrix whose columns are an orthonormal set of eigenvectors of M, i.e., the vectors $\vec{u}_j$ satisfy the eigenvalue equation, $$M \vec{u}_j = \lambda_j(\gamma) \vec{u}_j, \tag{A.11}$$

and the othonormality conditions, $$\sum_{l=1}^{N_s} u_i^l u_j^l = \delta_{j,i}, \tag{A.12a}$$

or the matrix equivalent, $$U^t U = I. \tag{A.12b}$$

where $\lambda_j(\gamma)$ is the eigenvalue of M associated with eigenvector $\vec{u}_j$. The $N_s \times N_s$ matrix $D_\gamma$ in eq. (A.10) is a diagonal matrix with the eigenvalues $\lambda_j(\gamma)$ on the diagonal. The above equations result from the orthonormality of the columns of the matrx M. Note that the operator M does not have a null space, i.e., it is positive definite for $\gamma>0$.

It can also be proven for orthogonal transformation square matrices like U that the rows are likewise orthonormal which leads to the equations, $$\sum_{l=1}^{N_s} u_j^l u_k^l = \delta_{j,k}, \tag{A.13a}$$

or its matrix equivalent, $$U U^s = 1. \tag{A.13b}$$

The operator $M_0$ has a non-trivial null space because the rank (denoted by r) of $M_0$, i.e., the dimension of its non-null space is less than $N_s$. $M_0$ has reduced rank because the data are not independent. This is typical of most inversion problems and mathematically the problem is underdetermined (more unknowns than measurements). In mathematical terms, $$M_o \vec{u}_j = \gamma_j(0) \vec{u}_j, \tag{A.14a}$$

for $j=1, 2, \ldots, r$ where the eigenvalues can be ordered so that $\lambda_{1l}(0) > \lambda_2(0) > \ldots > \lambda_r(0) > 0$. Also in the null space, $$M_o \vec{u}_j = 0, \tag{A.14b}$$

for $j=r+1, \ldots, N_s$. The operator $M_0$ can be diagonalized in its non-null space by the transformation, $$M_0 = U_r D_0 U_r^t, \tag{A.15}$$

where $U_r$ is an $N_s \times r$ matrix. whose columns are the eigenvectors $\vec{u}_j$ where $j=1, 2, \ldots r$, and $D_0$ is a diagonal matrix with eigenvalues $\lambda_j(0)$ for $j=1,2,\ldots,r$ as diagonal elements.

It follows from (A.7) that the eigenvalues $\lambda_j$ (7) of M are simply related to those of $M_0$, $$\lambda_j(\gamma_j(0) + \gamma. \tag{A.16}$$

To proceed, one uses the transformation (A.10) in eq. (A.5) to write, $$\vec{\alpha}_\gamma = M^{-1} \vec{d} = U D_\gamma^{-1} U^t \vec{d}, \tag{A.17}$$

and similarly using eq. (A.15) and (A.6), $$\vec{\alpha}^{(0)} = M_0^{-1} \vec{d}^{(0)} = U_r D_0^{-1} U_r^t \vec{d}^{(0)} \tag{A.18}$$

At this point, there are several ways to proceed which all lead to the same results. The most direct approach is to use the above equations, and write the solutions in eqs. (A.17) and (A.18) as eigenvector expansions, i.e., from (A.17) one finds $$\vec{\alpha}_\gamma = \sum_{i=1}^{r} \frac{Q_i \vec{u}_i}{\lambda_i(\gamma)}, \tag{A.19}$$

where $$Q_i = \vec{u}_i^t \cdot \vec{d} \tag{A.19a}$$

are the projections of the data onto the eigenvectors. Likewise from (A.18), $$\vec{\alpha}^0 = \sum_{i=1}^{r} \frac{Q_i^0 \vec{u}_i}{\lambda_i(0)}, \tag{A.20}$$

where $$Q_i^0 = \vec{u}_i^t \cdot \vec{d}^0 \equiv Q_i - Q_{0,i}. \tag{A.21}$$

In obtaining the above equation, I have used (A.8) and have defined the projections $Q_{0,i} = \vec{u}_i^t \cdot \vec{n}$ of the noise onto the non-null space of $M_0$. The criterion for selecting $\gamma$ is that the squared norm of the difference vector, $\vec{a}_\gamma - \vec{\alpha}^0$, be a minimum. Therefore, one is led to the minimization of the function $F_\gamma$ where $$F_\gamma = (\vec{a}_\gamma - \vec{\alpha}^0)^s \cdot (\vec{\alpha}_\gamma - \vec{a}^0), \tag{A.22}$$

where $(\cdot)$ denotes the ordinary scalar product.

Combining eqs. (A.19)–(A.22) and using the orthonormality conditions one finds that $$F_\gamma = \gamma^2 \sum_{i=1}^{r} \frac{Q_i^2}{\lambda_i^2(0) \lambda_i^2(\gamma)} + 2 \sum_{i=1}^{r} \frac{Q_i Q_{0,i}}{\lambda_i(0) \lambda_i(\gamma)} + C_1, \tag{A.23}$$

where $C_1$ is a constant independent of $\gamma$, i.e., $$C_1 = \sum_{i=1}^{r} \frac{Q_{0,i}^2 - 2Q_{0,i} Q_i}{\lambda_i^2(0)}. \tag{A.24}$$

To proceed with the minimization of $F_\gamma$, it is necessary to select a direction for the vector $\vec{Q}_0$. The function is maximized (minimized) with respect to the noise by choosing $\vec{Q}_0$ parallel (anti-parallel) to $\vec{Q}$. A conservative approach, also followed by Butler, Reeds and Dawson[9] is to assume that the vectors are parallel. This assumption is not rigorously justifiable but errs on the side of over smoothing (selecting too large a $\gamma$) which is much less dangerous than under smoothing which can result in a wildly oscillatory and meaningless inverse. Thus one is lead to write, $$\vec{Q}_0 = s\vec{Q}, \quad (A.24)$$

where the scalar s is determined below.

Requiring that the derivative of $F_\gamma$ with respect to $\gamma$, vanish, leads to a trancendental equation whose solution determines $\gamma_{opt}$, i.e., $$\gamma = \bar{s}\,\frac{N(\gamma)}{D(\gamma)}, \quad (A.26)$$

where, $$N(\gamma) = \sum_{i=1}^{r} \frac{Q_i^2}{\lambda_i^3(\gamma)}, \quad (A.27)$$

and, $$D(\gamma) = \sum_{i=1}^{r} \frac{Q_i^2}{\lambda_i^3(\gamma)\lambda_i(0)}, \quad (A.28)$$

and, $$\bar{s} = \frac{s}{1-s}. \quad (A.29)$$

According to the criterion used in this Appendix, an optimal value of $\gamma$ can be found by finding the non-negative roots of eq. (A.26). The equation is solved numerically, by using Newton's method. Note that, by inspection of (A.26) that for noise free data (i.e., s=0) that $\gamma$=0 as required. From (A.26) one can prove that the equation always has a unique non-negative solution for s<1 which is bounded in the interval, $$\gamma_l < \gamma_{opt} < \gamma_u, \quad (A.30)$$

where $\gamma_l = \bar{s}\gamma_r(0$ and $\gamma_u = \bar{s}\gamma_1(0)$.

To complete this Appendix, it remains to determine the scalar s in eq. (A.25). To this end, note that $$s = \sqrt{\frac{\vec{Q}_0^t \cdot \vec{Q}_0}{\vec{Q}^t \cdot \vec{Q}}}. \quad (A.31)$$

Using, (A.19a) one finds that, $$\vec{Q}^t \cdot \vec{Q} = \sum_{i,k=1}^{N_s} d_i d_k S_{i,k}, \quad (A.32)$$

where the $d_i$ are the components of the data vector defined in (A.3) and, $$S_{i,k} = \sum_{l=1}^{r} u_l^i u_l^k. \quad (A.33)$$

Similarly, using (A.21) one finds that, $$\langle \vec{Q}_0^t \cdot \vec{Q}_0 \rangle = \sum_{i,k=1}^{N_s} \langle n_i n_k \rangle S_{i,k}, \quad (A.34)$$

where the $n_i$ are the components of the noise vector defined in (A.9) and where it has been assumed that in computing s one can replace the random variable $\vec{Q}_0^t \cdot \vec{Q}_0$ by its expectation value.

Finally, using (A.9) and the statistical properties of the noise one finds that, $$\langle \vec{Q}_0^t \cdot \vec{Q}_0 \rangle = \psi \sum_{m=1}^{N_w} \sum_{i,k=1}^{N_s} \frac{S_{i,k} f_i f_k F_{m,m+1}(T_{2,i}) F_{m,m+1}(T_{2,k})}{\hat{\sigma}_{m,m+1}^2}. \quad (A.35)$$

Appendix B: Proof That M Is Positive Definite

Recall from (A.7) that, $$M_{l,k} = M_{l,k}^{(0)} + \gamma \delta_{l,k}, \quad (B.1)$$

where from (67) and (A.4), $$M_{l,k}^{(0)} = \sum_{m=1}^{N_w} \frac{f_k F_{m,m+1}(T_{2,k}) f_l F_{m,m+1}(T_{2,l})}{\hat{\sigma}_{m,m+1}^2}. \quad (B.2)$$

Note that $M_{l,k}^{(0)}$ can be written in the form, $$M_{l,k}^{(0)} = \sum_{m=1}^{N_w} B_{l,m}^t B_{m,k} = (B^t \cdot B)_{l,k}, \quad (B.3)$$

where I have defined the matrix, $$B_{m,k} = \frac{f_k F_{m,m+1}(T_{2,k})}{\hat{\sigma}_{m,m+1}}. \quad (B.4)$$

For an arbitrary vector $\vec{V} \in R^{N_s \times 1}$, note that $$\vec{V}^t B^t V \vec{V} \equiv \|B\vec{V}\|^2 \geq 0, \quad (B.5)$$

so that $M^{(0)}$ is positive semi-definite. More specifically, since $\vec{V}$ is arbitrary, one can choose it to be any eigenvector of $M^{(0)}$, e.g., $\vec{u}_j$ from which it follows that $\lambda_j(0) \geq 0$. For $\gamma > 0$, it follows from (A.15) that $\lambda_j(\gamma) > 0$ so that M is positive definite.

Appendix C: Calculation of $\Delta\phi$

Recall from eq. (44) that the free-fluid porosity is defined by, $$\phi_f = K_{tool} \sum_{l=N_c}^{N_s} \alpha_l + \Delta\phi, \quad (C.1)$$

where $K_{tool}$ is the tool constant.

This Appendix derives the correction $\Delta\phi$ in the above equation. This correction is needed because the bound-fluid porosity cut-off $T_c$ generally does not lie on the leftmost endpoint of the free-fluid porosity integration interval. The correction is in practice almost negligble. It does not affect $\phi_{nmr}$, only its partitioning into free and bound fluid porosity. It can be determined exactly by specifying the closed interval [$T_{min}$, $T_{max}$] and the number of integration points $N_s$ which determines a set of logarithmically spaced $T_{2,l}$ values for l=1, 2, . . . , $N_s$. The l-th integration element is a rectangular strip of height $P(T_{2,l})$, width $\delta_l$ and area $\alpha_l \equiv P(T_{2,l})\delta_l$ where, $$\delta_l = \frac{T_{2,l+1} - T_{2,l-1}}{2}. \quad (C.2)$$

The integer $N_c$ in (C.1) is defined such that $T_{2,l} \geq T_c$ for l=$N_c$, . . . $N_s$. The endpoints of the rectangular strips are at the midpoints of adjacent values of $T_2$,t. For example, let $\tau_l$ denote the midpoint (also the leftmost integration point for the area element $\alpha_l$). Then by definition, $$\tau_l = \frac{T_{2,l} + T_{2,l-1}}{2}. \quad (C.3)$$

Note that the widths ($\gamma_l$) of the rectangular strips can be written in terms of the $\tau_l$, i.e., $$\delta_l = \tau_{l+1} - \tau_l. \quad (C.4)$$

Figure 26:
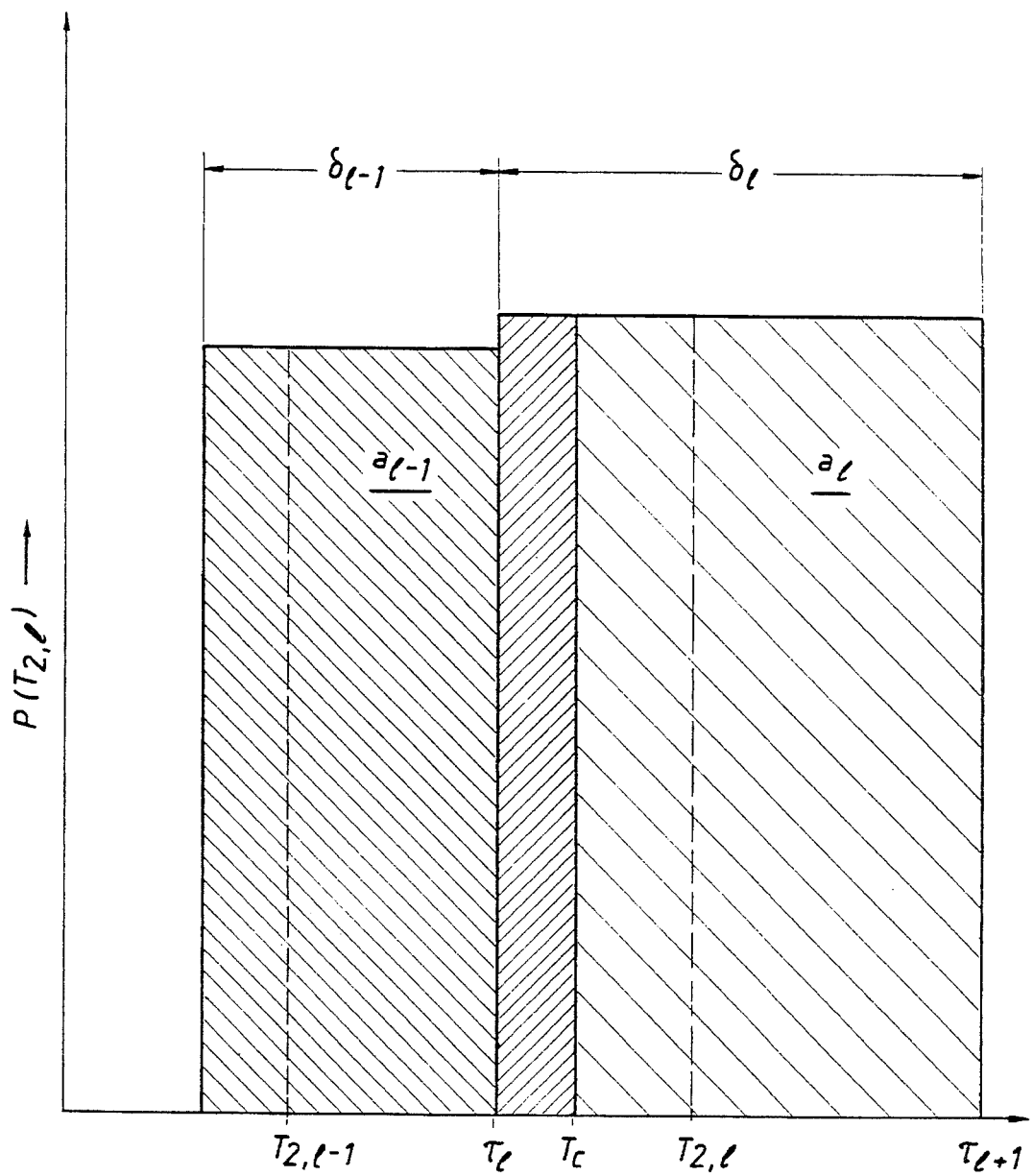
FIG. 26 illustrates a correction, $\Delta\phi$, used in equation C.1 associated with a calculation of the free-fluid porosity, $\phi_f$.

This above described picture is shown schematically in FIG. 26 for the two rectangular integration elements corresponding to $l=N_c-1$ and $l=N_c$.

In general, there are two cases to consider: (a)$\tau \leq T_c$ or (b)$\tau > T_c$. Case (a) is illustrated in FIG. 26. In case (a), the correction $\Delta\phi \leq 0$, so that the correction subtracts porosity from the summation in (C.1) which includes a small amount of bound fluid porosity. The porosity correction is the sand shaded area in FIG. 26 multiplied by the tool constant. This correction increases the bound fluid porosity by an equal amount. A simple calculation shows that for case (a):

$$\Delta\phi = -\frac{2K_{tool}(T_c - \tau) \alpha_{N_c}}{T_{2,N_c+1} - T_{2,N_c}}, \qquad (C.5)$$

and for case (b) one finds that, $$\Delta\phi = \frac{2K_{tool}(\tau - T_c) \alpha_{N_c-1}}{T_{2,N_c} - T_{2,N_c-2}}. \qquad (C.6)$$

B. Apparatus Including Multi-Wait Time Pulsed NMR Logging Method For Determining Accurate $T_2$-Distributions And Accurate $T_1/T_2$ Ratios And Generating a More Accurate Output Record Using The Updated $T_2$-Distributions And $T_1/T_2$ Ratios The specification of part B is divided into two parts:

(1) a Description of the Preferred Embodiment which provides a general, more understandable description of the present invention entitled "Apparatus Including Multi-Wait Time Pulsed NMR Logging Method For Determining Accurate $T_2$-Distributions And Accurate $T_1/T_2$ Ratios And Generating a More Accurate Output Record Using The Updated $T_2$-Distributions And $T_1/T_2$ Ratios."; and (2) a Detailed Description of the Preferred Embodiment which provides a more detailed description of the present invention.

Description of the Preferred Embodiment

The following paragraphs supplement the earlier discussion in the "Background of the Invention" section of this specification and discuss the problem which ultimately resulted in the development of the new method and apparatus of the present invention. The present invention is responsive to a plurality of multi-wait time spin echo pulse sequence data acquired by a pulsed NMR well logging tool for determining an updated (i.e., corrected) $T_1/T_2$ ratio, $\xi$, and a corresponding updated $T_2$-distribution (or a equivalently a set of corrected spectral amplitudes $\{\overset{\frown}{\alpha}_l\}$) and for generating a more accurate output record using the corrected $T_1/T_2$ ratio and updated spectral amplitudes.

In the following paragraphs, refer to FIGS. 2, 4, 5, 9a, 9b, 13, 16, 27, 28–30 and 31.

In FIGS. 2, 4, 5, 9a, and 9b, part A of this specification, which represents the disclosure in U.S. Pat. No. 5,291,137 issued to Freedman, a NMR well logging method is discussed. In this NMR well logging method, a static magnetic field $B_0$ is applied to a formation traversed by a wellbore, as shown in FIG. 2. A period of time or wait time, W, must elapse after application of the static magnetic field $B_0$ to the formation 19 or 22 in an attempt to align the magnetic moments "A" of FIG. 4. A perfect alignment of the magnetic moments "A" is shown in FIG. 5. When the period of time elapses, a plurality of oscillating RF pulses Bx90 and By180 of FIG. 9a, also known as the "Carr-Purcell-Meiboom-Gill (CPMG) sequence," energize the formation 19 or 22 via antennas 18 or 21. As a result, a spin echo pulse sequence, shown in FIG. 9b, is received in the antennas 18 or 22. This NMR well logging method is illustrated in more detail in FIGS. 27–30.

In FIGS. 1 and 27–30, assume that the NMR logging tool 13 of FIG. 1 is slowly moving up the borehole 10. Assume further that the formations 11 and 12 of FIG. 1 are homogeneous and that the static magnetic field $B_0$ is applied to the homogeneous formation via the magnets 17 or 20 of FIG. 1 while the logging tool 13 is moving up the borehole. In FIG. 27, after the $B_0$ field has been applied to the formation, a first wait time or period of time, $W_1=W$, is allowed to elapse before the RF pulses (Bx90 and By180) shown in FIG. 28 energize the formation via antennas 18 or 21 of FIG. 1. When the RF pulses of FIG. 28 energize the formation via antennas 18 or 21, a first spin echo pulse sequence 60 of FIG. 27 is received in the antennas 18 or 21. When the first spin echo pulse sequence 60 is received, while the NMR logging tool is still moving in the borehole, a second period of time, $W_2$, is allowed to elapse, where, $W_2=W_1=W$, before the RF pulses shown in FIG. 29 energize the formation via antennas 18 or 21. When the RF pulses of FIG. 29 energize the formation, a second spin echo pulse sequence 62 of FIG. 27 is received in the antennas 18 or 21. When the second spin echo pulse sequence 62 is received, while the NMR logging tool of FIG. 1 is still moving up the borehole, a third period of time, $W_3$, is allowed to elapse, where, $W_3=W_2=W_1=W$, before the RF pulses shown in FIG. 30 energize the formation via antennas 18 or 21. When the RF pulses of FIG. 30 energize the formation, a third spin echo pulse sequence 64 of FIG. 27 is received in the antennas 18 or 21. The set of CPMG pulses shown in FIGS. 28–30 provide an example of a single wait time CPMG pulse sequence as disclosed in the teachings of the Freedman patent since the wait times that precede each CPMG are all equal, i.e., $W_3=W_2=W_1=W$.

In FIGS. 4 and 5, the wait time (W) in FIGS. 28–30 should be long enough in order to allow the magnetic moments "A" shown in FIG. 4 enough time to align together in the idealized manner shown in FIG. 5. However, in practice, the wait time of FIGS. 28–30 is frequently not long enough to allow the magnetic moments of FIG. 4 to align to the extent that the nuclear magnetization can reach its thermal equilibrium value.

Figure 31:
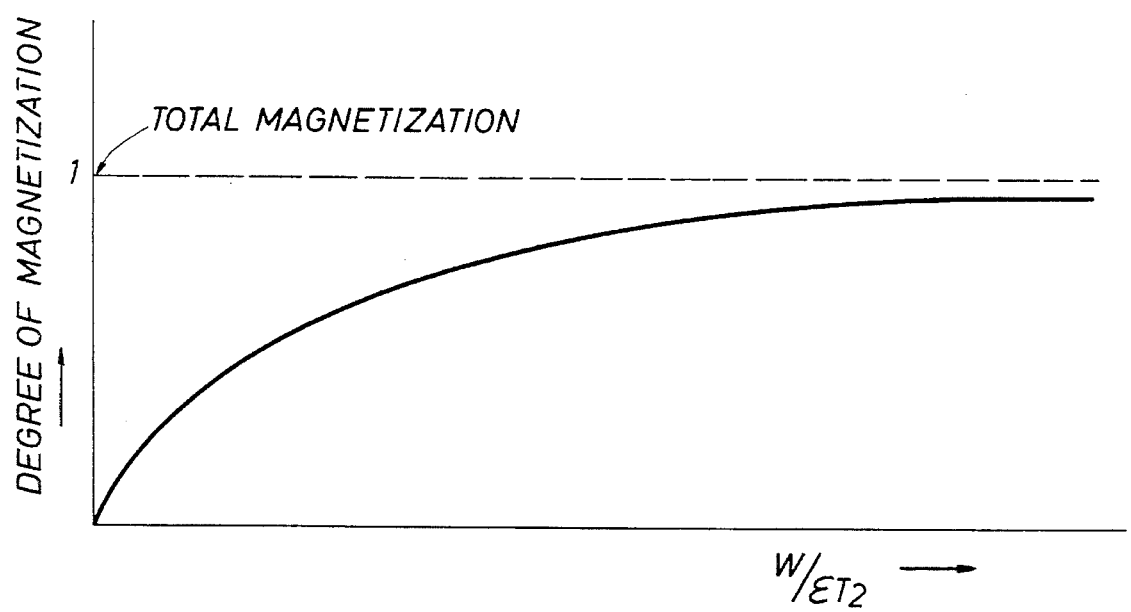
FIG. 31 illustrates a plot of degree of magnetization versus a term which is a function of wait time W, $T_1/T_2$ ratio, $\xi$, and transverse relaxation time $T_2$, this plot representing the actual time it takes for the magnetic moment vector M to change from the condition shown in FIG. 4 to the condition shown in FIG. 5.

In FIGS. 4, 5, 27, and 31, after applying the static magnetic field $B_0$ to the formation, the magnetic moments "A" of FIGS. 4 and 5 begin to achieve a degree of magnetization, the degree of magnetization building up exponentially, as shown in FIG. 31. The exponential build up of the degree of magnetization shown in FIG. 31 is mathematically represented by equation 34, set forth above and duplicated below as follows:

$$f_l = \left(1 - \exp\left(-\frac{W}{\xi_0 T_{2,l}}\right)\right), \qquad (34b)$$

where we have, for clarity, made a slight change in notation. The parameter has been changed from $\xi$ in equation (34) of part A of this specification to $\xi_0$ in equation 34b above. This conforms to the notation in part B of this specification where $\xi_0$ is used to denote an assumed or approximate value of the $T_1/T_2$ ratio and $\xi$ denotes the actual or true value of the ratio.

When the exponential curve approaches its asymptote as shown schematically in FIG. 31, the "total magnetization" approaches its thermal equilibrium value. When the total magnetization achieves its thermal equilibrium value, the magnetic moments "A" of FIG. 4 are aligned in the manner shown in FIG. 5 for the idealized case of perfect alignment. However, in practice, the wait time, W, for the single wait time pulse sequence shown in FIGS. 28–30 is frequently not long enough to allow the magnetic moments "A" of FIG. 4 to achieve its thermal equilibrium value as indicated in FIG. 31 by the magnetization curve approaching its asymptote.

In FIGS. 4, 5, 9b, 13 and 16, in order to remedy this deficiency, an approximate correction was applied by employing an assumed $T_1/T_2$ ratio, denoted by the parameter, $\xi_0$, in the polarization function in equation 34b above. The polarization function, $f_p$, in equation 34b was used in the calculations for the "logarithm of the likelihood function," block 4A3 of FIG. 13. The parameter $\xi_0$ is an approximation that represents the intrinsic or true $T_1/T_2$ ratio of the rock formations being traversed by the logging tool in a borehole. The relaxation time, $T_1$ is known as the "longitudinal relaxation time," which is the time it takes for the magnetization vector M to build up along the direction of the applied magnetic field $B_0$, that is, the relaxation time for the magnetization vector M to change from the condition shown in FIG. 4 to the condition shown in FIG. 5. The relaxation time, $T_2$, in the above ratio is defined to be the "spin-spin relaxation time," which describes the decay in the spin echo envelope, that is, the decay time shown in FIG. 9b of the Freedman patent which is annotated by the words "Decay Due to Proton Environment Effects." The logarithm of the likelihood function, $-\ln L$, of block 4A3 of FIG. 13 is defined by equation 42 set forth above in part A of this specification and appearing in column 27, lines 15–19 of the Freedman patent. The logarithm of the likelihood function, $-\ln L$, in equation 42 of part A of this specification and in the Freedman patent is a function of the window sums, $\bar{I}_{m,m+1}$. However, the window sums, $\bar{I}_{m,m+1}$, of equation 42 are defined by equation 40 set forth above and appearing in column 26, lines 45–50 of the Freedman patent. The expectation value of the window sum, $I_{m,m+1}(\{\alpha_l\})$ in equation 40 is a function of a polarization function, $f_p$. The polarization function is defined by equation 34b set forth above and appearing in column 25, line 25 of the Freedman patent except for a slight change in notation discussed following equation 34b. The polarization function, $f_p$, of column 25, line 25 is a function of the wait time, W, and the assumed (and therefore approximate) $T_1/T_2$ ratio. Since the wait time W is used in the single wait time pulse sequence shown in FIGS. 28–30, the polarization function requires an accurate value of the $T_1/T_2$ ratio in order to compensate for the insufficient wait time W. However, as noted below, the assumed $T_1/T_2$ ratio used in the polarization correction is only approximate and is frequently assumed to be constant. In fact, this ratio is not a constant for rock formations and depends upon the formation being excited. Therefore, in summary, the logarithm of the likelihood function, $-\ln L$, of block 4A3 of FIG. 13 is a function of the particular wait time, say $W_p$, used in the single wait time CPMG pulse sequence and the assumed (and therefore approximate) $T_1/T_2$ ratio, $\xi_0$. By minimization of $-\ln L$, of block 4A3 of FIG. 13, a single set of apparent spectral amplitudes $\{\hat{\alpha}_{l,p}\}$ corresponding to the particular wait time $W_p$ used in the pulse sequence is determined. Note that in FIG. 13 of part A of this specification and the Freedman patent, the dependence of the estimated spectral amplitudes (see the ouputs of block 4A3) on the wait time index "p" was not explicitly shown. The apparent spectral amplitudes $\{\hat{\alpha}_{l,p}\}$ are used to compute log outputs in block 4A4 and to generate the new output record medium shown in FIG. 16. The apparent set of spectral amplitudes are in many cases not equal to the true or intrinsic spectral amplitudes of the rock formations being logged because the correction made for insufficient wait time is inaccurate due to use of an incorrect value of the $T_1/T_2$ ratio (i.e., $\xi_0$) used in the polarization function defined by equation 34b above. Since the apparent spectral amplitudes, $\{\hat{\alpha}_{l,p}\}$, are used to generate the output record medium of FIG. 16, the output record medium of FIG. 16 is, to a certain extent, inaccurate.

In order to correct this deficiency relating to the accuracy of the output record medium of FIG. 16, a new signal processing method and apparatus in accordance with the present invention was developed which is responsive to a set of incoming multi-wait time CPMG spin echo pulse sequence data for determining an updated and more accurate estimate of the true $T_1/T_2$ ratio, denoted by $\hat{\xi}$, and also a corresponding set of updated or estimates of true spectral amplitudes, $\{\hat{\alpha}_l\}$, which are an intrinsic property of the rock formation being logged and therefore are independent of the pulse sequence wait times. The new updated spectral amplitudes are used to generate a more accurate output record medium. The multi-wait time "saturation recovery/CPMC" spin echo pulse sequence data is acquired by the new signal processing apparatus as a result of the use of a pulsed NMR well logging pulse sequence of the type disclosed in U.S. Pat. No. 5,023,551 to Kleinberg, et al. entitled "Nuclear Magnetic Resonance Pulse Sequences for Use With Borehole Logging Tools," the disclosure of which is incorporated by reference into this specification. In response to the multi-wait time spin echo pulse sequence data, the new signal processing apparatus of the present invention determines a "corrected" $T_1/T_2$ ratio, $\hat{\xi}$ and a corresponding set of "corrected" or updated spectral amplitudes, $\{\hat{\alpha}_l\}$; and, using the updated $T_1/T_2$ ratio and corresponding set of corrected spectral amplitudes, it generates a more accurate output record medium, similar to the output record shown in FIG. 16.

Referring to FIGS. 32–35, the multi-wait time pulsed NMR well logging method, which is used by the new signal processing apparatus of the present invention, is illustrated.

Figure 36:
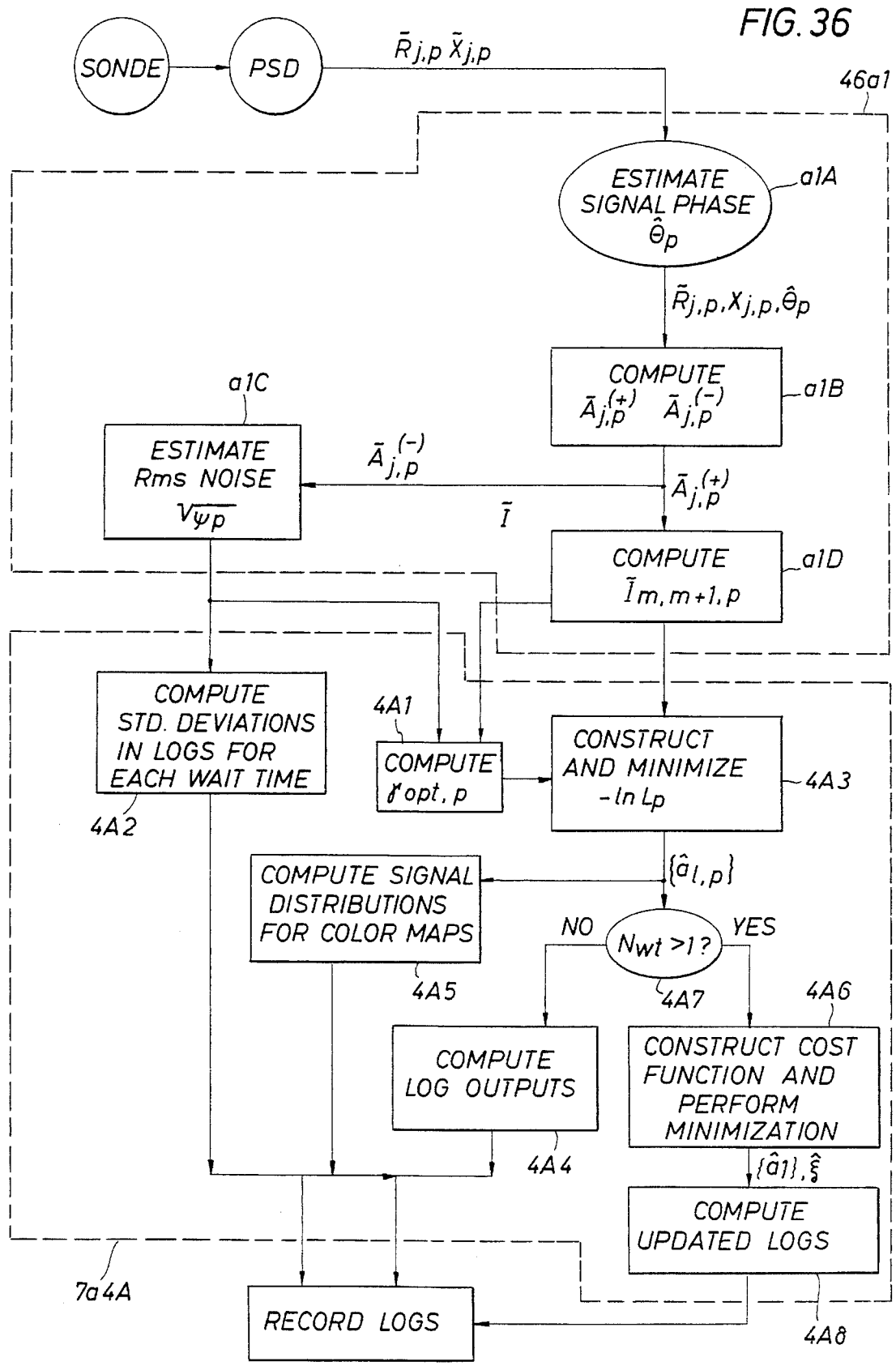
FIG. 36 illustrates a new block diagram or flow chart representing the new signal processing software associated with the new signal processing system in accordance with the present invention including a new decision triangle $N_{wt}>1$? and a new block entitled "Construct Cost Function Perform Minimization" which represents an improvement over the block diagram or flow chart of FIG. 13, the flowchart of FIG. 36 including a flow chart of the first part 46a1 of the signal processing method and apparatus of the present invention stored in the electronics cartridge 24 of the NMR tool and the second part 7a4A of the signal processing method and apparatus of the present invention stored in the surface oriented processing system 7a of FIG. 10, which first part and second part of the signal processing method and apparatus is embodied in the form of software stored in a memory of the electronics cartridge and the surface oriented processing system, respectively.

The new signal processing apparatus of the present invention is disposed within the NMR well logging tool of FIG. 1 and is illustrated in FIGS. 11, 12a, and 36 of the drawings. The multi-wait time NMR well logging pulse sequence of FIGS. 32–35 is similar to the pulse sequence disclosed in U.S. Pat. No. 5,023,551 to Kleinberg, et al. entitled "Nuclear Magnetic Resonance Pulse Sequences for Use With Borehole Logging Tools."

In FIGS. 32–35, assume that the static magnetic field $B_0$ is applied to the formation via magnets 17 or 20 of FIG. 1. In FIG. 32, when the NMR logging tool of FIG. 1 is being raised upwardly (or lowered) in the wellbore during a logging operation, a first period of time, $W_1$, is allowed to elapse before the RF pulses shown in FIG. 33 (i.e., the CPMG pulse sequence) energize the formation via antennas 18 or 21 of FIG. 1. When the RF pulses of FIG. 33 energize the formation via antennas 18 or 21, a first spin echo pulse sequence 66 of FIG. 32 is received in the antennas 18 or 21. The logging tool of FIG. 1 is still being raised upwardly in the wellbore during the logging operation. When the first spin echo pulse sequence 66 is received, a second period of time, $W_2$, is allowed to elapse, where, $W_2$, is different than (not equal to) $W_1$. For our example illustrated in FIG. 32, $W_2$ is greater than $W_1$. When the period of time $W_2$ elapses, the RF pulses shown in FIG. 34 energize the formation via antennas 18 or 21. When the RF pulses of FIG. 34 energize the formation, a second spin echo pulse sequence 68 of FIG. 32 is received in the antennas 18 or 21. The amplitudes of the second spin echo pulse sequence 68 are different than (in our example, are shown to be greater than) the amplitudes of the first spin echo pulse sequence 66. When the second spin echo pulse sequence 68 is received, the NMR logging tool is still moving upwardly in the wellbore during the logging operation. A third period of time $W_3$ is allowed to elapse, where $W_3$ is different than (not equal to) $W_2$ and $W_3$ is also different than (not equal to) $W_1$. In our example in FIG. 32, $W_3$ is shown to be greater than $W_2$ and greater than $W_1$. When the time period $W_3$ elapses, the RF pulses shown in FIG. 35 energize the formation via antennas 18 or 21. When the RF pulses of FIG. 35 energize the formation, a third spin echo pulse sequence 70 of FIG. 32 is received in the antennas 18 or 21. The amplitudes of the third spin echo pulse sequence 70 are different than (in our example of FIG. 32, are shown to be greater than) the amplitudes of both the first, and second spin echo pulse sequences 66 and 68.

Since the wait time periods $W_1$, $W_2$, and $W_3$ of FIG. 32 are now all different frown one another, the magnetic moments "A" shown in FIG. 4 have been given different periods of time to align together in the manner shown in FIG. 5. Therefore, the NMR logging system shown in FIG. 12b1 and FIG. 11 receives the spin echo pulse sequence data of FIG. 32, which data is now sensitive to the degree of total magnetization of the individual magnetic moments "A" in the formation traversed by the wellbore.

In FIG. 32, the spin echo pulse sequences 66, 68, and 70 of FIG. 32 are received by the antennas 18 or 21 of the well logging tool shown in FIG. 1 and are input to the new signal processing apparatus of the present invention. The hardware portion of the new signal processing apparatus is shown in FIGS. 11, 12a, and 12b1 of the drawings. The new software portion of the new signal signal processing apparatus of the present invention is illustrated in FIG. 36 of the drawings.

Referring to FIG. 36, the new software portion of the new signal processing apparatus of the present invention is illustrated.

Recall that, since the constant duration wait time, $W_p$, of FIG. 27 (which is used in the polarization function, $f_l$, of equation 34b) is often deemed to be insufficient in terms of time duration, the approximate or assumed $T_1/T_2$ ratio, $\xi_0$, was used in the polarization function $f_l$ of equation 34b to compensate for the insufficient wait time, $W_p$. However, the assumed $T_1/T_2$ ratio was always incorrectly assumed to be a constant. Recall also that the negative logarithm of the likelihood function, $-\ln L$, of equation 42, reflected in the "Construct and Minimize $-\ln L$" block 4A3 of FIG. 13 and the "Construct and Minimize $-\ln L_p$" block 4A3 of FIG. 36, is ultimately a function of the polarization function, $f_l$, of equation 34b, and the polarization function, $fl$, is in turn, a function of the insufficient wait time $W_p$ and the incorrect $T_1/T_2$ ratio, $\xi_0$. Furthermore, the "Construct and Minimize $-\ln L$" block 4A3 of FIG. 13 generates a single set (corresponding to a single wait time $W_p$) of apparent spectral amplitudes, $\{\hat{\alpha}_{l,p}\}$, in FIG. 13. The "Construct and Minimize $-\ln L_p$" of FIG. 36 also generates apparent sets of spectral amplitudes, $\{\hat{\alpha}_{l,p}\}$, for p=1, 2, . . . , $N_{wt}$ where $N_{wt}$ is an integer representing the total number of different wait times in a multi-wait time pulse sequence.

However, the single set of apparent spectral amplitudes, $\{\hat{\alpha}_{l,p}\}$, were used in FIG. 13 to compute log outputs 4A4 and to generate the output record medium shown in FIG. 16. Therefore, since the assumed $T_1/T_2$ ratio is inaccurate, the apparent spectral amplitudes $\{\hat{\alpha}_{l,p}\}$ of FIG. 13 are incorrect. Since, in FIG. 13, the single set of spectral amplitudes $\{\hat{\alpha}_{l,p}\}$ were used to generate the output record medium in FIG. 16, the output record medium of FIG. 16 is, to a certain extent, inaccurate. Therefore, in order to generate a more accurate output record medium similar to the output record shown in FIG. 16, the signal processing software represented by the flowchart of FIG. 13 must be improved to eliminate the inaccuracy of the output record medium shown in FIG. 16.

FIG. 36 illustrates the new software portion of the new signal processing apparatus in accordance with the present invention. The new software of FIG. 36 represents an improvement over the signal processing software of FIG. 13. In the flowchart of FIG. 36, the subscript, p=1,2, . . . , $N_{wt}$, is used to denote a measurement or output associated with a particular wait time $W_p$ in a multi-wait time CPMG pulse sequence having Not different wait times. For example, in FIG. 32, three (3) wait times $W_1$, $W_2$, $W_3$, were used to generate the three spin echo pulse sequences 66, 68, and 70. Therefore, in the example of FIG. 32, the number of wait times, $N_{wt}$=3. Consequently, as will be discussed in more detail below, the three (3) spin echo pulse sequences 66, 68, and 70 of FIG. 32 will be input to the signal processing system represented by the hardware of FIGS. 11 and 12b1 and the software of FIG. 36.

In FIG. 36, the first part 46a1 of the signal processing software flowchart shown in FIG. 13 is identical to the first part 46a1 of the signal processing software flowchart shown in FIG. 36. However, the second part 7a4A of the signal processing software flowchart shown in FIG. 13 is not identical to the second part 7a4A of the signal processing software flowchart of FIG. 36. More particularly, in FIG. 36, the second part 7a4A of the signal processing software flowchart includes three additional new blocks:

(1) a new decision triangle "$N_{wt}>1$?", block 4A7 of FIG. 36, (2) a new additional block entitled the "Construct Cost Function and Perform Minimization", block 4A6 of FIG. 36 (hereinafter called "the Construct Cost Function block"), and (3) a new "Compute Updated Logs" block 4A8 of FIG. 36 which is identical to the "Compute Log Outputs" block 4A4; however, it receives the new updated spectral amplitudes, $\{\hat{\alpha}_l\}$, which are output from the "Construct Cost Function" block 4A6.

In operation, referring by way of example to FIGS. 32 and 36, since three (3) wait times, $W_1$, $W_2$, $W_3$, are used, when the three (3) spin echo pulses sequences 66, 68, and 70 of FIG. 32 were received by the antennas 18 or 21 of FIG. 1, in our example, more than one wait time is being used. In our example, $N_{wt}$=3. As a result, since $N_{wt}$ is greater than 1, the decision triangle, block 4A7 of FIG. 36, would instruct the apparent sets of spectral amplitudes, $\{\hat{\alpha}_{l,p}\}$, which are output from the "Construct and Minimize $-\ln L_p$" block 4A3, to pass to the "Construct Cost Function and Perform Minimization" block 4A6. The block 4A6 will be discussed below in greater detail. Otherwise, if $N_{wt}$ is less than 2, (i.e., there is only one wait time, say for example, W, used in the pulse sequence) the single set of apparent spectral amplitudes $\{\hat{\alpha}_{l,1}\}$ passes to the "Compute Log Outputs" block 4A4 which would ultimately generate the output record medium shown in FIG. 16.

The Construct Cost Function block 4A6 of FIG. 36 receives the previously determined apparent sets of spectral amplitudes, $\{\hat{\alpha}_{l,p}\}$, which were output from the "Construct and Minimize $-\ln L_p$" block 4A3 and passed to the Construct Cost Function block 4A6 via decision triangle 4A7. However, in response to the sets of apparent spectral amplitudes, $\{\hat{\alpha}_{l,p}\}$, the "Construct Cost Function and Perform Minimization" block 4A6 generates a set of new or updated values of the spectral amplitudes, $\{\hat{\alpha}_l\}$. The set of new updated values of the spectral amplitudes are used to compute the updated log outputs, block 4A4, to compute the updated signal distributions, block 4A5, and to generate a more accurate output record medium similar to the output record shown in FIG. 16 of the drawings.

The cost function being constructed in the "Construct Cost Function" block 4A6 of FIG. 36 is defined by equation 78 of this specification, i.e., $$C(\xi_v, \{\alpha_{v,l}\}) = \sum_{p=1}^{N_{wt}} \sum_{l=1}^{N_s} \left( \alpha_{l,p} - \frac{\alpha_{v,l} f_l(W_p, \xi_v)}{f_l(W_p, \xi_0)} \right)^2, \quad (78)$$

The cost function $C(\xi_v, \{a_{v,l}\})$ of equation 78 is a function of the polarization functions, $f_l(W_p, \xi_0)$ and $f_l(W_p, \xi_v)$. The polarization functions are defined in Equations 74 and 75 of this specification and are repeated below as follows:

$$f_l(W_p, \xi_0) = \left(1 - \exp\left(-\frac{W_p}{T_{1\alpha,l}}\right)\right), \quad (74)$$

where the apparent longitudinal relaxation times $(T_{1\alpha,e})$ have been defined, $$(T_{1\alpha,l})^{-1} = (\xi_0 T_{2,l})^{-1} + (T_{mf})^{-1}, \quad (75)$$

where $T_{mf}$ is the NMR relaxation time of the mud filtrate. Note that equations 74 and 75 above also are used to define the function, $f_l(W_p, \epsilon_v)$, by replacing $\xi_0$ by $\xi_v$.

In the cost function equation 78 set forth above, the following terms are defined:

(1) The quantity, $W_p$, is a distinct wait time, such as one of the wait times, $W_1, W_2, \ldots, W_{N_{wt}}$ shown in FIG. 32;

(2) The quantity, $\xi_0$, is the assumed value of the $T_1/T_2$ ratio referred to earlier in this specification which is partly responsible for an inaccurate output record medium of FIG. 16;

(3) The quantity, $\xi_v$, is a variable representing the true or intrinsic $T_1/T_2$ ratio which is the "yet to be determined" new updated value of the $T_1/T_2$ ratio;

(4) The $N_s$ quantities, $\{\hat{\alpha}_{l,p}\}$, for each value of the wait time $W_p$ represent the sets of apparent spectral amplitudes output from the "Construct and Minimize –ln $L_p$" block 4A3 in FIG. 36; and (5) The $N_s$ quantities, $\{\hat{\alpha}_{v,l}\}$, are variables representing the "yet to be determined" estimates of intrinsic or true spectral amplitudes in the rock formation traversed by the wellbore and which are output from the "Construct Cost Function and Perform Minimization" block 4A6 in FIG. 36 and which, after being input to block 4A8 in FIG. 36, are ultimately responsible for generating a more accurate output record medium similar to the output record medium shown in FIG. 16 of the drawings.

The "Construct Cost Function and Perform Minimization" block 4A6 of FIG. 36 generates a plurality of new values of the spectral amplitudes, $\{\hat{\alpha}_l\}$, in response to the sets of apparent spectral amplitudes, $\{\alpha_{l,p}\}$, output from the "Construct and Minimize–ln $L_p$" block 4A3 by:

(1) constructing the cost function, $C(\xi_v, \{\alpha_{v,l}\})$, of equation 78 set forth above; and (2) the simultaneous minimization of the constructed cost function, $C(\xi_v, \{\alpha_{v,l}\})$, with respect to the $N_s+1$ variables, $\xi_v$ and $\{\hat{a}_{v,l}\}$.

The cost function, $C(\xi_v, \{\alpha_{v,l}\})$, can be minimized by using a standard non-linear optimization algorithm which starts with an given initial set of values of the variables and iteratively updates their values until the cost function attains its global minimum within the allowed (i.e., constrained) hyperspace of its variables. If we let, $\xi_v*$ and $\{\alpha_{v,l}*\}$, denote the values of the variables for which $C(\xi_v, \{\alpha_{v,l}\})$ attains its global minimum then the updated $T_1/T_2$ ratio and spectral amplitudes are obtained, as follows, $\hat{\xi} = \xi_v*$ and $\{\hat{\alpha}_l\} = \{\alpha_{v,l}*\}$.

The desired value of the spectral amplitude, $\{\hat{\alpha}_l\}$, the one which corresponds to the minimum of the cost function, is generated by the "Construct Cost Function" block 4A6. The "Compute Updated Logs" block 4A8 uses the set of updated spectral amplitudes, $\{\alpha_o\}$, to "record logs" and to generate a more accurate output record medium, similar to the output record medium shown in FIG. 16 of the drawings.

A functional description of the operation of the present invention will be set forth in the following paragraphs with reference to FIGS. 1, 11, 12a, 12b1, 32–35, and 36 of the drawings.

The NMR well logging tool of FIG. 1 is traversing a wellbore. The static field $B_0$ magnetizes the formation. A period of time, $W_1$, of FIG. 33 is allowed to elapse. When the period of time, $W_1$ of FIG. 33 elapses, the CPMG pulse sequence (the RF pulses) shown in FIG. 33 energizes the formation traversed by the wellbore. The first spin echo pulse sequence 66 of FIG. 32 is received in the antenna(s) 18 or 21 of FIG. 1. A second period of time, $W_2$, of FIG. 32 is allowed to elapse. The second period of time, $W_2$, is not equal to time period $W_1$,; in our example of FIG. 33, assume that time period, $W_2$, is greater than time period $W_1$. When the second period of time, $W_2$, elapses, the CPMG pulse sequence (the RF pulses) of FIG. 34 energizes the formation traversed by the wellbore via antenna 18 or 21 of FIG. 1. The second spin echo pulse sequence 68 of FIG. 32 is received in the antenna 18 or 21 of FIG. 1. A third period of time, $W_3$, of FIG. 35 is allowed to elapse. The third period of time, $W_3$, is not equal to $W_2$, nor is it equal to $W_1$; in our example of FIGS. 32, assume that time period, $W_3$, is greater than time period, $W_2$, and that $W_2$ is greater than the time period, $W_1$. When the third period of time, $W_3$, elapses, the CPMG pulse sequence (the RF pulses) of FIG. 35 energizes the formation traversed by the wellbore via antenna 18 or 21 of FIG. 1. The third spin echo pulse sequence 70 of FIG. 32 is received in the antenna 18 or 21 of FIG. 1.

The spin echo pulse sequences 66, 68, and 70 of FIG. 32 are received by the RF antenna 18 or 21 and are input to the downhole computer 46 as shown in FIG. 12. In the downhole computer 46, the plurality of spin echo pulse sequences 66, 68, and 70 are "sequentially processed" by the first part 46a1 of the signal processing system of FIG. 36, beginning with the pulse sequence 66 and ending with the pulse sequence 70, in the same manner discussed above in connection with FIG. 13, thereby generating a corresponding plurality of sequentially generated window sums. Then, the sequentially generated window sums are transmitted to and input to the surface oriented processing system 7a of FIGS. 10–11. In the surface oriented system 7a, the plurality of window sums are processed by the second part 7a4A of the signal processing system of FIG. 36. This "sequential processing" of the spin echo pulse sequences 66, 68, and 70 of FIG. 32 takes place in the following manner:

In FIGS. 32 and 36, in response to the first spin echo pulse sequence 66 of FIG. 32, a first window sum, $\bar{I}_{m,m+1,1}$ is generated by the "Compute $\bar{I}_{m,m+1,p}$" block a1D, associated with the first part 46a1 of the signal processing method and apparatus which comprises the software 46a of FIGS. 12b1 and 12b2. The first set of window sums is generated in the same manner as discussed above in connection with FIG. 13. The first set of window sums $\bar{I}_{m,m+1,1}$ is then passed to the "Construct and Minimize –ln $L_p$" block 4A3 associated with the second part 7a4A of the signal processing method and apparatus which comprises the software 7a4 of FIG. 11. The "Construct and Minimize –ln $L_p$" block 4A3 of FIG. 36 will now generate a first set of apparent spectral amplitudes $\{\hat{\alpha}_{l,1}\}$ in response to the first set of window sums, $\bar{I}_{m,m+1,1}$, corresponding to the first wait time $W_1$ of FIG. 32.

Then, in response to the second spin echo pulse sequence 68 of FIG. 34, a second set of window sums, $\bar{I}_{m,m+1,2}$, is generated by the "Compute $\tilde{I}_{m,m+1,p}$" block a1D associated with the first part 46a1 of the signal processing method and apparatus. The second set of window sums is generated in the same manner as discussed above in connection with FIG. 13. The second set of window sums, $\tilde{I}_{m,m+1,2}$, is then passed to the "Construct and Minimize $-\ln L_p$" block 4A3 associated with the second part 7a4A of the signal processing method and apparatus. The "Construct and Minimize $-\ln L_p$" block 4A3 of FIG. 36 will now generate a second set of apparent spectral amplitudes, $\{\hat{\alpha}_{l,2}\}$, in response to the second set of window sums, $\tilde{I}_{m,m+1,2}$, corresponding to the second wait time $W_2$ of FIG. 32.

Then, in response to the third spin echo pulse sequence 70 of FIG. 35, a third set of window sums, $\tilde{I}_{m,m+1,2}$, is generated by the "Compute $\tilde{I}_{m,m+1,p}$" block a1D, associated with the first part 46a1 of the signal processing method and apparatus. The third set window sums is generated in the same manner as discussed above in connection with FIG. 13. The third set of window sums, $\tilde{I}_{m,m+1,2}$, is then passed to the "Construct and Minimize $-\ln L_p$" block 4A3 associated with the second part 7a4A of the signal processing method and apparatus. The "Construct and Minimize $-\ln L_p$" block 4A3 of FIG. 36 will now generate a third set of apparent spectral amplitudes, $\{\hat{\alpha}_{l,e}\}$, in response to the third set of window sums, $\tilde{I}_{m,m+1,3}$, corresponding to the third wait time $W_3$ of FIG. 32.

Since three wait times $W_1$, $W_2$, and $W_3$ were used in FIG. 32 to generate the three spin echo pulse sequences 66, 68, and 70, the decision triangle of block 4A7 of FIG. 36 will pass the three sets of apparent spectral amplitudes $\{\hat{\alpha}_{l,1}\}$, $\{\hat{\alpha}_{l,2}\}$, and $\{\hat{\alpha}_{l,3}\}$, to the "Construct Cost Function and Perform Minimization" block 4A6 of FIG. 36.

The Construct Cost Function block 4A6 of FIG. 36 receives the sets of apparent spectral amplitudes, $\{\hat{\alpha}_{l,1}\}$, $\{\hat{\alpha}_{l,2}\}$, and $\{\hat{\alpha}_{l,3}\}$, which were output from decision triangle 4A7. However, in response to the sets of apparent spectral amplitudes the "Construct Cost Function and Perform Minimization" block 4A6: constructs a cost function, minimizes the cost function, and then generates a single set of new updated values of intrinsic spectral amplitudes, $\{\hat{\alpha}_l\}$. The new values of the spectral amplitudes, $\{\hat{\alpha}_l\}$, are used to compute the log outputs, block 4A4, to compute the signal distributions, block 4A5, and to generate a more accurate output record medium similar to the output record shown in FIG. 16 of the drawings.

The following paragraphs will provide a Detailed Description of the Preferred Embodiment, and in particular, a detailed description of the "Construct Cost Function and Perform Minimization" block 4A6 shown in FIG. 36 of the drawings.

It should be obvious to those skilled on the art that modifications to the preferred embodiment described above are contained within the scope of the present invention. These include determining the true $T_1/T_2$ ratios ($\xi$) and the true $T_2$-distributions, e.g., the set of intrinsic spectral amplitudes $\{\alpha_l\}$ by minimizing a generalized likelihood function. The generalization of equation 42 of part A of this specification is given below by equation 42b, $$-\ln L = \sum_{p=1}^{N_{wt}} \sum_{m=1}^{N_w} \frac{(\tilde{I}_{m,m+1,p} - I_{m,m+1,p}\{\alpha_l,\xi\})^2}{2\psi[N_{m+1,p} - N_{m,p} + \delta_{m,1}]} + \frac{\gamma}{2\psi} \sum_{l=1}^{N_s} \alpha_l^2, \quad (42b)$$

where $I_{m,m+1,p}\{\alpha_l,\xi\}$ is defined by equation 40b (a generalization of equation 40 of part A of this specification) below, i.e., $$<\tilde{I}_{m,m+1,p}> = \sum_{l=1}^{N_s} \alpha_l f_{l,p} F_{m,m+1,p}(T_{2,l}, N_m, N_{m+1}, \Delta) \equiv I_{m,m+1,p}\{\alpha_l,\xi\}, \quad (40b)$$

where we have also introduced a generalization of equation 34 of part A of this specification which we denote by equation 34c given below, i.e., $$f_{l,p} = \left(1 - \exp\left(-\frac{W_p}{\xi T_{2,l}}\right)\right). \quad (34c)$$

The true or intrinsic $T_1/T_2$ ratios and spectral amplitudes are determined by minimization of the genearalized likelihood function in equation 42b above. The log ouputs are then determined as described above from the set of spectral amplitudes and $T_1/T_2$ ratio at which $-\ln L$ in equation 42b attains its minimum value. In connection with this modification, the flowchart in FIG. 36 of this specification is modified accordingly. For example the generalized likelihood function in eq. (42b) above would be constructed in a block similar to block 4A3 of FIG. 36 of part B of this specification. The true spectral amplitudes output by minimizing the generalized likelihood function would then be passed through blocks similar to blocks 4A4 and 4A5 of FIG. 13 of part A of this specification. The blocks 4A7 and 4A6 of FIG. 36 would not be required for this modified embodiment.

DETAILED DESCRIPTION OF THE PREFERRED EMBODIMENT

An important ingredient in processing single wait time CPMG spin-echo pulse sequences is the polarization correction which accounts for incomplete recovery of the longitudinal magnetization during the wait time that precedes each CPMG spin-echo waveform. The polarization correction depends on a parameter representing the true $T_1/T_2$ ratio of the rock sample. Here $T_1$ is the longitudinal relaxation time and $T_2$ is the spin-spin or transverse relaxation time. Although the true $T_1/T_2$ ratios have been shown[11,12] to vary from one rock sample to another, a constant ratio (referred to here as $\xi_0$) is nevertheless assumed by the signal processing algorithm during logging.

The reason for using an assumed value of the $T_1/T_2$ ratio is that single wait time CPMG pulse sequences do not contain any information about $T_1$. Therefore to correct for the effects of a finite wait time one must guess at a value for the ratio. As shown below, use of incorrect values of the ratios leads to accuracy errors in the log outputs.

An alternative approach would be to make simultaneous estimates of $T_1$ and $T_2$-distributions; however, this problem is not numerically robust and also the required measurement times are too long for practical borehole applications. A method for simultaneously logging $T_1$ and $T_2$ was proposed by Kleinberg, et al.[10]

This method employs composite pulse sequences which combine fast inversion recovery (FIR) sequences and CPMG spin-echo sequences and are referred to as FIR/CPMG pulses.[10] The FIR/CPMG method of logging in a borehole proved to be impractical as later showed by Kleinberg, et al.[11] The latter publication showed that $T_1$ logs obtained from a moving NMR logging tool are not repeatable because the measurements are corrupted by the interfaces separating the different geological formations penetrated by the borehole. The root cause of the problem is the relatively long times required to perform the FIR/CPMG pulse sequences. The FIR/CPMG method, however, does provide an efficient method in the laboratory for measuring $T_1$ and $T_2$ as shown in two related publications.[1,6] The principal reason why the FIR/CPMG method is suitable for a laboratory environment but not for borehole depth logging is that in the laboratory there are no constraints on the measurement times. Another related reason is that the measurement S/N ratios in a laboratory NMR measurement are much higher than those in a borehole measurement.

The main objective of the aforementioned FIR/CPMC, patent was to obtain $T_1$ logs. It has since been realized[11] that at the frequencies at which modern pulsed NMR tools operate, e.g., in the vicinity of 2 MHz and for short inter-echo spacings (e.g., 500 μsec and less) $T_2$ measurements are not contaminated by molecular diffusion effects. Therefore, logs of $T_2$ obtained using CPMG pulse sequences provide substantially equivalent NMR information as would $T_1$ logs. As a result, the relatively simple single wait time CPMG pulse sequence which measures $T_2$ has become a standard means of obtaining continuous (depth) logs of NMR properties using pulsed NMR logging tools in boreholes.

The present specification shows that using single wait time CPMG pulse sequences involves an uncontrolled approximation that can lead to unacceptable errors in the log outputs. It is furthermore shown that increasing the wait time preceding each CPMG sequence is inefficient and leads to reduced logging speeds. This specification further discloses that the accuracy problem can be eliminated by employing multi-wait time CPMG pulse sequences and by employing a new processing method which provides estimates of true $T_1/T_2$ ratios and also provides improved log outputs. The multi-wait time CPMG pulse sequences are a special case of the more general FIR/CPMG sequences in the Kleinberg, et al.[10] patent. The multi-wait time pulse sequences were referred to as saturation recovery/CPMG pulses in the aforementioned patent and are obtained by setting the wait times in the FIR/CPMG sequences to zero and omitting the 180 degree inversion pulses.

The $\xi_0$ parameter is a processing input on the same footing, for example, as the cementation and saturation exponents used in resistivity logging. The purpose of this specification is to address several important problems associated with pulsed NMR logging. These problems have not been recognized in prior art inventions. First, we disclose an algorithm for estimating the true $T_1/T_2$ ratios (hereafter referred to by $\xi$) using multi-wait time CPMG spin-echo pulse sequences acquired by the CMR. The second purpose of this invention is to study the propagation of errors through the CMR signal processing algorithm to the CMR log outputs. The errors studied are those caused by using values of $\xi_0$ in the signal processing that are not equal to the true values, $\xi$. In particular, the dependence of these errors on wait time for four different model $T_2$-distributions is investigated. It is shown that these errors can cause inaccuracies in NMR derived porosities. It is shown that multi-wait time pulse sequences can be used to eliminate the accuracy problem.

In order to elucidate the nature and origin of the polarization correction, it is useful to pause here and discuss the CMR tool pulse sequence and the laboratory experimental results on which the correction is based.

One of the main features of NMR logging that sets it apart from other borehole logging measurements is the relatively long time required for a single unit of measurement. That is, the measurement time of a single measurement unit is of the order of several seconds. Here a single measurement unit refers to a combined phase alternated pair (PAP) of Carr-Purcell-Meiboom-Gill (CPMG) spin-echo waveforms which represent the basic unit of measurement in modern pulsed NMR well logging tools. The details of the CPMG pulse sequence and measurement principles are described fully in the NMR literature[is]. For this reason only a cursory introduction is provided here.

A CPMG consists of two time intervals: (1) an initial polarization period or wait time (W) that initiates each CPMG, followed by (2) a series of radio frequency (r.f.) pulses. The wait time interval normally accounts for most of the CPMG measurement time. A wait time is required in order to restore the nuclear magnetization. The r.f. pulses are applied to manipulate the magnetization vector and, as a result, produce the measured spin-echo signals. The reason that the nuclear magnetization must be restored is that at the end of each CPMG the total magnetization is practically zero.

In most NMR measurement environments, as for example in the laboratory, the measurement time for a CPMG is not a critical factor and a polarization correction is not required. That is, one can always select the wait time sufficiently long (e.g., typically 5–10 seconds is required) so that the longitudinal magnetization attains its thermal equilibrium value during the wait time interval. This luxury is not possible when logging with a moving tool. For continuous (e.g., depth) logging it is desirable to use shorter wait times in order to increase logging speed, improve signal-to-noise ratio and achieve better vertical resolution.

During the wait time, the macroscopic longitudinal magnetization approaches its equilibrium value in the static magnetic field produced by a permanent magnet in the tool sonde. This process can be described by a phenomenological relaxation time equation for the longitudinal magnetization. In simple physical systems, e.g., bulk water, the approach to equilibrium is exponential with a single time constant, $T_1$, known as the longitudinal relaxation time. In sedimentary rocks, the approach to equilibrium is described by a $T_1$-distribution. The physical basis for a distribution of $T_1$ values is the distribution of pore sizes in rocks. That is, pore fluids in different parts of a rock sample experience local variations in pore surface-to-volume ratios and concentrations of magnetic impurities, and therefore, exhibit different local relaxation rates. Mathematically, this process can be described by a model which expresses the longitudinal magnetization as a sum of single exponential basis functions with fixed relaxation times. The relaxation times are chosen equally spaced on a logarithmic scale over the assumed domain of the distribution function.

The amplitude of the longitudinal magnetization associated with each basis function can be determined in the laboratory by fitting inversion recovery measurements to the mathematical model. The set of amplitudes and their associated relaxation times represent the $T_1$-distribution. $T_1$-distributions estimated from laboratory inversion recovery measurements are presented as semilog plots of NMR signal amplitude versus $T_1$ (e.g., see ref. 3). Similar plots are used to display $T_2$-distributions.

Incomplete recovery of the longitudinal magnetization occurs frequently during continuous logging when wait times of the order of 1.0 second are used. In some sedimentary formations, the $T_1$-distributions contain relaxation times of the order of several seconds. This occurs, for example, for fluids in large pores that have negligible surface relaxation. The relaxation times in these pores then approach and are limited by the bulk fluid relaxation times. Clearly, the longitudinal magnetization in these formations does not reach its equilibrium value during the wait time interval. Thus, a polarization correction is required in order to obtain accurate estimates of $T_2$-distributions (and therefore CMR log outputs).

The polarization correction depends for its validity on assumptions derived from comparisons of $T_1$ and $T_2$-distributions estimated from laboratory NMR data. The experiments and the cross correlation analyses of the distributions on carbonate and sandstone rock suites were conducted at the Schlumberger-Doll Research Center[11-12] (SDR). The SDR experiments were conducted using a proton Larmor frequency of 2 MHz so that the results are applicable to the CMR tool which has operating frequencies that are close to 2 MHz.

The SDR results showed that, for many rock samples, $T_2$ and $T_1$-distributions are approximately congruent. Moreover, it was shown that a reasonable approximation to the $T_1$-distribution of many rock samples can be obtained from the $T_2$-distribution by the making the transformation, $T_1 = \xi T_2$ where the factor $\xi$ is referred to as the $T_1/T_2$ ratio. A mean value, $\bar{\xi} = 1.65$, was reported by SDR for a suite of 105 rock samples which included a wide range of rock lithologies, e.g., sandstones, carbonates, diatomites and shales[11].

Note that using the aforementioned transformation one can obtain a plot of the $T_1$-distribution of a rock by shifting a plot of its $T_2$-distribution by $\log \xi$ along the x-axis and then changing the x-axis label from $T_2$ to $T_1$. The similar shapes of the $T_1$ and $T_2$-distributions of rock samples observed at SDR is not a universal property and certainly depends on the frequency of the NMR measurements. The effects of molecular diffusion on $T_2$-distributions at higher frequencies and/or increased inter-echo spacings invalidate the SDR 2 MHz results on the approximate congruency of the $T_1$ and $T_2$-distributions. Indeed, it has been shown that the $T_1$ and $T_2$-distributions of two sandstone samples, for measurements made at 20 MHz, have very different shapes[4].

Algorithm For Estimating T1/T2 Ratios

As noted above, the simplest CMR tool pulse sequence is a repetition of PAP spin-echo waveforms which are acquired with a single fixed wait time (W) which precedes each CPMG. In this section pulse sequences with multiple wait times, $W_p$, where the index $p=1,2,\ldots,N_{wt}$ denotes the wait times are considered. Pulse sequences with multiple wait times are required in order to obtain data with sensitivity to the $T_1$-distribution and therefore to the $T_1/T_2$ ratio. In practice, as shown in the next section, only a few (e.g., $N_{wt}=3$) wait times are required to obtain good estimates of $\xi$. Using a notation similar to that in Eq. (1) of the Freedman patent, a multi-wait time phase alternated pair CPMG pulse sequence can be written in the form:

$$CPMG^{(\pm)}: \{n_p \{W_p - 90°(\pm x) - (t_{cp} - 180°(y) - t_{cp} - (echo)_j)_{j=1,2,\ldots,J_p}\}\}_{p=1,2,\ldots,N_{wt}}. \quad (72)$$

The integer $n_p$ is the number of times that wait time $W_p$ is repeated in a specific multi-wait time pulse sequence. In practice, it is often advantageous to collect and average multiple repeats of the waveforms with short wait times. The amplitude $\tilde{A}_{j,p}^{(+)}$ of the j-th spin-echo in a CPMG waveform can be related to the spectral amplitudes of the associated $T_2$-distribution by the equation, $$\tilde{A}_{j,p}^{(+)} = \sum_{l=1}^{N_s} \alpha_{l,p} f_l(W_p, \xi_0) \exp\left(-\frac{j\Delta}{T_{2\alpha,l}}\right) + N_{j,p}, \quad (73)$$

for $j=1, 2, \ldots, J_p$ where the index $p=1, 2, \ldots, N_{wt}$ denotes the p-th wait time in a pulse sequence with $N_{wt}$ wait times. Here $J_p$ is the total number of echoes collected for the p-th wait time. Due to duty cycle restrictions in the CMR tool hardware, the number of echoes collected ($J_p$) for each wait time within a multiple wait time pulse sequence depends on the wait time. Specifically, fewer echoes are collected for the shorter wait times in the sequence. In Eq. (73), the $\alpha_{l,p}$ are $N_s$ apparent spectral amplitudes associated with the intrinsic relaxation times ($T_{2,l}$) for the p-th wait time assuming a $T_1/T_2$ ratio equal to $\xi_0$. The factor $f_l(W_p, \xi_0)$ is called the polarization correction. For the CPMG pulse sequence the polarization correction is given by, $$f_l(W_p, \xi_0) = \left(1 - \exp\left(-\frac{W_p}{T_{1\alpha,l}}\right)\right), \quad (74)$$

where we have defined the apparent longitudinal relaxation times, $$(T_{1\alpha,l})^{-1} = (\xi_0 T_{2,l})^{-1} + (T_{mf})^{-1}, \quad (75)$$

which includes both the intrinsic longitudinal relaxation of the l-th spectral component and the bulk relaxation time of the mud filtrate ($T_{mf}$). Note that because of the shallow depth of investigation (i.e., 1 inch) of the CMR tool one can assume that the measurement volume is flushed by mud filtrate. The NMR filtrate relaxation time can be measured at the wellsite, however, in practice the mud filtrate correction is often negligble. In writing eq. (75), we have used the fact that the relaxation rates due to different mechanisms are additive. The intrinsic longitudinal relaxation times ($\xi T_{2,l}$) arise solely from surface relaxation at the pore surfaces and therefore provide rock pore size information. In eq. (73), we have also defined apparent spin-spin relaxation times, $$(T_{2\alpha,l})^{-1} = (T_{2,l})^{-1} + (T_{mf})^{-1}, \quad (76)$$

where as noted previously, the intrinsic spin-spin relaxation times, $T_{2,l}$ are chosen to be equally spaced on a logarithmic scale in the interval $(T_{min}, T_{max})$ which defines the domain of the $T_2$-distribution. The quantity, $\Delta$, in equation (1) is the inter-echo spacing which for the CMR tool has a nominal value of 320 μsec. It is the relatively short inter-echo spacings and the low proton Larmor frequency of the CMR tool spin-echo measurements that provide $T_2$-distributions that are free of molecular diffusion effects[12]. The last term ($N_{j,p}$) in eq. (73) accounts for thermal electronic noise on the j-th echo of the spin-echo waveform associated with the p-th wait time.

The first step in the algorithm is to estimate the $T_2$-distributions for each of the $N_{wt}$ wait times in the pulse sequence. The distributions are estimated using the assumed value of $\xi_0$. The next step utilizes the $N_{wt} \times N_s$ spectral amplitude estimates determined in the first step as "data" in the minimization of a non-linear cost function. The minimization provides estimates of the true $T_1/T_2$ ratio ($\xi$) and, in addition, an "updated" $T_2$-distribution which is a byproduct of the minimization. The updated $T_2$-distributions are computed simultaneously with the estimates of $\xi$ and, therefore, are computed using a more accurate polarization correction. The updated $T_2$-distributions are used to compute more accurate log outputs.

The derivation of the cost function is based on the following arguments. The apparent spectral amplitudes estimated from the multi-wait time data have an implicit dependence on wait time. The dependence on wait time occurs because the estimates are made using an approximate value of the $T_1/T_2$ ratio. The product of each spectral amplitude and its polarization correction, i.e., for some assumed $\xi_0$, is an invariant for any value of the wait time. That is, if another value of $\xi_0$ were used, then although the polarization correction and the apparent amplitudes would be different, the product would nevertheless be invariant.

The invariant product is determined only by the measured spin-echo amplitudes. Mathematically, this means that one can write the approximate equation, $$\hat{\alpha}_{l,p} f_l(W_p, \xi_0) \approx \alpha_l f_l(W_p, \xi), \qquad (77)$$

where the $\hat{\alpha}_{l,p}$ are the $N_{wt} \times N_s$ apparent spectral amplitudes estimated by the signal processing algorithm. In eq. (77), the approximate equality is used to express the invariant product because of the effects of random noise. The "hat" is used here to remind us that these are estimates rather than true values of the amplitudes.

On the right hand side of eq. (77), the $a_l$ are the true spectral amplitudes of the $T_2$-distribution computed using the true value of the $T_1/T_2$ ratio ($\xi$). Note that these latter amplitudes are independent of wait time since we are, in principle, making an exact polarization correction. Eq. (77) leads immediately to a cost function, $$C(\xi_\nu, \{\alpha_{\nu,l}\}) = \sum_{p=1}^{N_{wt}} \sum_{l=1}^{N_s} \left( \hat{\alpha}_{l,p} - \frac{\alpha_{\nu,l} f_l(W_p, \xi_\nu)}{f_l(W_p, \xi_0)} \right)^2, \qquad (78)$$

which is a function of a variable $\xi_\nu$ representing the $T_1/T_2$ ratio. The cost function is also a functional of a variable distribution of spectral amplitudes $\{\alpha_{\nu,l}\}$ representing the $T_2$-distribution. More generally, the terms in eq. (78) could be weighted by the data covariance matrix. Simultaneous minimization of the cost function with respect to $\xi_\nu$ and $\{\alpha_{\nu,l}\}$ provides estimates ($\hat{\xi}$) of the true $T_1/T_2$ ratios and also true spectral amplitude estimates ($\hat{\alpha}_l$). That is, let $\xi_\nu^*$ and $\{\alpha_{\nu,l}^*\}$ denote the feasible values at which the cost function attains its global minimum. Then, the estimates of the true ratios are given by, $\hat{\xi} = \xi_\nu^*$, and the true spectral amplitude estimates by, $\hat{\alpha}_l = \alpha_{\nu,l}^*$. As noted previously, the ($\hat{\alpha}_l$) are used to compute updated log outputs. In FIG. 36, a flowchart which summarizes the steps in the multi-wait time data acquisition and processing method is shown.

Monte Carlo Testing of the Algorithm

This section presents some typical results obtained from Monte Carlo type numerical experiments designed to test the algorithm. The algorithm was tested by processing synthetic multi-wait time CPMG spin-echo waveforms. The synthetic waveforms were computed using the four input $T_2$-distributions shown in FIG. 37. These distributions have shapes which are representative of $T_2$-distributions found in reservoir rocks. Futhermore, for the distributions in FIG. 37, the logarithmic mean relaxation times ($T_{2,log}$) cover a relatively broad range of values. The relaxation times are: 34 ms for the distribution labeled A, 170 ms for the distribution labeled B, 253 ms for the distribution labeled C, and 38 ms for the bimodal distribution labeled D. These distributions are hereafter referred to as the A-distribution, etc. If the total porosity, $\phi_{nmr}$, for each distribution is normalized to 100 p.u. then the flee-fluid porosities computed with a 33 ms cutoff (i.e., $\phi_f(33)$) are 51, 95, 96 and 55 p.u. for the A, B, C and D-distributions, respectively.

The use of numerical experiments, rather than real laboratory experiments, is important for testing the algorithm since in real rocks the true $T_1/T_2$ ratios are not known. The $T_1/T_2$ ratios determined at SDR were obtained by maximizing a cross correlation function of laboratory determined $T_1$ and $T_2$-distributions. The laboratory distributions are only approximately congruent. The signal processing algorithm and the $T_1/T_2$ ratio algorithm derived in the previous section both assume that the $T_1$ and $T_2$-distributions are exactly congruent. For this reason, the laboratory determined ratios are only approximately equal to the estimates, $\hat{\xi}$. The estimates ($\hat{\xi}$) determined by minimization of eq. (78) are based on the same assumptions on which the signal processing algorithm is based. Therefore, it is these estimates that provide a self-consistent polarization correction for the signal processing algorithm.

Three types of numerical experiments were performed and are discussed separately. The first type of simulation was aimed at determining the statistical properties of the $T_1/T_2$ ratio estimates ($\hat{\xi}$). The second type of experiment was performed to study how errors in the assumed value ($\xi_0$) of the $T_1/T_2$ ratio propagate through the signal processing algorithm to produce systematic errors in the CMR log outputs. The third type of simulation was performed to study the updated $T_2$-distributions (i.e., $\hat{\alpha}_l$) and log outputs which are computed simultaneously with the $T_1/T_2$ ratio estimates. Note that a nominal value of $\xi_0 = 1.5$ is typically used during logging and is also the nominal value used for the computations in this invention specification.

Estimation of $\hat{\xi}$

Figure 38:
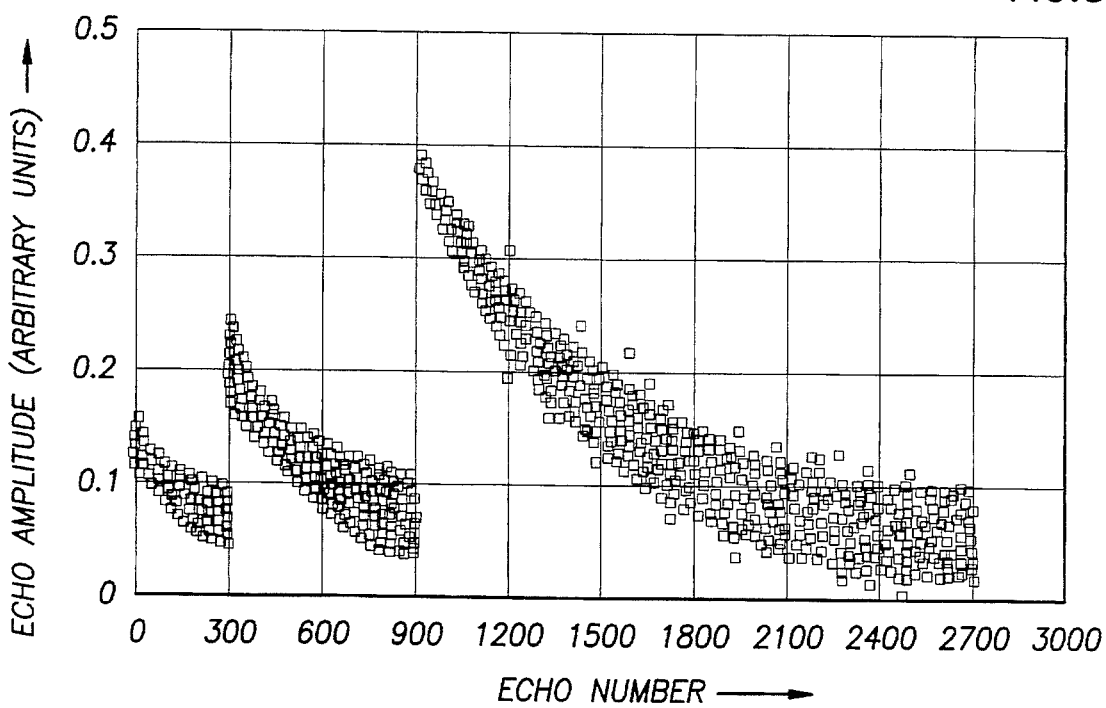
FIG. 38 illustrates a plot of echo amplitudes versus the number of the particular echo for each of three different wait times between adjacent spin echo pulse sequences.

For all of the simulations discussed in this subsection, multi-wait time CPMG waveforms similar to those shown in FIG. 38 were used to test the algorithm. Moreover, for each wait time psuedo random Gaussian noise, with an rms amplitude equal to 5 percent of the signal amplitude on the first echo, was added to each echo. This corresponds to a signal-to-noise (S/N) ratio of 26 dB which can be achieved with borehole tools by waveform stacking. Testing at lower values of S/N ratios has also been performed. These results proved that the method provides good estimates even at much reduced values of S/N ratio.

The pulse sequence parameters, e.g., $W_p$, $N_{wt}$, and $J_p$, used for all of the simulations in this subsection are identical to those shown in FIG. 38. The values used for the signal processing parameters were: $\xi_0 = 1.5$, $N_s = 50$, $T_{mf} = 500$ sec., $T_{min}$ and $T_{max}$ were selected to span the domain of the input $T_2$-distributions. Simulations using more than 3 wait times were also performed without significant improvement in the estimates. The latter results will not be shown here. For each simulation, the input waveforms were computed using an input value of $\xi$ (e.g., the true $T_1/T_2$ ratio). The algorithm shown in FIG. 36 was used to compute $\hat{\xi}$. For each case, the numerical experiments were repeated 100 times in order to sample different realizations of the psuedo random ensemble of input waveforms.

Figure 37:
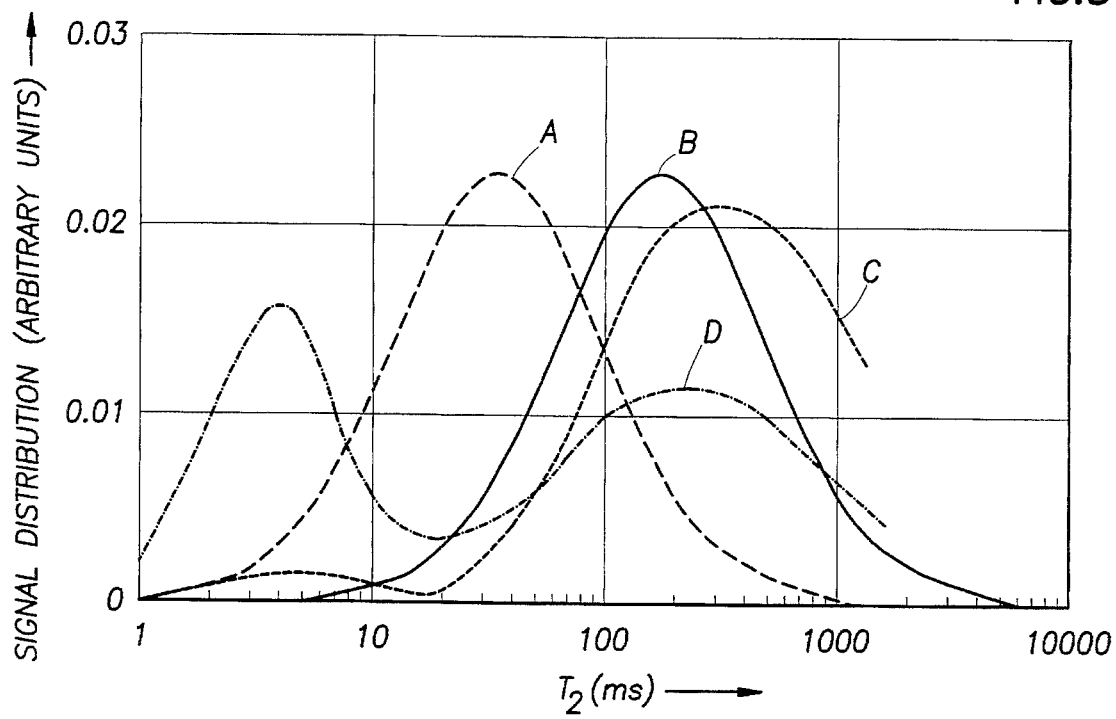
FIG. 37 illustrates a plurality of input $T_2$-distributions referred to in this specification.
Figure 39:
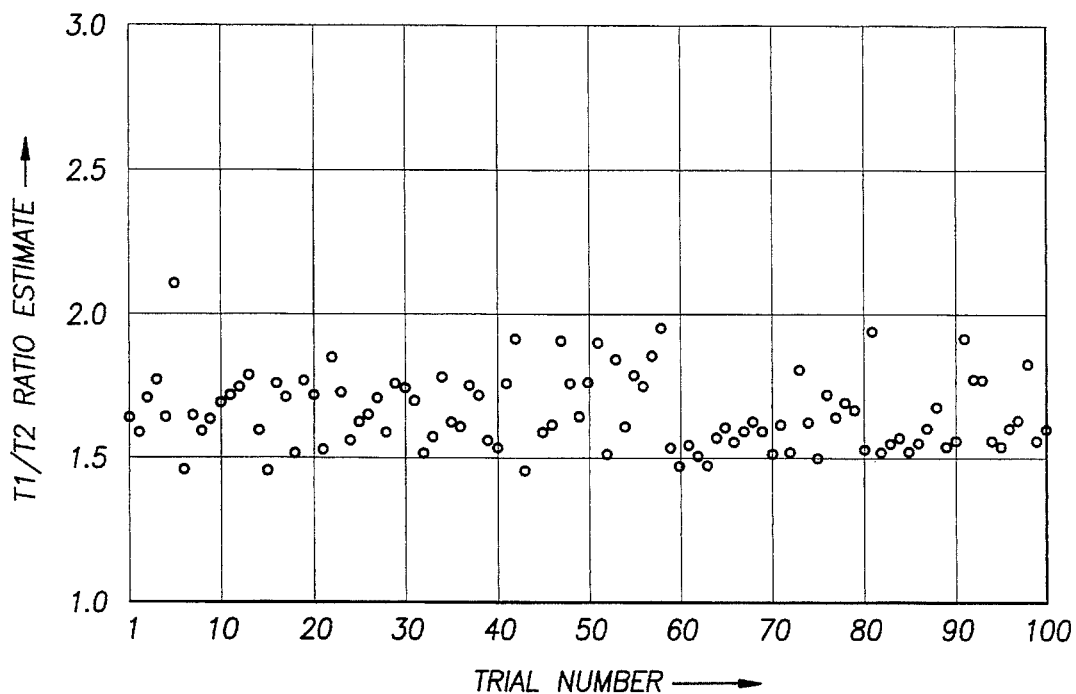
FIGS. 39–46 illustrate Monte Carlo estimates of $T_1/T_2$ ratios versus trial numbers.
Figure 40:
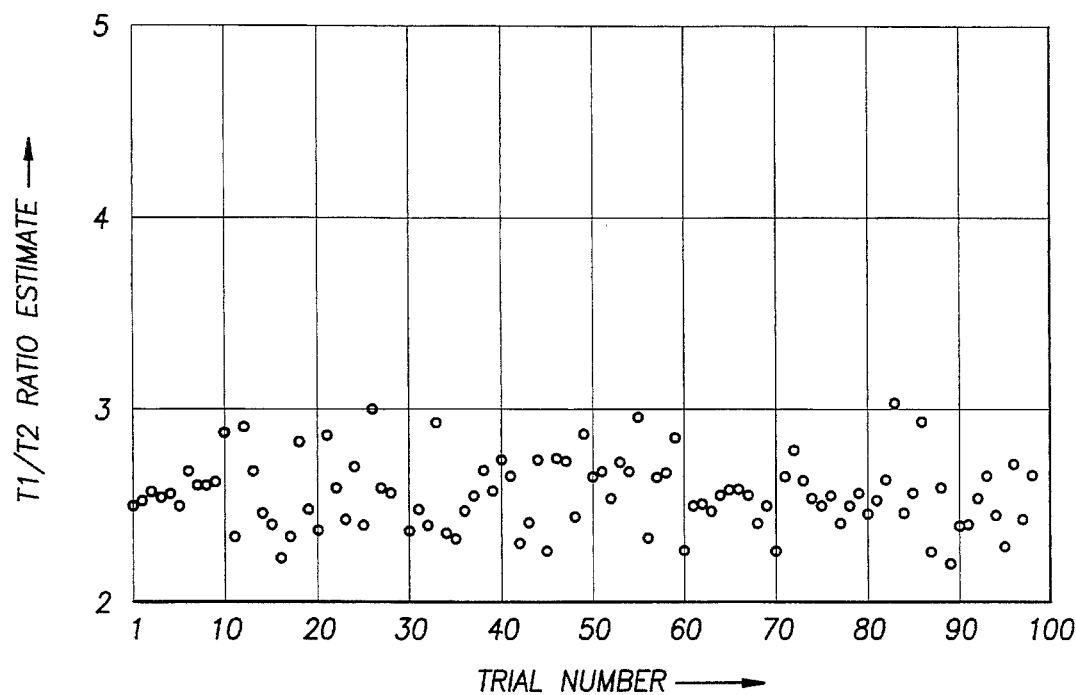

The first set of estimates are for the A-distribution in FIG. 37. The estimates ($\hat{\xi}$) are shown in FIGS. 39–40 for input or true values of $\xi$ equal to 1.5 and 2.5, respectively. Note that both sample means exhibit a positive bias. The rms total error in the estimates is comprised of contributions from both the bias error and the statistical error. The total rms error ($\Sigma$) in the estimator, $\hat{\xi}$, can be determined as follows. If we let $\Sigma^2$ denote the mean square total error then by definition, $$\Sigma^2 = \frac{1}{N_{trials}} \sum_{i=1}^{N_{trials}} (\delta\xi_i)^2, \quad (79)$$

where we have defined the deviations of the estimates from their true values, i.e., $$\delta\xi_i = \xi_i - \xi, \quad (80)$$

where the index, i=1, 2, ..., $N_{trials}$, denotes the i-th Monte Carlo trial and $N_{trials}$ denotes the total number of trials (equal to 100 here). On using eqs. (79) and (80) one finds that $\Sigma$=0.20 for the estimates shown in FIGS. 39–40. The true values (i.e., $\xi$ in eq. (80)) used in the computations were, of course, the input values 1.5 and 2.5, respectively. It should be noted that using different input values of $\xi$ produces comparable results. The fact that the total errors are equal (e.g., 0.20) in these two cases is coincidental. Based on these computations, it is reasonable to assume that for rocks with $T_2$-distributions similar to the A-distribution, that the true $T_1/T_2$ ratios can be estimated in the borehole to within a total error on the order of ±0.20.

Figure 41:
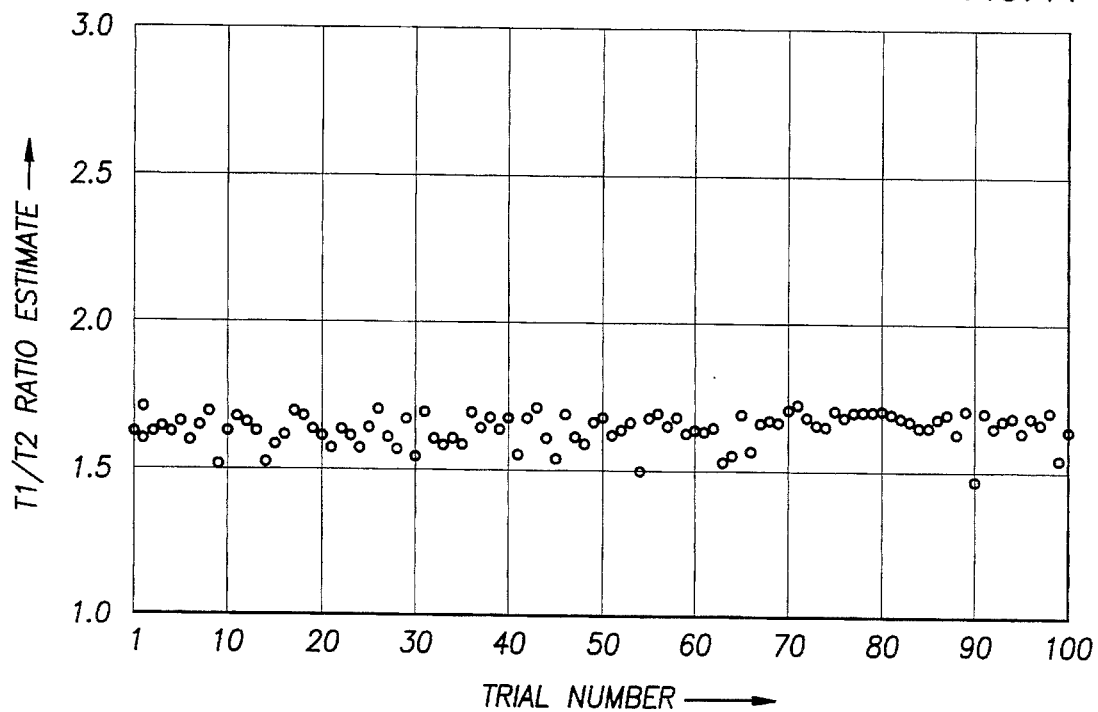
Figure 42:
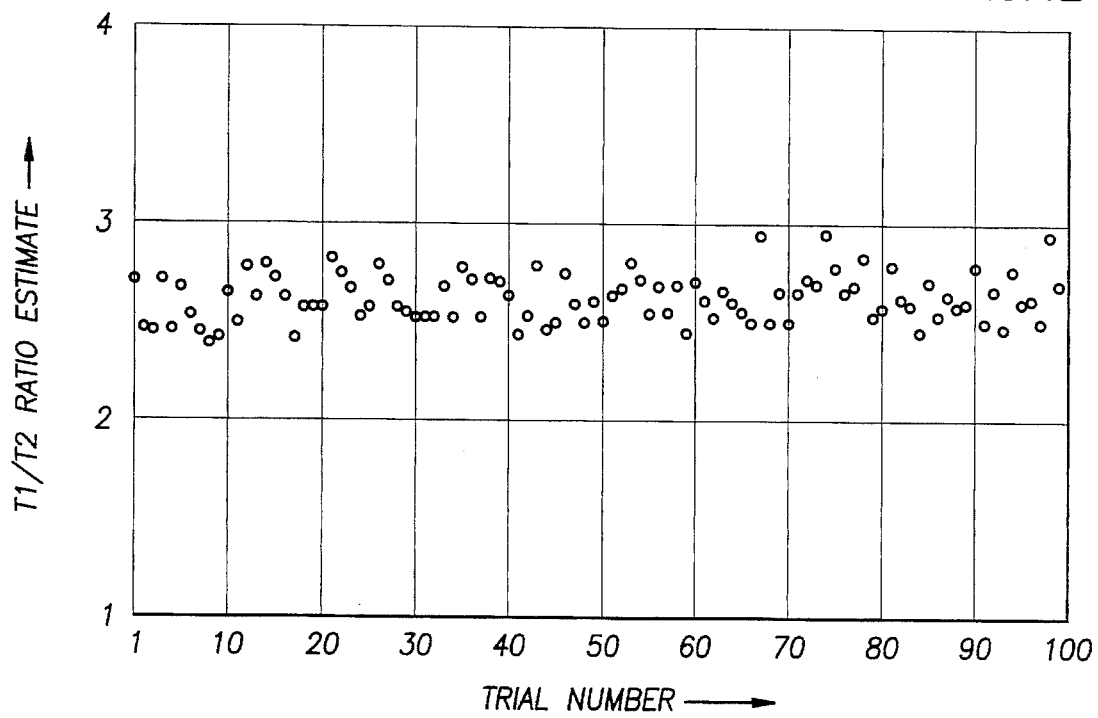
Figure 43:
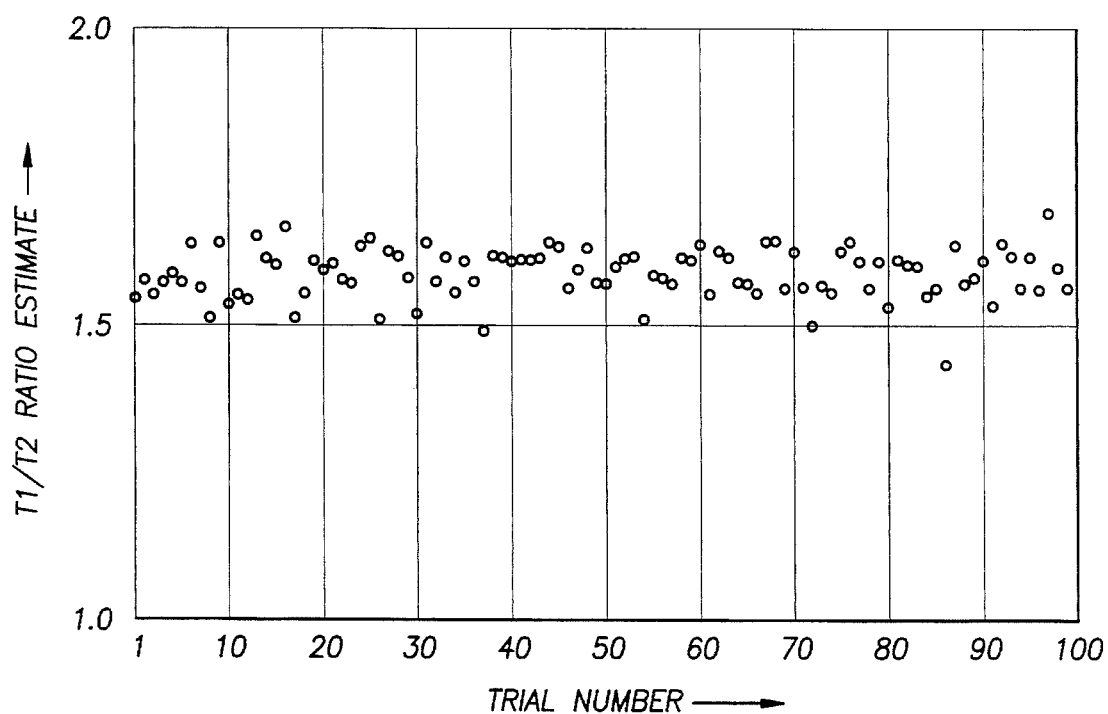
Figure 44:
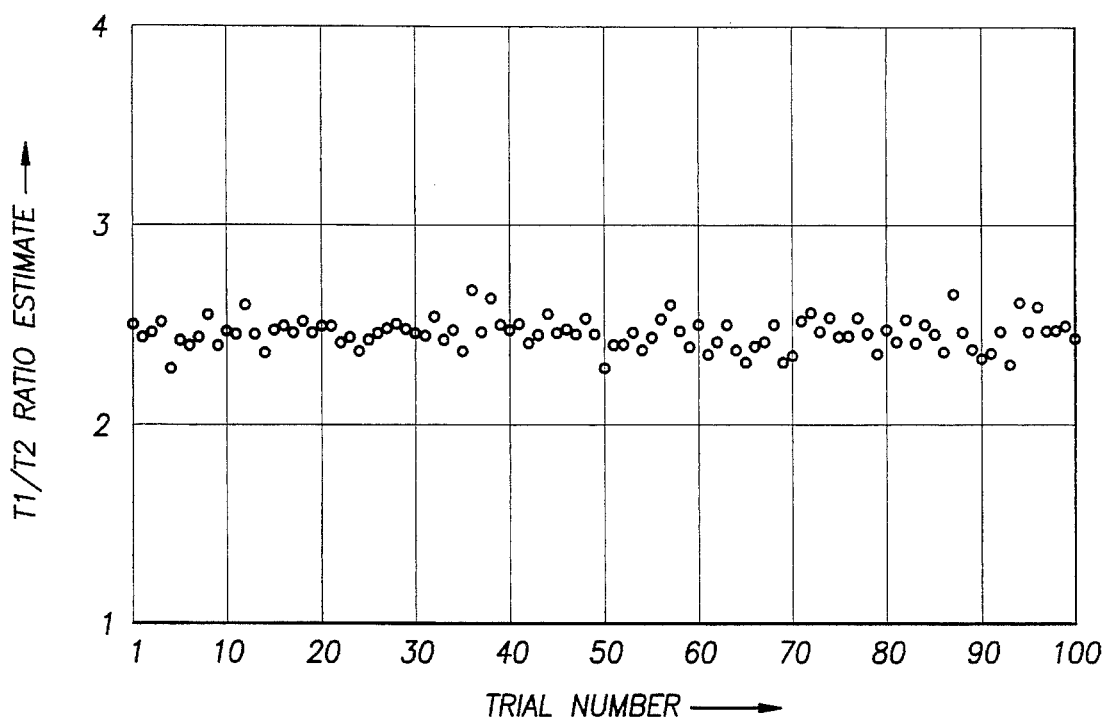
Figure 45:
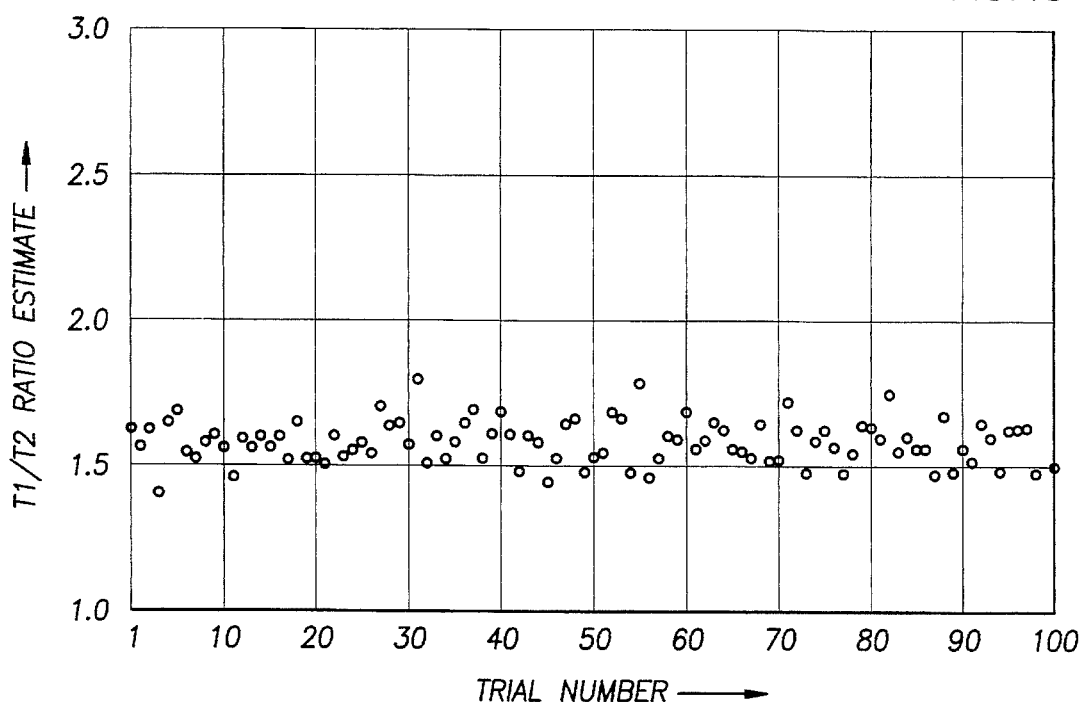
Figure 46:
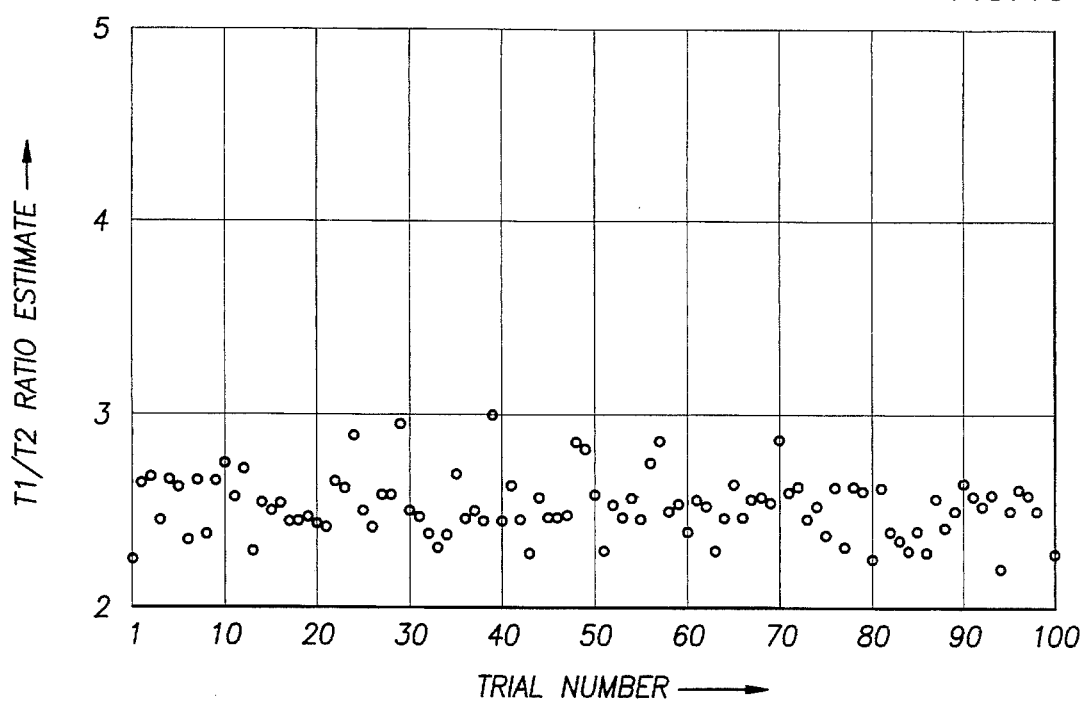

The second set of estimates for the B-distribution are shown in FIGS. 41–42. Note that the longer decay times in this distribution result in more sensitivity to the wait time. This is reflected in smaller standard deviations for the estimates. For these results the total rms errors (bias plus noise) in the estimates are: $\Sigma$=0.12 for $\xi$=1.5 and $\Sigma$=0.16 for $\xi$=2.5. The third set of estimates are shown in FIGS. 43–44 for the C-distribution for which $\Sigma$=0.09 for both $\xi$=1.5 and 2.5. Finally, in FIGS. 45–46 are shown estimates for the bimodal D-distribution for which $\Sigma$=0.12 for $\xi$=1.5 and $\Sigma$=0.15 for $\xi$=2.5, respectively. A simple expression relating the total rms sample error defined by eqs. (79) and (80) to the population standard deviation and bias error is derived in Appendix D.

Propagation of Errors

The foregoing results indicate that it should be possible to obtain borehole estimates of $\xi$ to within errors on the order of ±0.20.

These results, however, do not reveal how sensitive CMR log outputs are to errors in $\xi$ which is of practical importance.

Therefore an important question that remains to be answered is "how does use of an incorrect ratio, say e.g., $\xi_0$=1.5, in the signal processing algorithm propagate via the polarization correction to the CMR log outputs?"

To study this question further, synthetic CMR waveforms each consisting of 1800 spin echoes with a S/N ratio of 100 dB were computed for each of the $T_2$-distributions in FIG. 37. Each waveform was computed using a pulse sequence with a single wait time which corresponds to the conventional pulse sequence used by the CMR EXP tool during depth logging operations.

Eleven waveforms were computed for each distribution using equally spaced values of wait times in the range from 0.8 to 2.6 seconds. The high S/N ratio was chosen so that the results of the simulations would not be clouded by noise errors but instead would be strictly representative of the polarization correction errors. The waveforms were processed using the CMR tool signal processing algorithm and the results are shown in FIGS. 47–58.

The results are displayed as percent errors in total NMR porosity ($\phi_{nmr}$), free-fluid porosity ($\phi_f(33)$), and logarithmic mean relaxation time ($\overline{T}_{2,log}$) plotted versus wait time. In computing the errors a fixed value $\xi_0$=1.5 was used in the signal processing algorithm. The dashed curves represent bounds on the errors for $1.0 \leq \xi \leq 2.5$. The solid line was computed with, $\xi=\xi_0$=1.5, for which there should be zero percent error in all quantities for all wait times. That is, if one uses the correct $T_1/T_2$ ratio in the signal processing algorithm then the polarization correction will exactly correct for the effects of finite wait time. Note that the aforementioned theoretical result is only approximately attained due to numerical noise (e.g., roundoff errors) in the computations.

Figure 47:
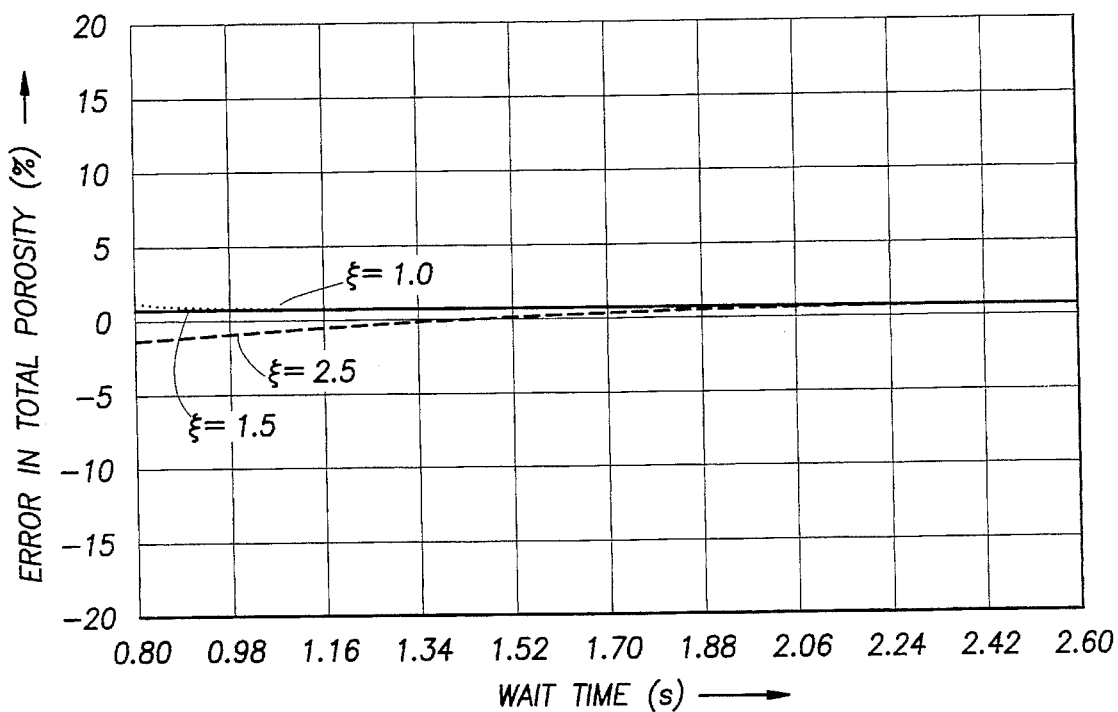
FIGS. 47–58 illustrate the percent error in total porosity, $\phi_{nmr}$, versus wait time shown in FIGS. 47, 50, 53, and 56, percent error in Free Fluid, $\phi_f(33)$, versus wait time shown in FIGS. 48, 51, 54, and 57, and percent error in $T_{2,log}$ versus wait time shown in FIGS. 49, 52, 55, and 58 for the following distributions relating to the signal distributions shown in FIG. 37: the A-distribution, B-distribution, C-distribution, and D-distribution, where the dashed curves represent the bounds for true $T_1/T_2$ ratios, where $\xi$ is is greater than or equal to 1.0 and less than or equal to 2.5, where the solid curve is $\xi$=1.5, and where all curves are computed for $\xi_0$=1.5.
Figure 48:
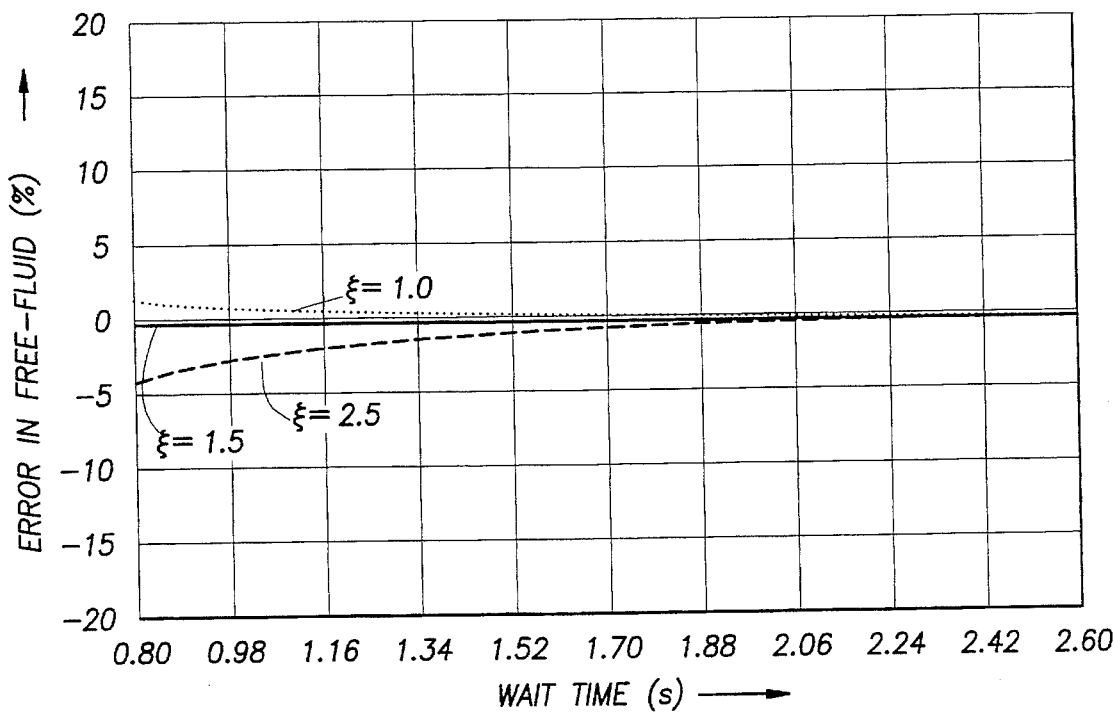
Figure 49:
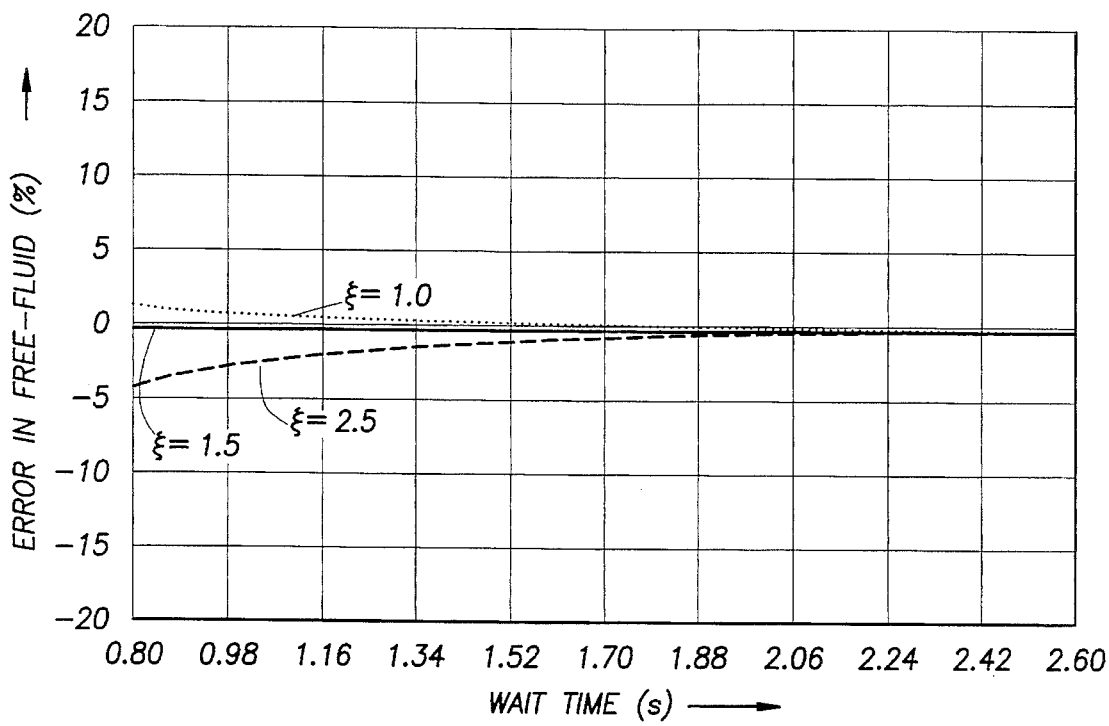

It is useful to point out a few important features of the results shown in FIGS. 47–58. First, as expected, for $T_2$-distributions like the A-distribution which have relatively fast relaxation times, the polarization correction is negligible for practical purposes as can be seen in FIGS. 47–49. In such formations, typically shaly sands, wait times can be shortened with minimal errors resulting from polarization corrections. Thus logging speeds can be increased since using the minimum acceptable wait time is equivalent to maximizing logging speed for a fixed sampling rate. Note also that the theoretical zero error line, i.e., for $\xi=\xi_0$, divides the porosity errors into two regions: (1) for $\xi<\xi_0$ the porosities are overestimated by the signal processing and (2) for $\xi>\xi_0$ the porosities are underestimated.

Figure 50:
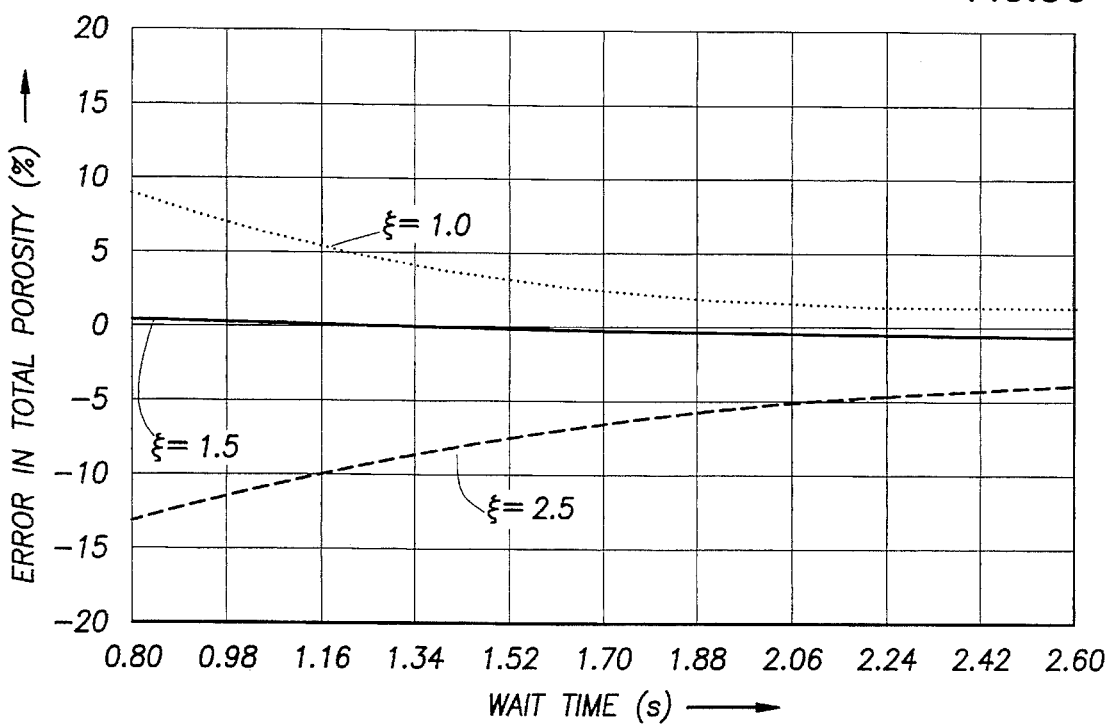
Figure 51:
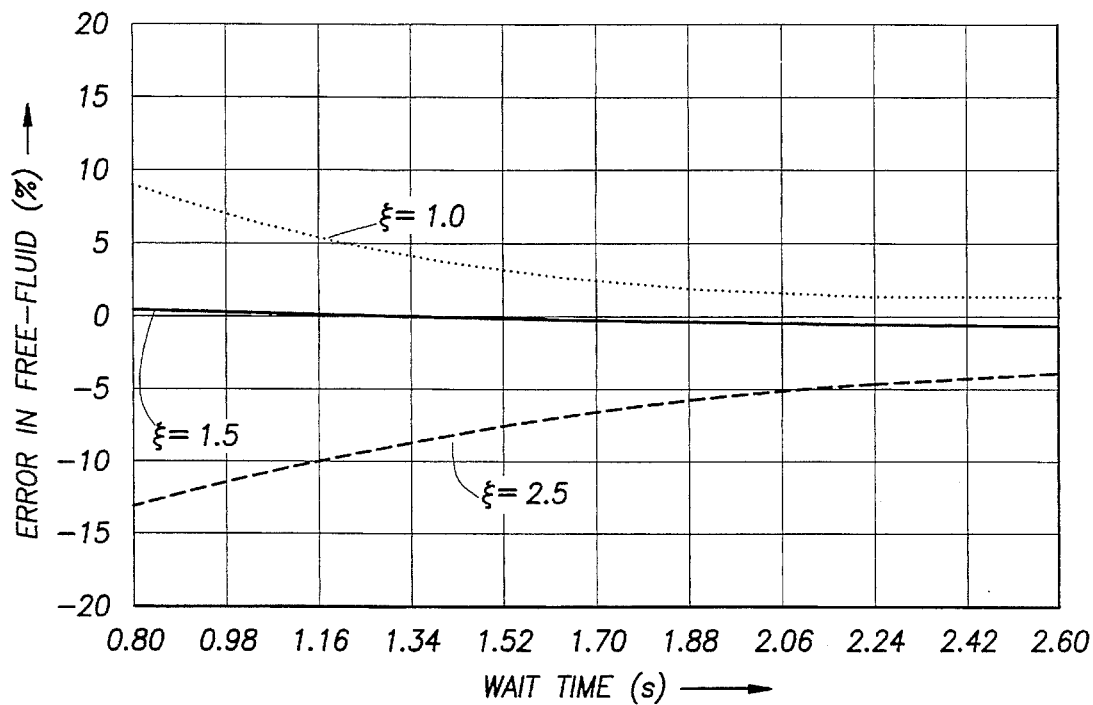
Figure 52:
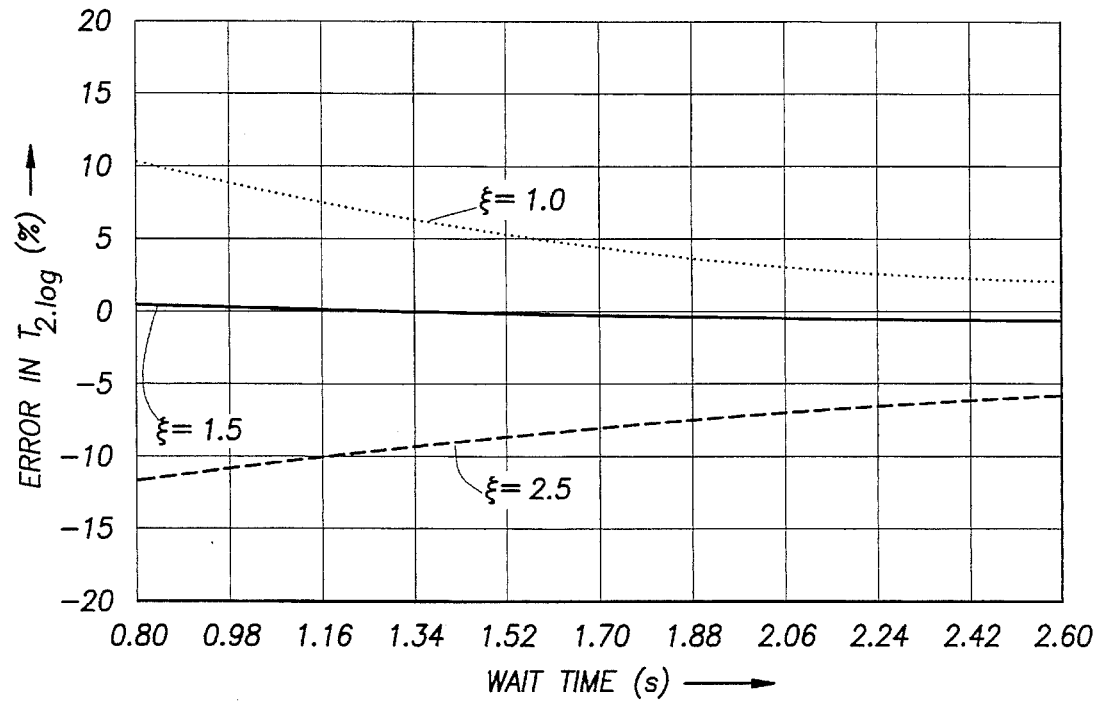
Figure 53:
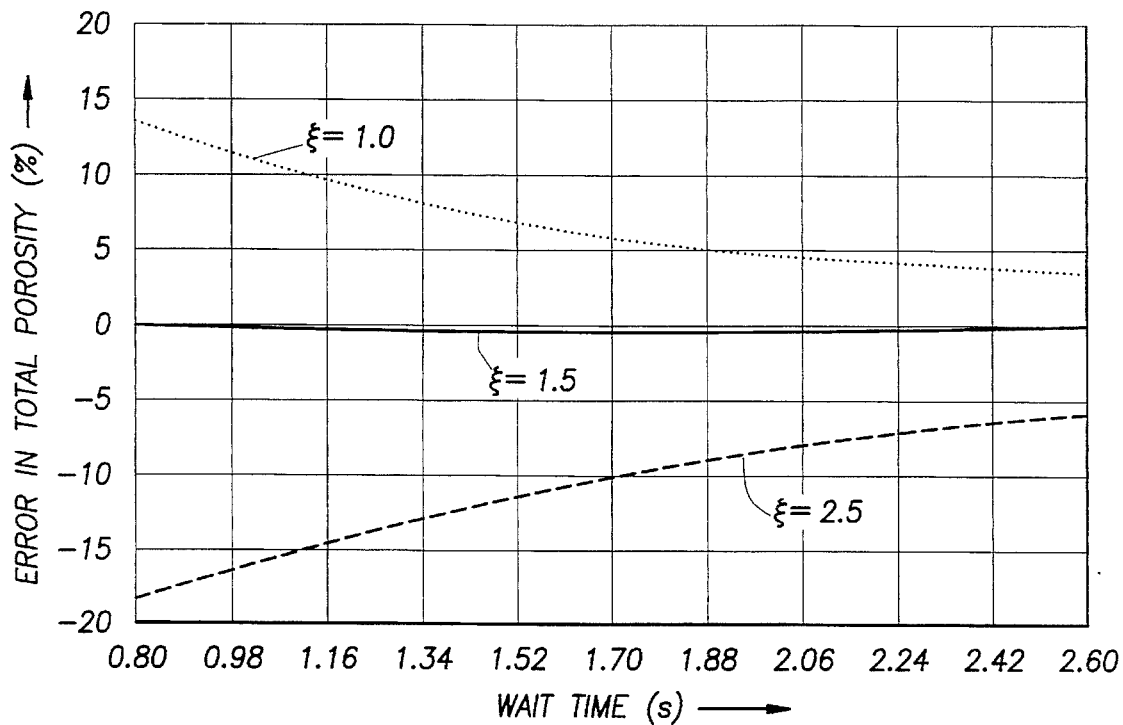
Figure 54:
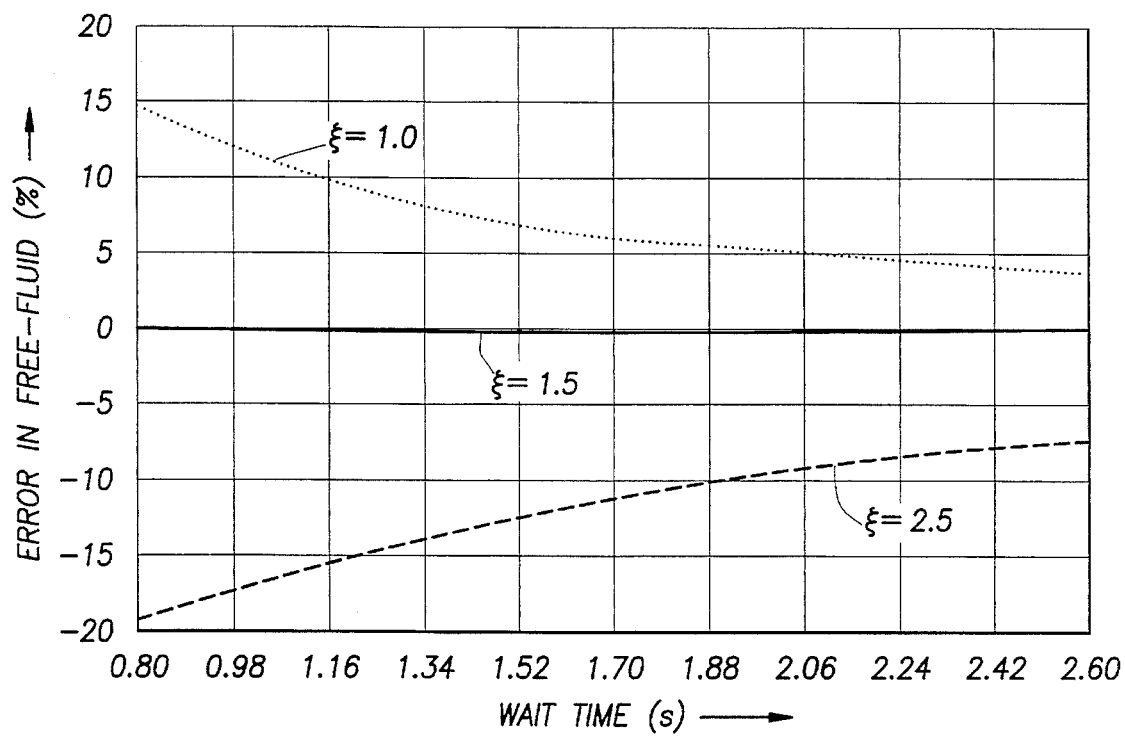
Figure 55:
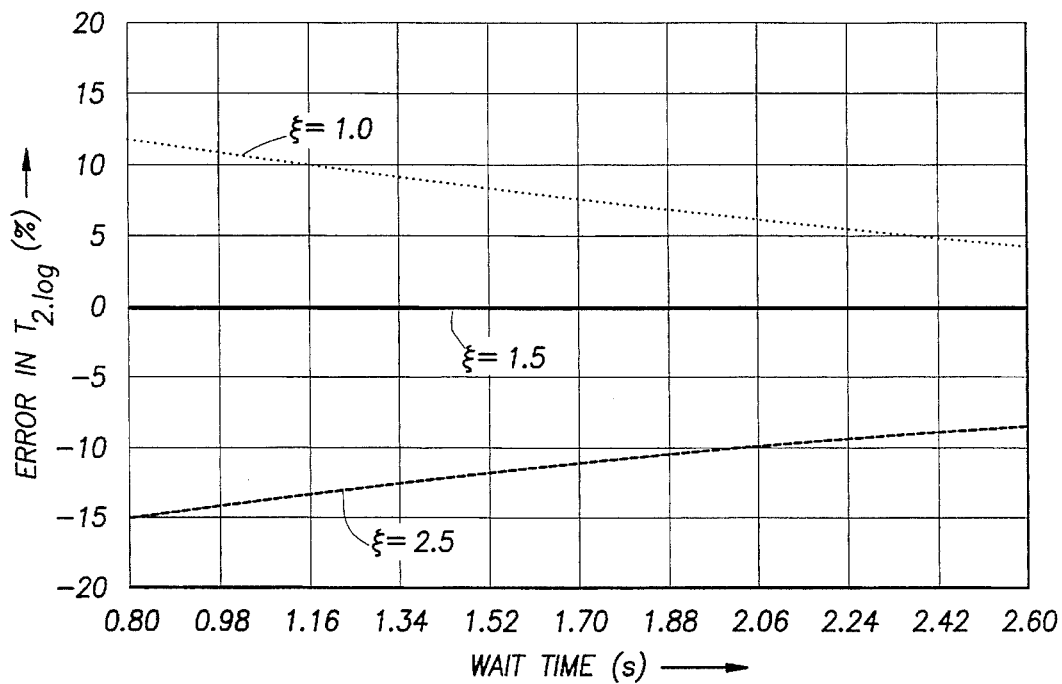
Figure 56:
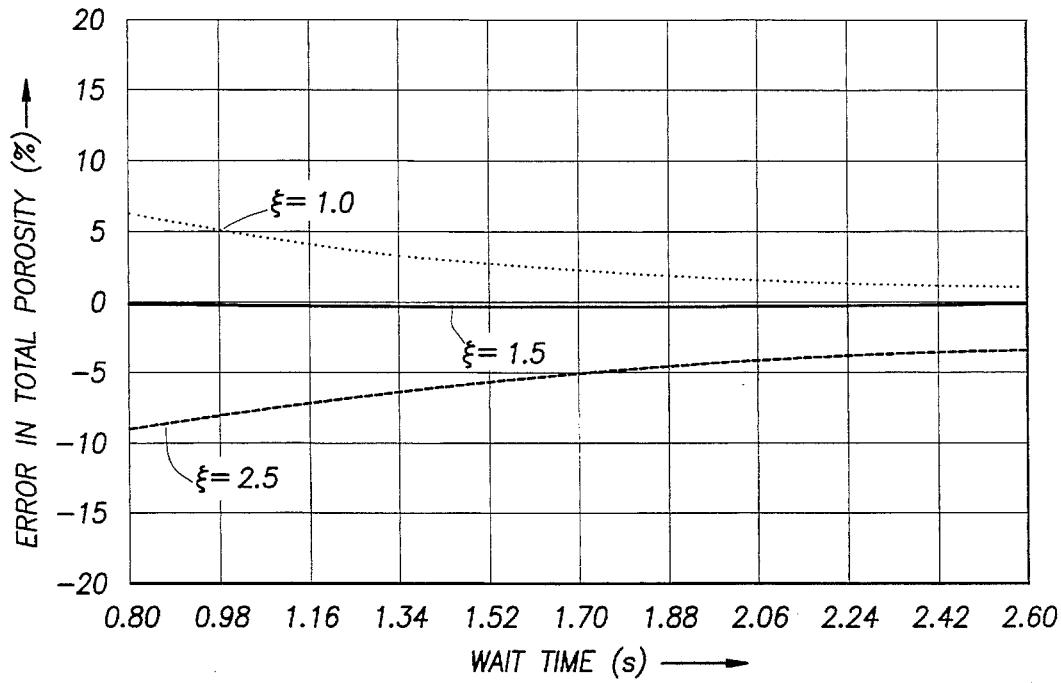
Figure 57:
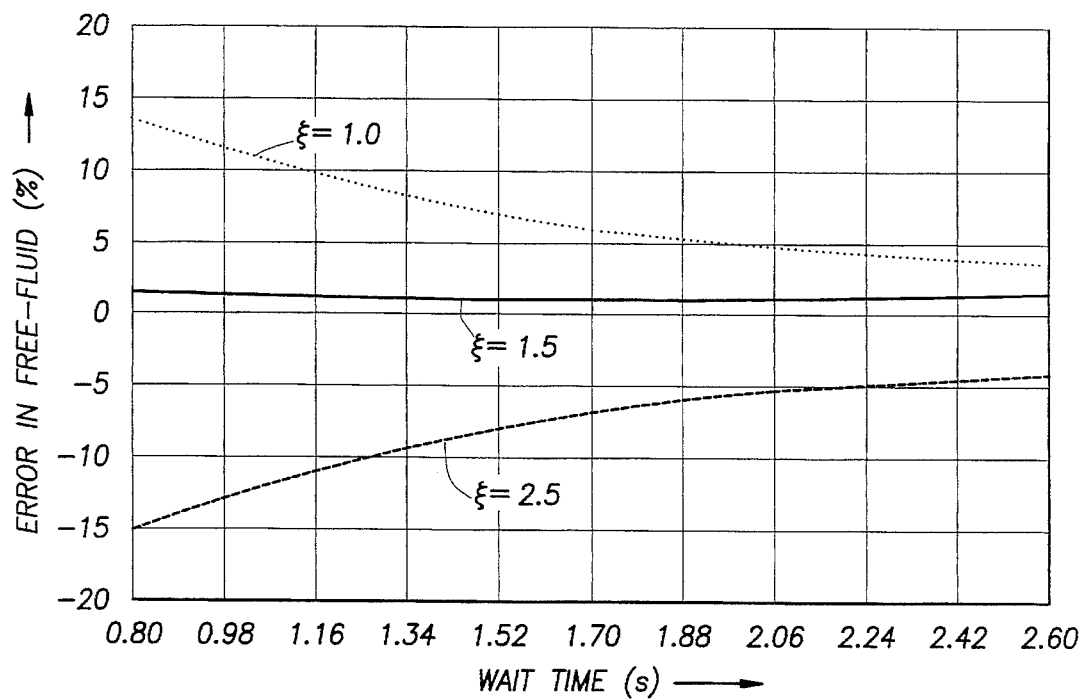
Figure 58:
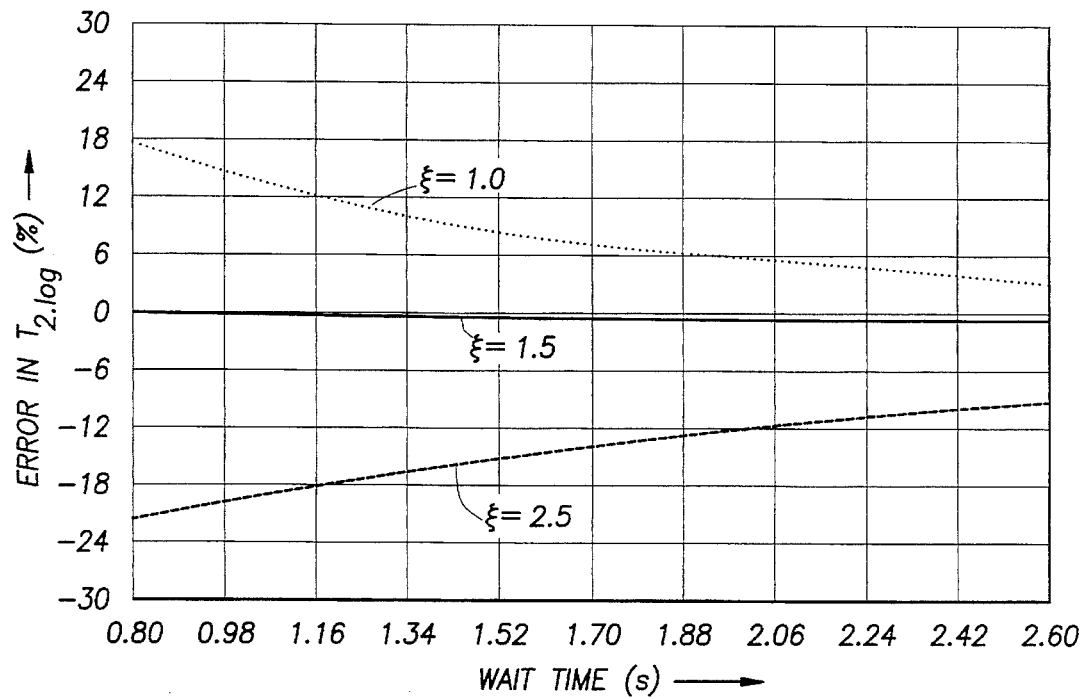

Secondly, as shown in FIGS. 50–52, the percent errors in formations with relatively long NMR decay times like the B-distribution can be significant. The errors can be reduced by increasing wait times or using values of $\xi_0$ close to the true ratios ($\xi$). The latter alternative, of course, requires using multi-wait time logging sequences in order to estimate the true ratios. The results in FIGS. 50–52 show that the errors initially decrease relatively quickly with increasing wait time and then flatten out. Thus, using longer wait times will produce diminishing returns once the error curves have flattened out. In FIGS. 53–58, similar plots for the C and D-distributions, respectively, are displayed.

Figure 59:
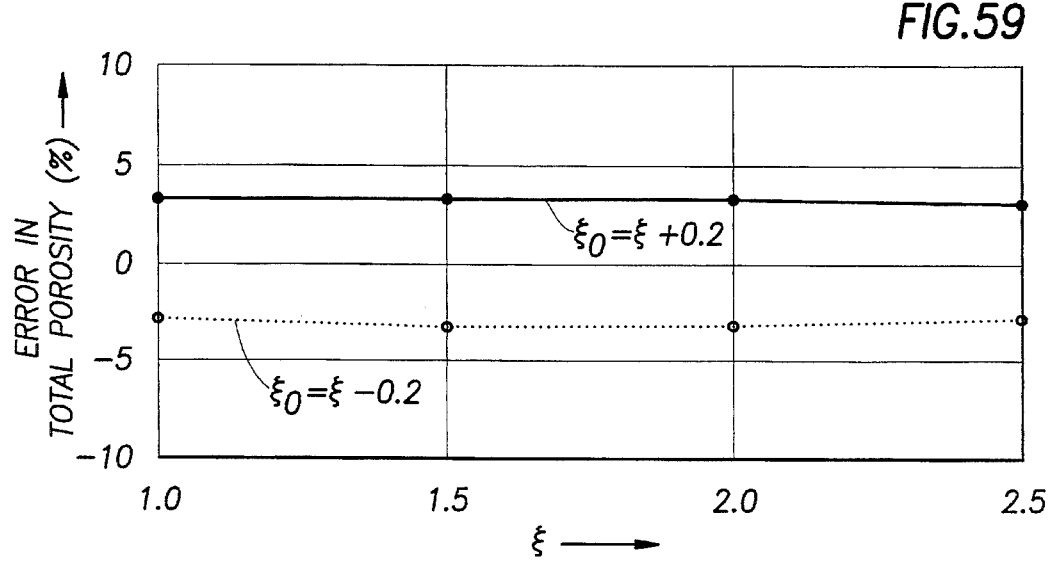
FIGS. 59–61 illustrate percent error in total porosity, FIG. 59, percent error in Free Fluid, FIG. 60, and percent error in $T_{2,log}$, FIG. 61, versus the true $T_1/T_2$ ratio, $\xi$, where the solid curves were computed for $\xi_0 = +0.2$, and the dashed curves were computed for $\xi_0 = \xi - 0.2$.
Figure 60:
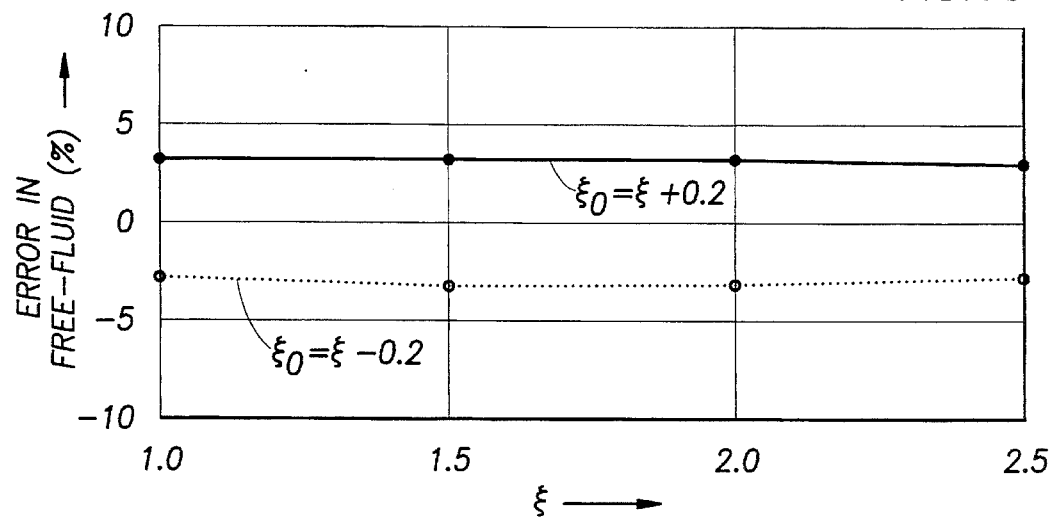
Figure 61:
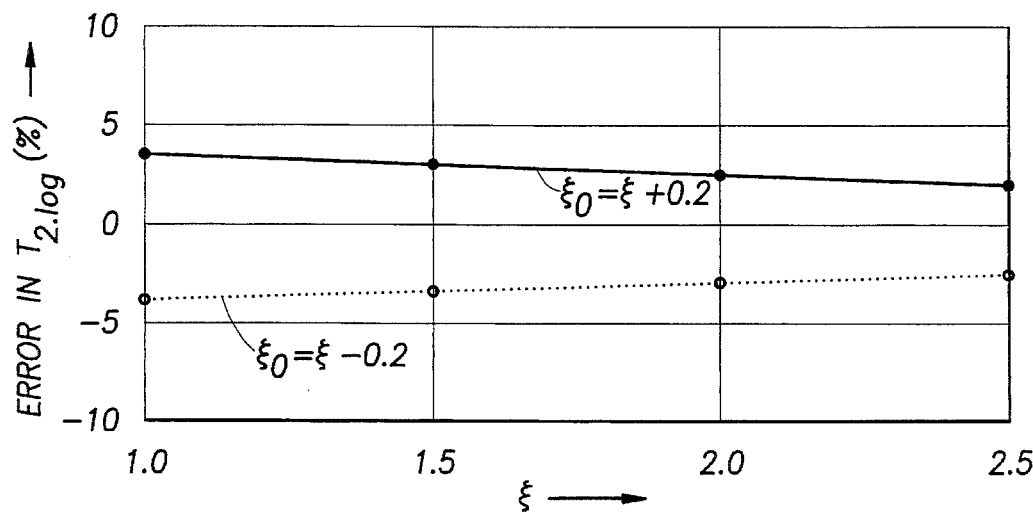

Finally, in FIGS. 59–61, the percent errors for the C-distribution are displayed assuming that $\xi$ is known to within 0.20 (e.g., $\xi_0=\xi\pm0.2$). The wait time is equal to 1.3 seconds for this example. Note that the percent errors are of the order of 3 percent in all quantities. Similar computations for the other three distributions in FIG. 37 have been performed and result in smaller percent errors. This example thus illustrates, for the distributions in FIG. 37, that under best conditions the maximum percent errors would be of the order of 3 percent. The 3 percent accuracy level is acceptable for practical petrophysical applications. This provides confidence that the estimates obtained from eq. (78) are sufficiently good to allow an accurate polarization correction to be applied.

Figure 62:
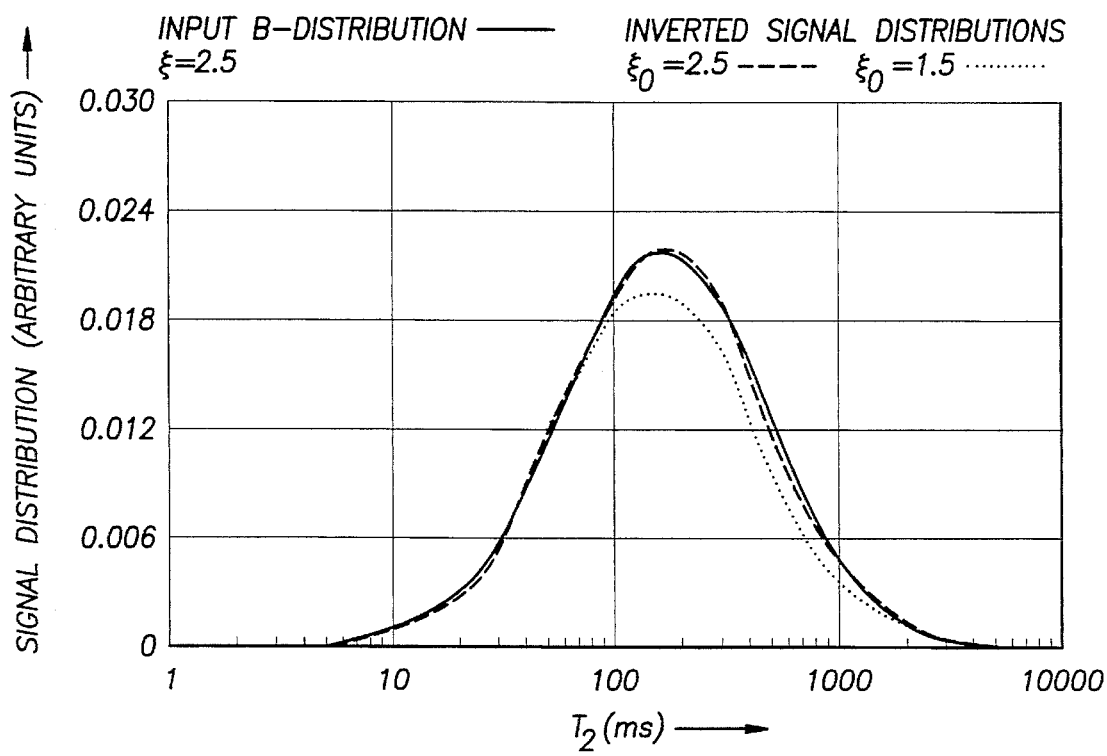
FIGS. 62–63 illustrates the effects of incorrect $T_1/T_2$ ratio on the $T_2$-distributions computed from the signal processing for a short (FIG. 62) and a long (FIG. 63) wait time, the two curves representing signal distribution versus relaxation time $T_2$, FIG. 62 representing input B-distribution where $\xi=2.5$, wait time $=0.8$ sec, 1800 echoes, 1 percent noise, $\xi_0=2.5$ for dashed curve and $\xi=1.5$ for dotted curve.
Figure 63:
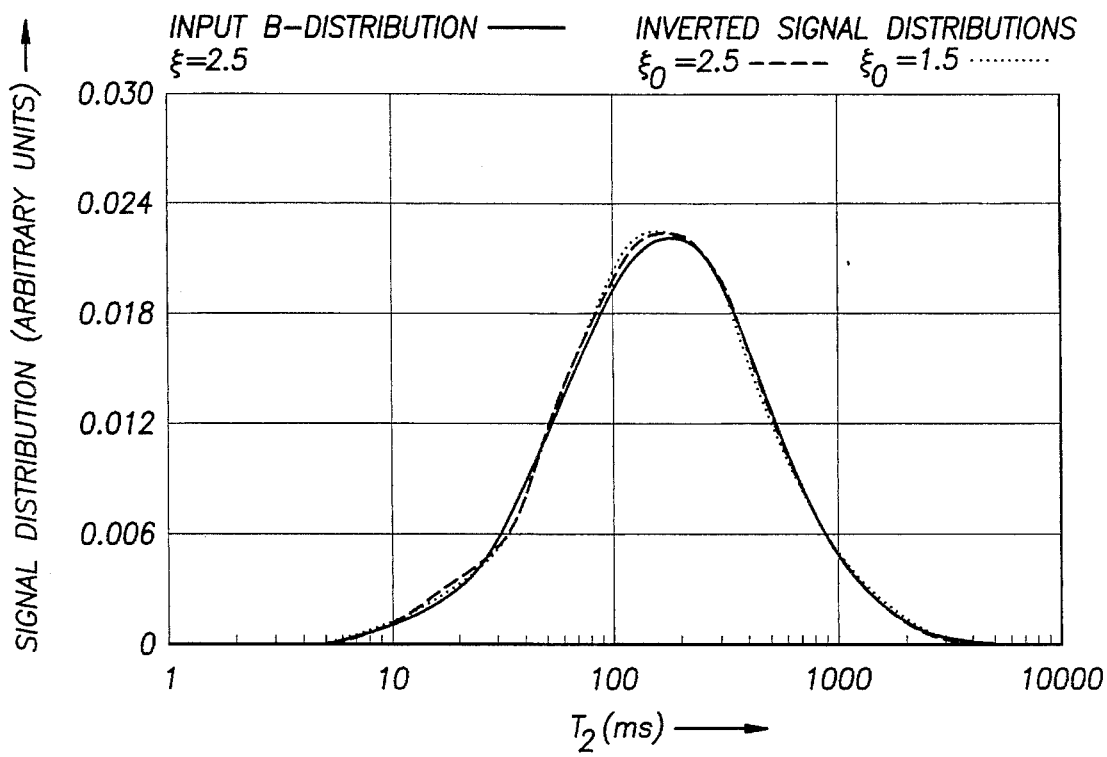

The foregoing results have displayed the percent errors in CMR log outputs, $\phi_{nmr}$, $\phi_f(33)$, and $T_{2,log}$, all of which are derived by performing various integrals over the computed $T_2$-distributions. In FIGS. 62–63, the effects of using an incorrect value of $\xi_0$ on the computed $T_2$-distributions themselves for a short (0.8 s) and a long (3.0 s) wait time are shown. For reference the $T_2$-distributions computed using the true ratio, $\xi=\xi_0$=2.5, are also shown. For the short wait time it is clear that the total porosity (proportional to the area under the distribution) is underestimated as shown previously in FIG. 50. Moreover, for the long wait time, note that the polarization correction is negligble. A high S/N ratio (40 dB) was used for the computations in FIGS. 62–63 so that noise effects on the computed $T_2$-distributions would not obscure the effect being studied here.

Updated $T_2$-Distributions and Log Outputs

The discussion in a previous section focussed attention on one of the outputs of the $T_1/T_2$ ratio algorithm, i.e., the estimate of the $T_1/T_2$ ratios. For each of the $N_{wt}$ wait times in a multi-wait time pulse sequence, there are the standard set of CMR log outputs such as $\phi_{nmr}$, $\phi_f(33)$, etc. An additional set of log outputs is computed from the updated $T_2$-distributions. That is, each log output is an array with the wait time as an index.

This section first shows an example of an updated $T_2$-distribution. As noted earlier, the updated $T_2$-distributions are improved estimates because they incorporate information obtained from all of the CPMG waveforms in a multi-wait time sequence. Additionally, the updated distributions are derived simultaneously with the $\xi$ estimates and therefore have the correct polarization correction automatically applied.

Figure 64:
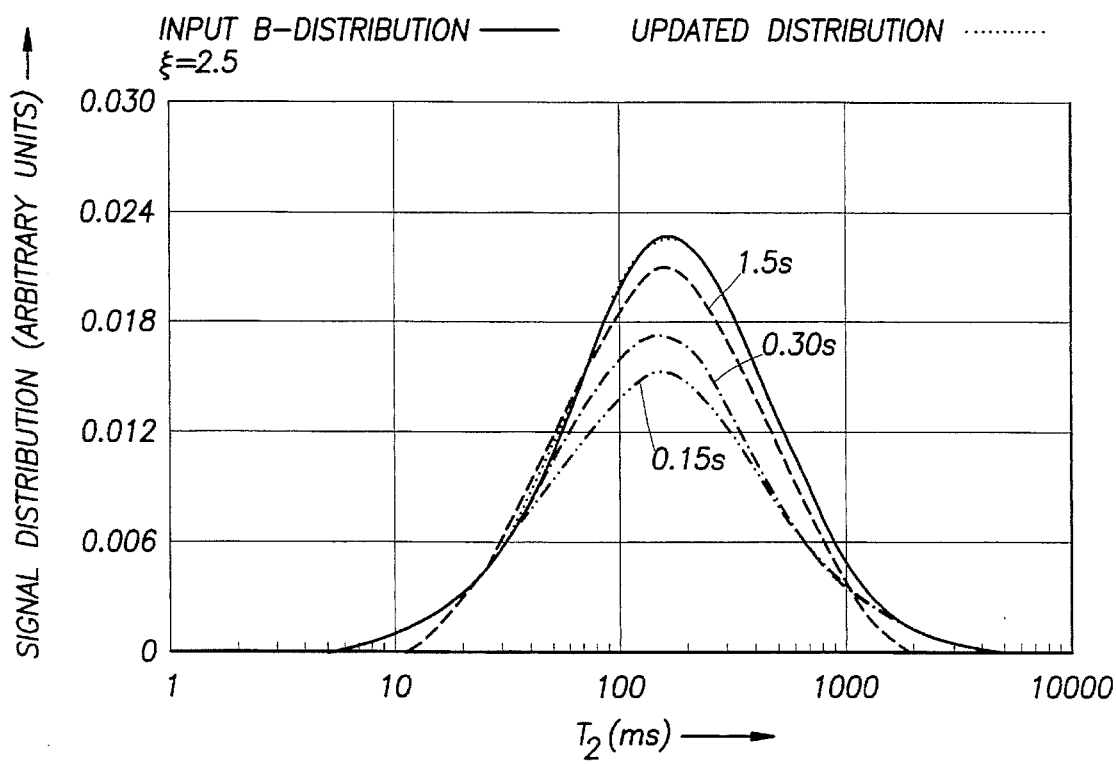
FIGS. 64–65 illustrates outputs of the multi-wait time method of the present invention, and in particular, an example showing an updated $T_2$-distribution computed using 300, 600, and 1800 echoes for wait times of 0.15 s, 0.30 s, and 1.5 s, respectively, FIGS. 64 and 65 both representing signal distribution versus time $T_2$ for the B-distribution having $\xi=2.5$, $\xi_0=1.5$, 1 percent noise, the estimated ratio, $\hat{\xi}$ for FIG. 64 being 2.47, $\hat{\xi}$ for FIG. 65 being 2.55.

In FIG. 64, three input $T_2$-distribution and outputs from minimization of the cost function in eq. (78) are shown for a multi-wait time sequence with three wait times. In this example, the multi-wait time CPMG waveforms each consists of 1800 spin echoes with a S/N ratio of 40 dB. Note that the updated $T_2$-distribution agrees closely with the input B-distribution. Also note that the estimate $\hat{\xi}=2.52$ agrees very closely with the true ratio of 2.5. In this example, the number of echoes is the same for all CPMG waveforms.

Figure 65:
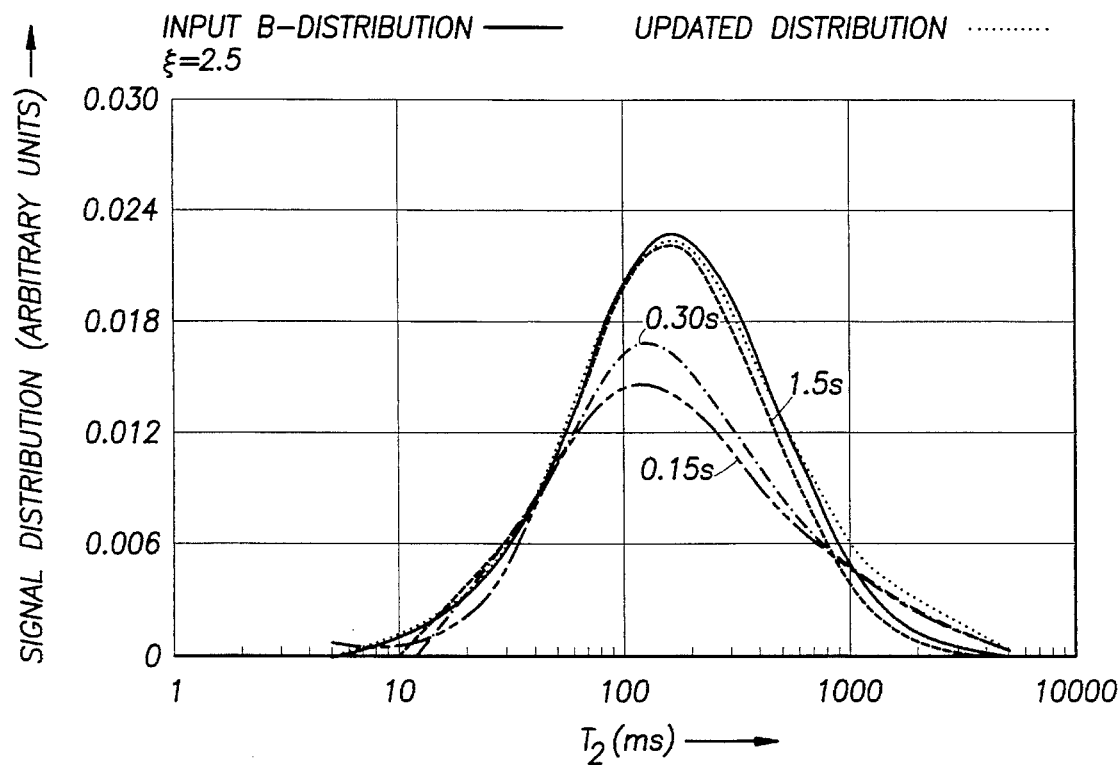

As noted previously, with the CMR tool it is necessary to collect fewer echoes for the shorter wait times due to tool duty cycle restrictions. In FIG. 65, we show an example where the waveforms corresponding to the shorter wait times consist of fewer spin-echoes. The effect of collecting too few echoes is to result in inverted $T_2$-distributions not matching the true distributions for long $T_2$ times. The minimum number of echoes required depends on the distribution being inverted but the long $T_2$ components must be well represented in the data.

The next set of simulations shows how the algorithm can be used to obtain improved log outputs while depth logging in formations with $T_2$-distributions that have high porosities and long $T_1$ decay times. This includes many carbonate and sandstone formations. To illustrate the point, the simulations are based on the C-distribution in FIG. 37 for which relatively large errors can result in the log outputs (see FIG. 53–55). Below we show the results of a set of numerical simulations for a sample that has a total porosity of 20 p.u. and a true $T_1/T_2$ ratio, $\xi=2.5$. The simulations were conducted with a S/N ratio of 20 dB (10 percent noise). An assumed $T_1/T_2$ ratio, $\xi_0=1.5$, was used in the signal processing algorithm.

Figure 66:
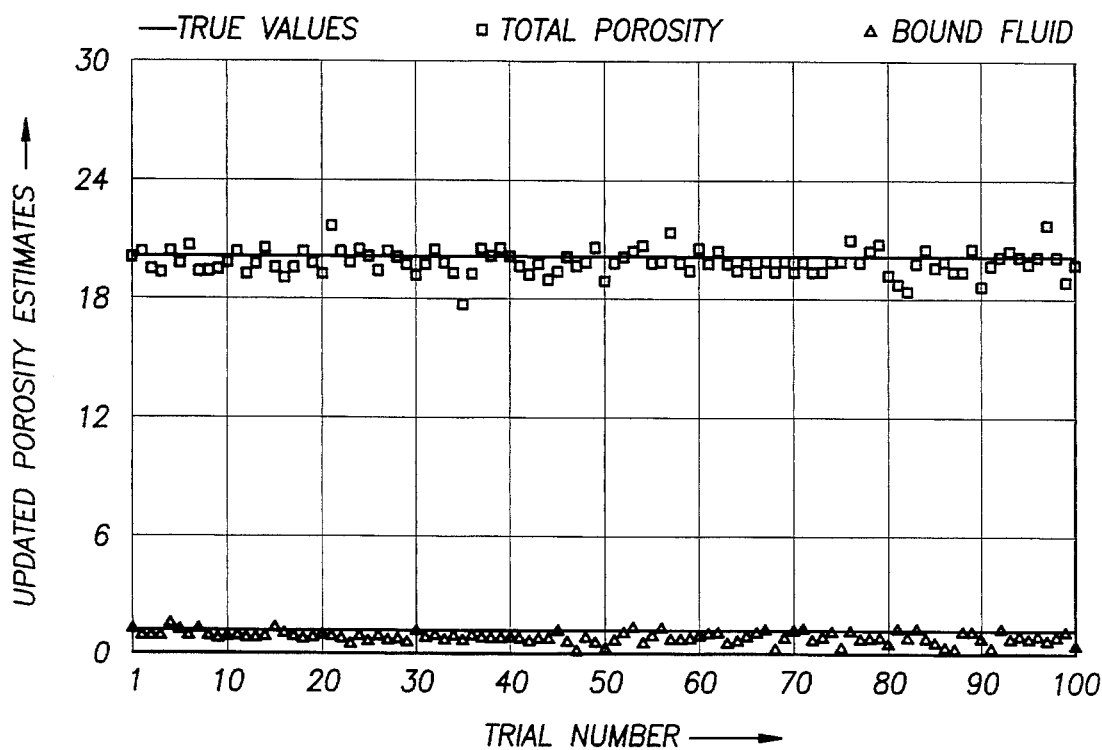
FIGS. 66–68 illustrates multi-wait time depth logging, and in particular, the estimated total and bound fluid porosities computed from the updated $T_2$-distributions using a pulse sequence with 3 wait times, FIGS. 66–68 representing updated porosity estimates versus trial number.
Figure 67:
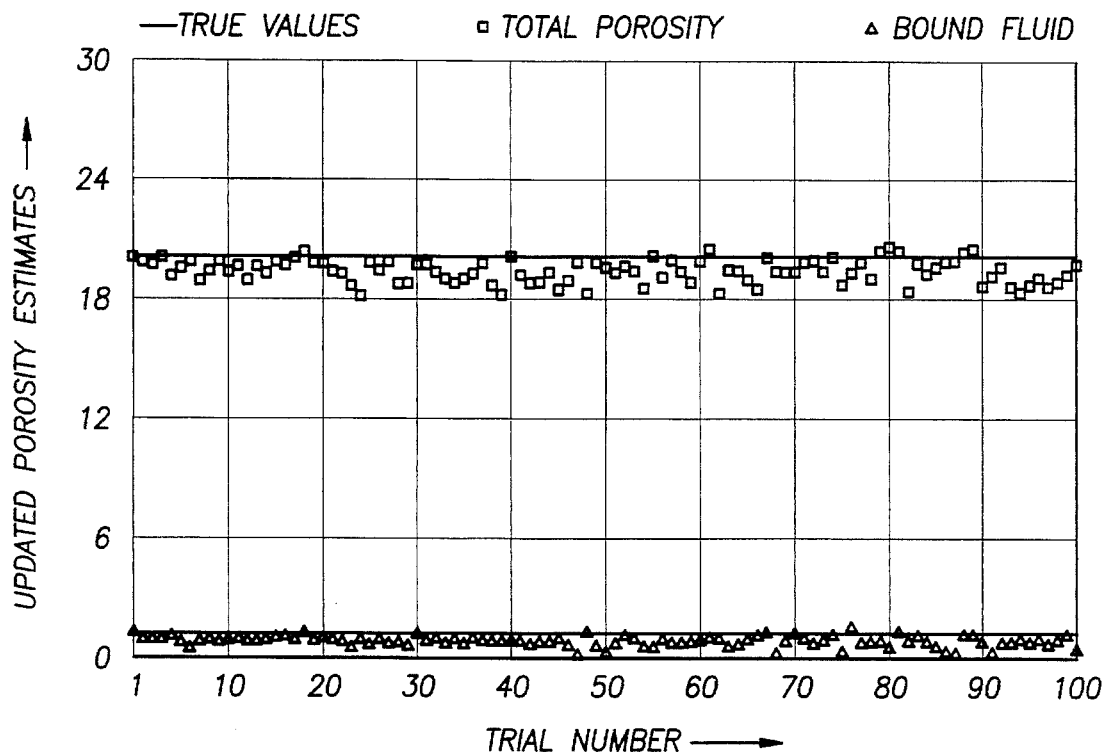
Figure 68:
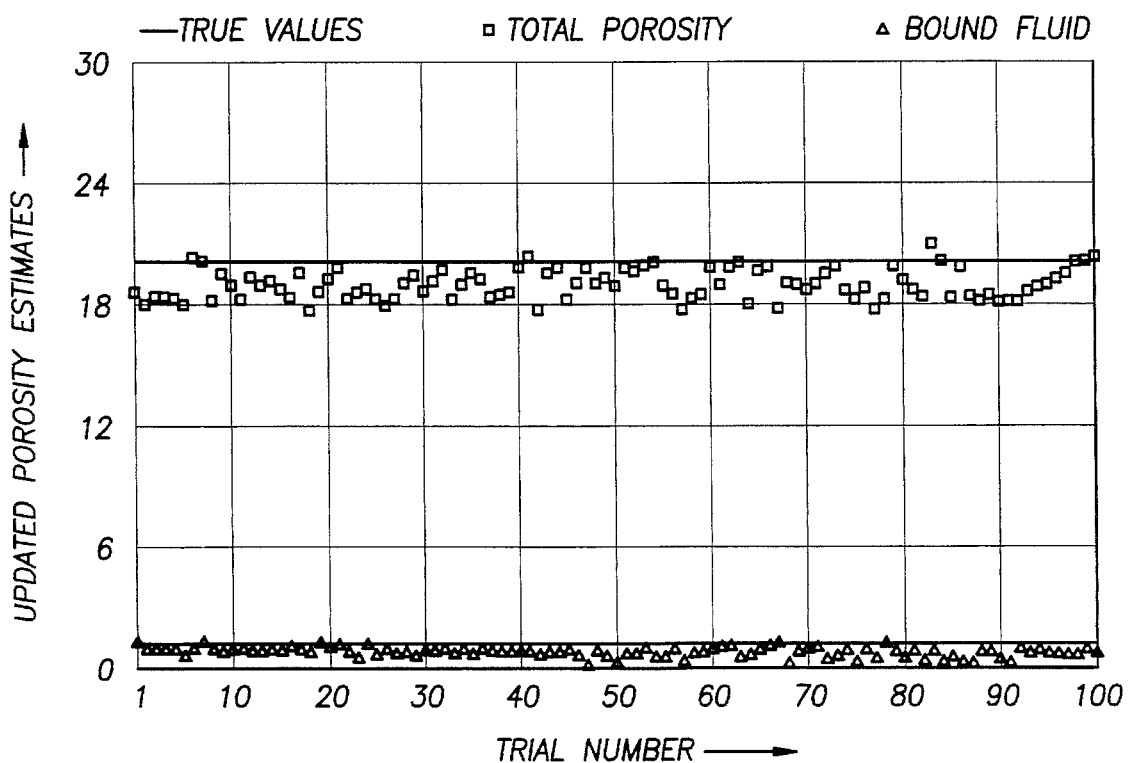

In FIGS. 66–68, three simulations each consisting of 100 trials, are shown for three different multi-wait time pulse sequences. The results for the first pulse sequence are shown in the plot in FIG. 66. This pulse sequence consists of three CPMG spin-echo waveforms with wait times of (0.15, 0.30, 1.2) seconds and corresponding echo numbers of (1200, 1200, 1200). The total time for a single measurement is 2.8 seconds (a PAP is 5.6 seconds). This assumes an inter-echo spacing of 0.32 ms. Note that the accuracy and precision of the updated total porosity estimates are excellent. Similarly for the updated bound fluid estimates which have superior precision compared to a single wait time pulse sequence. The reason for the improved precision is that the updated bound fluid is determined from all three input distributions each of which have comparable precision on bound fluid. The result is akin to averaging three measurements; hence the bound fluid standard deviation is reduced by the factor $\sqrt{3}$.

The plot in FIG. 67 is for a pulse sequence with wait times of (0.15, 0.30, 1.2) seconds with corresponding echo numbers of (300, 600, 1200). The total measurement time is 2.3 seconds. Note that accurate total porosities are still recovered with only a small negative bias. Finally the plot in FIG. 68 shows the updated porosity estimates for a 1.92 second total measurement time with wait times of (0.15, 0.30, 0.8) seconds and with echo numbers of (300, 600, 1200).

Figure 69:
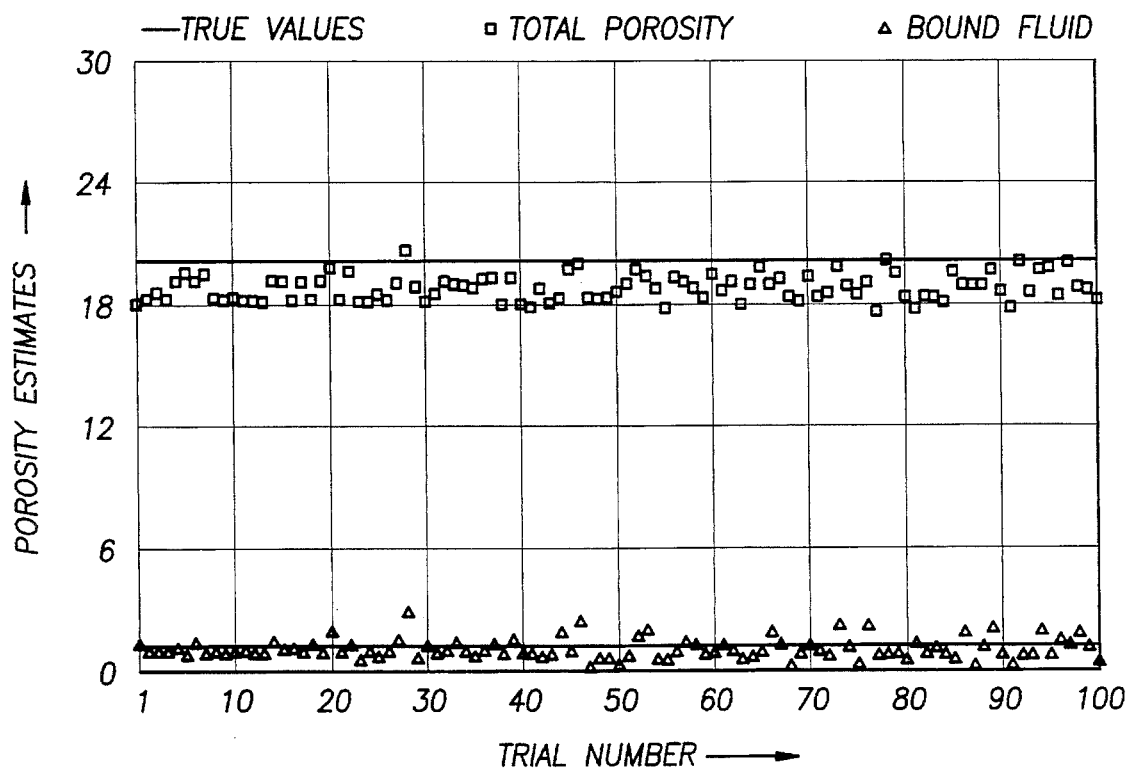
FIGS. 69–71 illustrates single wait time depth logging, and in particular, the estimated total and bound fluid porosities using a standard pulse sequence with one wait time, total times including the wait time and the 1200 echoes in each pulse sequence, FIGS. 69–71 representing porosity estimates versus trial number.
Figure 70:
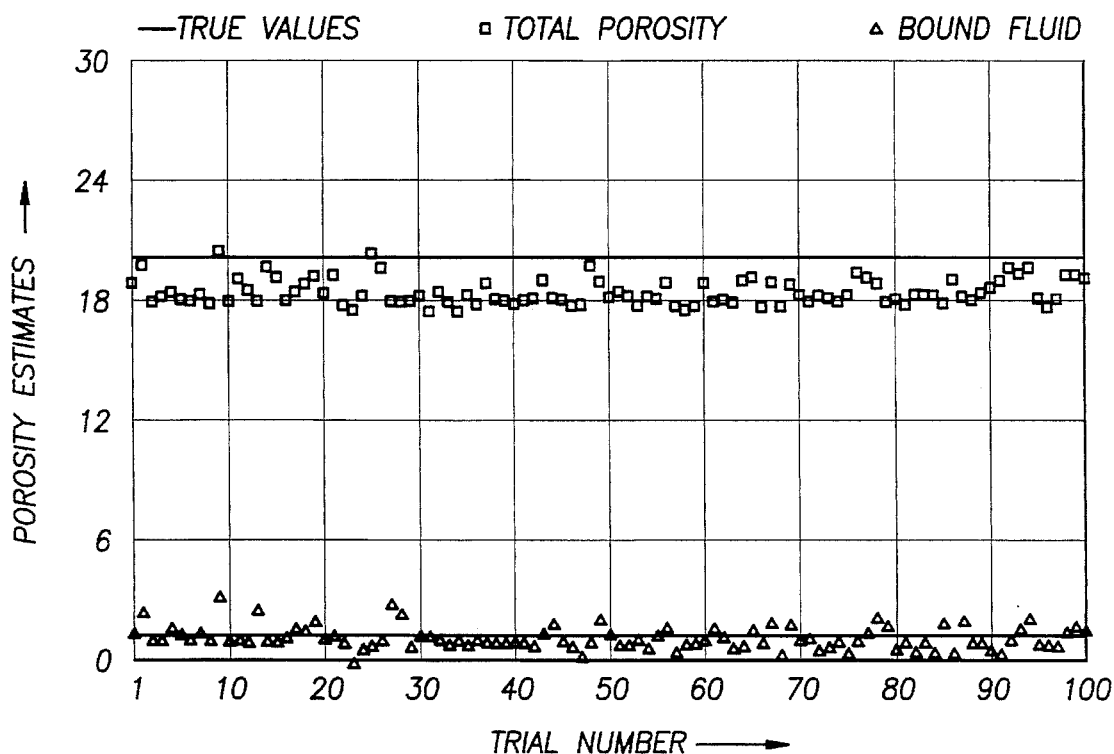
Figure 71:
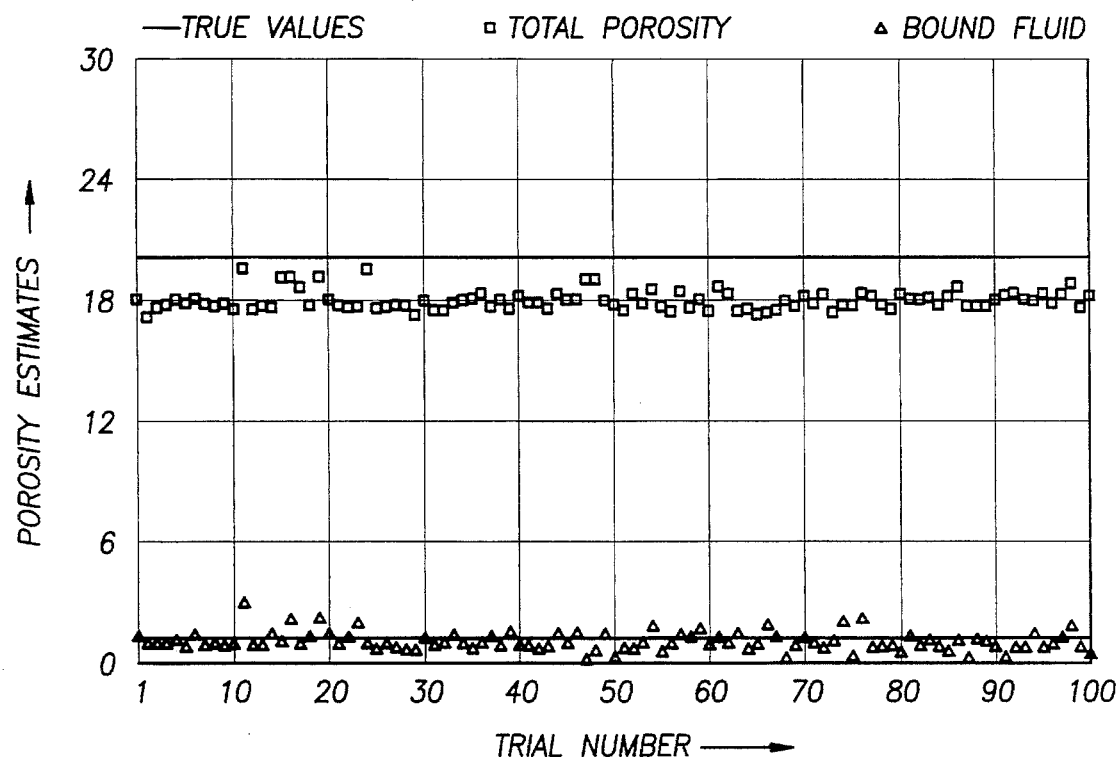
Figure 72:
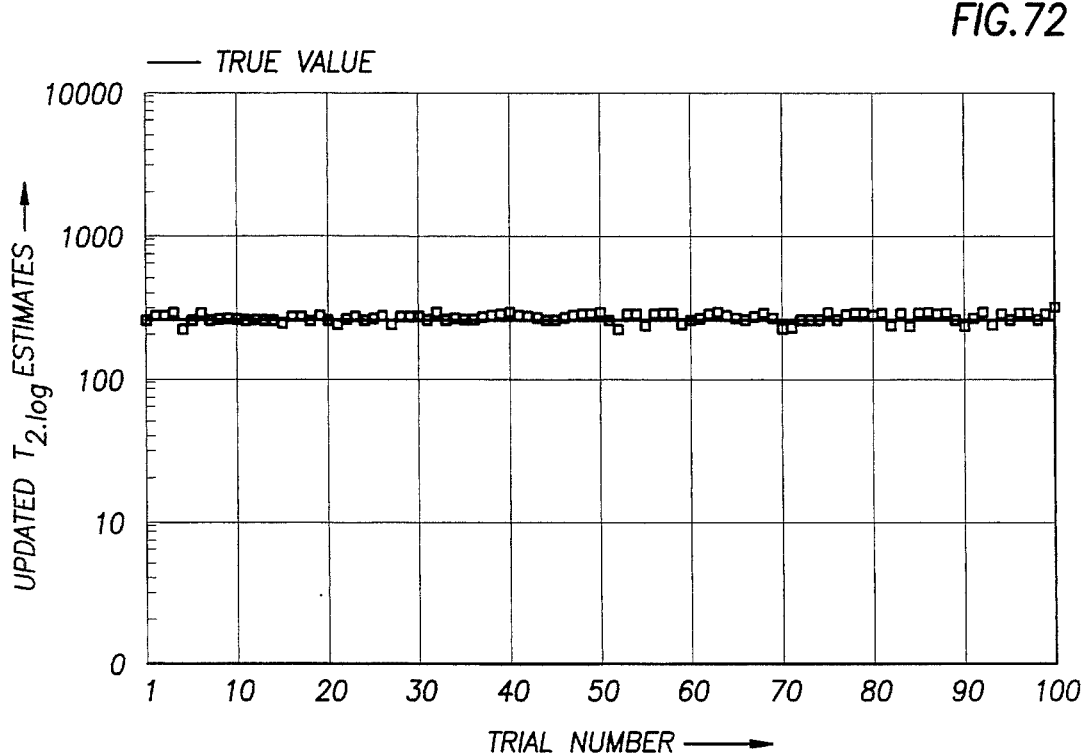
FIGS. 72–74 illustrates multi-wait time depth logging, and in particular, the estimated mean relaxation times ($T_{2,log}$) computed from the updated $T_2$-distributions using a pulse sequence with 3 wait times, total times including all 3 wait times and all echoes in 3 pulse sequences, FIGS. 72–74 representing updated $T_{2,log}$ estimates versus trial number.
Figure 73:
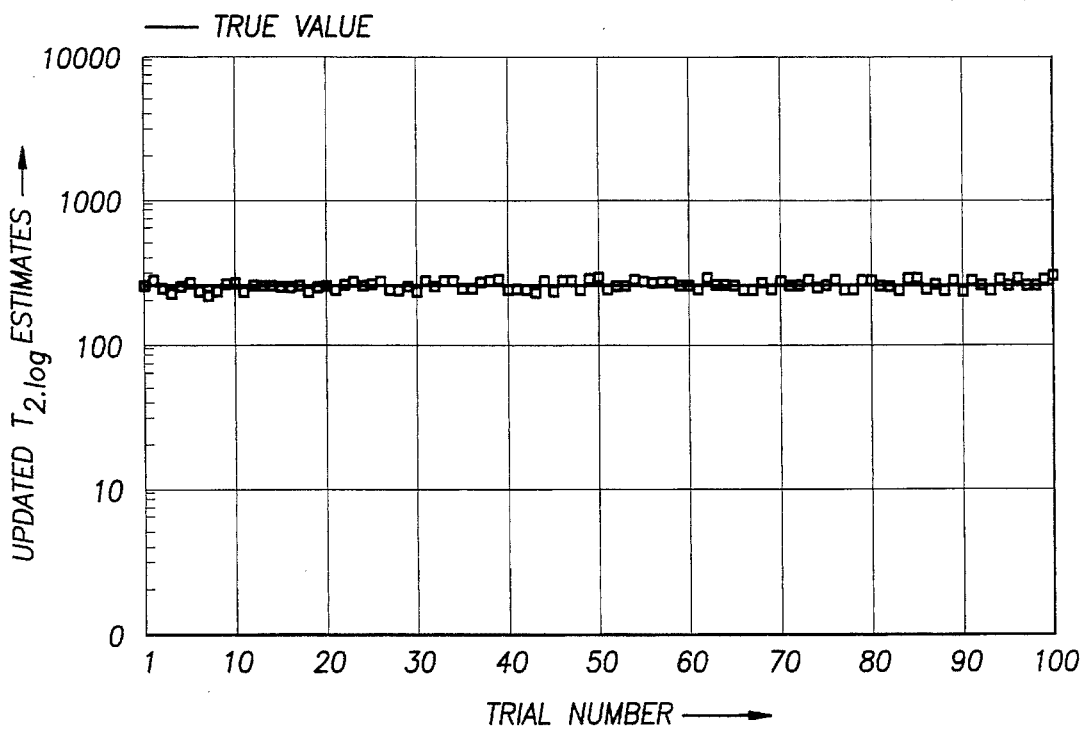
Figure 74:
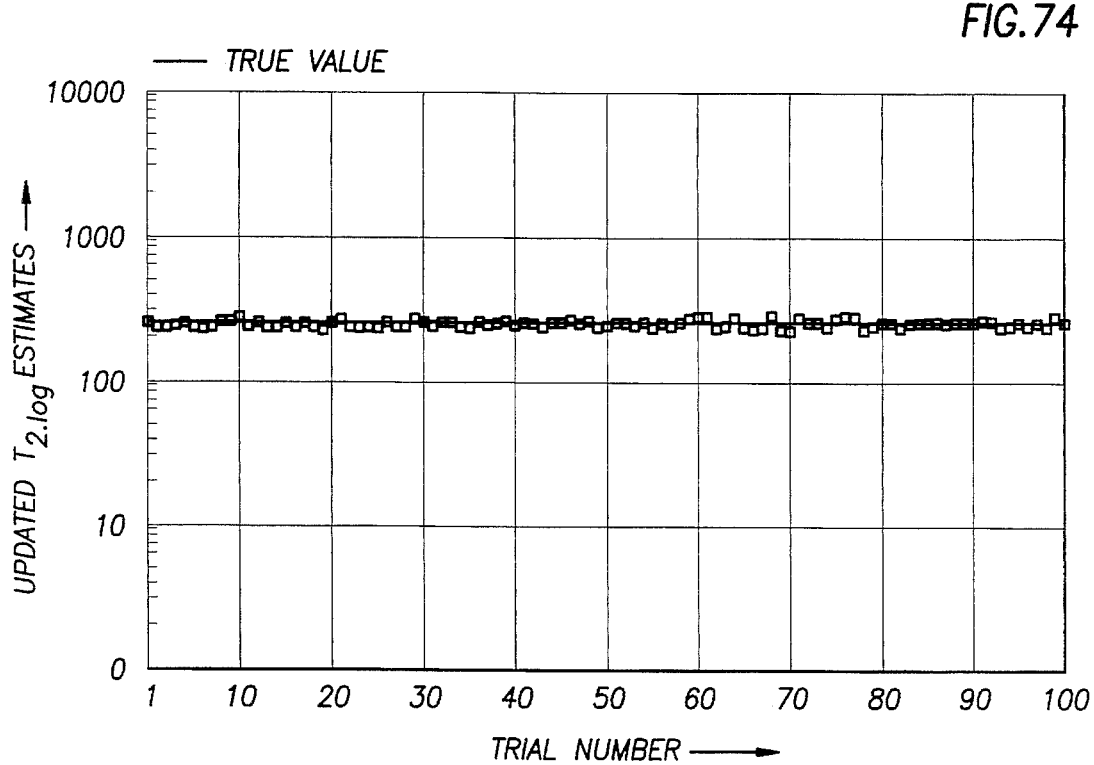
Figure 75:
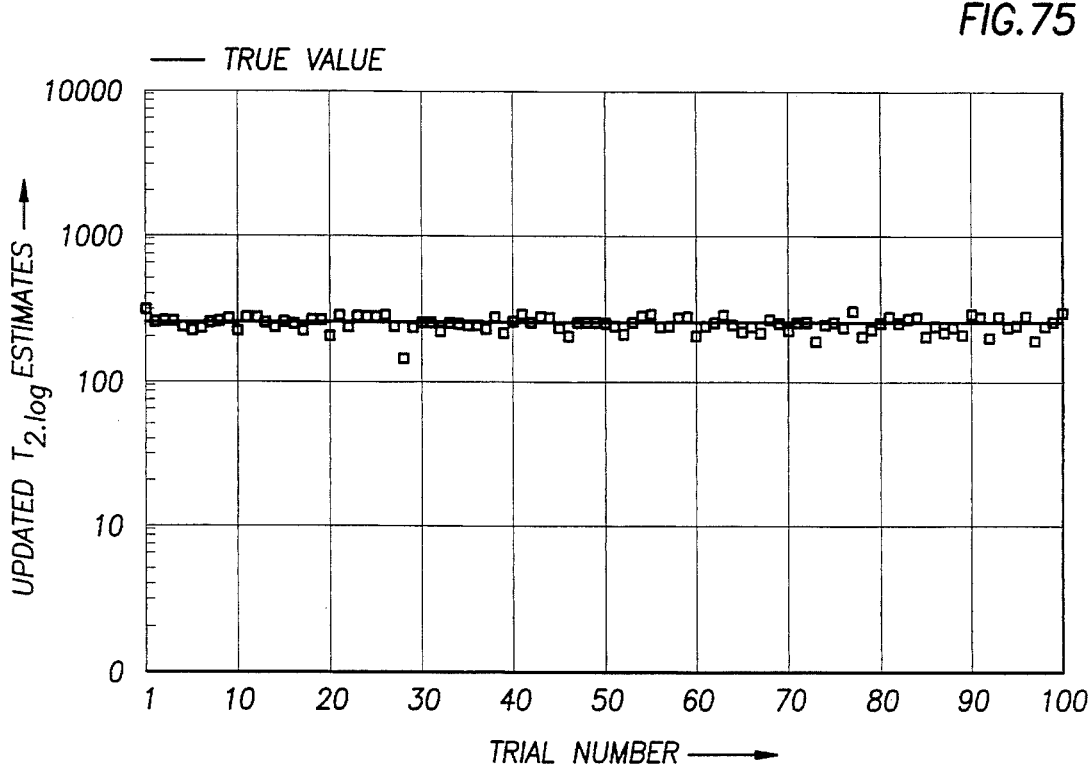
FIGS. 75–77 illustrates single wait time depth logging, and in particular, the estimated mean relaxation times ($T_{2,log}$) using a standard pulse sequence with one wait time, total times including the wait time and the 1200 echoes in each pulse sequence, FIGS. 75–77 representing $T_{2,log}$ estimates versus trial number.
Figure 76:
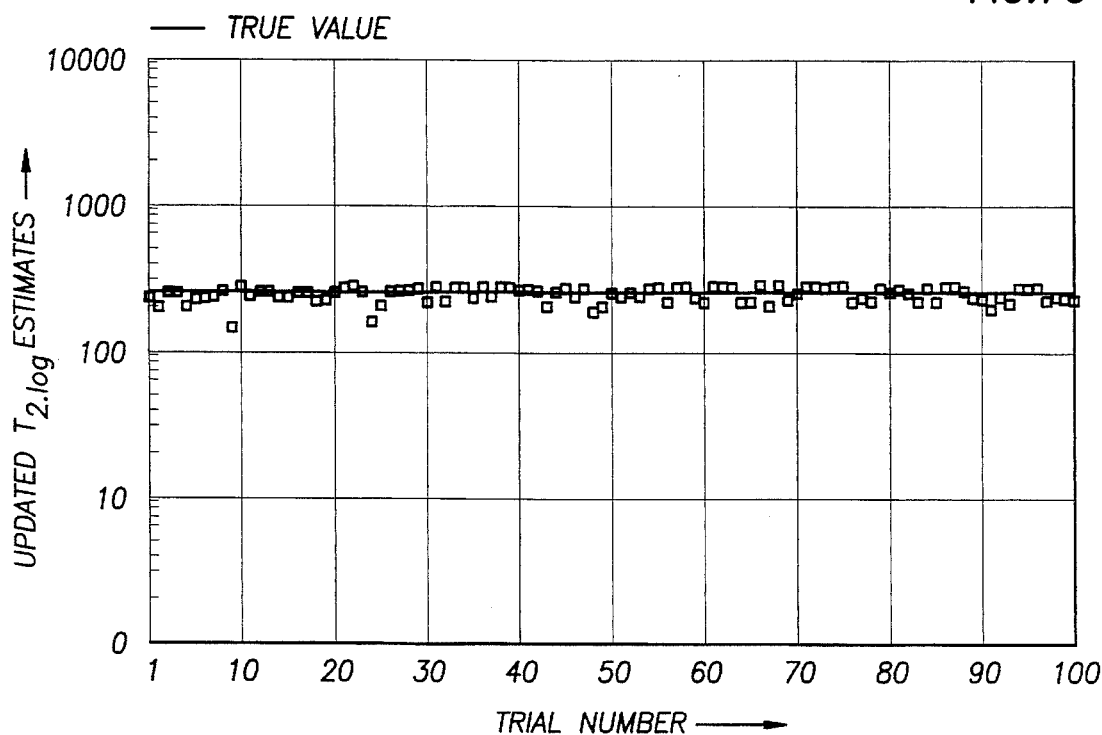
Figure 77:
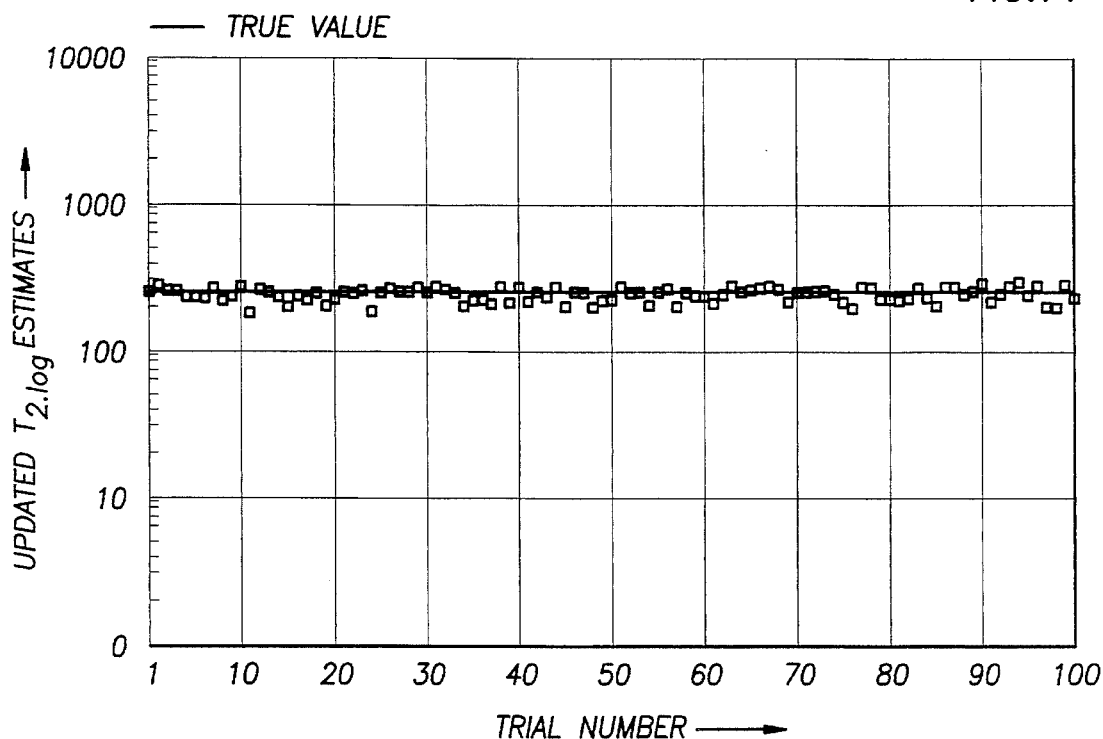

In order to have a basis for evaluating the results in FIGS. 66–68, analogous simulations were performed using pulse sequences with a single wait time, 1200 echoes and the same total time budget as used in the plots in FIG. 66–68. The results are shown in FIGS. 69–71. First observe that the total porosity estimates obtained using the multi-wait time sequence with 1.92 second measurement time are comparable to those obtained using the 2.8 second single wait time pulse. Thus, the multi-wait time pulse sequence is more efficient since comparable results can be achieved while logging 1.46 times faster than with a single wait time pulse sequence. The plot in FIG. 71 corresponds to a wait time of 1.54 seconds. The total porosity can be seen to be underestimated by about 2.0 p.u. This is consistent with the error propagation results in FIGS. 53–55 which predict that the total porosity will be underestimated by approximately 10 percent (see FIG. 53) or about 2 p.u. in the present situation. Observe also that the bound fluid porosity estimates for the single wait time sequence are, as noted earlier, poorer by almost a factor of two. Finally, in FIGS. 72–74 and 75–77 are shown the estimated mean relaxation times for the multi-wait time and single wait time depth logging examples. The precision of the multi-wait time pulse sequence estimates is clearly seen to be superior.

Conclusions

It has been shown that pulsed NMR logging using single wait time CPMG spin-echo pulse sequences involves an uncontrolled approximation. The approximation can result in log outputs with significant errors. The source of the errors is the use of incorrect $T_1/T_2$ ratios in the signal processing. The problem is amplified in high porosity rock formations with variable $T_1/T_2$ ratios and long $T_1$ components. In such formations the error propagation results show that the variations in $T_1/T_2$ ratios can result in significant uncontrolled accuracy errors in CMR log outputs. It was shown that increasing the wait times for single wait time pulse sequence logging is not a practical solution to the problem because it is inefficient and leads to reduced logging speeds.

It was shown that the aforementioned accuracy problems can be eliminated by using pulse sequences with several wait times. It was also shown that bound-fluid porosities derived from multiple wait time pulse sequences have superior precision compared to those derived from conventional single wait time pulse sequences.

Numerical simulations were conducted, using four model $T_2$-distributions. The numerical experiments were conducted to study: (1) the accuracy and precision of the $T_1/T_2$ ratio estimates, (2) the propagation of errors through the signal processing when single wait time pulse sequences are processed using incorrect $T_1/T_2$ ratios, and (3) the accuracy and precision of the updated log outputs. The results demonstrate the necessity of using multi-wait time pulse sequences in certain logging environments.

The adverse effects on log repeatability at bed interfaces predicted[11] for $T_1$ logging are not expected to be a problem for the pulse sequences employed here. The repeatability problem was due to the long distances traversed during a measurement cycle. This can be traced to the FIR/CPMG pulse sequences used for $T_1$ logging and the relatively poor S/N ratio of the underlying stretched exponential relaxational model studied by Kleinberg, et al.[11]

Tool motion is not expected to cause a log repeatability problem for the CPMG multi-wait time pulse sequences used here. For example, for one of the pulse sequences studied, with wait times of (0.15, 0.30, 0.8) seconds and corresponding echo numbers of (300, 600, 1200), the total measurement time for a PAPs is 4 seconds. A tool moving at 600 ft/hour (2 inches/second) will traverse 8 inches during a PAPs acquisition. Thus any bed boundary effects will be well localized at the bed interfaces.

NOMENCLATURE

Arabic

| | |
|---|---|
| $a_l$ | True spectral amplitudes corresponding to relaxation time $T_{2,l}$. Note that true amplitudes are independent of wait time. |
| $\{a_l\}$ | Set of true spectral amplitudes of a rock sample which is referred to as its $T_2$-distribution. |
| $a_{l,p}$ | Apparent spectral amplitudes defined in eq. (73) for wait time $W_p$ corresponding to relaxation time $T_{2,l}$ when an assumed (incorrect) $T_1/T_2$ ratio is used in the polarization correction. |
| $\tilde{A}_{j,p}^{(+)}$ | Amplitude of j-th spin-echo associated with p-th wait time in a multi-wait time pulse sequence. |
| $a_{v,l}$ | Variable spectral amplitude in the cost function defined in eq. (78). |
| $a_{v,l}^*$ | Optimal value of $a_{v,l}$ at which the cost function in eq. (78) attains its global minimum. The distribution $\{a_{v,l}^*\}$ is equal to the estimated true $T_2$-distribution, i.e., $\{\hat{a}_l\}$. |
| $C(\xi_v, \{a_{v,l}\})$ | Cost function that is minimized to estimate true $T_1/T_2$ ratios and updated $T_2$-distributions (see eq. (78)). |
| $f_l(W_p, \xi)$ | Polarization correction function for wait time $W_p$ and $T_1/T_2$ ratio, $\xi$. |
| $J_p$ | Number of spin-echoes per CPMG with wait time $W_p$. |
| $N_s$ | Number of spectral components in multi-exponential signal processing model. |
| $N_{wt}$ | Number of wait times in a multi-wait time CPMG pulse sequence. |

Greek

| | |
|---|---|
| $N_{j,p}$ | Gaussian noise on j-th spin-echo in CPMG initiated by wait time $W_p$. |
| $N_{trials}$ | Number of trials or samples in a numerical experiment. |
| $T_{1a,l}$ | Apparent longitudinal relaxation times defined in eq. (75). |
| $T_{2a,l}$ | Apparent spin-spin relaxation times defined in eq. (76). |
| $\overline{T}_{2,log}$ | Logarithmic mean relaxation time of a $T_2$-distribution (e.g., a CMR log output). |
| $T_{mf}$ | Mud filtrate relaxation time. Used as an input in the signal processing algorithm. |
| $T_{2,l}$ | $N_s$ equally spaced values, on a logarithmic scale, of $T_2$ in a domain assumed to span the intrinsic $T_2$-distribution. |
| $T_{min}$ | Smallest relaxation time assumed for inversion of a $T_2$-distribution. Used as an input in the signal processing algorithm. |
| $T_{max}$ | Largest relaxation time assumed for inversion of a $T_2$-distribution. Used as an input in the signal processing algorithm. |
| $W_p$ | The p-th wait time in a multi-wait time CPMG pulse sequence. |
| $\Delta$ | Inter-echo spacing. A value of 0.32 ms is used for all the computations in this specification. |
| $\xi$ | True $T_1/T_2$ ratio of a porous rock sample. |
| $\xi_0$ | Assumed $T_1/T_2$ ratio used in signal processing algorithm during single wait time logging (e.g., a nominal value $\xi_0 \cong 1.5$ is used when logging sandstone formations). |
| $\xi_r$ | Used in Appendix D to denote population random variable representing $T_1/T_2$ ratio estimator. |
| $\overline{\xi}$ | Used in the Appendix D to denote mean of $\xi_r$. |
| $\xi_v$ | Variable in the cost function representing the $T_1/T_2$ ratio (see eq. (78)). |
| $\xi_v^*$ | Optimal value of $\xi_v$ at which the cost function in eq. (78) attains its global minimum. Equal to estimate of true $T_1/T_2$ ratio $(\xi)$. |
| $\phi_{bf}(33)$ | Bound-fluid NMR porosity (e.g., a CMR log output) using a 33 ms cutoff. |
| $\phi_{nmr}$ | Total NMR porosity (e.g., a CMR log output). |
| $\phi_f(33)$ | Free-fluid NMR porosity (e.g., a CMR log output) using a 33 ms cutoff for the bound-fluid porosity. |
| $\sigma_{bias}$ | Used in Appendix D to denote bias error in the $T_1/T_2$ ratio estimator. |
| $\sigma(\xi_r)$ | Used in Appendix D to denote statistical error in the $T_1/T_2$ ratio estimator. |
| $\Sigma$ | Total rms error in estimator. Includes bias and statistical errors. |

Overbars

| | |
|---|---|
| $\hat{\phantom{x}}$ | Used to denote estimates. For example, if x is a true value of a random variable then $\hat{x}$ is an estimate of x. |

Subscripts

| | |
|---|---|
| j | Used to denote the echo number of an echo in a CPMG. |
| l | Used to denote a particular spectral component. |

REFERENCES

The following references are incorporated into this specification by reference:

10. Kleinberg, Robert L., Sezginer, Abdurrahman and Fukuhara, Masafumi, "Nuclear Magnetic Resonance Pulse Sequences For Use With Borehole Logging Tools," U.S. Pat. No. 5,023,551 issued Jun. 11, 1991.
11. Kleinberg, R. L., Straley, C., Kenyon, W. E., Akkurt, R. and Farooqui, S. A., 1993b, Nuclear Magnetic Resonance of rocks: $T_1$ vs. $T_2$: SPE 26470, Proceedings 1993 SPE Ann. Tech. Conf. And Exhibition, Houston, Tx., Oct. 3–6, 553–563.
12. Kleinberg, R. L., Farooqui, S. A., and Horsfield, M. A., 1993a, $T_1/T_2$ ratio and frequency dependence of nmr relaxation in porous sedimentary rocks: *J. of Colloid and Interface Science*, v. 158, 195–198.
13. Farrar, T. C. and Becker, E. D., 1971, *Pulse and fourier transform nmr.* Academic Press, 27–29.
14. Morriss, C. E., Macinnis, J., Freedman, R., Smaardyk, J., Straley, C., Kenyon, W. E., Vinegar, H. J., and Tutunjian, P. N., 1993, Field test of an experimental pulsed nuclear magnetism tool, paper GGG in 34th Annual Logging Symposium Transactions: Soc. of Professional Well Log Analysts.

APPENDIX D

The mean square total error in the estimates e as defined in eqs. (79) and (80) is for a sample drawn from the population of all possible experimental trials. Here we show that the mean square total error for the population can be expressed as the sum of the statistical variance and the square of the bias error. The latter expression is readily derived by considering the probability distribution for the population of $T_1/T_2$ estimates. Let $\xi_r$ be the random variable representing the population of all possible estimates. Moreover, let $\overline{\xi}$ denote the expectation value of $\xi_r$, i.e., $\langle \xi_r \rangle = \overline{\xi}$ where the angular brackets are used to denote a statistical average. Moreover, let $\xi$ denote the true value of the $T_1/T_2$ ratio (e.g., the target of the estimator). Define the bias error, $$\sigma_{bias} = \bar{\xi}_r - \xi. \qquad (D.1)$$

Then the mean square error $\Sigma^2$ including both bias and statistical error is given by, $$\Sigma^2 = \langle(\xi_r - \xi)^2\rangle, \qquad (D.2)$$

which can also be written in the form, $$\Sigma^2 = \langle(\xi_r - \bar{\xi}_r)^2\rangle + 2\sigma_{bias}\langle(\tau_r - \bar{\xi}_r)\rangle + \sigma_{bias}^2. \qquad (D.3)$$

In the above equation the middle term on the right hand side vanishes by definition and the first term is by definition the statistical variance in $\xi_r$. Using these facts one finds that, $$\Sigma^2 = \sigma^2(\xi_r) + \sigma_{bias}^2. \qquad (D.4)$$

Thus, eqs. (79) and (80) are equivalent for a sufficiently large sample to eq. (D.4).

The invention being thus described, it will be obvious that the same may be varied in many ways. Such variations are not to be regarded as a departure from the spirit and scope of the invention, and all such modifications as would be obvious to one skilled in the art arc intended to be included within the scope of the following claims.

We claim:

1. A logging system, comprising:

first means adapted to be disposed in a wellbore for receiving a plurality of spin echo pulse sequences from a formation penetrated by said wellbore, generating a plurality of signals in response thereto, and transmitting said plurality of signals uphole when said first means is disposed in said wellbore;

second means adapted to be disposed at a surface of said wellbore for receiving said plurality of signals, said second means including, spectral amplitude generation means responsive to said plurality of signals for generating a true polarization correction and a set of true spectral amplitudes corresponding to the true polarization correction, and means responsive to the true polarization correction and said set of true spectral amplitudes corresponding to the true polarization correction for generating an output record medium illustrating a set of characteristics of said formation penetrated by said wellbore.

2. The logging system of claim 1, wherein said spectral amplitude generation means comprises:

first spectral amplitude generation means responsive to said plurality of signals received from said first means for generating a set of apparent spectral amplitudes, and second spectral amplitude generation means responsive to said set of apparent spectral amplitudes for generating said true polarization correction and said set of true spectral amplitudes corresponding to the true polarization correction in response to said set of apparent spectral ampltiudes.

3. The logging system of claim 2, wherein said second spectral amplitude generation means comprises:

cost function construction and minimization means responsive to said set of apparent spectral amplitudes for constructing a cost function, determining a plurality of said cost functions as a function of a respective plurality of different polarization corrections and different spectral amplitudes, and determining a minimum one of said plurality of cost functions, said cost function construction and minimization means determining a polarization correction and a set of spectral amplitudes which corresponds to said minimum one of said plurality of cost functions, said polarization correction and said set of spectral amplitudes determined by said cost function construction and minimization means representing said true polarization correction and said set of true spectral amplitudes generated by said second spectral amplitude generation means.

4. The logging system of claim 2, wherein said spectral amplitude generation means comprises:

generalized likelihood function construction and minimization means responsive to said plurality of signals received from said first means for constructing a generalized likelihood function as a function of a polarization correction and a set of spectral amplitudes corresponding to the polarization correction, said generalized likelihood function construction and minimization means determining a plurality of the likelihood functions as a function of different ones of the polarization correction and different ones of the set of spectral amplitudes, and determining a minimum one of said plurality of likelihood functions, the polarization correction and the set of spectral amplitudes which correspond to said minimum one of said plurality of likelihood functions being said true polarization correction and said set of true spectral amplitudes generated by said second spectral amplitude generation means.

5. The logging system of claim 1, wherein said first means comprises:

transmission means for transmitting a first set of oscillating magnetic field pulses into said formation in the presence of a static magnetic field; and receiving means for receiving a first one of said plurality of spin echo pulse sequences from said formation in response to the transmission of said first set of oscillating magnetic field pulses into said formation, said transmission means transmitting a second set of oscillating magnetic field pulses into said formation in the presence of said static magnetic field when a first time period has elapsed following the receipt of said first one of said plurality of spin echo pulse sequences from said formation, said receiving means receiving a second one of said plurality of spin echo pulse sequences from said formation in response to the transmission of said second set of oscillating magnetic field pulses into said formation, said transmission means transmitting a third set of oscillating magnetic field pulses into said formation in the presence of said static magnetic field when a second time period has elapsed following the receipt of said second one of said plurality of spin echo pulse sequences from said formation, said second time period being different than said first time period.

6. The logging system of claim 5, wherein said spectral amplitude generation means comprises:

first spectral amplitude generation means responsive to said plurality of signals received from said first means for generating a set of apparent spectral amplitudes, and second spectral amplitude generation means responsive to said set of apparent spectral amplitudes for generating said true polarization correction and said set of true spectral amplitudes corresponding to the true polarization correction in response to said set of apparent spectral ampltiudes.

7. The logging system of claim 6, wherein said second spectral amplitude generation means comprises:

cost function construction and minimization means responsive to said set of apparent spectral amplitudes for constructing a cost function, determining a plurality of said cost functions as a function of a respective plurality of different polarization corrections and different spectral amplitudes, and determining a minimum one of said plurality of cost functions, said cost function construction and minimization means determining a polarization correction and a set of spectral amplitudes which corresponds to said minimum one of said plurality of cost functions, said polarization correction and said set of spectral amplitudes determined by said cost function construction and minimization means representing said true polarization correction and said set of true spectral amplitudes generated by said second spectral amplitude generation means.

8. The logging system of claim 6, wherein said spectral amplitude generation means comprises:

generalized likelihood function construction and minimization means responsive to said plurality of signals received from said first means for constructing a generalized likelihood function as a function of a polarization correction and a set of spectral amplitiudes corresponding to the polarization correction, said generalized likelihood function construction and minimization means determining a plurality of the likelihood functions as a function of different ones of the polarization correction and different ones of the set of spectral amplitudes, and determining a minimum one of said plurality of likelihood functions, the polarization correction and the set of spectral amplitudes which correspond to said minimum one of said plurality of likelihood functions being said true polarization correction and said set of true spectral amplitudes generated by said second spectral amplitude generation means.

9. The logging system of claim 1, wherein said first means comprises:

transmission means for transmitting a first set of oscillating magnetic field pulses into said formation in the presence of a static magnetic field; and receiving means for receiving a first one of said plurality of spin echo pulse sequences from said formation in response to the transmission of said first set of oscillating magnetic field pulses into said formation, said transmission means transmitting a second set of oscillating magnetic field pulses into said formation in the presence of said static magnetic field when a first time period has elapsed following the receipt of said first one of said plurality of spin echo pulse sequences from said formation, said receiving means receiving a second one of said plurality of spin echo pulse sequences from said formation in response to the transmission of said second set of oscillating magnetic field pulses into said formation, said transmission means transmitting a third set of oscillating magnetic field pulses into said formation in the presence of said static magnetic field when a second time period has elapsed following the receipt of said second one of said plurality of spin echo pulse sequences from said formation, said second time period being different than said first time period, said receiving means receiving a third one of said plurality of spin echo pulse sequences from said formation in response to the transmission of said third set of oscillating magnetic field pulses into said formation, said transmission means transmitting a fourth set of oscillating magnetic field pulses into said formation in the presence of said static magnetic field when a third time period has elapsed following the receipt of said third one of said plurality of spin echo pulse sequences from said formation, said third time period being different than said second time period and said third time period being different than said first time period.

10. The logging system of claim 9, wherein said spectral amplitude generation means comprises:

first spectral amplitude generation means responsive to said plurality of signals received from said first means for generating a set of apparent spectral amplitudes; and second spectral amplitude generation means responsive to said set of apparent spectral amplitudes for generating said true polarization correction and said set of true spectral amplitudes corresponding to the true polarization correction in response to said set of apparent spectral ampltiudes.

11. The logging system of claim 10, wherein said second spectral amplitude generation means comprises:

cost function construction and minimization means responsive to said set of apparent spectral amplitudes for constructing a cost function, determining a plurality of said cost functions as a function of a respective plurality of different polarization corrections and different spectral amplitudes, and determining a minimum one of said plurality of cost functions, said cost function construction and minimization means determining a polarization correction and a set of spectral amplitudes which corresponds to said minimum one of said plurality of cost functions, said polarization correction and said set of spectral amplitudes determined by said cost function construction and minimization means representing said true polarization correction and said set of true spectral amplitudes generated by said second spectral amplitude generation means.

12. The logging system of claim 10, wherein said spectral amplitude generation means comprises:

generalized likelihood function construction and minimization means responsive to said plurality of signals received from said first means for constructing a generalized likelihood function as a function of a polarization correction and a set of spectral amplitudes corresponding to the polarization correction, said generalized likelihood function construction and minimization means determining a plurality of the likelihood functions as a function of different ones of the polarization correction and different ones of the set of spectral amplitudes, and determining a minimum one of said plurality of likelihood functions, the polarization correction and the set of spectral amplitudes which correspond to said minimum one of said plurality of likelihood functions representing said true polarization correction and said set of true spectral amplitudes generated by said second spectral amplitude generation means.

13. In a system including a logging tool adapted to be disposed in a wellbore and a surface unit electrically connected to the logging tool adapted to be disposed at a surface of the wellbore, a method of logging said wellbore, comprising the steps of:

(a) magnetizing a formation penetrated by said wellbore with a static magnetic field;

(b) exciting the formation in the presence of said static magnetic field with an oscillating magnetic field;

(c) receiving a first set of spin echo pulses into said logging tool from said formation;

(d) transmitting a first set of signals uphole from said logging tool to said surface unit representative of said first set of spin echo pulses;

(e) waiting a first time period following the receiving step (c) and, when the first time period elapses, exciting the formation in the presence of said static magnetic field with another of said oscillating magnetic field;

(f) receiving a second set of spin echo pulses into said logging tool from said formation;

(g) transmitting a second set of signals uphole from said logging tool to said surface unit representative of said second set of spin echo pulses;

(h) waiting a second time period following the receiving step (f), where said second time period is different than said first time period, and, when the second time period elapses, exciting the formation in the presence of said static magnetic field with another of said oscillating magnetic field;

(i) receiving a third set of spin echo pulses into said logging tool from said formation;

(j) transmitting a third set of signals uphole from said logging tool to said surface unit representative of said third set of spin echo pulses;

(k) in response to the first, second, and third set of signals, generating in said surface unit a true polarization correction and a set of true spectral amplitudes; and (l) generating in said surface unit a new output record medium representative of a set of characteristics of said formation penetrated by said wellbore in response to said true polarization correction and said set of true spectral amplitudes.

14. The method of claim 13, wherein the generating step (k) comprises the steps of:

(m) generating in said surface unit a first set of apparent spectral amplitudes in response to the first set of signals, generating a second set of apparent spectral amplitudes in response to the second set of signals, and generating a third set of apparent spectral amplitudes in response to the third set of signals; and (n) generating said true polarization correction and said set of true spectral amplitudes in response to the first, second, and third set of apparent spectral amplitudes.

15. The method of claim 14, wherein the generating step (n) comprises the steps of: constructing a cost function; and generating a plurality of the cost functions as a function of different ones of said polarization correction and said spectral ampltiudes and noting a minimum one of the cost functions, the polarization correction and the set of spectral amplitudes associated with said minimum one of the plurality of cost functions being said true polarization correction and said set of true spectral amplitudes generated during the generating step (n).

16. The method of claim 13, wherein the generating step (k) comprises the steps of:

constructing a generalized likelihood function as a function of a polarization correction and a set of spectral amplitudes; and minimizing said generalized likelihood function thereby generating a plurality of likelihood functions, the polarization correction and the spectral amplitudes associated with a minimum one of the likelihood functions representing the true polarization correction and the set of true spectral amplitudes generated during the generating step (k).

17. The method of claim 13, further comprising:

(m) following the transmitting step (j), waiting a third time period following the receiving step (i), where said third time period is different than said second time period, and, when the third time period elapses, exciting the formation in the presence of said static magnetic field with another of said oscillating magnetic field;

(n) receiving a fourth set of spin echo pulses into said logging tool from said formation;

(o) transmitting a fourth set of signals uphole from said logging tool to said surface unit representative of said fourth set of spin echo pulses;

(p) in response to the first, second, third, and fourth set of signals, generating in said surface unit said true polarization correction and said set of true spectral amplitudes; and (q) generating in said surface unit said new output record medium representative of said set of characteristics of said formation penetrated by said wellbore in response to said true polarization correction and said set of true spectral amplitudes.

18. The method of claim 1, wherein the generating step (p) comprises the steps of:

(r) generating in said surface unit a first set of apparent spectral amplitudes in response to the first set of signals, generating a second set of apparent spectral amplitudes in response to the second set of signals, generating a third set of apparent spectral amplitudes in response to the third set of signals, and generating fourth set of apparent spectral amplitudes in response to the fourth set of signals; and (s) generating said true polarization correction and said set of true spectral amplitudes in response to the first, second, third and, fourth set of apparent spectral amplitudes.

19. The method of claim 18, wherein the generating step, (s) comprises the steps of: constructing a cost function; and generating a plurality of the cost functions as a function of different ones of the polarization correction and the spectral ampltiudes and noting a minimum one of the cost functions, the polarization correction and the set of spectral amplitudes associated with said minimum one of the cost functions representing said true polarization correction and said set of true spectral amplitudes generated during the generating step (s).

20. The method of claim 17, wherein the generating step (p) comprises the steps of:

constructing a generalized likelihood function as a function of a polarization correction and a set of spectral amplitudes; and minimizing said generalized likelihood function thereby generating a plurality of likelihood functions, the polarization correction and the spectral amplitudes associated with a minimum one of the likelihood functions representing the true polarization correction and the set of true spectral amplitudes generated during the generating step (p).

21. The method of claim 13, further comprising:

(m) following the transmitting step (j), waiting a third time period following the receiving step (i), where said third time period is different than said second time period, and, when the third time period elapses, exciting the formation in the presence of said static magnetic field with another of said oscillating magnetic field;

(n) receiving a fourth set of spin echo pulses into said logging tool from said formation;

(o) transmitting a fourth set of signals uphole from said logging tool to said surface unit representative of said fourth set of spin echo pulses;

(p) waiting a fourth time period following the receiving step (n), where said fourth time period is different than said third time period, and, when the fourth time period elapses, exciting the formation in the presence of said static magnetic field with another of said oscillating magnetic field;

(q) receiving a fifth set of spin echo pulses into said logging tool from said formation;

(r) transmitting a fifth set of signals uphole from said logging tool to said surface unit representative of said fifth set of spin echo pulses;

(s) in response 1;o the first, second, third, fourth, and fifth set of signals, generating in said surface unit said true polarization correction and said set of true spectral amplitudes; and (t) generating said new output record medium representative of said set of characteristics of said formation penetrated by said wellbore in response to said true polarization correction and said set of true spectral amplitudes.

22. The method of claim 21, wherein the generating step (s) comprises the steps of:

(u) generating in said surface unit a fast set of apparent spectral ampltudes in response to the first set of signals, generating a second set of apparent spectral amplitudes in response to the second set of signals, generating a third set of apparent spectral amplitudes in response to the third set of signals, generating a fourth set of apparent spectral amplitudes in response to the fourth set of signals, and generating a fifth set of apparent spectral amplitudes in response to the fifth set of signals; and (v) generating said true polarization correction and said set of true spectral amplitudes in response to the first, second, third, fourth and fifth set of apparent spectral ampltides.

23. The method of claim 22, wherein the generating step (v) comprises the steps of: constructing a cost function; and generating a plurality of the cost functions as a function of different ones of the polarization correction and the set of spectral ampltiudes and noting a minimum one of the cost functions, the polarization correction and the set of spectral amplitudes associated with said minimum one of the cost functions representing said true polarization correction and said set of true spectral amplitudes generated during the generating step (v).

24. The method of claim 21, wherein the generating step (s) comprises the steps of:

constructing a generalized likelihood function as a function of a polarization correction and a set of spectral amplitudes; and minimizing said generalized likelihood function thereby generating a plurality of likelihood functions, the polarization correction and the spectral amplitudes associated with a minimum one of the plurality of likelihood functions representing the true polarization correction and the set of true spectral amplitudes generated during the generating step (s).

25. The method of claim 24, wherein said true polarization correction comprises a true $T_1/T_2$ ratio, said set of true spectral amplitudes including a set of true spectral amplitudes $\{\hat{\alpha}_l\}$, and said set of apparent spectral amplitudes including a set of apparent spectral amplitudes $\{\hat{\alpha}_{l,p}\}$, where p represents a particular wait time.

26. A logging system, comprising:

first means adapted to be disposed in a wellbore for waiting a plurality of time periods when said first means is disposed in said wellbore and responsive thereto for receiving a plurality of spin echo pulse sequences from a formation penetrated by said wellbore which correspond, respectively, to said plurality of time periods, said first means generating a plurality of signals corresponding, respectively, to said plurality of spin echo pulse sequences and transmitting said plurality of signals uphole when said first means is disposed in said wellbore; and second means adapted to be disposed at a surface of said wellbore for receiving said plurality of signals, said second means including, spectral amplitude generation means for generating a set of apparent spectral amplitudes in response to said plurality of signals, said spectral amplitude generation means generating a true polarization correction and a set of true spectral amplitudes in response to said set of apparent spectral amplitudes when said plurality of time periods are different from each other, and output record generation means responsive to said set of apparent spectral amplitudes when said plurality of time periods are approximately equal to each other and to said true polarization correction and said set of true spectral amplitudes when said plurality of time periods are different from each other for generating an output record medium illustrating a set of characteristics of said formation penetrated by said wellbore.

27. The logging system of claim 26, wherein said spectral amplitude generation means comprises:

first spectral amplitude generation means responsive to said plurality of signals received from said first means for generating said set of apparent spectral amplitudes, and second spectral amplitude generation means responsive to said set of apparent spectral amplitudes for generating said true polarization correction and said set of true spectral amplitudes corresponding to the true polarization correction in response to said set of apparent spectral ampltiudes when said plurality of time periods are different from each other.

28. The logging system of claim 27, wherein said second spectral amplitude generation means comprises:

cost function construction and minimization means responsive to said set of apparent spectral amplitudes for constructing a cost function, determining a plurality of said cost functions as a function of a respective plurality of different polarization corrections and different spectral amplitudes, and determining a minimum one of said plurality of cost functions, said cost function construction and minimization means determining a selected polarization correction and a selected set of spectral amplitudes which corresponds to said minimum one of said plurality of cost functions, said selected polarization correction and said selected set of spectral amplitudes determined by said cost function construction and minimization means representing said true polarization correction and said set of true spectral amplitudes generated by said second spectral amplitude generation means.

29. In a logging system including a first means adapted to be disposed in a wellbore and a second means adapted to be disposed at a surface of said wellbore, a method of logging said wellbore, comprising the steps of:

waiting by said first means a plurality of time periods when said first means is disposed in said wellbore; exciting a formation penetrated by said wellbore a plurality of times which correspond, respectively, to said plurality of time periods;

receiving in said first means a plurality of spin echo pulse sequences from said formation which correspond, respectively, to said plurality of times and to said plurality of time periods;

generating in said first means a plurality of signals corresponding, respectively, to said plurality of spin echo pulses sequences and transmitting said plurality of signals uphole when said first means is disposed in said wellbore;

receiving in said second means said plurality of signals and generating a set of apparent spectral amplitudes in response to said plurality of signals;

generating in said second means a true polarization correction and a set of true spectral amplitudes in response to said set of apparent spectral amplitudes when said plurality of times periods are different from each other;

generating in said second means an output record medium illustrating a set of characteristics of said formation in response to said set of apparent spectral amplitudes when said plurality of time periods are approximately equal to each other; and generating in said second means said output record medium in response to said true polarization correction and said set of true spectral amplitudes when said plurality of time periods are different from each other.

30. The method of claim 29, wherein the step of generating in said second means a true polarization correction and a set of true spectral amplitudes in response to said set of apparent spectral amplitudes comprises the steps of:

constructing a cost function; and minimizing said cost function.

\* \* \* \* \*